US007153878B2

(12) United States Patent
Conner et al.

(10) Patent No.: US 7,153,878 B2
(45) Date of Patent: Dec. 26, 2006

(54) PEROXISOME PROLIFERATOR ACTIVATED RECEPTOR MODULATORS

(75) Inventors: Scott Eugene Conner, Elizabethtown, IN (US); James Allen Knobelsdorf, Noblesville, IN (US); Nathan Bryan Mantlo, Brownsburg, IN (US); Jeffrey Michael Schkeryantz, Fishers, IN (US); Quanrong Shen, Fishers, IN (US); Alan M Warshawsky, Carmel, IN (US); Guoxin Zhu, Noblesville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/505,089

(22) PCT Filed: Feb. 13, 2003

(86) PCT No.: PCT/US03/02679

§ 371 (c)(1),
(2), (4) Date: Aug. 17, 2004

(87) PCT Pub. No.: WO03/072100

PCT Pub. Date: Sep. 4, 2003

(65) Prior Publication Data

US 2005/0107449 A1 May 19, 2005

Related U.S. Application Data

(60) Provisional application No. 60/359,808, filed on Feb. 25, 2002.

(51) Int. Cl.
| | |
|---|---|
| A61K 31/426 | (2006.01) |
| A61K 31/429 | (2006.01) |
| A61K 31/421 | (2006.01) |
| A61K 31/5377 | (2006.01) |
| A61K 31/506 | (2006.01) |
| A61K 31/497 | (2006.01) |
| A61K 31/443 | (2006.01) |
| A61K 31/4439 | (2006.01) |
| A61K 31/4525 | (2006.01) |

(52) U.S. Cl. ............ 514/365; 514/367; 514/374; 514/236.8; 514/256; 514/255.05; 514/340; 514/342; 514/326; 548/204; 548/153; 548/236; 544/333; 544/405; 546/269.1; 546/268.7; 546/209

(58) Field of Classification Search .......... 548/203, 548/204, 205, 235, 236, 153; 544/333, 405; 546/269.1, 268.7, 209
See application file for complete search history.

(56) References Cited

U.S. PATENT DOCUMENTS 6,787,552 B1 * 9/2004 Sakuma et al. .......... 514/256

FOREIGN PATENT DOCUMENTS

| EP | 0 930 299 A | 7/1999 |
|---|---|---|
| WO | WO 01 00603 A | 1/2001 |
| WO | WO 02 18355 A | 3/2002 |
| WO | WO 02 062774 A | 8/2002 |
| WO | WO 03 072100 A | 9/2003 |

* cited by examiner

*Primary Examiner*—Kamal A. Saeed
*Assistant Examiner*—Jason M. Nolan
(74) *Attorney, Agent, or Firm*—MaCharri Vorndran-Jones

(57) ABSTRACT

The present invention is directed to compounds represented by the following structural formula, and pharmaceutically acceptable salts thereof, Formula I. (Formula I); wherein: (a) R5 is selected from the group consisting of $(C_1–C_6)$alkyl, $(C_1–C_6)$alkenyl, aryl $(C_0–C_4)$alkyl, aryloxy$(C_0–C_4)$alkyl, arylthio$(C_0–C_4)$alkyl, and further wherein when R5 is alkyl, R5 can optionally combine with W to form a 6 membered cycloheteroalkyl ring that is fused with the oxazole or thiazole ring to which the R5 group is attached; (b) R9 is selected from the group consisting of $C_1–C_5$alkyl, $C_1–C_5$alkenyl, and aryl$C_0–C_3$alkyl. (c) $T_1$ is selected from the group consisting of C and N, (d) W is selected from the group consisting of $CH_2$, $C(O)N(R21)$, $N(R21)$, $N(R21)CH_2$, O, $OCH_2$, S, and $SO_2$; and (e) X is selected from the group consisting of C, $CH_2C$, and $CCH_2$ (I)

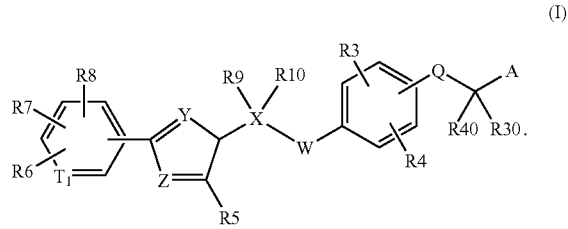

25 Claims, No Drawings

PEROXISOME PROLIFERATOR ACTIVATED RECEPTOR MODULATORS

This Application claims the benefit of U.S. Provisional Application Ser. No. 60/359,808, filed Feb. 25, 2002, and PCT Application Ser. No. PCT/US03/02679, filed Feb. 13, 2003.

BACKGROUND OF THE INVENTION

Peroxisome Proliferator Activated Receptors (PPARs) are members of the nuclear hormone receptor super family, which are ligand-activated transcription factors regulating gene expression. Various subtypes of PPARs have been discovered. These include PPARα, NUC1, PPARγ and PPARδ.

The PPARα receptor subtypes are reported to be activated by medium and long-chain fatty acids. They are involved in stimulating beta-oxidation of fatty acids and with the activity of fibrates reportedly producing a substantial reduction in plasma triglycerides and moderate reduction in low density lipoprotein (LDL) cholesterol. PPARα, PPARγ and PPARδ receptors have been implicated in diabetes mellitus, cardiovascular disease, obesity, Syndrome X and gastrointestinal disease, such as, inflammatory bowel disease. Syndrome X is the combination of symptoms including hyperinsulemia combined with hypertension, elevated body weight, elevated triglycerides and elevated LDL.

Current PPAR agonist treatment for Syndrome X relates to the use of thiazolidinediones (TZDs) or other insulin sensitivity enhancers (ISEs). TZDs are a class of PPAR gamma agonists which have been shown to increase the sensitivity of insulin sensitive cells. Increasing insulin sensitivity rather than the amount of insulin in the blood reduces the likelihood of hypoglycemic coma. However, TZDs and ISEs typically have little effect in preventing the cardiovascular part of Syndrome X in that their administration usually dose not result in the lowering of triglycerides and LDL-cholesterol while raising HDL-cholesterol. Furthermore, side effects commonly associated with treatment with TZDs can include significant weight gain, and, for troglitazone, can include liver toxicity. Therefore, a need exists for new pharmaceutical agents which affect treat or prevent cardiovascular disease, particularly that associated with Syndrome X, while preventing or minimizing weight gain, and more preferably while improving insulin sensitivity. It may be especially desirable when the active pharmaceutical agent selectively modulates a PPAR receptor subtype to provide an especially desirable pharmacological profile.

SUMMARY OF THE INVENTION

The present invention is directed to compounds represented by the following structural Formula I:

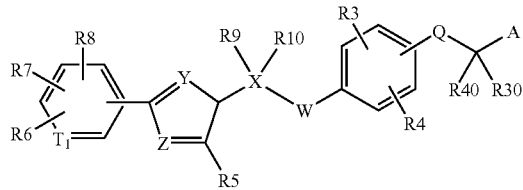

and pharmaceutically acceptable salts thereof, wherein:

(a) R3 and R4 are each independently selected from the group consisting of hydrogen, $(C_1-C_4)$alkyl, halo, and $(C_1-C_6)$alkoxy;

(b) R30 and R40 are each independently selected form the group consisting of hydrogen, $(C_1-C_4)$alkyl, and $(C_1-C_6)$alkoxy;

(c) R5 is selected from the group consisting of $(C_1-C_6)$ alkyl, $(C_1-C_6)$alkenyl, aryl$(C_0-C_4)$alkyl, aryloxy$(C_0-C_4)$alkyl, arylthio$(C_0-C_4)$alkyl, wherein said aryl $(C_0-C_4)$alkyl, aryloxy$(C_0-C_4)$alkyl, and arylthio $(C_1-C_4)$alkyl are each independently optionally substituted with from one to three substituents each independently selected from R5', and further wherein when R5 is alkyl, R5 can optionally combine with W to form a 6 membered cycloheteroalkyl ring that is fused with the oxazole or thiazole ring to which the R5 group is attached;

(d) R5' are each independently selected from the group consisting of halo, —(O)—$(C_1-C_5)$alkylCOOH, $C_1-C_5$alkyl, $C_1-C_5$alkylCOOH, and $CF_3$;

(e) R6 is selected from the group consisting of trihalomethyl, trihalomethoxy, hydroxy$(C_0-C_3)$alkyl, $(C_1-C_4)$ alkyl, $(C_1-C_6)$alkylNC(O)—, tetramethyldioxaborolanyl, halo, —C(O)$(C_1-C_4)$alkyl, —O—$(C_1-C_2)$alkyl-$CO_2H$, aryloxy, arylthio, —C(O)N$(C_1-C_6)$alkyl, $(C_1-C_4)$alkoxy, tetrahydropyranyloxy, morpholinyl, $(C_5-C_6)$cycloalkyloxy, $(C_5-C_6)$heterocyclo-oxy, pyridinyl, pyrimidinyl, pyrazinyl and aryl$(C_0-C_4)$alkyl, wherein said pyridinyl, pyrimidinyl, pyrazinyl, aryl $(C_0-C_4)$alkyl, aryloxy, $(C_5-C_6)$heterocyclo-oxy, and arylthio are each optionally substituted with from one to three substituents independently selected from R6';

(f) R6' and R9' are each independently selected from the group consisting of $CF_3$, $C_1-C_4$ alkyl, halo, hydroxy $(C_1-C_3)$alkyl, $C_1-C_3$alkoxy, and —C(O)$CH_3$;

(g) R7 and R8 are each independently selected from the group consisting of hydrogen, $CF_3$, and $(C_1-C_4)$ alkyl;

(h) R9 is selected from the group consisting of $C_1-C_5$alkyl, $C_1-C_5$alkenyl, and aryl$C_0-C_3$alkyl, wherein said arylalkyl is optionally substituted with from one to three substituents each independently selected from R9';

(i) R10 is selected from the group consisting of hydrogen, and $C1-C_5$alkyl;

(j) Q is selected from the group consisting of O, a single bond, and C;

(k) $T_1$ is selected from the group consisting of C and N;

(l) W is selected from the group consisting of $CH_2$, C(O)N(R21), N(R21), N(R21)$CH_2$, O, $OCH_2$, S, and $SO_2$;

(m) R21 is selected from the group consisting of hydrogen and $C_1-C_2$alkyl;

(n) X is selected from the group consisting of C, $CH_2C$, and $CCH_2$;

(O) Y and Z are each independently selected from the group consisting of O, N and S, wherein at least one of Y and Z is selected from the group consisting of O and S;

(p) A is an functional group selected from the group consisting of carboxyl, $C_1-C_3$alkylnitrile, carboxamide, and $(CH_2)_n$ COOR19;

(q) n is 0, 1, 2 or 3; and (r) R19 is selected from the group consisting of hydrogen, and $C_1-C_3$alkyl.

Another embodiment of the present invention is a compound of Formula I':

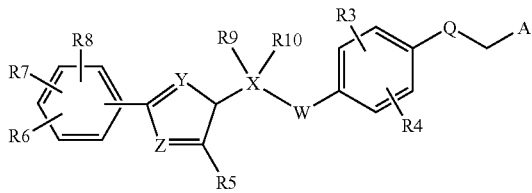

and pharmaceutically acceptable salts thereof, wherein:
(a) R3 and R4 are each independently selected from the group consisting of hydrogen, $(C_1-C_4)$alkyl, halo, and $(C_1-C_6)$alkoxy;
(b) R5 is selected from the group consisting of $(C_1-C_6)$alkyl, $(C_1-C_6)$alkenyl, substituted aryl$(C_0-C_4)$alkyl, substituted aryloxy$(C_1-C_4)$alkyl, substituted arylthio $(C_0-C_4)$alkyl, unsubstituted aryl$(C_0-C_4)$alkyl, unsubstituted aryloxy$(C_0-C_4)$alkyl, and unsubstituted arylthio$(C_0-C_4)$alkyl;
(c) R6 is selected from the group consisting of trihalomethyl, halo, hydroxy, hydroxy$(C_1-C_3)$alkyl, $(C_1-C_4)$alkyl, —C(O) $(C_2-C_4)$alkyl, —C(O)N$(C_1-C_6)$alkyl, —O—$(C_1-C_2)$alkyl-$CO_2H$, $(C_1-C_4)$alkyloxy, $(C_5-C_6)$cycloalkyloxy, $(C_5-C_6)$heterocyclic, $(C_5-C_6)$heterocyclo-oxy, substituted $(C_5-C_6)$heterocyclo-oxy, aryl $(C_0-C_4)$alkyl, substituted aryl$(C_0-C_4)$alkyl;
(d) R7 and R8 are each independently selected from the group consisting of hydrogen, $CF_3$, and $(C_1-C_4)$alkyl;
(e) R9 is selected from the group consisting of $C1-C_5$alkenyl, unsubtituted aryl$C_0-C_3$alkyl, substituted aryl$C_0-C_3$alkyl, substituted arylthio$C_1-C_2$alkyl, unsubstituted arylthio$C_1-C_2$alkyl, substituted aryloxy$C_1-C_2$alkyl, unsubstituted aryloxy$C_1-C_2$alkyl and $C1-C_5$alkyl;
(f) R10 is hydrogen or methyl;
(g) Q is selected from the group consisting of O and C;
(h) W is selected from the group consisting of O, S, and $SO_2$;
(i) X is selected from the group consisting of CH, $CH_2$CH, and $CHCH_2$;
(j) Y and Z are each independently selected from the group consisting of O, N and S;
(k) A is an functional group selected from the group consisting of carboxyl, $C_1-C_3$alkylnitrile, carboxamide, and $(CH_2)_n$ COOR19;
(l) n is 0, 1, 2 or 3; and
(m) R19 is selected from the group consisting of hydrogen, optionally substituted $C1-C4$alkyl and optionally substituted arylmethyl.

In one embodiment, the present invention also relates to pharmaceutical compositions which comprising at least one compound of the present invention, or a pharmaceutically acceptable salt thereof, and a pharmaceutically acceptable carrier.

In another embodiment, the present invention relates to a method of selectively modulating a PPAR delta receptor by contacting the receptor with at least one compound represented by Structural Formula I, and pharmaceutically acceptable salts thereof.

In another embodiment, the present invention relates to a method of modulating one or more of the PPAR alpha, beta, gamma, and/or delta receptors.

In a further embodiment, the present invention relates to a method of making a compound represented by Structural Formula I.

The compounds of the present invention are believed to be effective in treating and preventing Syndrome X, Type II diabetes, hyperglycemia, hyperlipidemia, obesity, coagaulopathy, hypertension, atherosclerosis, and other disorders related to Syndrome X and cardiovascular diseases. In addition, the compounds can be associated with fewer clinical side effects than compounds currently used to treat these conditions. Further, compounds of this invention can be useful for lowering fibrinogen, increasing HDL levels, treating renal disease, controlling desirable weight, treating demyelinating diseases, treating certain viral infections, and treating liver disease.

DETAILED DESCRIPTION OF THE INVENTION

The terms used to describe the instant invention have the following meanings herein.

As used herein, alkyl groups include straight chained and branched hydrocarbons, which are completely saturated.

Cycloalkyl groups, as used herein, include cyclic hydrocarbons, which are completely saturated.

As used herein, the term "halo" means Cl, F, or Br. Especially preferred halo groups are Cl and F.

An especially preferred trihalomethyl group is —$CF_3$.

As used herein, when Q is a single bond means that Q is absent and the —C(R30)(R40) group is directly bonded to the phenyl.

As used herein, when arylalkyl is aryl$C_0$alkyl, then the aryl group is bonded directly to the group to which the arylalkyl group is bonded. For example (but not limited to), if aryl is phenyl then aryl$C_0$alkyl means a phenyl group and aryl$C_1$alkyl means a benzyl.

As used herein, aryl groups include carbocyclic aromatic ring systems (e.g. phenyl), fused polycyclic aromatic ring systems (e.g. naphthyl and anthracenyl) and aromatic ring systems fused to carbocyclic non-aromatic ring systems (e.g., 1,2,3,4-tetrahydronaphthyl and benzodioxyl). One especially preferred aryl group is phenyl.

Heterocyclic and heterocyclo group, as used herein, is a ring system having at least one heteroatom such as nitrogen, sulfur or oxygen. Heterocyclic/heterocyclo groups include benzofuranyl, benzothiazolyl, benzothienyl, isoquinolyl, isoxazolyl, morpholino, oxadiazolyl, pyridyl, pyrimidinyl, pyrrolyl, quinolyl, tetrahydropyranyl, dioxaborolan-2-yl and thienyl.

Suitable substituents when at least one of said R5, R6, R9 and R19 is substituted is one or more independently selected from the group consisting halo, —(O)—$(C_1-C_5)$alkyl-COOH, $C_1-C_5$alkyl, and $CF_3$. When R19 is substituted, it is preferred that there are from 1–3 substitutions on said R19 group. When R9, R5 or R6 are substituted, it is especially preferred that there are 1 or 2 independent substituents on said R9, R5 or R6 group.

As used herein, the phrase "selectively modulate" means a compound whose EC50 for the stated PPAR receptor is at least ten fold lower than its EC50 for the other PPAR receptor subtypes.

When a compound represented by Structural Formula I has more than one chiral substituent it may exist in diastereoisomeric forms. The diastereoisomeric pairs may be separated by methods known to those skilled in the art, for example chromatography or crystallization and the individual enantiomers within each pair may be separated using methods familiar to the skilled artisan. The present invention includes each diastereoisomer of compounds of Structural Formula I and mixtures thereof.

Certain compounds of Structural Formula I may exist in different stable conformational forms that may be separable. Torsional asymmetry due to restricted rotation about an asymmetric single bond, for example because of steric hindrance or ring strain, may permit separation of different conformers. The present invention includes each conformational isomer of compounds of Structural Formula I and mixtures thereof.

Certain compounds of Structural Formula I may exist in zwitterionic form and the present invention includes each zwitterionic form of compounds of Structural Formula I and mixtures thereof.

"Pharmaceutically-acceptable salt" refers to salts of the compounds of the Structural Formula I that are generally clinically acceptable for use in mammals. Typical pharmaceutically-acceptable salts include those salts prepared by reaction of the compounds of the present invention with a mineral or organic acid or an organic or inorganic base. Such salts are known as base addition salts, respectively. It should be recognized that the particular counterion forming a part of any salt of this invention is not of a critical nature, so long as the salt as a whole is pharmaceutically-acceptable and as long as the counterion does not contribute undesired qualities to the salt as a whole. These salts may be prepared by methods known to those skilled in the art.

The term, active ingredient means the compounds generically described by Structural Formula I as well as the salts of such compounds.

The term pharmaceutically acceptable means that the carrier, diluent, excipients and salt must be compatible with the other ingredients of the composition, and having acceptable safety profile for use in a mammal. It is preferred that such mammal is a human patient. Pharmaceutical compositions of the present invention are prepared by procedures known in the art using well-known and readily available ingredients.

Preventing refers to reducing the likelihood that the recipient will incur or develop any of the pathological conditions described herein. The term preventing is particularly applicable to a patient that is susceptible to the particular patholical condition.

Treating refers to mediating a disease or condition and preventing, or mitigating, its further progression or ameliorate the symptoms associated with the disease or condition.

"Pharmaceutically-effective amount" means that amount of a compound, or of its salt thereof, that will elicit the biological or medical response of a tissue, system, or mammal. Such an amount can be administered prophylactically to a patient thought to be susceptible to development of a disease or condition. Such amount when administered prophylactically to a patient can also be effective to prevent or lessen the severity of the mediated condition. Such an amount is intended to include an amount sufficient to modulate a selected PPAR receptor or to prevent or mediate a disease or condition. Generally, the effective amount of a Compound of Formula I will be between 0.02 through 5000 mg per day. Preferably 1 through 1,500 mg per day. The desired dose may be presented in a single dose or as divisded doses administered at appropriate intervals.

A "mammal" is an individual animal that is a member of the taxonomic class Mammalia. The class Mammalia includes humans, monkeys, chimpanzees, gorillas, cattle, swine, horses, sheep, dogs, cats, mice, and rats.

Administration to a human is most preferred. The compounds and compositions of the present invention are useful for the treatment and/or prophylaxis of cardiovascular disease, for raising serum HDL cholesterol levels, for lowering serum triglyceride levels and for lower serum LDL cholesterol levels. Elevated triglyceride and LDL levels, and low HDL levels, are risk factors for the development of heart disease, stroke, and circulatory system disorders and diseases.

The compounds and compositions of the present invention can also be useful for treating and/or preventing obesity.

Further, these compounds and compositions can be useful for the treatment and/or prophylaxis of non-insulin dependent diabetes mellitus (NIDDM) with reduced or no body weight gains by the patients. Furthermore, compounds and compositions of the present invention can be useful to treat or prevent acute or transient disorders in insulin sensitivity, such as sometimes occur following surgery, trauma, myocardial infarction, and the like. Additionally, compounds of this invention can be useful for treating certain autoimmune conditions. The physician of ordinary skill will know how to identify humans who will benefit from administration of the compounds and compositions of the present invention.

The present invention further provides a method for the treatment and/or prophylaxis of hyperglycemia in a human or non-human mammal which comprises administering an effective, non-toxic amount of a compound of the general formula (I), or a tautomeric form thereof and/or a pharmaceutically acceptable salt thereof to a hyperglycemic human or non-human mammal in need thereof.

The invention also relates to the use of a compound of Formula I as described above, for the manufacture of a medicament for treating a PPAR receptor mediated condition.

A therapeutically effective amount of a compound of Structural Formula I can be used for the preparation of a medicament useful for treating Syndrome X, diabetes, treating obesity, lowering tryglyceride levels, lowering serum LDL levels, raising the plasma level of high density lipoprotein, and for treating, preventing or reducing the risk of developing atherosclerosis, and/or for preventing or reducing the risk of having a first or subsequent atherosclerotic disease event in mammals, particularly in humans. In general, a therapeutically effective amount of a compound of the present invention typically reduces serum triglyceride levels of a patient by about 20% or more, and increases serum HDL levels in a patient. It is especially preferred that HDL levels will be increased by about 30% or more. In adition, a therapeutically effective amount of a compound, used to prevent or treat NIDDM, typically reduces serum glucose levels, or more specifically HbAlc, of a patient by about 0.7% or more.

Advantageously, compositions containing the compound of Structural Formula I or the salts thereof may be provided in dosage unit form, preferably each dosage unit containing from about 1 to about 500 mg be administered although it will, of course, readily be understood that the amount of the compound or compounds of Structural Formula I actually to be administered will be determined by a physician, in the light of all the relevant circumstances.

When used herein Syndrome X includes pre-diabetic insulin resistance syndrome and the resulting complications thereof, insulin resistance, non-insulin dependent diabetes, dyslipidemia, hyperglycemia obesity, coagulopathy, hypertension and other complications associated with diabetes. The methods and treatments mentioned herein include the above and encompass the treatment and/or prophylaxis of any one of or any combination of the following: pre-diabetic insulin resistance syndrome, the resulting complications thereof, insulin resistance, Type II or non-insulin dependent diabetes, dyslipidemia, hyperglycemia, obesity and the complications associated with diabetes including cardiovascular disease, especially atherosclerosis.

The compositions are formulated and administered in the same general manner as detailed herein. The compounds of the instant invention may be used effectively alone or in combination with one or more additional active agents depending on the desired target therapy. Combination therapy includes administration of a single pharmaceutical dosage composition which contains a compound of Structural Formula I and one or more additional active agents, as well as administration of a compound of Structural Formula I and each active agent in its own separate pharmaceutical dosage formulation. For example, a compound of Structural Formula I or salt thereof and an insulin secretogogue such as biguanides, thiazolidinediones, sulfonylureas, insulin, or α-glucosidose inhibitors can be administered to the patient together in a single oral dosage composition such as a tablet or capsule, or each agent administered in separate oral dosage formulations. Where separate dosage formulations are used, a compound of Structural Formula I and one or more additional active agents can be administered at essentially the same time, i.e., concurrently, or at separately staggered times, i.e., sequentially; combination therapy is understood to include all these regimens.

An example of combination treatment or prevention of atherosclerosis may be wherein a compound of Structural Formula I or salts thereof is administered in combination with one or more of the following active agents: antihyperlipidemic agents; plasma HDL-raising agents; antihypercholesterolemic agents, fibrates, vitamins, aspirin, and the like. As noted above, the compounds of Structural Formula I can be administered in combination with more than one additional active agent.

Another example of combination therapy can be seen in treating diabetes and related disorders wherein the compounds of Structural Formula I, salts thereof can be effectively used in combination with, for example, sulfonylureas, biguanides, thiazolidinediones, α-glucosidase inhibitors, other insulin secretogogues, insulin as well as the active agents discussed above for treating atherosclerosis.

The compounds of the present invention, and the pharmaceutically acceptable salts, have valuable pharmacological properties and can be used in pharmaceutical compositions containing a therapeutically effective amount of a compound of the present invention, or pharmaceutically acceptable salts thereof, in combination with one or more pharmaceutically acceptable excipients. Excipients are inert substances such as, without limitation, carriers, diluents, fillers, flavoring agents, sweeteners, lubricants, solubilizers, suspending agents, wetting agents, binders, disintegrating agents, encapsulating material and other conventional adjuvants. Proper formulation is dependent upon the route of administration chosen. Pharmaceutical compositions typically contain from about 1 to about 99 weight percent of the active ingredient that is a compound of the present invention.

Preferably, the pharmaceutical formulation is in unit dosage form. A "unit dosage form" is a physically discrete unit containing a unit dose, suitable for administration in human subjects or other mammals. For example, a unit dosage form can be a capsule or tablet, or a number of capsules or tablets. A "unit dose" is a predetermined quantity of the active compound of the present invention, calculated to produce the desired therapeutic effect, in association with one or more pharmaceutically-acceptable excipients. The quantity of active ingredient in a unit dose may be varied or adjusted from about 0.1 to about 1000 milligrams or more according to the particular treatment involved.

The dosage regimen utilizing the compounds of the present invention is selected by one of ordinary skill in the medical or veterinary arts, in view of a variety of factors, including, without limitation, the species, age, weight, sex, and medical condition of the recipient, the severity of the condition to be treated, the route of administration, the level of metabolic and excretory function of the recipient, the dosage form employed, the particular compound and salt thereof employed, and the like.

Preferably, the compounds of the present invention are administered in a single daily dose, or the total daily dose may be administered in divided doses, two, three, or more times per day. Where delivery is via transdermal forms, of course, administration is continuous.

Suitable routes of administration of pharmaceutical compositions of the present invention include, for example, oral, eyedrop, rectal, transmucosal, topical, or intestinal administration; parenteral delivery (bolus or infusion), including intramuscular, subcutaneous, intramedullary injections, as well as intrathecal, direct intraventricular, intravenous, intraperitoneal, intranasal, or intraocular injections. The compounds of the invention can also be administered in a targeted drug delivery system, such as, for example, in a liposome coated with endothelial cell-specific antibody.

Solid form formulations include powders, tablets and capsules.

Sterile liquid formulations include suspensions, emulsions, syrups, and elixirs.

Pharmaceutical compositions of the present invention can be manufactured in a manner that is itself known, e.g., by means of conventional mixing, dissolving, granulating, dragee-making, levigating, emulsifying, encapsulating, entrapping or lyophilizing processes.

The following pharmaceutical formulations 1 and 2 are illustrative only and are not intended to limit the scope of the invention in any way. "Active Ingredient", refers to a compound according to Structural Formula I or salts thereof.

Formulation 1

Hard gelatin capsules are prepared using the following ingredients:

|  | Quantity (mg/capsule) |
| --- | --- |
| Active Ingredient | 250 |
| Starch, dried | 200 |
| Magnesium stearate | 10 |
| Total | 460 mg |

Formulation 2

A tablet is prepared using the ingredients below:

|  | Quantity (mg/tablet) |
| --- | --- |
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

In yet another embodiment of the compounds of the present invention, the compound is radiolabelled, such as with carbon-14, or tritiated. Said radiolabelled or tritiated compounds are useful as reference standards for in vitro assays to identify new selective PPAR receptor agonists.

The compounds of the present invention can be useful for modulating insulin secretion and as research tools. Certain compounds and conditions within the scope of this invention are preferred. The following conditions, invention embodiments, and compound characteristics listed in tabular form may be independently combined to produce a variety of preferred compounds and process conditions. The following list of embodiments of this invention is not intended to limit the scope of this invention in any way.

Some prefered characteristics of compounds of formula I are:
- (a) R3 is methyl;
- (b) R4 is hydrogen;
- (c) R30 is methyl;
- (d) R30 is alkoxy;
- (e) R3 and R4 are each hydrogen;
- (f) R3 and R4 are each methyl;
- (g) A is carboxyl;
- (h) w is —O—;
- (i) w is —S—;
- (j) W is —NH—;
- (k) W is selected from the group consisting of C(O)N(R21), N(R21), N(R21)CH$_2$, OCH$_2$, and SO$_2$;
- (l) X is C;
- (m) X is CH$_2$C;
- (n) R9 is methyl;
- (o) R9 is benzyl;
- (p) R9 is C$_1$–C$_3$alkyl;
- (q) R10 is hydrogen;
- (r) R10 is methyl
- (s) Z is N;
- (t) Z is O;
- (u) Y is O;
- (v) Y is S;
- (w) Q is O;
- (x) Q is C;
- (y) Q is attached to the phenyl ring in a meta orientation with respect to the W group that is attached to the phenyl ring;
- (z) Q is attached to the phenyl ring in a para orientation with respect to the W group that is attached to the phenyl ring;
- (aa) R5 is methyl;
- (bb) R5 is C$_2$–C$_4$alkyl;
- (cc) R5 is isopropyl;
- (dd) R5 is arylalkyl;
- (ee) R$_5$ combines with W to form a 6 membered cycloheteroalkyl ring that is fused to the thiazole or oxazole ring from which the R5 group originates;
- (ff) R6 is CF$_3$;
- (gg) R6 is an optionally substituted group selected from the group consisting of trihalomethoxy, (C$_1$–C$_6$)alkylNC(O)—, tetramethyldioxaborolanyl, —C(O)(C$_1$–C$_4$)alkyl, —O—(C$_1$–C$_2$)alkyl-CO$_2$H, aryloxy, arylthio, —C(O)N(C$_1$–C$_6$)alkyl, tetrahydropyranyloxy, morpholinyl, (C$_5$–C$_6$)cycloalkyloxy, (C$_5$–C$_6$)heterocyclooxy, pyridinyl, pyrimidinyl, pyrazinyl and aryl(C$_0$–C$_4$)alkyl;
- (hh) R7 is CF$_3$;
- (ii) R8 is CF$_3$;
- (jj) R7 is halo;
- (kk) R8 is hydrogen;
- (ll) T$_1$ is C;
- (mm) T$_1$ is N;
- (nn) Aryl is a phenyl group;
- (oo) Heterocyclic group contains on O;
- (pp) A compound of Formula I that selectively modulates a delta receptor;
- (qq) A compound of Formula I that is a PPAR coagaonist that modulates a gamma receptor and a delta receptor;
- (rr) A compound of Formula I for use in the treatment of cardiovascular disease;
- (ss) A compound of Formula I for use in the treatment of Syndrome X;
- (tt) A compound of Formula I for use in the control of obesity;
- (uu) A compound of Formula I for use in treating diabetes.
- (vv) A compound of Formula I that is a PPAR receptor agonist.
- (ww) Preferred compounds of Formula I are selected from the group consisting of (4-{1-[4-[2-(2-Chloro-6-fluoro-phenyl)-ethyl]-2-(4-trifluoromethyl-phenyl)-thiazol-5-yl]-ethylsulfanyl}-2-methyl-phenoxy)-acetic acid, (2-Methyl-4-{1-[4-methyl-2-(4-trifluoromethyl-phenyl)-thiazol-5-yl]-2-phenyl-ethylsulfanyl}-phenoxy)-acetic acid, 3-(2-Methyl-4-{1-[4-methyl-2-(4-trifluoromethyl-phenyl)-thiazol-5-yl]-2-phenyl-ethoxy}-phenyl)-propionic acid, (4-{1-[4-[2-(2-Chloro-6-fluoro-phenyl)-ethyl]-2-(4-trifluoromethyl-phenyl)-thiazol-5-yl]-ethoxy}-2-methyl-phenoxy)-acetic acid, 3-(4-{1-[4-[2-(2-Chloro-6-fluoro-phenyl)-ethyl]-2-(4-trifluoromethyl-phenyl)-thiazol-5-yl]-ethoxy}-2-methyl-phenyl)-propionic acid, (2-Methyl-4-{1-[4-phenethyl-2-(4-trifluoromethyl-phenyl)-thiazol-5-yl]-ethylsulfanyl}-phenoxy)-acetic acid, (2-Methyl-4-{1-[4-phenethyl-2-(4-trifluoromethyl-phenyl)-thiazol-5-yl]-ethoxy}-phenoxy)-acetic acid, 3-(2-Methyl-4-{1-[4-phenethyl-2-(4-trifluoromethyl-phenyl)-thiazol-5-yl]-ethoxy)-phenyl)-propionic acid, (2-Methyl-4-{1-(4-phenyl-2-(4-trifluoromethyl-phenyl)-thiazol-5-yl]-ethylsulfanyl}-phenoxy)-acetic acid, 3-(2-Methyl-4-{1-[4-phenyl-2-(4-trifluoromethyl-phenyl)-thiazol-5-yl]-ethoxy}-phenyl)-propionic acid, (4-{1-[4-Isopropyl-2-(4-trifluoromethyl-phenyl)-thiazol-5-yl]-ethylsulfanyl}-2-methyl-phenoxy)-acetic acid, (4-{1-[4-Isopropyl-2-(4-trifluoromethyl-phenyl)-thiazol-5-yl]-ethoxy}-2-methyl-phenoxy)-acetic acid, 3-(4-{1-[4-Isopropyl-2-(4-trifluoromethyl-phenyl)-thiazol-5-yl]-ethoxy}-2-methyl-phenyl)-propionic acid, 3-(4-{1-[4-Isopropyl-2-(4-trifluoromethyl-phenyl)-thiazol-5-yl]-ethylsulfanyl}-2-methyl-phenyl)-propionic acid, (2-Methyl-4-(1-[4-phenylsulfanylmethyl-2-(4-trifluoromethyl-phenyl)-thiazol-5-yl]-ethylsulfanyl}-phenoxy)-acetic acid, (4-{1-[4-(3,5-Bis-trifluoromethyl-phenoxymethyl)-2-(4-trifluoromethyl-phenyl)-thiazol-5-yl]-ethylsulfanyl}-2-methyl-phenoxy)-acetic acid, (4-{1-[4-(2-Chloro-6-fluoro-phenoxymethyl)-2-(4-trifluoromethyl-phenyl)-thiazol-5-yl]-ethylsulfanyl}-2-methyl-phenoxy)-acetic acid, 3-(4-{1-[4-(3,5-Bis-trifluoromethyl-phenoxymethyl)-2-(4-trifluoromethyl-phenyl)-thiazol-5-yl]-ethoxy}-2-methyl-phenyl)-propionic acid, 3-(4-{1-[4-(2-Chloro-6-fluoro-phenoxymethyl)-2-(4-trifluoromethyl-phenyl)-thiazol-5-yl]-ethoxy}-2-methyl-phenyl)-propionic acid, 3-(2-Methyl-4-{1-[4-methyl-2-(4-trifluoromethyl-phenyl)-thiazol-5-yl]-ethoxy}-phenyl)-propionic acid, 3-(2-Methyl-4-{2-[5-methyl-2-(4-trifluoromethyl-phenyl)-thiazol-4-yl]-propoxy}-phenyl)-propionic acid, 3-(2-Methyl-4-{2-methyl-2-[5-methyl-2-(4-trifluoromethyl-phenyl)-thiazol-4-yl]-propoxy}-phenyl)-propionic acid, 3-(2-Methyl-4-{2-methyl-2-[5-methyl-2-(4-trifluoromethyl-phenyl)-thiazol-4-yl]-propoxy}-phenyl)-propionic acid, 3-(2-Methyl-4-{2-[5-methyl-2-(4-trifluoromethyl-phenyl)-oxazol-4-yl]-propoxy}-phenyl)-propionic acid, (R)-3-(2-Methyl-4-[2-[5-methyl-2-(4-trifluoromethyl-phenyl)-thiazol-4-yl]-propylsulfanyl)-phenyl)-propionic acid, (4-{1R-[4-[2-(2-Chloro-6-fluoro-phenyl)-ethyl]-2-(4-trifluoromethyl-phenyl)-thiazol-5-yl]-ethylsulfanyl}-2-methyl-phenoxy)-acetic acid, _(4-{1S-[4-[2-(2-Chloro-6-fluoro-phenyl)-ethyl]-2-(4-trifluoromethyl-phenyl)-thiazol-5-yl]-ethylsulfanyl}-2-methyl-phenoxy)-acetic acid, (2-Methyl-4-{1S-[4-phenethyl-2-(4-trifluoromethyl-phenyl)-thiazol-5-yl]-ethoxy}-phenoxy)-acetic acid, (2-Methyl-4-({R-[4-phenethyl-2-(4-trifluoromethyl-phenyl)-thiazol-5-yl]-ethoxy}-phenoxy)-acetic acid, _(2-Methyl-4-{1R-[4-phenethyl-2-(4-trifluoromethyl-phenyl)-thiazol-5-yl]-ethylsulfanyl}-phenoxy)-acetic acid, (R)-(4-{1-[4-Isopropyl-2-(4-trifluoromethyl-phenyl)-thiazol-5-yl]-ethylsulfanyl}-2-methyl-phenoxy)-acetic acid, (S)-(4-{1-(4-Isopropyl-2-(4-trifluoromethyl-phenyl)-thiazol-5-yl]-ethylsulfanyl}-2-methyl-phenoxy)-acetic acid, (S)-(4-{1-[4-Isopropyl-2-(4-trifluoromethyl-phenyl)-thiazol-5-yl]-ethoxy}-2-methyl-phenoxy)-acetic acid, (R)-(4-{1-[4-Isopropyl-2-(4-trifluoromethyl-phenyl)-thiazol-5-yl]-ethoxy}-2-methyl-phenoxy)-acetic acid, (S)-3-(4-{1-[4-Isopropyl-2-(4-trifluoromethyl-phenyl)-thiazol-5-yl]-ethoxy}-2-methyl-phenyl)-propionic acid, (R)-3-(4-{1-[4-Isopropyl-2-(4-trifluoromethyl-phenyl)-thiazol-5-yl]-ethoxy}-2-methyl-phenyl)-propionic acid, (R)-3-(4-{1-[4-(2-Chloro-6-fluoro-phenoxymethyl)-2-(4-trifluoromethyl-phenyl)-thiazol-5-yl]-ethoxy}-2-methyl-phenyl)-propionic acid,_ (S)-3-(4-{1-[4-(2-Chloro-6-fluoro-phenoxymethyl)-2-(4-trifluoromethyl-phenyl)-thiazol-5-yl]-ethoxy}-2-methyl-phenyl)-propionic acid, (R)-(4-{1-[4-(2-Chloro-6-fluoro-phenoxymethyl)-2-(4-trifluoromethyl-phenyl)-thiazol-5-yl]-ethylsulfanyl}-2-methyl-phenoxy)-acetic acid, (S)-(4-{1-[4-(2-Chloro-6-fluoro-phenoxymethyl)-2-(4-trifluoromethyl-phenyl)-thiazol-5-yl]-ethylsulfanyl}-2-methyl-phenoxy)-acetic acid, (S)-(2-Methyl-4-{1-[4-phenylsulfanylmethyl-2-(4-trifluoromethyl-phenyl)-thiazol-5-yl]-ethylsulfanyl}-phenoxy)-acetic acid, (R)-(2-Methyl-4-{1-[4-phenylsulfanylmethyl-2-(4-trifluoromethyl-phenyl)-thiazol-5-yl]-ethylsulfanyl}-phenoxy)-acetic acid, _(R)-3-(2-Methyl-4-{1-[4-methyl-2-(4-trifluoromethyl-phenyl)-thiazol-5-yl]-ethoxy}-phenyl)-propionic acid, (S)-3-(2-Methyl-4-{1-[4-methyl-2-(4-trifluoromethyl-phenyl)-thiazol-5-yl]-ethoxy}-phenyl)-propionic acid, 3-(4-{1-[4-Ethyl-2-(4-trifluoromethyl-phenyl)-oxazol-5-yl]-ethoxy}-2-methyl-phenyl)-propionic acid, (4-{1-[4-Ethyl-2-(4-trifluoromethyl-phenyl)-oxazol-5-yl]-ethoxy}-2-methyl-phenoxy)-acetic acid, (4-{1-[4-Ethyl-2-(4-trifluoromethyl-phenyl)-oxazol-5-yl]-ethylsulfanyl}-2-methyl-phenoxy)-acetic acid, (4-{1R-[4-Ethyl-2-(4-trifluoromethyl-phenyl)-oxazol-5-yl]-ethylsulfanyl}-2-methyl-phenoxy)-acetic acid, (4-{1S-[4-Ethyl-2-(4-trifluoromethyl-phenyl)-oxazol-5-yl]-ethylsulfanyl}-2-methyl-phenoxy)-acetic acid, 3-(2-Methyl-4-{1S-[4-methyl-2-(4-trifluoromethyl-phenyl)-oxazol-5-yl]-2-phenyl-ethoxy}-phenyl)-propionic acid, 3-(2-Methyl-4-{1R-[4-methyl-2-(4-trifluoromethyl-phenyl)-oxazol-5-yl]-2-phenyl-ethoxy}-phenyl)-propionic acid, 3-(2-Methyl-4-{1-[4-methyl-2-(4-trifluoromethyl-phenyl)-oxazol-5-yl]-ethoxy}-phenyl)-propionic acid, 3-(2-Methyl-4-{1-[4-methyl-2-(4-trifluoromethyl-phenyl)-oxazol-5-yl]-propoxy}-phenoxy)-acetic acid, 3-(2-Methyl-4-{1-(4-methyl-2-(4-trifluoromethyl-phenyl)-oxazol-5-yl]-propoxy}-phenyl)-propionic acid, 3-(2-Methyl-4-{1-[4-methyl-2-(4-trifluoromethyl-phenyl)-oxazol-5-yl]-but-3-enyloxy}-phenyl)-propionic acid, 3-(2-Methyl-4-{1-[4-methyl-2-(4-trifluoromethyl-phenyl)-oxazol-5-yl]-pentyloxy}-phenyl)-propionic acid, 3-(4-{1-[4-tert-Butyl-2-(4-trifluoromethyl-phenyl)-oxazol-5-yl]-ethoxy}-2-methyl-phenyl)-propionic acid, 3-(4-{1-[4-Isopropyl-2-(4-trifluoromethyl-phenyl)-oxazol-5-yl]-ethoxy}-2-methyl-phenyl)-propionic acid, 3-(4-{2-[4-Isopropyl-2-(4-trifluoromethyl-phenyl)-oxazol-5-yl]-propoxy}-2-methyl-phenyl)-propionic acid, (R)-3-(2-Methyl-4-{1-[4-methyl-2-(4-trifluoromethyl-phenyl)-oxazol-5-yl]-ethoxy}-phenyl)-propionic acid, 3-(2-Methyl-4-{1-[4-methyl-2-(4-trifluoromethyl-phenyl)-oxazol-5-yl]-butoxy}-phenyl)-propionic acid, 3-[4-(1-{4-Isopropyl-2-[4-(4,4,5,5-tetramethyl-[1,3,2]dioxaborolan-2-yl)-phenyl]-oxazol-5-yl}-ethoxy)-2-methyl-phenyl]-propionic acid methyl ester, 3-(4-{1-[2-(4-Hydroxy-phenyl)-4-isopropyl-oxazol-5-yl]-ethoxy}-2-methyl-phenyl)-propionic acid methyl ester, 3-(4-{1-[4-Isopropyl-2-(4-methoxy-phenyl)-oxazol-5-yl]-ethoxy}-2-methyl-phenyl)-propionic acid, 3-(4-{1-[2-(3-Cyclopentyloxy-phenyl)-4-isopropyl-oxazol-5-yl]-ethoxy}-2-methyl-phenyl)-propionic acid, 3-[4-(1-{4-Isopropyl-2-[3-(tetrahydro-pyran-4-yloxy)-phenyl]-oxazol-5-yl}-ethoxy)-2-methyl-phenyl)-propionic acid, 3-(4-{1-[2-(4-Cyclopentyloxy-phenyl)-4-isopropyl-oxazol-5-yl]-ethoxy}-2-methyl-phenyl)-propionic acid, 3-(4-{1-[4-Isopropyl-2-(4-piperidin-1-yl-phenyl)-oxazol-5-yl]-ethoxy}-2-methyl-phenyl)-propionic acid, 3-(4-{1-[4-Isopropyl-2-(3-piperidin-1-yl-phenyl)-oxazol-5-yl]-ethoxy}-2-methyl-phenyl)-propionic acid, 3-(4-{1-[4-Isopropyl-2-(3-morpholin-4-yl-phenyl)-oxazol-5-yl]-ethoxy}-2-methyl-phenyl)-propionic acid, 3-(4-{1-[4-Isopropyl-2-(4-morpholin-4-yl-phenyl)-oxazol-5-yl]-ethoxy}-2-methyl-phenyl)-propionic acid, and 3-(4-{1-[2-(4-Hexylcarbamoyl-phenyl)-4-isopropyl-oxazol-5-yl]-ethoxy}-2-methyl-phenyl)-propionic acid.

SYNTHESIS

Compounds of the present invention have been formed as specifically described in the examples. Further, many compounds are prepared as more generally using a Mitsunobu protocol (O. Mitsunobu, 1981 Synthesis, p1) and other methods known to the skilled artisan. Alternative synthesis methods may also be effective and known to the skilled artisan.

For example, an intermediate like A is alkylated with an alkyl halide like agent B in the presence of a base (e.g. K2CO3, Cs2CO3 etc.). Hydrolysis in the presence of aqueous NaOH or LiOH gave the acid product.

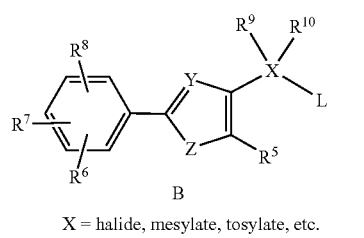
B
X = halide, mesylate, tosylate, etc.

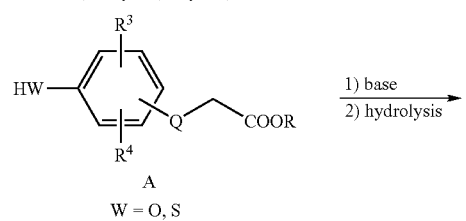
A
W = O, S

-continued

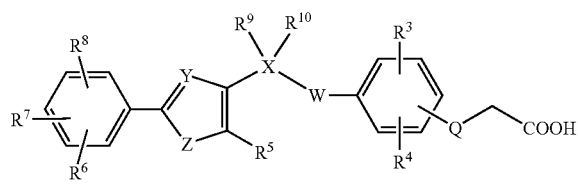

Alternatively, an intermediate like A is coupled with an alcohol C under Mitsunobu reaction condition (DEAD/ PPh3, ADDP/Pbu3 etc.). Hydrolysis in the presence of aqueous NaOH or LiOH gave the acid product:

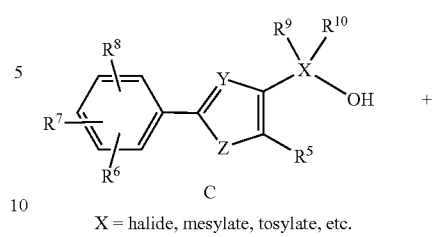
C
X = halide, mesylate, tosylate, etc.

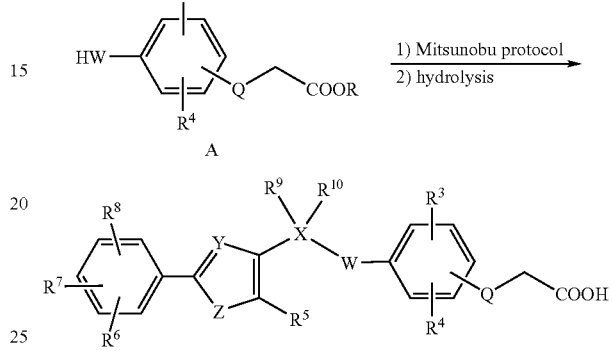
A

For the compounds with nitrogen in the linker, reductive amination protocol is used, for example:

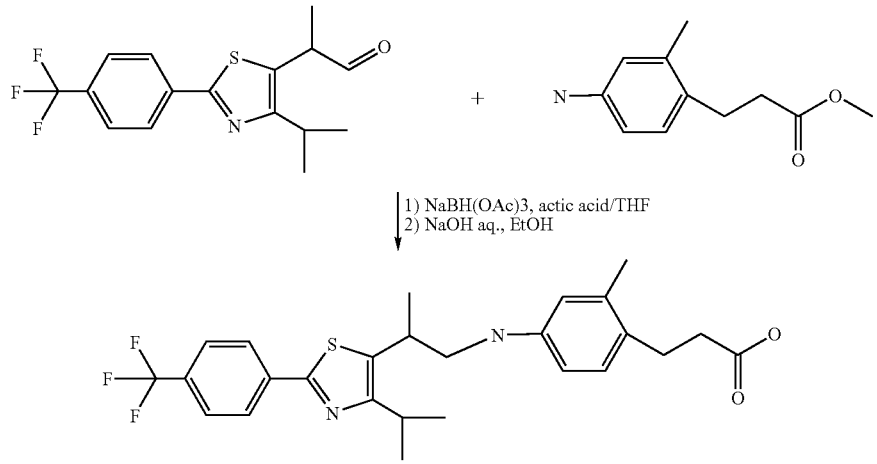

Suzuki coupling or Stille coupling reactions are used for the synthesis of biaryl compounds:

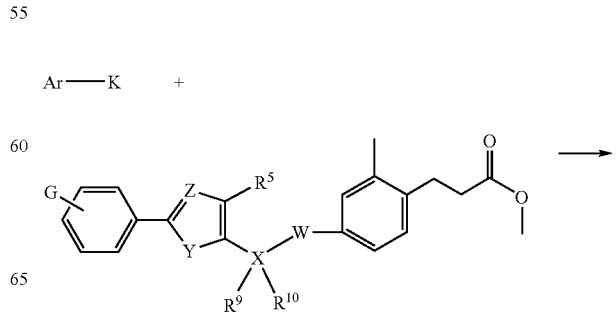

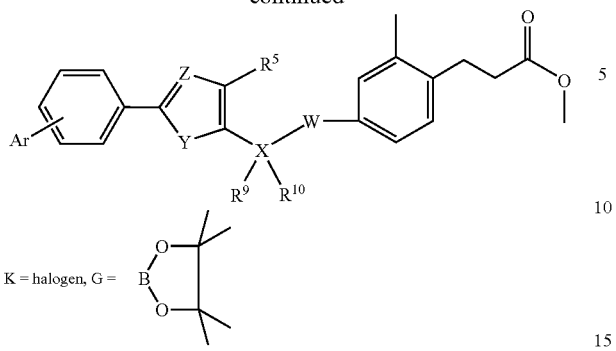

K = halogen, G = [pinacol boronate]

or: K = B(OH)₂, G = halogen
or: K = Sn(Bu)₃, G = Halogen

EXEMPLIFICATION

The Examples provided herein are illustrative of the invention claimed herein and are not intended to limit the scope of the claimed invention in any way.

Instrumental Analysis

Infrared spectra are recorded on a Perkin Elmer 781 spectrometer. $^1$H NMR spectra are recorded on a Varian 400 MHz spectrometer at ambient temperature. Data are reported as follows: chemical shift in ppm from internal standard tetramethylsilane on the δ scale, multiplicity (b=broad, s=singlet, d=doublet, t=triplet, q=quartet, qn=quintet and m=multiplet), integration, coupling constant (Hz) and assignment. $^{13}$C NMR are recorded on a Varian 400 MHz spectrometer at ambient temperature. Chemical shifts are reported in ppm from tetramethylsilane on the δ scale, with the solvent resonance employed as the internal standard (CDCl$_3$ at 77.0 ppm and DMSO-d$_6$ at 39.5 ppm). High resolution mass spectra are obtained on VG ZAB 3F or VG 70 SE spectrometers.

Preparation 1

3-Oxo-5-phenyl-pentanoic acid ethyl ester

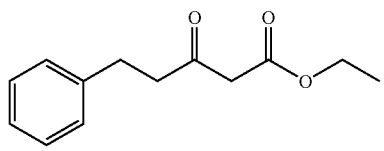

Ethyl acetoacetate (2.32 g, 20 mmol) is added to a pre-cold solution of LDA (2.0 M, 20 mL, 40 mmol) in THF (100 mL) at 0° C. After addition, the mixture is stirred for 30 min, then benzyl bromide (3.42 g, 20 mmol) is added dropwise. After stirred at 0° C. for 30 min, the reaction is quenched by 5 N HCl, extracted with ethyl ether. The combined organic layers are washed with water and brine until it is neutral.

Concentration and column chromatography gave 1.6 g of the title compounds.

The following compounds are made in a similar manner:

Preparation 2

5-(2-Chloro-6-fluoro-phenyl)-3-oxo-pentanoic acid ethyl ester

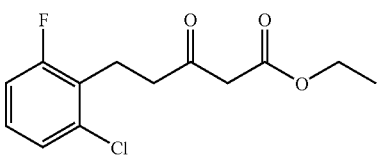

Preparation 3

2-Chloro-3-Oxo-5-phenyl-pentanoic acid ethyl ester

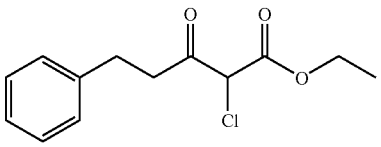

To a solution of 3-oxo-5-phenyl-pentanoic acid ethyl ester (1.6 g, 7.76 mmol) in methylene chloride (18 mL) is added sulfuryl chloride (1.15 g, 8.53 mmol) dropwise. After stirred at room temperature for 6 hours, the reaction mixture is poured into water, extracted with methylene chloride, is washed water and brine, dried over sodium sulfate. Concentration gave the crude title compound, which is used for the next step without further purification.

The following compounds are made in a similar manner:

Preparation 4

5-(2-Chloro-6-fluoro-phenyl)-2-chloro-3-oxo-pentanoic acid ethyl ester

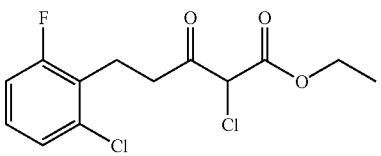

Preparation 5

2-Chloro-4-methyl-3-oxo-pentanoic acid ethyl ester

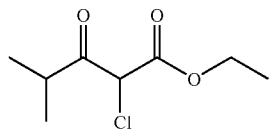

Preparation 6

2-(4-Bromo-phenyl)-4-methyl-thiazole-5-carboxylic acid ethyl ester

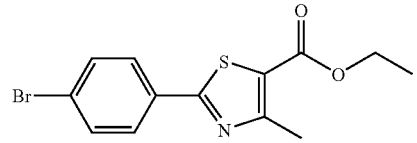

4-Bromo-thiobenzamide (5 g) in toluene is heated at reflux for 1 h in a flask equipped with a Dean-Stark trap. The dry 4-bromo-thioamide (3.4 g, 15 mmol) and ethyl 2-chloroacetoacetate (2.71 g, 16.4 mmol) are heated in ethanol (1000 mL) for overnight. The cooled reaction is concentrated and purified by short path chromatrography. The fractions that contained pure product are concentrated to yield 1.5 g (30.6%) ester as a solid.

Th following thiazoles are made in a similar manner:

Preparation 7

4-Isoproyl-2-(4-trifluoromethyl-phenyl)-thiazole-5-carboxylic acid ethyl ester

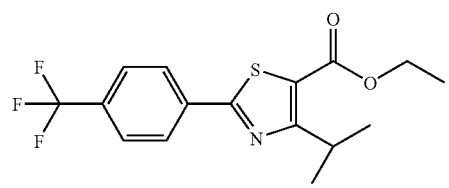

Preparation 8

4-Phenethyl-2-(4-trifluoromethyl-phenyl)-thiazole-5-carboxylic acid ethyl ester

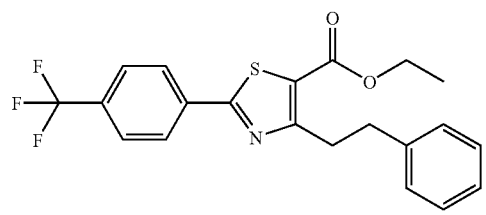

Preparation 9

4-[2-(2-Chloro-6-fluoro-phenyl)-ethyl-]2-(trifluoromethyl-phenyl)-thiazole-5-carboxylic acid ethyl ester

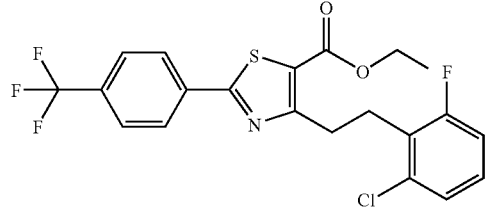

Preparation 10

4-Phenyl-2-(4-trifluoromethyl-phenyl)-thiazole-5-carboxylic acid ethyl ester

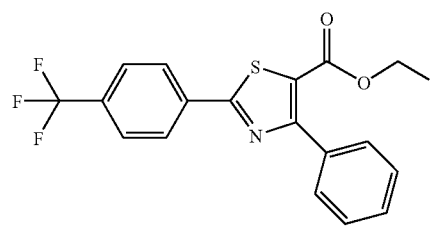

Preparation 11

4-Phenoxymethyl-2-(4-trifluoromethyl-phenyl)-thiazole-5-carboxylic acid ethyl ester

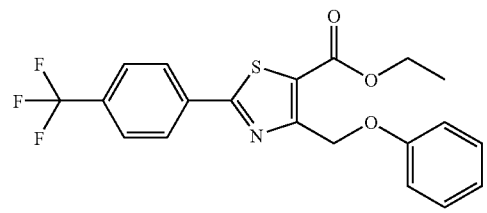

Step A

4-Bromomethyl-2-(4-trifluoromethyl-phenyl)-thiazole-5-carboxylic acid ethyl ester

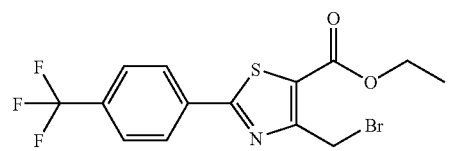

4-Methyl-2-(4-trifluoromethyl-phenyl)-thiazole-5-carboxylic acid ethyl ester (1.6 g, 5.00 mmol) is dissolved into chloroform (50 mL) then N-bromosuccinimide (1.0 g, 5.5 mmol) and 2,2'-azobisisobutyronitrile (0.412 g, 2.5 mmol) are added and the reaction is heated to reflux. The reaction is monitored by TLC until no starting material remained. The reaction is allowed to cool to room temperature, then diluted with more chloroform (100 mL). Water (50 mL) is added and the two phases are separated. The organic layer is washed with brine, then dried over anhydrous sodium sulfate. The material is then concentrated and further purified using flash column chromatography to yield 1.97 g or 99% yield.

Step B

4-Phenoxymethyl-2-(4-trifluoromethyl-phenyl)-thiazole-5-carboxylic acid ethyl ester Phenol (0.518 g, 5.5 mmol) is combined with anhydrous acetonitrile (20 mL) and cesium carbonate (2.3 g, 10 mmol) and allowed to stir at room temperature under nitrogen. To the reaction is added 4-bromomethyl-2-(4-trifluoromethyl-phenyl)-thiazole-5-carboxylic acid ethyl ester (1.97 g, 5.00 mmol). The reaction is monitored by TLC until all of the bromide is consumed. The reaction is diluted with ethyl ether (100 mL), then 0.1N NaOH (50 mL) is added. The two phases are separated, then the organic layer is washed with water (50 mL) and brine (50 mL). The organic layer is dried over anhydrous sodium sulfate, then concentrated. The material is further purified using flash chromatography to yield 1.75 g or 86% yield of the product.

The following compounds are made in a similar manner:

Preparation 12

4-(3,5-Bis-trifluoromethyl-phenoxymethyl)-2-(4-trifluoromethyl-phenyl)-thiazole-5-carboxylic acid ethyl ester

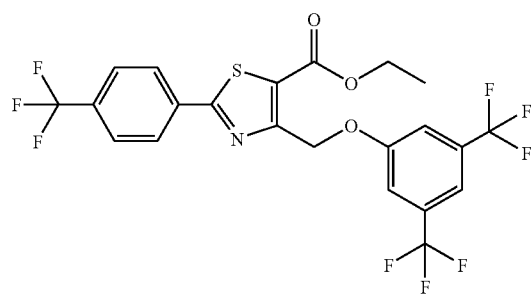

Preparation 13

4-(2-Chloro-6-fluoro-phenoxymethyl)-2-(4-trifluoromethyl-phenyl)-thiazole-5-carboxylic acid ethyl ester

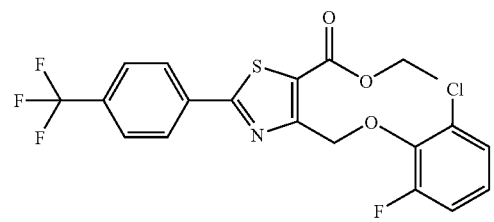

Preparation 14

4-(4-Bromo-phenylsulfanylmethyl)-2-(4-trifluoromethyl-phenyl)-thiazole-5-carboxylic acid ethyl ester

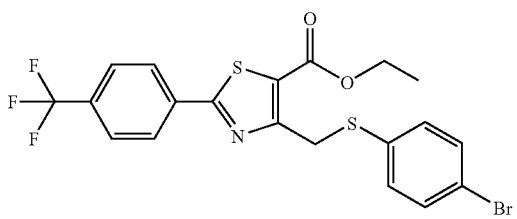

Preparation 15

4-Phenylsulfanylmethyl-2-(4-trifluoromethyl-phenyl)-thiazole-5-carboxylic acid ethyl ester

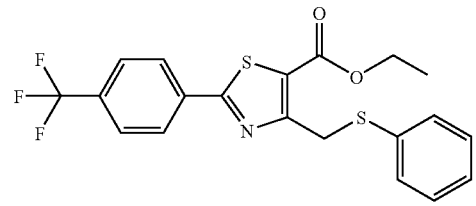

Preparation 16

[4-Methyl-2-(4-trifluoromethyl-phenyl)-thiazol-5-yl]-methanol

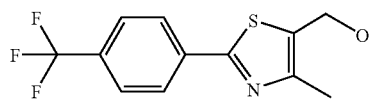

A THF (60 mL) solution of 4-Methyl-2-(4-trifluoromethyl-phenyl)-thiazole-5-carboxylic acid ethyl ester (14.9 g, 47.3 mmol) is cooled to 0° C. and a 1M LiAlH₄ (47.3 mL, 47.3 mmol) is added slowly. The reaction is warmed to room temperature slowly, after stirring at room temperature for 2 h, tlc (15% EtOAc/hexane) showed that all the starting ester had been consumed. The reaction is cooled and carefully quenched with 2.4 mL water, 2.4 mL 5N NaOH and 7 mL water. The light tan solid is filter through celite and dried to give 7.70 g crude product. Recrystallization from methanol gave pure alcohol.

The following compounds are made in a similar manner:

Preparation 17

[4-Isopropyl-2-(4-trifluoromethyl-phenyl)-thiazol-5-yl]-methanol

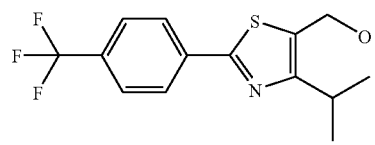

Preparation 18

4-Phenethyl-2-(4-trifluoromethyl-phenyl)-thiazol-5-yl]-methanol

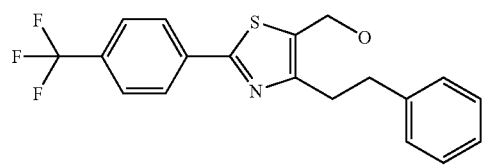

Preparation 19

4-[2-(2-Chloro-6-fluoro-phenyl)-ethyl]-2-(4-trifluoromethyl-phenyl)-thiazol-5-yl]-methanol

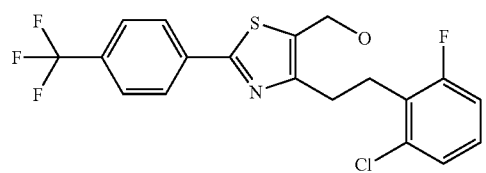

Preparation 20

[4-Phenyl-2-(4-trifluoromethyl-phenyl)-thiazol-5-yl]-methanol

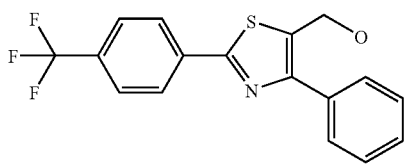

Preparation 21

[4-Phenoxymethyl-2-(4-trifluoromethyl-phenyl)-thiazol-5-yl]-methanol

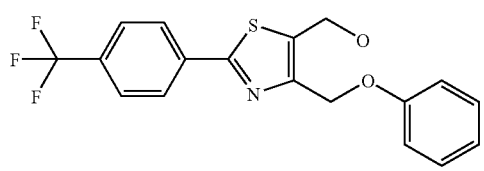

Preparation 22

[4-(2-Chloro-6-fluoro-phenoxymethyl)-2-(4-trifluoromethyl-phenyl)-thiazol-5-yl]-methanol

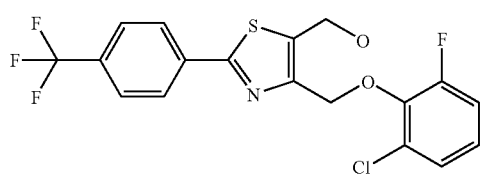

Preparation 23

[4-(3,5-Bis-trifluoromethyl-phenoxymethyl)-2-(4-trifluoromethyl-phenyl)-thiazol-5-yl]-methanol

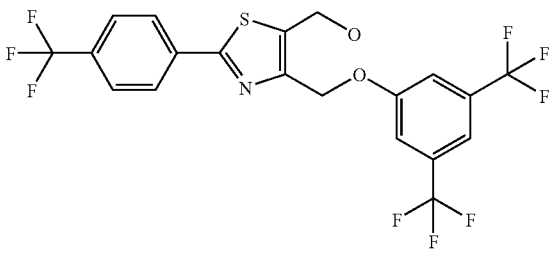

Preparation 24

[4-Phenylsulfanylmethyl-2-(4-trifluoromethyl-phenyl)-thiazol-5-yl]-methanol

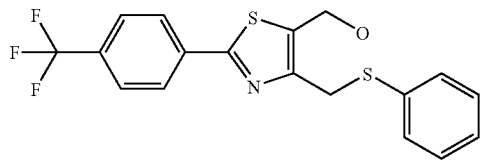

Preparation 25

[4-(4-Bromo-phenylsulfanylmethyl)-2-(4-trifluoromethyl-Phenyl)-thiazol-5-yl]-methanol

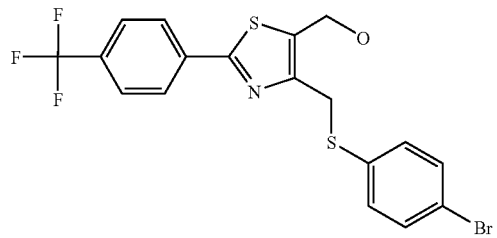

Preparation 26

4-Ethyl-2-(4-trifluoromethylphenyl)-oxazole-5-carboxylic acid methyl ester

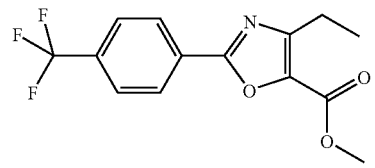

To a solution of 4-trifluoromethyl benzoic acid (0.100 g, 0.239 mmole) in methanol (2.0 mL), is added sodium hydroxide (0.093 g, 0.287 mmole) and stirred at room temperature for 2 hours. The mixture is concentrated to dryness in vacuo to give sodium 4-trifluoromethyl-benzoate as a white solid. It is then mixed with $NH_4OAc$ (8.329, 107.9 mmole) in glacial acetic acid (500 mL) and heated at 100° C. for 16 hours. After removed the solvents on rota-vapor, the residue is partitioned between ethyl acetate (300 mL) and saturated sodium bicarbonate (300 mL). Extracted the aqueous layer with ethyl acetate (300 mL) one more time. The combined organic is ish with brine (3×500 mL), dried over $Na_2SO_4$, filtered and concentrated. The crude product is purified by chromatography on silica gel column, gradient elute with 0 to 10% ethyl acetate in hexane and concentrated to provide the titled compound as a white solid. Mass [EI+] 300 $(M^++H)$.

Preparation 27

[4-Ethyl-2-(4-trifluoromethyl-phenyl)-oxazol-5-yl]-methanol

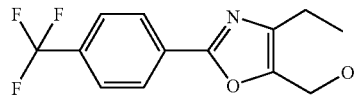

To a solution of 4-Ethyl-2-(4-trifluoromethyl-phenyl)-oxazole-5-carboxylic acid methyl ester (4.63 g, 15.47 mmole) in THF (100 mL), is added $LiBH_4$ in one portion at 0° C. The reaction is warmed up to room temperature and stirred for an hour. Additional $LiBH_4$ is added and the reaction is heated at 60° C. for 30 minutes. The excess amount of $LiBH_4$ is destroyed using 6N HCl (50 mL) dropwise at 0° C. The mixture is partitioned between ethyl acetate (300 mL) and brine (300 mL). The organic layer is washed with brine (3×300 mL), dried over $Na_2SO_4$, filtered and concentrated. The crude product is purified by flash chromatography, eluting with 60% ethyl acetate in hexane and concentrated to provide the titled compound as a white solid. Mass [EI+] 272 $(M+H)^+$.

Preparation 28

1-[4-Ethyl-2-(4-trifluoromethyl-phenyl)-oxazol-5-yl]-ethanol

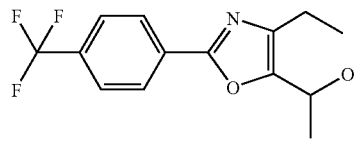

Step A

4-Ethyl-2-(4-trifluoromethyl-phenyl)-oxazole-5-carbaldehyde

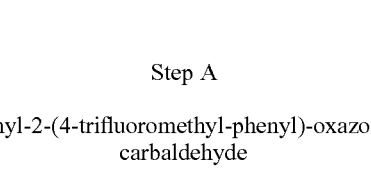

To a solution of oxalyl chloride (2.0M/DCM, 3.52 mL, 7.04 mmloe) in DCM (50 mL), is injected DMSO (0.998 mL, 14.1 mmole) and stirred for 15 minute at −78° C. A solution of [4-Ethyl-2-(4-trifluoromethyl-phenyl)-oxazol-5-yl]-methanol (1.59 g, 5.86 mmole) in DCM (10 mL) is then added. After stirred for 30 minutes, triethyl amine (4.08 mL, 29.3 mmole) is added. The reaction is kept at −78° C. for another 30 minutes, then warmed up to room temperature for 2 hours, washed with brine (3×50 mL), dried over $Na_2SO_4$, filtered and concentrated. The crude product is purified by flash chromatography (silica gel, 10% ethyl acetate in hexane) and concentrated to provide the titled compound as a white solid. Mass [EI+] 270 $(M+H)^+$.

Step B

1-[4-Ethyl-2-(4-trifluoromethyl-phenyl)-oxazol-5-yl]-ethanol

To a solution of 4-ethyl-2-(4-trifluoromethyl-phenyl)-oxazole-5-carbaldehyde (0.793 g, 2.95 mmole) in THF (30 mL) at 0° C., is added a solution of methyl magnesium bromide in diethyl ether (3.0M, 2.0 mL, 0.60 mmole) dropwise. The reaction is stirred for 5 minutes and then warmed up to room temperature for 30 minutes. The reaction is quenched with $NH_4Cl_{(aq)}$ (10 mL), partitioned between ethyl acetate (50 mL) and water (50 mL). Extracted the aqueous layer with ethyl acetate (2×50 mL). The combined organic is washed with brine (3×100 mL), dried over $Na_2SO_4$, filtered and concentrated to provide the titled compound as a white solid. The crude product is used for the next step without further purification. Mass [EI+] 286 $(M+H)^+$.

Preparation of 29

1-[4-Methyl-2-(4-trifluoromethyl-phenyl)-thiazol-5-yl]-ethanol

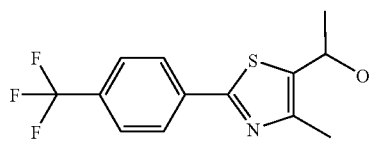

Step A

4-Methyl-2-(4-trifluoromethyl-phenyl)-thiazole-5-carbaldehyde

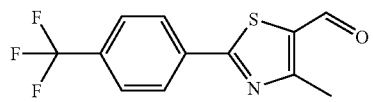

A mixture of [4-methyl-2-(4-trifluoromethyl-phenyl)-thiazol-5-yl]-methanol (5.0 g, 18.3 mmol) and MnO2 (2.4 g, 27.5 mmol) in chloroform (110 mL) are heated to reflux for 48 hrs, cooled to room temperature, filtered through celite. Concentration gave 5 gram of the title compound.

Step B

1-[4-Methyl-2-(4-trifluoromethyl-phenyl)-thiazol-5-yl]-ethanol

To a solution of 4-methyl-2-(4-trifluoromethyl-phenyl)-thiazole-5-carbaldehyde (1.5 g, 5.53 mmole) in THF (50 mL) at 0° C., is added a solution of methyl magnesium bromide in diethyl ether (3.0M, 2.0 mL, 6.0 mmole) dropwise. The reaction is stirred for 5 minutes and then warmed up to room temperature for 2 hrs. The reaction is quenched with $NH_4Cl_{(aq)}$ (10 mL), partitioned between ethyl ether (50 mL) and water (50 mL). Extracted the aqueous layer with ethyl ether (2×50 mL). The combined organic is washed with brine (3×100 mL), dried over $Na_2SO_4$, filtered and concentrated. Column chromatography on silica gel gave 1.35 gram of the title compound.

The following compounds are made in a similar manner:

Preparation of 30

1-[4-isopropyl-2-(4-trifluoromethyl-phenyl)-thiazol-5-yl]-ethanol

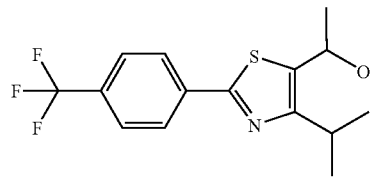

Preparation of 31

1-[4-Phenethyl-2-(4-trifluoromethyl-phenyl)-thiazol-5-yl]-ethanol

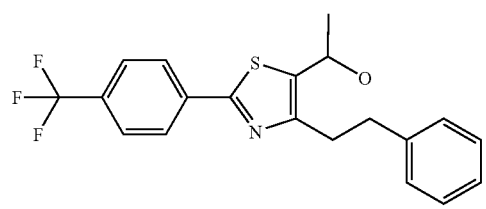

Preparation of 32

1-[4-[2-(2-Chloro-6-fluoro-phenyl)-ethyl]-2-(4-trifluoromethyl-phenyl)-thiazol-5-yl]-ethanol

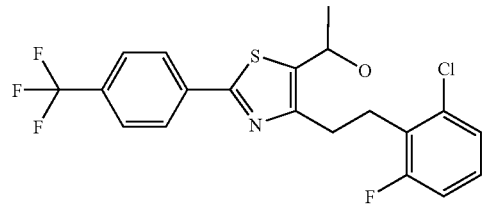

Preparation of 33

1-[4-Phenylsulfanylmethyl-2-(4-trifluoromethyl-phenyl)-thiazol-5-yl]-ethanol

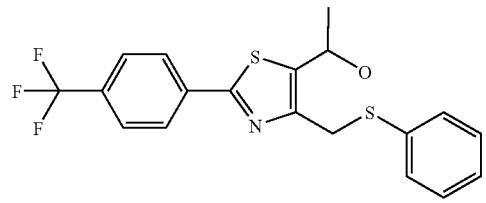

Preparation of 34

1-[4-(2-Chloro-6-fluoro-phenoxymethyl)-2-(4-trifluoromethyl-phenyl)-thiazol-5-yl]-ethanol

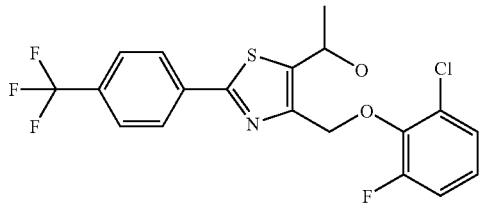

Preparation of 35

1-[4-(3,5-Bis-trifluoromethyl-phenoxymethyl)-2-(4-trifluoromethyl-phenyl)-thiazol-5-yl]-ethanol

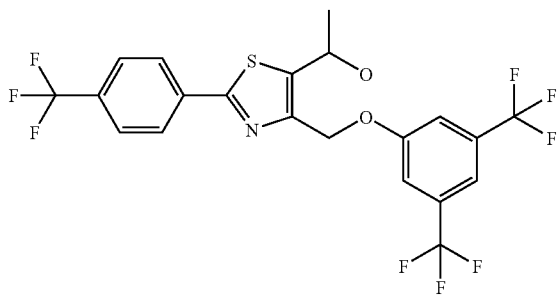

Preparation 36

1-[4-Phenyl-2-(4-trifluoromethyl-phenyl)-thiazol-5-yl]-ethanol

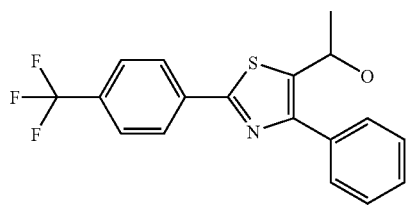

Preparation 37

1-[4-Methyl-2-(4-trifluoromethyl-phenyl)-thiazol-5-yl]-2-phenyl-ethanol

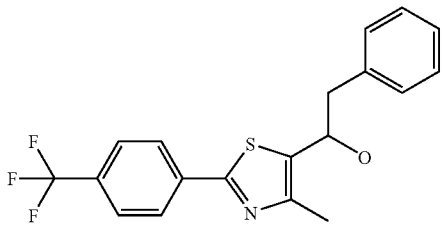

To a solution of 4-methyl-2-(4-trifluoromethyl-phenyl)-thiazole-5-carbaldehyde (0.5 g, 1.84 mmole) in THF (20 mL) at 0° C., is added a solution of benzyl magnesium chloride in tetrahedronfuran (2.0M, 1.0 mL, 2 mmole) dropwise. The reaction is stirred for 5 minutes and then warmed up to room temperature for 2 hrs. The reaction is quenched with $NH_4Cl_{(aq)}$, partitioned between ethyl ether and water. Extracted the aqueous layer with ethyl ether. The combined organic is washed with brine, dried over $Na_2SO_4$, filtered and concentrated. Column chromatography on silica gel gave the title compound.

Preparation 38

1-[2-(4-Bromo-phenyl)-4-isopropyl-oxazol-5-yl]-ethanol

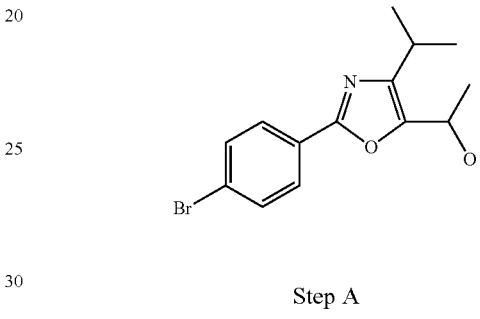

Step A 2-(4-Bromo-phenyl)-4-isopropyl-oxazole-5-carboxylic acid ethyl ester

A solution of 4-bromo-benzoic acid (34.0 g, 0.169 mol) in DMF (450 mL) is treated at ambient temperature portionwise with NaH (6.4 g, 0.16 mol, 60% oil dispersion). The suspension is heated to 90° C. and 2-choro-4-methyl-3-oxo-pentanoic acid ethyl ester (27.7 g, 0.144 mol) is added neat. The remaining chloride is washed into the reaction flask using DMF (25 mL). The reaction mixture is stirred for 18 h, cooled, and treated with water (600 mL). The mixture is extracted with EtOAc (750 mL). The organic layer is washed with brine (2×250 mL), dried ($Na_2SO_4$), and concentrated to a foam (56 g). This diester is dissolved in acetic acid (500 mL), treated at ambient temperature with ammonium acetate (80 g, 1.0 mol)$_1$ and heated at 120° C. for 20 h. The reaction mixture is cooled, concentrated, and partitioned between EtOAc (500 mL) and saturated $NaHCO_3$ solution (3×125 mL). The organic layer is dried ($Na_2SO_4$), and concentrated. The crude product is purified by silica gel flash chromatography using hexanes:ethyl acetate (6:1) to give the title compound (26.6 g, 55%).

Step B

[2-(4-Bromo-phenyl)-4-isopropyl-oxazol-5-yl]-methanol

A solution of 2-(4-bromo-phenyl)-4-isopropyl-oxazole-5-carboxylic acid ethyl ester (20.6 g, 60.9 mmol) in THF (300 mL) is cooled in an ice-water bath and treated portionwise with $LiAlH_4$ (2.8 g, 73 mmol). The reaction is complete after 1.5 h. Ice chips (~10 g) are added to quench the excess hydride reagent, and anhydrous $Na_2SO_4$ (~50 g) is added. The thick suspension is stirred 30 min, filtered through celite, and washed with THF (600 mL). The filtrate is dried (Na$_2$SO$_4$) and concentrated. The crude product is purified by silica gel flash chromatography using hexanes:ethyl acetate (3:1) to give a white solid (17.9 g, 99%).

Step C 2-(4-Bromo-phenyl)-4-isopropyl-oxazole-5-carbaldehyde

A solution of [2-(4-bromo-phenyl)-4-isopropyl-oxazol-5-yl]-methanol (17.9 g, 60.4 mmol) in CH$_2$Cl$_2$ (450 mL) is treated at ambient temperature with acetic acid 1,1-diacetoxy-3-oxo-1-$^5$-ioda-2-oxa-indan-1-yl ester (39 g, 92 mmol, Dess Martin reagent). The suspension is stirred 1 h and is partitioned between 10% aqueous Na$_2$S$_2$O$_3$ solution (250 mL) and CH$_2$Cl$_2$ (150 mL). The organic layer is washed with saturated NaHCO$_3$ (2×250 mL), and the combined aqueous layers are back-extracted with Et$_2$O (300 mL). The combined organic layers are dried (Na$_2$SO$_4$) and concentrated. The crude product is purified by silica gel flash chromatography using hexanes:ethyl acetate (6:1) to give an offwhite solid (14.4 g, 81%).

Step D

1-[2-(4-Bromo-phenyl)-4-isopropyl-oxazol-5-yl]-ethanol

A solution of 2-(4-bromo-phenyl)-4-isopropyl-oxazole-5-carbaldehyde (14.4 g, 84.9 mmol) in THF (300 mL) is cooled to −78° C. and treated dropwise with methyl magnesium bromide (25 mL, 75 mmol, 3M Et$_2$O). After 1 h, more methyl magnesium bromide (12 mL, 36 mmol) is added. The reaction mixture is stirred 1.5 h, and saturated NH$_4$Cl solution (10 ml) is added dropwise. The mixture is partitioned between saturated NH$_4$Cl solution (10 ml), 1N HCl (25 mL), and Et$_2$O (300 mL). The organic layer is washed with brine (150 mL), dried (Na$_2$SO$_4$), and concentrated. The crude product is purified by silica gel flash chromatography using hexanes:ethyl acetate (9:1 to 5:1) to give an offwhite solid (9.5 g, 63%).

Preparation 39

1-[2-(-bromo-phenyl)-4-isopropyl-oxazol-5-yl]-ethanol

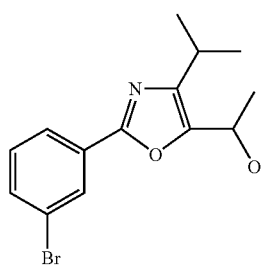

By the sequence above as preparation 38, 4-bromobenzoic acid is converted to 1-[2-(4-bromo-phenyl)-4-isopropyl-oxazol-5-yl]-ethanol.
2-(3-Bromo-phenyl)-4-isopropyl-oxazole-5-carboxylic acid ethyl ester: 135 mmol scale, 35%
[2-(3-Bromo-phenyl)-4-isopropyl-oxazol-5-yl]-methanol: 45 mmol scale, 100%
2-(3-Bromo-phenyl)-4-isopropyl-oxazole-5-carbaldehyde: 45 mmol, 69%
1-[2-(3-Bromo-phenyl)-4-isopropyl-oxazol-5-yl]-ethanol: 29 mmol scale, 100%

Preparation 40

1-[4-Methyl-2-(4-trifluoromethyl-phenyl)-oxazol-5-yl]-ethanol

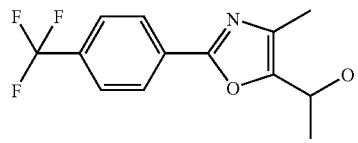

Step 1

2-(4-tert-Butyl-benzoylamino)-propionic acid methyl ester

D,L Alanine methyl ester (18.5 g, 132 mmol), triethylamine (42 mL, 300 mmol) and dichloromethane (300 mL) are stirred in an ice/water bath. 4-(Trifluromethyl)benzoyl chloride (25 g, 120 mmol) is added dropwise and the resulting mixture is allowed to stir for 20 hr at room temperature. 500 mL water and 100 mL 1M hydrochloric acid are successively added. The organic layer is separated, washed with 250 mL each of saturated sodium hydrogen carbonate, water, and brine, dried over anhydrous magnesium sulfate, filtered, and concentrated to 100 mL volume. The mixture is diluted with 200 mL hexanes, cooled to 0° C. for 1 hr, and the white solid filtered and dried under vacuum to afford 2-(4-tert-Butyl-benzoylamino)-propionic acid methyl ester, 26.5 g, 80%. MS (ES): 276 (M$^+$+1).

Step 2

2-(4-tert-Butyl-benzoylamino)-propionic acid

A mixture of 2-(4-tert-Butyl-benzoylamino)-propionic acid methyl ester (26.3 g, 95.6 mmol), 200 mL 1M sodium hydroxide, and 100 mL tetrahydrofuran is stirred at room temperature 20 hr. The resulting clear solution is cooled on an ice/water bath and the pH is adjusted to 2 with concentrated hydrochloric acid. The product is extracted with three 250 mL portions of ethyl acetate. The combined extracts are washed with 100 mL each of water and brine, dried over anhydrous magnesium sulfate, filtered, and concentrated to afford 2-(4-tert-Butyl-benzoylamino)-propionic acid as a white solid, 24.6 g, 95%. MS M$^+$+1 260.

Step 3

[4-Methyl-2-(4-trifluoromethyl-phenyl)-oxazol-5-yl]-methanol

To a solution of 2-(4-Trifluoromethyl-benzoylamino)-propionic acid (33.4 g, 128 mmol) is added oxalyl chloride (111 mL, 1.27 Mol) and 1 drop of DMF and the solution stirred overnight. The volatiles are removed in vacuo and toluene (20 mL) is added. The toluene is then removed in vacuo. To the resultant crude oil is dissolve in 50 mL methylene chloride, cooled to 0° C. and triethylamine (27 mL, 192 mmol) is added followed by methanol (50 mL). After 3 hrs the volatiles are removed in vacuo and the crude oil is purified by flash column chromatography (20%–50% ethyl acetate/hexanes) to provide 12.6 g (35%) of 4-Methyl-2-(4-trifluoromethyl-phenyl)-oxazole-5-carboxylic acid methyl ester. This ester (2.0 g, 7.0 mmol) is reduced to the alcohol by dissolution in THF (50 mL) and adding 4 eq. $LiBH_4$ (0.610 g, 28.0 mmol) to provide 1.8 g (100%) [4-Methyl-2-(4-trifluoromethyl-phenyl)-oxazol-5-yl]-methanol. MS $M^++1$ 258.

Step 4

4-Methyl-2-(4-trifluoromethyl-phenyl)-oxazole-5-carbaldehyde [4-Methyl-2-(4-trifluoromethyl-phenyl)-oxazol-5-yl]-methanol (2.42 g, 9.41 mmol) and 100 mL dichloromethane are stirred at room temperature. Dess-Martin periodinane (8.0 g, 18.8 mmol) is added and the resulting mixture is stirred 4 hr at room temperature. The mixture is diluted with 100 mL saturated sodium hydrogen carbonate. The organic layer is separated, washed with 50 mL each of water and brine, dried over anhydrous magnesium sulfate, filtered, and concentrated. The crude product is purified by silica gel chromatography eluting with a mixture of 8:2 hexanes:ethyl acetate affording 4-methyl-2-(4-trifluoromethyl-phenyl)-oxazole-5-carbaldehyde as a white solid, 2.12 g, 89%. MS ($M^++1$) 256.

Step 5

1-[4-Methyl-2-(4-trifluoromethyl-phenyl)-oxazol-5-yl]-ethanol

A solution of 4-methyl-2-(4-trifluoromethyl-phenyl)-oxazole-5-carbaldehyde (1.32 g, 5.16 mmol) and 50 mL tetrahydrofuran is stirred at 0° C. Methyl magnesium bromide (2.2 mL, 6.71 mmol, 3M) is added dropwise and the resulting mixture is allowed to stir at room temperature 30 min. The reaction is not complete, so an additional amound of methyl magnesium bromide (1 mL, 3 mmol) is added and the reaction stirred an additional 1 hr at room temperature. The mixture is cooled on an ice/water bath and aqueous ammonium chloride (10 mL) is added. The product is extracted with three 75 mL portions of ethyl acetate, the combined extracts are dried over anhydrous magnesium sulfate, filtered and concentrated. The crude product is purified by silica gel chromatography eluting with a mixture of 1:1 hexanes:ethyl acetate to afford 1-[4-Methyl-2-(4-trifluoromethyl-phenyl)-oxazol-5-yl]-ethanol as an ivory solid, 1.12 g, 80%. MS ($M^++1$) 272.

Preparation 41

2-Methyl-1-[4-methyl-2-(4-trifluoromethyl-phenyl)-oxazol-5-yl]-propan-1-ol

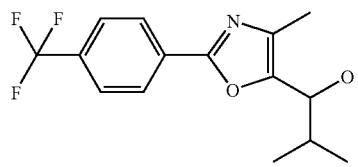

This compound is prepared in analogous fashion using preparation 40. Steps 1–4 are identical as previously described. Step 5 is performed using isoproyl magnesium bromide to afford 2-methyl-1-[4-methyl-2-(4-trifluoromethyl-phenyl)-oxazol-5-yl]-propan-1-ol.

Preparation 42

1-[4-Isopropyl-2-(4-trifluoromethyl-phenyl)-oxazol-5-yl]-ethanol

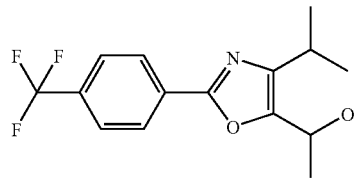

Step 1

2-chloro-4-methyl-3-oxo-pentanoic acid ethyl ester ethyl isobutyryl acetate (12.0 g, 75.85 mmol) is stirred at 0° C. in dichloromethane (75 mL). Sulfuryl chloride (6.5 mL, 80 mmol) is added dropwise and the resulting mixture is allowed to stir 20 hr at room temperature. The reaction mixture is cooled to 0° C. and aqueous saturated sodium hydrogen carbonate (200 mL) is added cautiously. The layers are separated, the aqueous layer is washed with dichloromethane (100 mL), the combined organic layers are washed with water and brine (100 mL each), dried over anhydrous magnesium sulfate, filtered, and concentrated to constant weight to give 2-chloro-4-methyl-3-oxo-pentanoic acid ethyl ester as a colorless oil, 14.6 g, 100%. MS ($M^++1$) 193.

Step 2

4-Isopropyl-2-(4-trifluoromethyl-phenyl)-oxazole-5-carboxylic acid ethyl ester

Sodium Hydride, 60% mineral oil (1.9 g, 46.3 mmol) and dimethylformamide (50 mL) are stirred at room tmperature and 4-(trifluoromethyl)benzoic acid (8.0 g, 42.1 mmol) is added. To the resulting slurry is added 2-chloro-4-methyl-3-oxo-pentanoic acid ethyl ester (8.5 g, 44.2 mmol) and the resulting mixture is heated to 90° C. for 3 hr. The reaction mixture is cooled, diluted with water (100 mL), and product is extracted with ethyl acetate (100 mL). The organic layer is washed with water (three 100 mL portions) and brine (100 mL), dried over anhydrous magnesium sulfate, filtered, and concentrated to constant weight to give 4-trifluoromethyl-benzoic acid 1-ethoxycarbonyl-3-methyl-2-oxo-butyl ester as a colorless oil, 14.6 g, 100%. The resulting oil is stirred in a mixture of acetic acid (100 mL) and ammonium acetate (9.75 g, 126.5 mmol) at reflux 1 hr, then 20 hr at room temperature. The solvent is removed in vacuo and the residue is partioned between aqueous saturated sodium hydrogen carbonate (100 mL) and ethyl acetate (100 mL. The layers are separated, the aqueous layer is washed with ethyl acetate (100 mL). The organic extracts are combined, washed with water and brine (100 mL each) dried over anhydrous magnesium sulfate, filtered, and concentrated. The residue is purified over silica eluting with 9:1 hexanes: ethyl acetate to afford 4-Isopropyl-2-(4-trifluoromethyl-phenyl)-oxazole-5-carboxylic acid ethyl ester as a white solid, 8.1 g, 60%. MS ($M^++1$) 328.

33

Step 3

[4-Isopropyl-2-(4-trifluoromethyl-phenyl)-oxazol-5-yl]-methanol

4-Isopropyl-2-(4-trifluoromethyl-phenyl)-oxazole-5-carboxylic acid ethyl ester (0.53 g, 1.62 mmol) is stirred in tetrahydrofuran (25 mL) at 0° C. Lithium aluminum hydride (0.122 g, 3.23 mmol) is added and the mixture is stirred 18 hr at room temperature. The mixture is diluted carefully with 1M aqueous hydrochloric acid (10 mL), and the product is extracted with ethyl acetate (three 75 mL portions). The extracts are combined, dried over anhydrous magnesium sulfate, filtered, and concentrated to afford [4-Isopropyl-2-(4-trifluoromethyl-phenyl)-oxazol-5-yl]-methanol as a white solid, 0.46 g, 100%. MS (M$^+$+1) 286.

Step 4

4-Isopropyl-2-(4-trifluoromethyl-phenyl)-oxazole-5-carbaldehyde

[4-Isopropyl-2-(4-trifluoromethyl-phenyl)-oxazol-5-yl]-methanol (0.46 g, 1.612 mmol), Dess-Martin periodinane (1.36 g, 3.22 mmol) and dichloromethane (25 mL) are stirred 1 hr at room temperature. The mixture is diluted with aqueous saturated sodium hydrogen carbonate (100 mL) and dichloromethane (100 mL). The layers are separated, the aqueous layer is washed with dichloromethane (100 mL). The organic ishes are combined, washed with brine (50 mL), dried over anhydrous magnesium sulfate, filtered, and concentrated in vacuo. The product is purified over silica eluting with 3:1 hexanes:ethyl acetate to afford 4-Isopropyl-2-(4-trifluoromethyl-phenyl)-oxazole-5-carbaldehyde as a white solid, 0.41 g, 90%. %. MS (M$^+$+1) 284.

Step 5

1-[4-Isopropyl-2-(4-trifluoromethyl-phenyl)-oxazol-5-yl]-ethanol

Followed a similar procedure in step 5 of preparation 40.

Preparation 43

1-[4-tert-Butyl-2-(4-trifluoromethyl-phenyl)-oxazol-5-yl]-ethanol

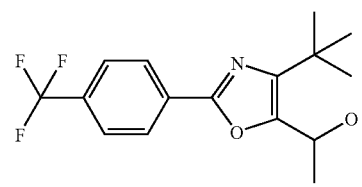

This compound is prepared in a similar manner as Preparation 42 using ethyl pivaloyl acetate as starting material at step 1.

34

Preparation 44

1-[4-Methyl-2-(4-trifluoromethyl-phenyl)-oxazol-5-yl]-propan-1-ol

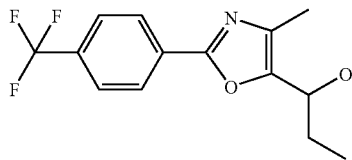

Step 1

4-methyl-2-(4-trifluoromethyl-phenyl)-oxazole-5-carboxylic acid methoxy-methyl-amide To a solution of 2-(4-Trifluoromethyl-benzoylamino)-propionic acid (5.0 g, 19.14 mmol) is added oxalyl chloride (16.7 mL, 191.4 mmol) and 2 drops of DMF and the solution stirred overnight. The volatiles are removed in vacuo and toluene (20 mL) is added. The toluene is then removed in vacuo. To the resultant crude oil is dissolve in dichloromethane (100 mL), cooled to 0° C. and triethylamine (13.4 mL, 96 mmol) is added followed by N,O-dimethyl hydroxylamine hydrochloride (9.4 g, 96 mmol). After 1 hr the mixture is partioned between 1M aqueous hydrochloric acid and ethyl acetate. The organic layer is dried over anhydrous magnesium sulfate, filtered, concentrated in vacuo. The product is purified over silica eluting with 8:2 hexanes:ethyl acetate to afford 4-methyl-2-(4-trifluoromethyl-phenyl)-oxazole-5-carboxylic acid methoxy-methyl-amide as a white crystalline solid, 2.4 g, 40%. MS (M$^+$+1) 315.

Step 2

1-[4-methyl-2-(4-trifluoromethyl-phenyl)-oxazol-5-yl]-propan-1-one 4-methyl-2-(4-trifluoromethyl-phenyl)-oxazole-5-carboxylic acid methoxy-methyl-amide (1.0 g, 3.18 mmol) is stirred in tetrahydrofuran (15 mL) at −78° C. ethyl magnesium bromide, 3M/ether (2.1 mL, 4.14 mmol) is added and the mixture is warmed to room temperature. The mixture is diluted with aqueous saturated ammonium chloride and washed with ethyl acetate (three 50 mL portions). The combined ishes are dried over anhydrous magnesium sulfate, filtered and concentrated in vacuo. The residue is purified over silica eluting with 7:3 hexanes:ethyl acetate to afford 1-[4-methyl-2-(4-trifluoromethyl-phenyl)-oxazol-5-yl]-propan-1-one as an ivory solid, 0.70 g, 78%. MS (M$^+$+1) 284.

Step 3

1-[4-methyl-2-(4-trifluoromethyl-phenyl)-oxazol-5-yl]-propan-1-ol

1-[4-methyl-2-(4-trifluoromethyl-phenyl)-oxazol-5-yl]-propan-1-one (0.68 g, 2.4 mmol) and tetrahydrofuran (5 mL) are stirred at 0° C. Lithium borohydride (0.14 g, 6.36 mmol) is added and the mixture is stirred 10 min at 0° C., and 30 min at room temperature. The mixture is diluted with 1M aqueous hydrochloric acid and washed with ethyl acetate (three 50 mL portions). The organic ishes are dried over anhydrous magnesium sulfate, filtered, and concentrated in vacuo. The residue is purified over silica eluting with 8:2 hexanes:ethyl acetate to 1:1 hexanes ethyl acetate to afford 1-[4-methyl-2-(4-trifluoromethyl-phenyl)-oxazol-5-yl]-propan-1-ol as ivory solid, 0.69 g, 100%. MS (M$^+$+1) 286.

Preparation 45

1-[4-Methyl-2-(4-trifluoromethyl-phenyl)-oxazol-5-yl]-but-3-en-1-ol

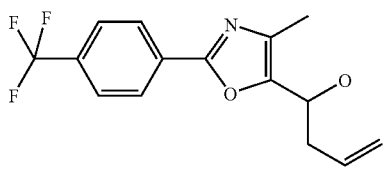

This compound is prepared in a similar manner as Preparation 44 using allyl magnesium bromide in step 2 as reagent.

Preparation 46

1-[4-Methyl-2-(4-trifluoromethyl-phenyl)-oxazol-5-yl]-pentan-1-ol

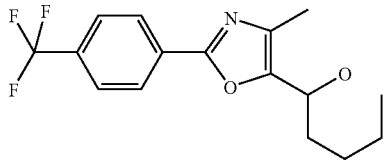

This compound is prepared in a similar manner as Preparation 44 using n-butyl lithium in step 2 as reagent.

Preparation 47

1-[4-Isopropyl-2-(4-trifluoromethoxy-phenyl)-oxazol-5-yl]-ethanol

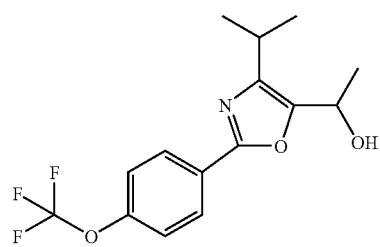

Preparation 48

1-[2-(4-Bromo-phenyl)-4-isopropyl-oxazol-5-yl]-ethanol

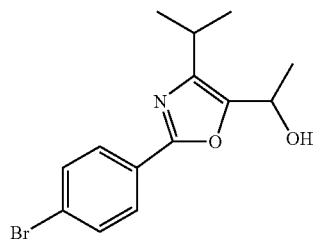

Preparation 49

2-[4-Isopropyl-2-(4-trifluoromethyl-phenyl)-oxazol-5-yl]-propan-1-ol

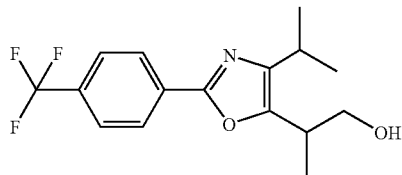

Step 1

4-Isopropyl-2-(4-trifluoromethyl-phenyl)-4H-oxazol-5-one

3-Methyl-2-(4-trifluoromethyl-benzoylamino)-butyric acid methyl ester (4.75 g, 16.42 mmol) is dissolved in acetic anhydride (25 mL) and heated to 95° C. for 3 hr. The mixture is concentrated in vacuo and the residue is partitioned between aqueous saturated sodium hydrogen carbonate (100 mL) and ethyl acetate (100 mL) the layers are separated, the organic phase is washed with water and brine (100 mL each), dried over anhydrous magnesium sulfate, filtered, concentrated in vacuo, and purified over silica gel eluting with 9:1 hexanes:ethyl acetate to afford 4-Isopropyl-2-(4-trifluoromethyl-phenyl)-4H-oxazol-5-one as a colorless oil which solidifies to a white crystalline solid on standing, 4.14 g, 93%. MS (M$^{++}$1) 272.

Step 2

2-[4-Isopropyl-2-(4-trifluoromethyl-Phenyl)-oxazol-5-yl]-propionic acid ethyl ester 4-Isopropyl-2-(4-trifluoromethyl-phenyl)-4H-oxazol-5-one (1.0 g, 3.69 mmol) and (carbethoxyethylidine)triphenylphosphorane (2.67 g, 7.37 mmol) are stirred in toluene (20 mL) at reflux 3 hr. The mixture is concentrated in vacuo and the residue is purified over silica eluting with 9:1 hexanes: ethyl acetate affording 2-[4-Isopropyl-2-(4-trifluoromethyl-phenyl)-oxazol-5-yl]-propionic acid ethyl ester as a pale orange oil, 1.11 g, 85%. MS (M$^+$+1) 356.

Step 3

2-[4-Isopropyl-2-(4-trifluoromethyl-phenyl)-oxazol-5-yl]-propan-1-ol

2-[4-Isopropyl-2-(4-trifluoromethyl-phenyl)-oxazol-5-yl]-propionic acid ethyl ester (1.11 g, 3.12 mmol) and tetrahydrofuran (50 mL) are cooled to 0° C. Lithium aluminum hydride (0.24 g, 6.25 mmol) is added and the resulting mixture is stirred 20 hr at room temperature. The mixture is cooled to 0° C. and 1M aqueous hydrochloric acid (50 mL) is carefully added. The mixture is then diluted with ethyl acetate (100 mL) and the layers are separated. The aqueous layer is washed with ethyl acetate (100 mL) and the organic ishes are combined, washed with water and brine (50 mL each), dried over anhydrous magnesium sulfate, filtered and concentrated to constant weight to give 2-[4-Isopropyl-2-(4-trifluoromethyl-phenyl)-oxazol-5-yl]-propan-1-ol as a pale orange oil, 1.03 g, 100%. MS (M$^+$+1) 314.

The following compound is made in similar manner:

Preparation 50

2-[4-Isopropyl-2-(4-trifluoromethoxy-phenyl)-oxazol-5-yl]-propan-1-ol

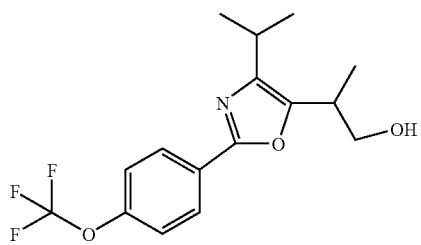

Preparation 51

2-[4-Isopropyl-2-(4-phenoxy-phenyl)-oxazol-5-yl]-propan-1-ol

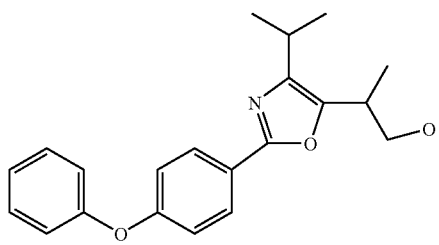

Preparation 52

2-[2-(4-Bromo-phenyl)-4-isopropyl-oxazol-5-yl]-propan-1-ol

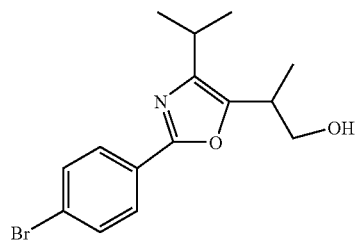

Preparation 53

2-[5-Methyl-2-(4-trifluoromethyl-phenyl)-thiazol-4-yl]-propan-1-ol and 2-Methyl-2-[5-methyl-2-(4-trifluoromethyl-phenyl)-thiazol-4-yl]-propan-1-ol

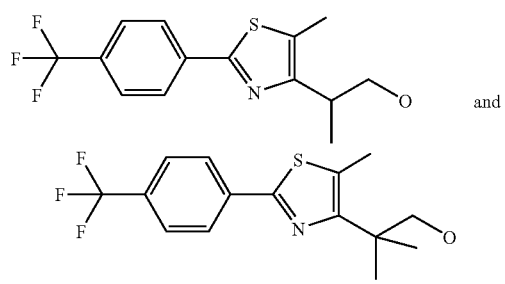

Step A

4-Bromo-2-methyl-3-oxo-pentanoic acid methyl ester and 4-Bromo-2,2-dimethyl-3-oxo-pentanoic acid methyl ester A solution of bromine (18.4 g, 115 mmol) in chloroform (30 mL) is added to a mixture of 2-methyl-3-oxo-pentanoic acid methyl ester and 2,2-dimethyl-3-oxo-pentanoic acid methyl ester (16.5 g) in chloroform (120 mL) at 0–5° C. dropwise. After the addition of bromine, the mixture is allowed to warm up to room temperature slowly and stirred overnight. The reaction is then quenched by ice water, the layers are separated. The organic layer is washed with cold water and brine, dried over sodium sulfate. Concentration gave the title compounds, which is used for next step without further purification.

Step B

2-[5-Methyl-2-(4-trifluoromethyl-phenyl)-thiazol-4-yl]-propionic acid methyl ester and 2-Methyl-2-[5-methyl-2-(4-trifluoromethyl-phenyl)-thiazol-4-yl]-propionic acid methyl ester A mixture of 4-Trifluoromethyl-thiobenzamide (7.70 g, 37.5 mmol) and the crude product from step A (9.0 g, 40 mmol) in ethanol (500 mL) is heated to reflux for 4 days. Solvent is evaporated and the residue is purified by chromatography on silica gel yielding the title compounds (11 g).

Step C

2-[5-Methyl-2-(4-trifluoromethyl-phenyl)-thiazol-4-yl]-propan-1-ol and 2-Methyl-2-[5-methyl-2-(4-trifluoromethyl-phenyl)-thiazol-4-yl]-propan-1-ol To a solution of 2-[5-Methyl-2-(4-trifluoromethyl-phenyl)-thiazol-4-yl]-propionic acid methyl ester and 2-Methyl-2-[5-methyl-2-(4-trifluoromethyl-phenyl)-thiazol-4-yl]-propionic acid methyl ester (10.6 g) in THF (50 mL) is added a solution of lithium aluminum hydride in THF (1.0 M, 33 mL) at 0° C. After 2 hrs, the reaction is quenched by water and sodium hydroxide, filtered, concentrated. Chromatography on silica gel gave 2-[5-Methyl-2-(4-trifluoromethyl-phenyl)-thiazol-4-yl]-propan-1-ol (4.3 g) and 2-Methyl-2-[5-methyl-2-(4-trifluoromethyl-phenyl)-thiazol-4-yl]-propan-1-ol (2.6 g).

Preparation 54

2-[5-Methyl-2-(4-trifluoromethyl-phenyl)-oxazol-4-yl]-propan-1-ol and 2-Methyl-2-[5-methyl-2-(4-trifluoromethyl-phenyl)-oxazol-4-yl]-propan-1-ol

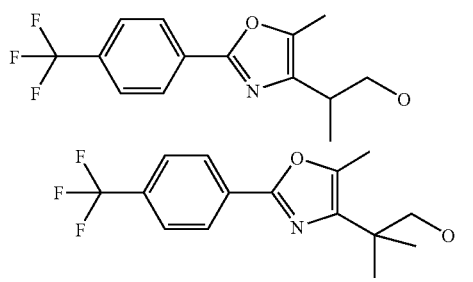

and

Step A

4-Bromo-2-methyl-3-oxo-pentanoic acid methyl ester and 4-Bromo-2,2-dimethyl-3-oxo-pentanoic acid methyl ester A solution of bromine (18.4 g, 115 mmol) in chloroform (20 mL) is added to a mixture of 2-methyl-3-oxo-pentanoic acid methyl ester and 2,2-dimethyl-3-oxo-pentanoic acid methyl ester (ca. 115 mmol) in chloroform (120 mL) at 0–5° C. dropwise. After the addition of bromine, the mixture is allowed to warm up to room temperature slowly and stirred overnight. The reaction is then quenched by ice water, the layers are separated. The organic layer is washed with cold water and brine, dried over sodium sulfate. Concentration gave the title compounds, which is used for next step without further purification.

Step B

2-[5-Methyl-2-(4-trifluoromethyl-phenyl)-oxazol-4-yl]-propionic acid methyl ester and 2-Methyl-2-[5-methyl-2-(4-trifluoromethyl-phenyl)-oxazol-4-yl]-propionic acid methyl ester To a solution of 4-Trifluoromethyl-benzoic acid (7.6 g, 40 mmol) in methanol (100 mL) is added sodium hydroxide (1.6 g, 40 mmol), stirred for 30 min, methanol is evaporated. The residue is taken into DMF (50 mL) and the crude product from step A (10 g) is added. The mixture is stirred overnight, diluted with ethyl acetate, washed with water and brine, dried over sodium sulfate, concentrated. The residue is taken into ethanol (150 mL) and treated with ammonium acetate (6.17 g) and heated at 70° C. for 12 hrs. Ethanol is evaporated, the residue is mixed with ammonium acetate (12.3 g) in glacial acid (750 mL) and heated at 100° C. for 2 days. Solvent is evaporated and the residue is taken into ethyl acetate, washed with water and brine, dried. Chromatography on silica gel gave 2-[5-Methyl-2-(4-trifluoromethyl-phenyl)-oxazol-4-yl]-propionic acid methyl ester (3.40 g) and 2-Methyl-2-[S-methyl-2-(4-trifluoromethyl-phenyl)-oxazol-4-yl]-propionic acid methyl ester (2.80 g).

Step C

2-[5-Methyl-2-(4-trifluoromethyl-phenyl)-oxazol-4-yl]-propan-1-ol

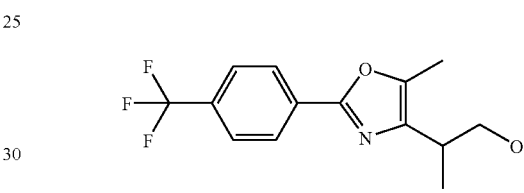

To a solution of 2-[5-methyl-2-(4-trifluoromethyl-phenyl)-ozazol-4-yl]-propionic acid methyl ester (3.4 g) from step B in THF (20 mL) is added a solution of lithium aluminum hydride in THF (1.0 M, 14 mL) at 0° C. After 2 hrs, the reaction is quenched by water and sodium hydroxide, filtered, concentrated. Chromatography on silica gel gave 2-[5-Methyl-2-(4-trifluoromethyl-phenyl)-oxazol-4-yl]-propan-1-ol (0.88 g).

Step D and 2-Methyl-2-[5-methyl-2-(4-trifluoromethyl-phenyl)-oxazol-4-yl]-propan-1-ol

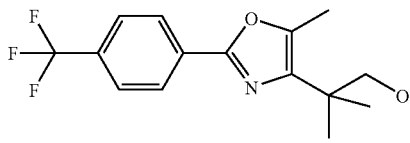

To a solution of 2-methyl-2-[5-methyl-2-(4-trifluoromethyl-phenyl)-oxazol-4-yl]-propionic acid methyl ester (2.8 g) from step B in THF (14 mL) is added a solution of lithium aluminum hydride in THF (1.0 M, 13 mL) at 0° C. After 2 hrs, the reaction is quenched by water and sodium hydroxide, filtered, concentrated. Chromatography on silica gel gave 2-Methyl-2-[5-methyl-2-(4-trifluoromethyl-phenyl)-oxazol-4-yl]-propan-1-ol (2.3 g).

Preparation 55

2-Methyl-2-[5-ethyl-2-(4-trifluoromethyl-phenyl)-thiazol-4-yl]-propan-1-ol

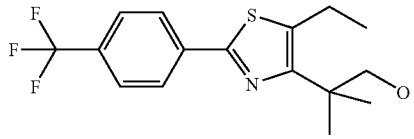

Step A

4-Bromo-2,2-dimethyl-3-oxo-hexanoic acid methyl ester

A solution of bromine (24 g, 150 mmol) in chloroform (30 mL) is added to 2,2-dimethyl-3-oxo-hexanoic acid methyl ester (25.9 g, 150 mmol) in chloroform (126 mL) at 0–5° C. dropwise. After the addition of bromine, the mixture is allowed to warm up to room temperature slowly and stirred overnight. The reaction is then quenched by ice water, the layers are separated. The organic layer is washed with cold water and brine, dried over sodium sulfate. Concentration gave the title compounds (36.9 g), which is used for next step without further purification.

Step B

2-Methyl-2-[5-ethyl-2-(4-trifluoromethyl-phenyl)-thiazol-4-yl]-propionic acid methyl ester A mixture of 4-Trifluoromethyl-thiobenzamide (12.3 g, 60 mmol) and the crude product from step A (16.6 g, 66 mmol) in ethanol (600 mL) is heated to reflux for 3 days. Solvent is evaporated and the residue is purified by chromatography on silica gel yielding the title compounds (14.5 g).

Step C

2-Methyl-2-[5-ethyl-2-(4-trifluoromethyl-phenyl)-thiazol-4-yl]-propan-1-ol

To a solution of 2-Methyl-2-[5-ethyl-2-(4-trifluoromethyl-phenyl)-thiazol-4-yl]-propionic acid methyl ester (14.5 g, 40.6 mmol) in THF (100 mL) is added a solution of lithium aluminum hydride in THF (1.0 M, 41 mL) at 0° C. After 2 hrs, the reaction is quenched by water and sodium hydroxide, filtered, concentrated. Chromatography on silica gel gave 2-Methyl-2-[5-ethyl-2-(4-trifluoromethyl-phenyl)-thiazol-4-yl]-propan-1-ol (12.3 g).

Preparation 56

2-[4-Methyl-2-(4-trifluoromethyl-phenyl)-thiazol-5-yl]-propan-1-ol

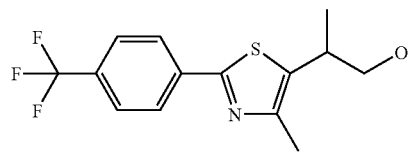

Step A

1-[4-Methyl-2-(4-trifluoromethyl-phenyl)-thiazol-5-yl]-ethanone

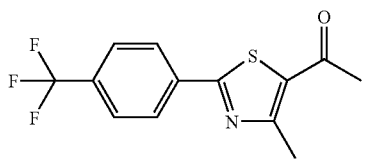

A mixture of 1-[4-Methyl-2-(4-trifluoromethyl-phenyl)-thiazol-5-yl-]-ethanol (1.0 g, 3.48 mmol) and MnO2 (0.45 g, 5.22 mmol) in chloroform (30 mL) is heated to reflux, after 24 hrs, additional MnO2 (300 mg) is added and refluxed for another 9 hrs, the reaction mixture is filtered through celite. Concentration of filtrate gave the title compound (1.0 g).

Step B 5-(2-Methoxy-1-methyl-vinyl)-4-methyl-2-(4-trifluoromethyl-phenyl)-thiazole

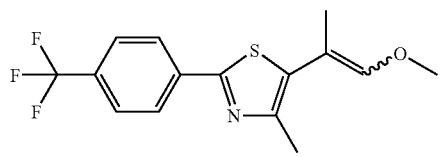

To a solution of (methoxymethyl)triphenyl phosphonium chloride (15.5 g, 45.2 mmole) in toluene (330 mL) is added potassium t-butoxide (5.07 g, 45.2 mmole) in one portion and stirred for 30 minutes, then a solution of 1-[4-Methyl-2-(4-trifluoromethyl-phenyl)-thiazol-5-yl]-ethanone (8.6 g, 30.1 mmole) in toluene (20 mL) is added. The reaction is stirred for 4 hours, quenched by NH4Cl aqueous solution, extracted with ethyl acetate and then concentrated on rota vapor. The residue is purified on a silica gel column, eluting with 0–10% ethyl acetate in hexane and concentrated to provide the title compound (7.0 g).

Step C

2-[4-Methyl-2-(4-trifluoromethyl-phenyl)-thiazol-5-yl]-propionaldehyde

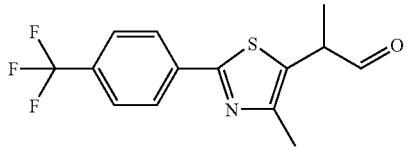

5-(2-Methoxy-1-methyl-vinyl)-4-methyl-2-(4-trifluoromethyl-phenyl)-thiazole (7.0 g, 22.3 mmol) in THF (200 mL) is treated with concentrated HCl aqueous solution (7 mL) at 50° C. for 2 hours. The reaction mixture is diluted with ethyl acetate, washed with sodium bicarbonate aqueous solution, dried over sodium sulfate. Concentration and column chromatography on silica gel provided the title compound (3.5 g).

Step D

2-[4-Methyl-2-(4-trifluoromethyl-phenyl)-thiazol-5-yl]-propan-1-ol

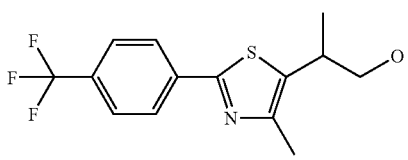

To a solution of 2-[4-methyl-2-(4-trifluoromethyl-phenyl)-thiazol-5-yl]-propionaldehyde (2.0 g, 6.68 mmol) in ethanol (30 mL) is added to NaBH, (0.25 g, 6.6 mmol) in portions at 0° C. The reaction is kept at 0° C. for 15 minutes and warmed up to room temperature for 2 hours. The reaction is quenched using water, extracted with ethyl acetate, dried over sodium sulfate. Concentration and column chromatography on silica gel eluted with hexanes and ethyl acetate gave the title compound (2.0 g).

Preparation 57

2-[5-Ethyl-2-(4-trifluoromethyl-phenyl)-thiazol-4-yl]-propan-1-ol

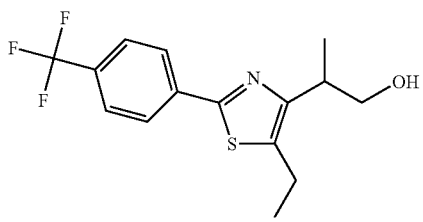

Step A

3-Oxo-hexanoic acid ethyl ester (29.5 g, 0.1865 Mol) is dissolved into anhydrous dichloromethane (DCM) (400 mL) and then cooled to 0° C.–5° C. while stirring. A solution of bromine (30.4 g, 0.190 Mol) in DCM (80 mL) is added dropwise over 2 h. to the solution of the beta keto-ester. After the addition, the mixture is allowed to stir 0.5 h. at 0° C., then the ice bath is removed and the mixture is allowed to stir at room temperature for 18 h. TLC will show complete consumtion of starting material, then ice water (200 g) is added with stirring. The organic layer is collected and washed with cold water (2×) and brine. The filtered solution is dried over anhydrous sodium sulfate, then concentrated to a clear liquid. The crude 4-Bromo-3-oxo-hexanoic acid ethyl ester (40.2 g, 0.1695 Mol), 91% yield, is used without further purification.

Step B

4-Bromo-3-oxo-hexanoic acid ethyl ester (4.68 g, 20.98 mmol) is dissolved into denatured ethanol (100 mL) and para-trifluoromethyl thiobenzamide (4.31 g, 21 mmol) is added in one portion. The reaction is purged of air and flushed with nitrogen then heated to reflux. The reaction is monitored by TLC and HPLC and when complete, the reaction is allowed to cool to room temperature. The solvent is removed and the reaction is diluted with ethyl acetate (200 mL), followed by ishes with saturated sodium bicarbonate solution, water, and brine. The ethyl acetate solution is dried over anhydrous sodium sulfate, then concentrated and further purified using flash column chromatography (10% EtOAc/Hexanes) to yield pure [5-Ethyl-2-(4-trifluoromethyl-phenyl)-thiazol-4-yl]-acetic acid ethyl ester (5.09 g, 14.82 mmol) or 71% yield.

Step C

[5-Ethyl-2-(4-trifluoromethyl-phenyl)-thiazol-4-yl]-acetic acid ethyl ester (2.02 g, 6.13 mmol) is dissolved into anhydrous tetrahydrofuran (THF) (10 mL) and lithium diisopropylamide (LDA) is slowly added at room temperature. This solution is allowed to stir at room temperature and monitored by TLC. After complete conversion, methyl iodide (582 mg, 4.00 mmol) is added slowly and the reaction is followed by TLC. After 18 h., the reaction is not complete, but is quenched with saturated ammonium chloride solution and diluted with diethyl ether. The two phases are separated and the organic layer is washed with water and brine, dried over anhydrous sodium sufate, then concentrated and purified using flash column chromatography (10% EtOAc/Hexanes). The pure 2-[5-Ethyl-2-(4-trifluoromethyl-phenyl)-thiazol-4-yl]-propionic acid ethyl ester (1.30 g, 3.64 mmol) is obtained in 59% yield.

Step D

2-[5-Ethyl-2-(4-trifluoromethyl-phenyl)-thiazol-4-yl]-propionic acid ethyl ester (1.05 g, 3.06 mmol) is dissolved into anhydrous tetrahydrofuran (THF) (10 mL) and then cooled to 0° C. with stirring. Lithium aluminum hydride (3.10 mL, 1M in THF, 3.10 mmol) is slowly added by syringe and the reaction is monitored by TLC. Upon complete conversion, the reaction is carefully quenched using water, base, and water. Celite is added to the reaction, followed by diethyl ether and the mixture is then filtered through a celite plug. The two phases are then separated and the organic layer is washed using water and brine. The organic layer is the dried over anhydrous sodium sulfate and concentrated. The pure 2-[5-Ethyl-2-(4-trifluoromethyl-phenyl)-thiazol-4-yl]-propan-1-ol (0.930 g, 2.95 mmol) is obtained in 95% yield after flash column chromatography.

Preparation 58

2-[4-Isopropyl-2-(4-trifluoromethyl-phenyl)-thiazol-5-yl]-propan-1-ol

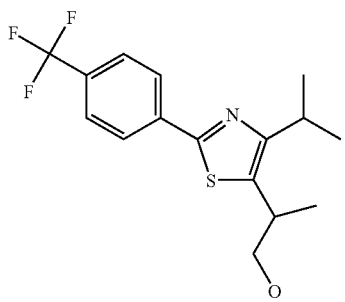

Step A

4-Isopropyl-2-(4-trifluoromethyl-phenyl)-thiazole-5-carboxylic acid methyl ester (14 g, 40.1 mmol) is dissolved into anhydrous tetrahydrofuran (THF) (200 mL) and then cooled to −30° C. while stirring under nitrogen. N-methyl, N-methoxy amine hydrochloride (0.881 g, 9.04 mmol) is then added to the solution in one portion. Isopropyl magnesium chloride (8.73 mL, 2M soln. in THF, 17.46 mmol) is slowly added to the cooled suspension over 1 h. TLC will show complete consumtion of starting material, then 30% solution of ammonium chloride is added with stirring. The reaction is diluted with diethyl ether and extracted. The organic layer is collected and washed with cold water (2×) and brine. The solution is then dried over anhydrous sodium sulfate, filtered, and concentrated. The 4-Isopropyl-2-(4-trifluoromethyl-phenyl)-thiazole-5-carboxylic acid methoxy-methyl-amide (0.705 g, 1.97 mmol) is obtained in pure form after flash column chromatography.

Step B

4-Isopropyl-2-(4-trifluoromethyl-phenyl)-thiazole-5-carboxylic acid methoxy-methyl-amide (7.56 g, 21.09 mmol) is suspended in anhydrous tetrahydrofuran (100 mL), and cooled to 0° C. with stirring under nitrogen. Methyl magnesium bromide (28 mL, 3.0M in diethyl ether, 84.36 mmol) is slowly added to the reaction over 1 h. The reaction is allowed to warm slowly to room temperature and monitored by TLC. Upon complete consumption of starting material, the reaction is carefully neutralized with 1N hydrochloric acid, extracted with diethyl ether, washed, dried, and concentrated. The 1-[4-Isopropyl-2-(4-trifluoromethyl-phenyl)-thiazol-5-yl]-ethanone (5.4 g, 17.23 mmol) 82% yield, is used without further purification.

Step C (Methoxymethyl)triphenylphosphinium chloride (8.86 g, 25.84 mmol) is suspended in anhydrous toluene (75 mL) and potassium tert-butoxide (2.90 g, 25.84 mmol) is carefully added. The solution is allowed to cool and stir at room temperature for 1 h. 1-[4-Isopropyl-2-(4-trifluoromethyl-phenyl)-thiazol-5-yl]-ethanone (5.4 g, 17.23 mmol) is then dissolved into anhydrous toluene (25 mL) and added to the reaction mixture by syringe. The reaction is allowed to stir at room temperature for several hours and is monitored by TLC. Upon complete consumption of starting material, the reaction is carefully quenched with saturated ammonium chloride solution, extracted with diethyl ether, washed, dried, and concentrated. The 4-Isopropyl-5-(2-methoxy-1-methyl-vinyl)-2-(4-trifluoromethyl-phenyl)-thiazole is used in the next step without further purification.

Step D

4-Isopropyl-5-(2-methoxy-1-methyl-vinyl)-2-(4-trifluoromethyl-phenyl)-thiazole is dissolved into anhydrous tetrahydrofuran (100 mL) and concentrated hydrochloric acid (5 mL) is added with stirring under nitrogen. The reaction is heated to 50° C. and monitored by TLC. Upon complete consumption of starting material, the reaction is carefully neutralized with sodium hydroxide, extracted with diethyl ether, washed, dried, and concentrated. The 2-[4-Isopropyl-2-(4-trifluoromethyl-phenyl)-thiazol-5-yl]-propionaldehyde (4.6 g, 14.05 mmol), 82% two steps, is obtained in pure form after flash column chromatography.

Step E

2-[4-Isopropyl-2-(4-trifluoromethyl-phenyl)-thiazol-5-yl]-propionaldehyde (4.05 g, 12.5 mmol) is dissolved into denatured ethanol (60 mL) at room temperature then cooled to 0° C. in an ice bath. Sodium borohydride (0.467 g, 12.5 mmol) is then carefully added in small portions. The reaction is allowed to warm slowly to room temperature and is monitored by TLC. Upon complete consumption of starting material, the reaction is carefully quenched with water and diluted with ethyl acetate. The ethanol is removed and the residue is extracted with ethyl acetate, washed, dried, and concentrated. The 2-[4-Isopropyl-2-(4-trifluoromethyl-phenyl)-thiazol-5-yl]-propan-1-ol (4.0 g, 12.14 mmol), 97%, is obtained in pure form after flash column chromatography.

Preparation 59

Toluene-4-sulfonic acid 2-[5-ethyl-2-(4-trifluoromethyl-phenyl)-oxazol-4-yl]-ethyl ester

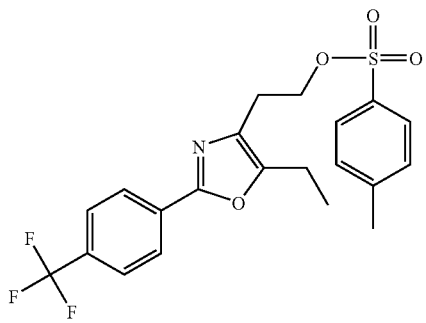

Step A

To a solution of •••••-trifluoromethyl-para-toluic acid (5.0 g, 26.3 mmol) in anhydrous acetone (100 mL) at 0° C. under nitrogen is added 4-bromo-3-oxo-hexanoic acid ethyl ester (6.4 g, 27 mmol) and triethyl amine (3.5 mL, 27 mmol). The mixture is allowed to stir 0.5 h. at 0° C., then the ice bath is removed and the mixture allowed to stir at room temperature for 18 h. The reaction is monitored by TLC and HPLC until complete consumtion of starting material, then ice water added with stirring and the mixture is extracted.

The organic layer is collected and washed with brine, then dried over anhydrous sodium sulfate. The crude 4-Trifluoromethyl-benzoic acid 3-ethoxycarbonyl-1-ethyl-2-oxo-propyl ester is used in the next step without further purification.

Step B

4-Trifluoromethyl-benzoic acid 3-ethoxycarbonyl-1-ethyl-2-oxo-propyl ester (25 mmol) is dissolved in acetic acid (100 mL) and dry ammonium acetate (10 g, 100 mmol) is added, then the reaction is heated under nitrogen to reflux. The reaction is monitored by TLC and HPLC but complete consumption of the starting material is never observed, and then allowed to cool. The cooled reaction is concentrated and diluted with 250 mL ethyl acetate. The residue is washed with 100 mL saturated sodium bicarbonate followed by water and brine. The organic layer is dried over anhydrous sodium sulfate, then concentrated and purified by column chromatrography. The fractions that contained pure product are concentrated to yield [5-Ethyl-2-(4-trifluoromethyl-phenyl)-oxazol-4-yl]-acetic acid ethyl ester (4.0 g, 12.22 mmol) or 50% yield.

Step C

[5-Ethyl-2-(4-trifluoromethyl-phenyl)-oxazol-4-yl]-acetic acid ethyl ester (4.0 g, 12.22 mmol) in anhydrous tetrahydrofuran (100 mL) is cooled to 0° C. and a 1M LiAlH$_4$ (12.2 mL, 12.2 mmol) solution is added slowly. The reaction is monitored by TLC until complete consumption of the starting material. The reaction is then carefully quenched with 2.4 mL water, 2.4 mL 5N NaOH and 7 mL water. The light tan solid is filter through celite and dried to give crude 2-[5-Ethyl-2-(4-trifluoromethyl-phenyl)-oxazol-4-yl]-ethanol (2.74 g, 9.60 mmol) or 79% yield.

Step D

To a solution of 2-[5-Ethyl-2-(4-trifluoromethyl-phenyl)-oxazol-4-yl]-ethanol 2.74 g, 9.60 mmol) in anhydrous dichloromethane (50 mL) is added dimethylamino pyridine (0.500 g, 4.00 mmol), tosic anhydride (8.4 g, 24 mmol), and pyridine (3.4 mL, 42 mmol) at room temperature. The reaction is monitored by TLC, and upon complete consumption of the starting alcohol, the reaction is diluted with DCM and extracted against saturated sodium bicarbonate solution. The organic layer is washed with water and brine, then dried over anhydrous sodium sulfate and concentrated. The pure toluene-4-sulfonic acid 2-[5-ethyl-2-(4-trifluoromethyl-phenyl)-oxazol-4-yl]-ethyl ester (3.0 g, 6.82 mmol) is obtained after flash column chromatography.

Preparation 60

Toluene-4-sulfonic acid 2-methyl-2-[5-methyl-2-(4-trifluoromethyl-phenyl)-thiazol-4-yl]-propyl ester

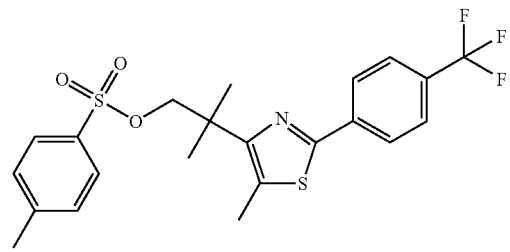

Preparation 61

Toluene-4-sulfonic acid 2-methyl-2-[5-methyl-2-(4-trifluoromethyl-phenyl)-oxazol-4-yl]-propyl ester

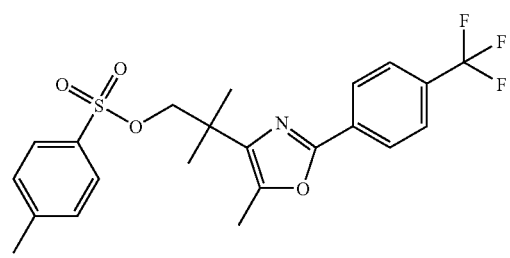

Preparation 62

1-[5-Ethyl-2-(4-trifluoromethyl-phenyl)-thiazol-4-yl]-propan-2-ol

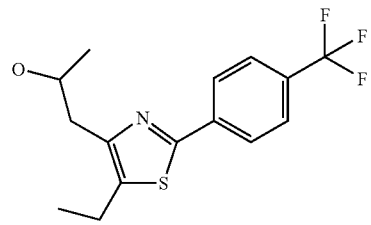

Step A

To a solution of 2-[5-Ethyl-2-(4-trifluoromethyl-phenyl)-thiazol-4-yl]-ethanol (1.25 g, 4.16 mmol) in anhydrous dichloromethane (25 mL) at 0° C. under nitrogen is slowly added Dess-Martin periodinane (2.6 g, 6.24 mmol). The reaction is allowed to warm slowly to room temperature and monitored by TLC. After complete consumption of the starting material, the reaction is diluted with dichloromethane and the two phases are seperated. The organic layer is washed, dried, filtered and concentrated. The crude [5-Ethyl-2-(4-trifluoromethyl-phenyl)-thiazol-4-yl]-acetaldehyde (0.253 g, 0.840 mmol), 21% yield, is further purified using flash column chromatography.

Step B

[5-Ethyl-2-(4-trifluoromethyl-phenyl)-thiazol-4-yl]-acetaldehyde (0.253 g, 0.840 mmol), is dissolved in anhydrous tetrahydrofuran (5 mL) and cooled to 0° C. with stirring under nitrogen. Methylmagnesium bromide, 3.0M in ether, (0.300 mL, 1.00 mmol) is added and the ice bath removed. After slowly warming to room temperature, the reaction is monitored by TLC. After the starting material is completely consumed, the reaction is quenched with saturated ammonium chloride solution and diluted with ether. The two phases are separated and the organic washed with water and brine, dried over sodium sulfate, then concentrated. The residue is further purified using flash column chromatography. The 1-[5-Ethyl-2-(4-trifluoromethyl-phenyl)-thiazol-4-yl]-propan-2-ol (0.222 g, 0.7049 mmol) is formed in 70% yield.

Preparation 63

C-[5-Methyl-2-(4-trifluoromethyl-phenyl)-oxazol-4-yl]-methylamine

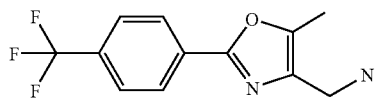

4-Azidomethyl-5-methyl-2-(4-trifluoromethyl-phenyl)-oxazole

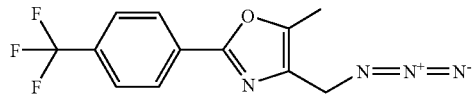

To a solution of 4-chloromethyl-5-methyl-2-(4-trifluoromethyl-phenyl)-oxazole (2.4 g, 8.71 mmol) in methanol (13 mL) is added sodium azide (1.13 g, 17.4 mmol) in water (10 mL). The mixture is heated to reflux for 3 hrs, cooled to room temperature, majority of the methanol is evaporated, the residue is extracted with ethyl acetate, dried, concentrated and colun chromatography on silica gel gave the title compound (2.10 g).

Step B

C-[5-Methyl-2-(4-trifluoromethyl-phenyl)-oxazol-4-yl]-methylamine

A mixture of 4-azidomethyl-5-methyl-2-(4-trifluoromethyl-phenyl)-oxazole (1.70 g) and PtO2 (0.106 g) in ethyl acetate (50 mL) at room temperature under 60 psi of hydrogen for 5 hrs, the reaction mixture is filtered through celite and filtrate is concentrated giving the title compound (1.3 g, 84.2% yield).

Preparation 64

2R-[5-Methyl-2-(4-trifluoromethyl-phenyl)-thiazol-4-yl]-propan-1-ol

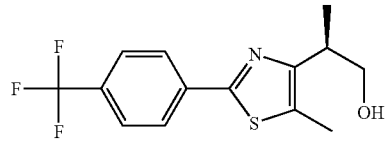

The racemic alcohol 2-[5-methyl-2-(4-trifluoromethyl-phenyl)-thiazol-4-yl]-propan-1-ol is resolved on a Chiralpak AD column (4.6×250 mm). Eluted with ethanol in heptane and concentrated the fractions to provide pure enantiomers.

Preparation 65

2S-[5-Methyl-2-(4-trifluoromethyl-phenyl)-oxazol-4-yl]-propan-1-ol

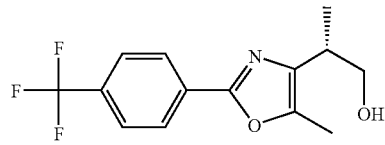

This compound is obtained in preparation 64.

Preparation 66

2-(4-Hydroxy-2-methyl-phenoxy)-2-methyl-propionic acid

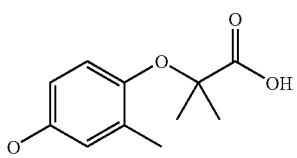

Step A 2-(4-Benzyloxy-2-formylphenoxy)-2-methyl propionic acid ethyl ester

5-Benzyloxy-2-hydroxy-benzaldehyde (Kappe, T.; Witoszynskyj, T. Arch. Pharm., 1975, 308 (5), 339–346) (2.28 g, 10.0 mmol), ethyl bromoisobutyrate (2.2 mL, 15 mmol), and cesium carbonate (3.26 g, 10.0 mmol) in dry DMF (25 mL) are heated at 80° C. for 18 h. The reaction mixture is cooled and partitioned between water (30 mL) and ether (75 mL). The organic layer is washed with brine (15 mL). The aqueous layers are back-extracted with ethyl acetate (30 mL), and the organic layer is washed with brine (20 mL). The combined organic layers are dried ($Na_2SO_4$) and concentrated to a brown oil. The crude product is purified by flash chromatography using hexanes:ethyl acetate (2.5:1) to give a pale yellow solid (3.04 g, 89%): mp 65° C.; $^1$H NMR (400 MHz, $CDCl_3$) δ 1.24 (t, 3H, J=7.1 Hz), 1.62 (s, 6H), 4.23 (q, 2H, J=7.1 Hz), 6.81 (d, 1H, J=8.8 Hz), 7.10 (dd, 1H, J=4.6, 9.0 Hz), 7.30–7.43 (m, 6H); MS (ES) m/e 343.1 [M+1].

Step B

2-(4-Hydroxy-2-methyl-phenoxy)-2-methyl-propionic acid ethyl ester 2-(4-Benzyloxy-2-formyl-phenoxy)-2-methyl-propionic acid ethyl ester (9.00 g, 26.3 mmol) in ethanol (250 mL) is treated with 5% Pd/C (1.25 g) and hydrogen (60 psi, rt, overnight). Additional 5% Pd/C (1.25 g) is added, and the reaction is continued for 6 h at 40° C. The mixture is filtered and concentrated to a tan oil (6.25 g). This oil contained 9 mol % of 2-(4-Hydroxy-2-hydroxymethyl-phenoxy)-2-methyl-propionic acid ethyl ester. $^1$H NMR (400 MHz, CDCl) δ 1.26 (t, 3H, J=7.3 Hz), 1.51 (s, 6H), 2.14 (s, 3H), 4.24 (q, 2H, J=7.3 Hz), 5.68 (brs, 1H), 6.47 (dd, 1H, J=3.4, 8.8 Hz), 6.59 (d, 1H, J=8.3 Hz), 6.60 (brs, 1H).

The following compound is prepared in a similar manner:

Preparation 67

2-(4-Hydroxy-2-methyl-phenoxy)-acetic acid

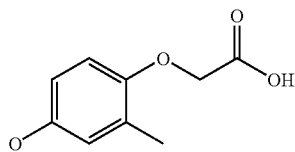

$^1$H NMR (400 MHz, CDCl3) δ 1.28 (t, 3H, J=7.1 Hz), 2.24 (s, 3H), 4.25 (q, 2H, J=7.1 Hz), 4.55 (s, 2H), 6.56 (dd, 1H, J=2.7, 8.5 Hz), 6.61 (d, 1H, J=8.3 Hz), 6.65 (d, 2H, J=2.9 Hz).

Preparation 68

(4-Hydroxy-2-propyl-phenoxy)-acetic acid ethyl ester

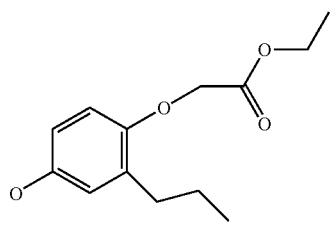

Step A

4-Benzyloxy-2-propylphenol

2-Allyl-4-benzyloxyphenol (WO 9728137 A1 19970807, Adams, A. D. et al.) (5.00 g, 20.8 mmol) in ethyl acetate (40 mL) is treated with 5% Pd/C (0.25 g) and hydrogen (1 atm) at ambient temperature for 18 h. The mixture is filtered and concentrated. The crude product is purified on a Biotage medium pressure chromatography system using a 40 L normal phase cartridge and eluted with 10% ethyl acetate in hexanes to give a tan solid (2.8 g, 56%). Rf=0.33 (25% EtOAc/Hexanes); $^1$H NMR (400 MHz, CDCl$_3$) δ 7.44–7.31 (m, 5H), 6.78 (s, 1H), 6.69 (d, J=1.5 Hz, 2H), 5.00 (s, 2H), 4.31 (s, 1H), 2.55 (t, J=7.6 Hz, 2H), 1.64 (q, J=7.5 Hz, 2H), 0.97 (t, J=7.3 Hz, 3H).

Step B

(4-Benzyloxy-2-propylphenoxy)acetic acid ethyl ester

A solution of 4-benzyloxy-2-propylphenol (0.50 g, 1.94 mmol) in dry DMF (7 mL) is cooled in an ice bath and treated with NaH (0.15 g, 3.8 mmol, 60% oil dispersion). The ice bath is removed, ethyl bromoacetate (0.43 mL, 3.9 mmol) is added, and the mixture is placed in an oil bath (T=85° C.). After 18 h, the reaction mixture is cooled and concentrated in vacuo. The residue is diluted with EtOAc, washed with brine (2×), dried (Na$_2$SO$_4$), and concentrated. The crude product is purified by radial chromatography using 10% ethyl acetate in hexanes to give a tan solid (0.62 g, 97%). $^1$H NMR (400 MHz, CDCl$_3$) δ 7.44–7.31 (m, 5H), 6.82 (d, J=2.9 Hz, 1H), 6.72 (dd, J=8.8, 2.9 Hz, 1H), 6.66 (d, J=8.8 Hz, 1H), 5.00 (s, 2H), 4.57 (s, 2H), 4.25 (q, J=7.0 Hz, 2H), 2.63 (t, J=7.6 Hz, 2H), 1.64 (q, J=7.5 Hz, 2H), 1.29 (t, J=7.1 Hz, 3H), 0.95 (t, J=7.3 Hz, 3H); MS (FIA) m/e 329 (M+1).

Step C

(4-Hydroxy-2-propylphenoxy)acetic acid ethyl ester

A solution of (4-benzyloxy-2-propylphenoxy)acetic acid ethyl ester (0.60 g, 1.83 mmol) in THF (15 mL) is treated with 5% Pd/C (75 mg) and hydrogen (60 psi) at ambient temperature for 24 h. The mixture is filtered and concentrated. The crude product is purified by radial chromatography using 15% ethyl acetate in hexanes to give a tan solid (0.25 g, 57%). $^1$H NMR (400 MHz, CDCl$_3$) δ 6.66 (d, J=2.9 Hz, 1H), 6.62 (d, J=8.8 Hz, 1H), 6.57 (dd, J=8.8, 2.9 Hz, 1H), 4.56 (s, 1H), 4.40 (s, 1H), 4.25 (q, J=7.2 Hz, 2H), 2.61 (t, J=7.6 Hz, 2H), 1.63 (q, J=7.5 Hz, 2H), 1.29 (t, J=7.1 Hz, 3H), 0.95 (t, J=7.3 Hz, 3H); MS (FIA) m/e 239 (M+1).

Preparation 69

(4-Mercapto-phenoxy)-acetic acid ethyl ester

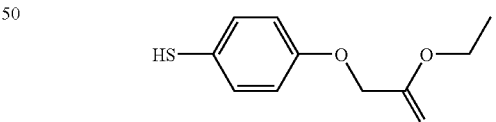

Step A

(4-Chlorosulfonyl-phenoxy)-acetic acid ethyl ester

Phenoxy-acetic acid ethyl ester (9.1 mL) is added to chlorosulfonic acid (15 mL) at 0° C. dropwise. The reaction is stirred at 0° C. for 30 min, it is allowed to warm to room temperature. After 2 hrs, the reaction mixture is poured into ice, solid product is collected by filtration and dried under vacuum.

Step B

(4-Mercapto-phenoxy)-acetic acid ethyl ester

To a mixture of (4-chlorosulfonyl-phenoxy)-acetic acid ethyl ester (0.98 g, 3.5 mmol) and tin powder (2.1 g) in ehtanol (4.4 mL) is added HCl in dioxane (1.0 M, 4.4 mL) under nitrogen. The mixture is heated to reflux for 2 hrs, it is poured into ice and methylene chloride and filtered. The layers are separated and extracted with methylene chloride, dried and concentrated. The crude product is used for next step without purification.

The following compounds are made in a similar manner:

Preparation 70

(4-Mercapto-2-methyl-phenoxy)-acetic acid ethyl ester

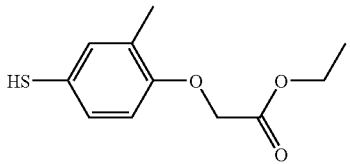

This compound can also be made by the following procedure: To a stirred suspension of Zn powder (10 μm, 78.16 g, 1.2 mol) and dichlorodimethyl silane (154.30 g, 145.02 mL, 1.2 mol) in 500 mL of dichloroethane is added a solution of (4-chlorosulfonyl-2-methyl-phenoxy)-acetic acid ethyl ester (100 g, 0.34 mol) and 1,3-dimethylimidazolidin-2-one (116.98 g, 112.05 mL, 1.02 mol) in 1 L of DCE. Addition is at a rate so as to maintain the internal temperature at ~52° C., cooling with chilled water as necessary. After addition is complete, the mixture is heated at 75° C. for 1 hour. It is then cooled to room temperature, filtered and concentrated iv. Add MTBE, washed twice with saturated LiCl solution concentrate iv again. Take up the residue in CH$_3$CN, ish with hexane (4×) and concentrate iv to yield a biphasic mixture. Let stand in a separatory funnel and separate layers, keeping the bottom layer for product. Filtration through a plug of silica gel (1 Kg, 25% EtOAc/hexane) and subsequent concentration yielded 61 g (79%) of a clear, colorless oil.

NMR (DMSO-d$_6$) δ 7.1 (s, 1H), 7.05 (dd, 1H), 6.75 (d, 1H), 5.03 (s, 1H), 4.75 (s, 2H), 4.15 (q, 2H), 2.15 (s, 3H), 1.2 (t, 3H).

Preparation 71

(4-Mercapto-2-propyl-phenoxy)-acetic acid ethyl ester

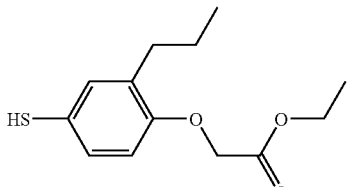

Preparation 72

3-(4-Mercapto-2-methyl-phenyl)-propionic acid methyl ester

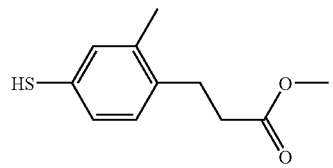

Step A

3-(4-Dimethylthiocarbamoyloxy-2-methyl-phenyl)-propionic acid methyl ester 3-(4-Hydroxy-2-methyl-phenyl)-propionic acid methyl ester (5.0 g, 25.75 mmol) is dissolved into dry dioxane (100 mL) and combined with 4-dimethylamino pyridine (0.500 g, 2.6 mmol), triethylamine (7.0 mL, 51.5 mmol), and dimethylaminothiocarbomoyl chloride (4.5 g, 32.17 mmol). The reaction is heated to reflux under nitrogen. The reaction is monitored by TLC until all of the phenol is consumed, 20 h. After cooling to room temperature, the reaction is diluted with ethyl acetate (200 mL). Water (75 mL) is added and the two layers are seperated. The organic layer is washed with brine (75 mL) then dried over anhydrous sodium sulfate. The solvent is removed and the residue is dried under vacuum.

Step B

3-(4-Dimethylcarbamoylsulfanyl-2-methyl-phenyl)-propionic acid methyl ester 3-(4-Dimethylthiocarbamoyloxy-2-methyl-phenyl)-propionic acid methyl ester, taken crude from the previous step, is diluted with 75 mL of tetradecane and heated to reflux under nitrogen. The reaction is monitored by TLC until all the conversion is complete, 20 h. The reaction is allowed to cool to room temperature, then the tetradecane is decanted away from the resulting oil. The residue is rinsed several times with hexanes. This oil is then purified using flash column chromatography, yielding 5.01 g, or 69% (2 steps) of the product.

Step C

3-(4-Mercapto-2-methyl-phenyl)-propionic acid methyl ester 3-(4-Dimethylcarbamoylsulfanyl-2-methyl-phenyl)-propionic acid methyl ester (5.01 g, 17.8 mmol) is diluted with methanol (30 mL) and to this is added sodium methoxide (1.7 mL of 4M in methanol, 7.23 mmol). The reaction is heated to reflux under nitrogen and monitored by TLC. After complete conversion, 20 h., the reaction is allowed to cool to room temperature. The reaction is nuetralized with 1N HCl (7.23 mL) and diluted with ethyl acetate (150 mL). The two phases are seperated and the organic layer is washed with water (75 mL), then brine (75 mL). The organic layer is then dried over anhydrous sodium sulfate, then concentrated to yield 4.43 g crude product that is used without further purification.

Preparation 73

4-(2-Methoxycarbonyl-ethyl)-3-methyl-benzoic acid

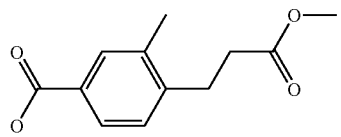

Step A

4-Bromo-3-methyl-benzoic acid benzyl ester

To a solution of 4-Bromo-3-methyl-benzoic acid benzyl (25.3 g, 0.118 mol) in DMF (200 mL) is added Cs2CO3 (76.6 g, 0.235 mol), followed by benzyl bromide (15.4 mL). After stirred at room temperature for 2 h, the reaction mixture is diluted with ethyl acetate, filtered through celite. The filtrate is washed with water and brine, dried over sodium sulfate, concentration gave the title product.

Step B 4-(2-Methoxycarbonyl-vinyl)-3-methyl-benzoic acid benzyl ester

To a solution of 4-bromo-3-methyl-benzoic acid benzyl ester (36 g, 118 mmol) in propronitrile (1000 mL) is added methyl acrylate (43.3 mL) and diisopropylethyl amine (42 mL), the solution is degassed and filled with nitrogen for three times. To this mixture are added tri-o-tolyl-phosphane (14.5 g) and palladium acetate (5.34 g) under nitrogen, then heated at 110° C. overnight, cooled to room temperature, filtered through celite. The solvent is evaporated, the residue is taken into ethyl acetate and washed with water and brine, dried over sodium sulfate. Concentration and column chromatography on silica gel eluted with hexanes and ethyl acetate gave the title compound (31 g, 84.7%).

Step C 4-(2-Methoxycarbonyl-ethyl)-3-methyl-benzoic acid

A mixture of 4-(2-methoxycarbonyl-vinyl)-3-methyl-benzoic acid benzyl ester (11.6 g, 37.4 mmol) and Pd/C (5%, 1.5 g) in THF (300 mL) and methanol (100 mL) is stirred under 60 psi of hydrogen overnight. Catalyst is filtered off, filtrate is concentrated giving the title compound (8.3 g, 100%).

Preparation 74

(4-Hydroxy-2-methyl-phenyl)-acetic acid methyl ester

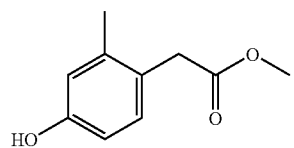

Step A

4-Methoxy-2-methylbenzoic acid (2.5 g, 15.04 mmol) is stirred in thionyl chloride (50 mL) at reflux 2 hr. The mixture is concentrated and diluted with toluene (10 mL) and concentrated. The resulting solid is dried under vacuum 18 hr. The resulting acid chloride is stirred in 20 mL ether at 0 deg C. A solution of diazomethane (39.6 mmol) in ether (150 mL) is added to the acid chloride solution and stirred 18 hr. The resulting diazoketone solution is concentrated. The residue is stirred in methanol (100 mL) and a solution of silver benzoate in triethylamine (1.0 g in 10 mL) is added and the reaction is heated to 60 deg C. and stirred 1 hr. The mixture is concentrated, diluted with 1.0 N aqueous hydrochloric acid (20 mL), extracted to three portions of ethyl acetate (50 mL each). The extracts are combined, washed with aqueous saturated sodium hydrogen carbonate, water, and brine (50 mL each), dried over anhydrous magnesium sulfate, filtered and concentrated. The residue is purified via silica gel chromatography eluting with 9:1 hexanes:ethyl acetate to afford 1.5 g (51%) of the homologated ester as a white solid.

Step B (4-Methoxy-2-methyl-phenyl)-acetic acid methyl ester (1.5 g, 7.72 mmol) is stirred in dichloromethane (50 mL) at 0 deg. C. Aluminum chloride (4.13 g, 31 mmol) is added followed by ethane thiol (2.9 mL, 38.6 mmol). The resulting mixture is stirred at room temperature for 2 hr. Water (50 mL) is added and the product is extracted into ethyl acetate (3×50 ml), the extracts are combined, dried over anhydrous magnesium sulfate, filtered, and concentrated to afford the title compound as a colorless oil, 1.4 g, 100%. MS M$^+$+1 181. The structure is confirmed by $^1$H NMR spectroscopy.

Preparation 75

(3-Hydroxy-phenyl)-acetic acid methyl ester

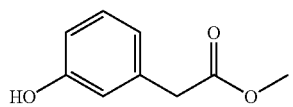

Step A (3-Hydroxy-phenyl)-acetic acid methyl ester (3-Hydroxy-phenyl)-acetic acid (5.0 g, 32.86 mmol) is stirred in methanol (100 mL) and concentrated (98%) sulfuric acid (3.0 mL.,) is added. The mixture is heated to reflux 18 hr. The reaction is cooled and concentrated. The residue is diluted with water (100 mL) and extracted with ethyl acetate (3×50 mL). The combined extracts are dried over anhydrous magnesium sulfate, filtered, and concentrated to yield the title compound as an orange oil, 5.46 g, 100%. MS M$^+$+1 167. The structure is confirmed by $^1$H NMR spectroscopy.

The following compounds are made in a similar manner:

Preparation 76

(3-Hydroxy-4-methoxy-phenyl)-acetic acid methyl ester

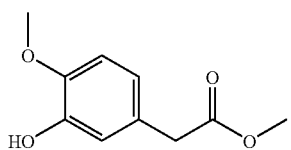

An orange oil. MS M⁺+1 197. The structure is confirmed by $^1$H NMR spectroscopy.

Preparation 77

3-(3-Hydroxy-phenyl)-propionic acid methyl ester

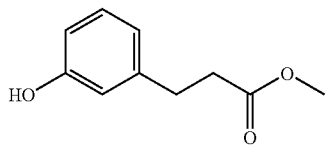

Step A 3-(3-Hydroxy-phenyl)-propionic acid methyl ester

An orange oil. MS M⁺+1 181. The structure is confirmed by $^1$H NMR spectroscopy.

Preparation 78

(3-Mercapto-phenyl)-acetic acid methyl ester

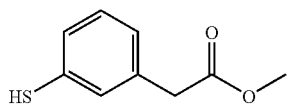

Step A (3-Dimethylthiocarbamoyloxy-phenyl)-acetic acid methyl ester

A mixture of (3-Hydroxy-phenyl)-acetic acid methyl ester (5.5 g, 33.1 mmol), N,N-dimethyl thiocarbamoyl chloride (5.11 g, 41.38 mmol), triethylamine (9.2 mL, 66.2 mmol), N,N-dimethylamino pyridine (0.4 g, 3.31 mmol) and dioxane (50 mL) is stirred at reflux 18 hr. The mixture is concentrated, partioned between 1M aqueous hydrochloric acid (200 mL) and ethyl acetate (3×75 mL). The combined organic extracts are dried over anhydrous magnesium sulfate, filtered, concentrated, and purified via silica chromatography eluting the product with dichloromethane to afford the title compound as a brown oil, 6.8 g, 81%. MS M⁺+1 254. The structure is confirmed by $^1$H NMR spectroscopy.

Step B (3-Dimethylcarbamoylsulfanyl-phenyl)-acetic acid methyl ester (3-Dimethylthiocarbamoyloxy-phenyl)-acetic acid methyl ester (6.8 g, 26.84 mmol) is stirred in tetradecane (30 mL) at 255 deg C. for 8 hr. The mixture is cooled, the residue is purified by silica chromatography eluting the product with hexanes to 1:1 hexanes:ethyl acetate to afford the title compound as an orange oil, 4.9 g, 58%. MS M⁺+1 254. The structure is confirmed by $^1$H NMR spectroscopy.

Step C (3-Mercapto-phenyl)-acetic acid methyl ester

A mixture of (3-dimethylcarbamoylsulfanyl-phenyl)-acetic acid methyl ester (2.0 g, 7.9 mmol), potassium hydroxide (1.4 g, 24 mmol) methanol (50 mL), and water (5 mL) is stirred at reflux 3 hr. The mixture is concentrated, and product partitioned between 1M aqueous hydrochloric acid (50 mL) and ethyl acetate (3×75 mL). The combined extracts are dried over anhydrous magnesium sulfate, filtered and concentrated. The residue is taken up in methanol (50 mL), 2 mL concentrated sulfuric acid is added, and the mixture refluxed 3 hr. The mixture is concentrated, and the residue purified by silica chromatography eluting with 7:3 hexanes:ethyl acetate to afford the title compound as a pale yellow oil, 1.0 g, 69%. MS M⁺+1 183. The structure is confirmed by $^1$H NMR spectroscopy.

Preparation 79

3-(4-Iodomethyl-2-methyl-phenyl)-propionic acid methyl ester

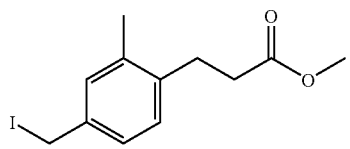

Step A 3-(4-Hydroxymethyl-2-methyl-phenyl)-acrylic acid methyl ester

A mixture of methyl-4-bromo-3-methylbenzoate (5.7 g, 24.88 mmol), lithium aluminum hydride (29 mL, 29 mmol, 1 M solution in tetrahydrofuran) and tetrahydrofuran (100 mL) is stirred in ice/water for 1 hr. The reaction is quenched with aqueous hydrochloric acid (50 mL, 1 M). The product is extracted into ethyl acetate (3×100 mL). The combined extracts are dried over anhydrous magnesium sulfate, filtered and concentrated. The crude product is taken up in propionitrile (100 mL). Methylacrylate (10 mL, 121.5 mmol), palladium acetate (1.12 g, 5 mmol), tri-o-tolylphosphine (3.0 g, 10 mmol), and N,N-diisopropyl ethylamine (8.7 mL, 50 mmol) are sequentially added and the resulting reaction mixture is heated to 110 deg C. 3 hr. The mixture is concentrated, and the residue diluted with aqueous hydrochloric acid (100 mL, 1M). The product is extracted with dichloromethane (2×100 mL) and ethyl acetate (100 mL). The combined extracts are dried over anhydrous magnesium sulfate, filtered, concentrated, and purified via silica chromatography eluting with 7:3 hexanes:ethyl acetate to 1:1 hexanes:ethyl acetate to afford the pure product as a yellow oil, 4.7 g, 91%. MS M$^+$+1 207. The structure is confirmed by $^1$H NMR spectroscopy.

Step B 3-(4-Hydroxymethyl-2-methyl-phenyl)-propionic acid methyl ester

A mixture of 3-(4-Hydroxymethyl-2-methyl-phenyl)-acrylic acid methyl ester (4.7 g, 22.8 mmol), Raney nickel (0.668 g) and tetrahydrofuran (618 mL) is shaken under 60 psig. Hydrogen 24 hr. The catalyst is filtered off, and the mixture is concentrated to afford the product as a pale yellow oil, 4.3 g, 91%. The structure is confirmed by $^1$H NMR spectroscopy.

Step C 3-(4-Iodomethyl-2-methyl-phenyl)-propionic acid methyl ester

A mixture of 3-(4-Hydroxymethyl-2-methyl-phenyl)-propionic acid methyl ester (0.62 g, 2.98 mmol), triphenyl phosphine (0.86 g, 3.27 mmol) and dichloromethane (10 mL) is stirred at room temperature. A solution of iodine (0.83 g, 3.27 mmol) in benzene (5 mL) is added and the black mixture is stirred at room temperature 2 hr. The brown mixture is diluted with 10% aqueous sodium hydrogen sulfite (5 mL) and the resulting clear mixture is washed with ethyl acetate (3×50 mL). The combined extracts are dried over anhydrous magnesium sulfate, filtered and concentrated. The residue is purified via silica chromatography eluting with 9:1 hexanes:ethyl acetate to afford the title compound as a crystalline ivory solid, 0.689, 72%. MS M$^+$+1 319. The structure is confirmed by $^1$H NMR spectroscopy.

Preparation 80

(4-Bromo-2-methyl-phenoxy)-acetic acid methyl ester

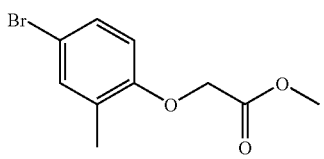

Step A (4-Bromo-2-methyl-phenoxy)-acetic acid methyl ester

A mixture of 4-bromo-2-methylphenol (1.0 g, 5.35 mmol), sodium hydride (0.26 g, 6.42 mmol, 60% mineral oil), N,N-dimethylformamide (10 mL), and methyl-2-bromoacetate (0.56 mL, 5.88 mmol) is stirred at room temperature 18 hr. The mixture is diluted with water (50 mL) and the product extracted to ethyl acetate (3×50 mL). The combined extracts are dried over anhydrous magnesium sulfate, filtered, concentrated and purified via silica chromatography eluting with 8:2 hexanes:ethyl acetate to afford title compound as a colorless oil, 1.03 g, 74%. MS M$^+$ 259. The structure is confirmed by $^1$H NMR spectroscopy.

Preparation 81

3-(4-Amino-2-methyl-phenyl)-propionic acid methyl ester

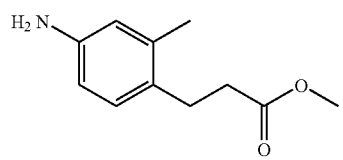

Step A 3-(2-Methyl-4-nitro-phenyl)-acrylic acid methyl ester

To a solution of 2-bromo-5-nitrotoluene (3.11 g, 14.39 mmol) in propionitrile (105 mL) is added DIPEA (5.1 mL, 29.28 mmol). The mixture is degassed three times. Methyl acrylate (5.2 mL, 57.74 mmol) is added and the mixture is degassed. Tri-o-tolylphosphine (1.77 g, 5.82 mmol) and Pd(OAc)$_2$ (0.64 g, 2.85 mmol) are added and the mixture is degassed a final two times followed by heating at 110° C. for 4 h. Upon cooling, the mixture is passed through Celite and the filtrate is concentrated. The residue is partitioned between Et$_2$O and 1N HCl. The organics are washed with saturated NaHCO$_3$ and brine, and dried with Na$_2$SO$_4$. The crude material is purified by flash chromatography to yield the title compound (2.90 g, 91%).

Step B 3-(4-Amino-2-methyl-phenyl)-propionic acid methyl ester

A mixture of 3-(2-Methyl-4-nitro-phenyl)-acrylic acid methyl ester (1.47 g, 6.64 mmol) and 5% Pd/C (0.29 g) in MeOH (100 mL) is exposed to a hydrogen atmosphere (60 psi) for 12 h. The mixture is filtered through Celite and purified by flash chromatography to yield the title compound (0.99 g, 77%).

Preparation 82

3-(2-Methyl-4-methylaminomethyl-phenyl)-propionic acid methyl ester TFA salt

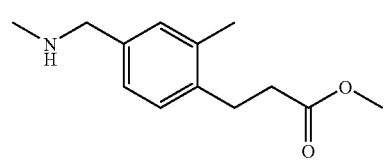

-continued

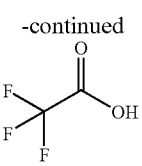

Step A

3-(4-Formyl-2-methyl-phenyl)-propionic acid methyl ester

A mixture of 3-(4-Hydroxymethyl-2-methyl-phenyl)-propionic acid methyl ester (0.49 g, 2.35 mmol) and MnO$_2$ (0.80 g, 9.20 mmol) in chloroform (5 mL) is stirred at RT for 4 days. The mixture is filtered through Celite; the Celite is washed with copious amounts of EtOAc. The filtrate is concentrated and purified by flash chromatography to yield the title compound (0.29 g, 60%).

Step B

3-(2-Methyl-4-methylaminomethyl-phenyl)-propionic acid methyl ester trifluoroacetic acid To a mixture of 3-(4-Formyl-2-methyl-phenyl)-propionic acid methyl ester (0.27 g, 1.31 mmol) and methylamine (2M in THF, 0.60 mL, 1.20 mmol) in anhydrous CH$_2$Cl$_2$ (10 mL) is added 4 Å molecular sieves followed by acetic acid (0.090 mL, 1.57 mmol). The mixture is stirred at RT for 1.5 h. Sodium triacetoxyborohydride (0.39 g, 1.85 mmol) is added, and the mixture is stirred overnight. The reaction is quenched with saturated NaHCO$_3$. The organics are washed with saturated NaHCO$_3$ and brine, and dried with MgSO$_4$. Upon concentration, the mixture is purified by reverse phase chromatography to yield the title compound (0.12 g, 45%).

Preparation 83

3-(4-Aminomethyl-2-methyl-phenyl)-propionic acid methyl ester

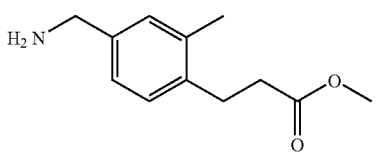

Step A

3-(4-Chloromethyl-2-methyl-phenyl)-propionic acid methyl ester

To a 0° C. solution of 3-(4-Hydroxymethyl-2-methyl-phenyl)-propionic acid methyl ester (1.02 g, 4.90 mmol) in anhydrous CH$_2$Cl$_2$ (15 mL) is added triethylamine (0.75 mL, 5.38 mmol) followed by thionyl chloride (0.40 mL, 5.48 mmol). The mixture is allowed to warm to RT overnight. Water is added, and the mixture is extracted with CH$_2$Cl$_2$. The organics are dried with MgSO$_4$ and concentrated. The crude material is purified by flash chromatography to yield the title compound (1.01 g, 91%).

Step B

3-(4-Azidomethyl-2-methyl-phenyl)-propionic acid methyl ester

To a solution of 3-(4-Chloromethyl-2-methyl-phenyl)-propionic acid methyl ester (0.52 g, 2.31 mmol) in DMF (7 mL) is added sodium azide (0.25 g, 3.84 mmol). The mixture is stirred overnight. Water is added, and the mixture is extracted with EtOAc. The organics are dried with Na$_2$SO$_4$ and concentrated to yield the title compound (0.49 g, 91%). The material is used without further purification.

Step C

3-(4-Aminomethyl-2-methyl-phenyl)-propionic acid methyl ester

A mixture of 3-(4-Azidomethyl-2-methyl-phenyl)-propionic acid methyl ester (0.20 g, 0.86 mmol) and 5% Pd/C (32 mg) in EtOH (50 mL) is exposed to a hydrogen atmosphere (60 psi) at RT overnight. Upon filtering the mixture through Celite, the filtrate is concentrated to yield the title compound (0.14 g, 78%). The material is used without further purification.

Preparation 84

3-(4-{2-[2-(4-Bromo-phenyl)-5-methyl-oxazol-4-yl]-propoxy}-2-methylphenyl)propionic acid methyl ester

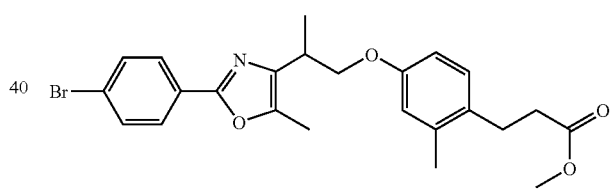

Step A

[2-(4-Bromo-phenyl)-5-methyl-oxazol-4-yl]-acetic acid methyl ester

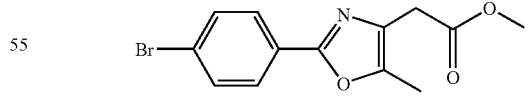

Aspartic acid methyl ester hydrochloride salt (15.2 g, 82 mmol) is dissolved in water (200 mL) and cooled to 0° C. in an ice water bath. Sodium carbonate (25.3 g, 239 mmol) is slowly added in several portions and the mixture is allowed to stir at 0° C. for 30 minutes. 4-Bromobenzoyl chloride (16.8 g, 77.4 mmol) is dissolved into acetone (20 mL) at room temperature and transferred to an additional funnel. The addition funnel is connected to the aspartic acid mixture and slowly added over a period of two hours. The reaction is allowed to continue at 0° C. for two hours, then the ice bath is removed. Upon reaching room temperature, the reaction is complete. The reaction is diluted with dichloromethane and acidified with concentrated hydrochloric acid. The two phases are separated and the organic layer is washed with water and brine. The organic layer is then dried over anhydrous sodium sulfate, filtered, and concentrated. The white solid is used without further purification, and the yield is quantitative.

2-(4-Bromo-benzoylamino)-succinic acid 4-methyl ester (25.5 g, 77.4 mmol) is dissolved in ethyl acetate (200 mL) at room temperature and pyridine (37.2 mL, 387 mmol), acetic acid anhydride (39.1 mL, 348.3 mmol), and 4-N,N-dimethylamino pyridine (2.0 g, 7.74 mmol) are added. The reaction is heated to 90° C. under nitrogen. The reaction is monitored by HPLC and upon complete consumption of the starting material, is allowed to cool to room temperature. The reaction is diluted with additional ethyl acetate and the two phases are separated. The organic layer is washed a few times with 1N HCl, then saturated sodium bicarbonate solution, and finally brine. The organic layer is then dried over anhydrous sodium sulfate, filtered, and concentrated. The 3-(4-Bromo-benzoylamino)-4-oxo-pentanoic acid methyl ester is used in the next step without further purification.

3-(4-Bromo-benzoylamino)-4-oxo-pentanoic acid methyl ester is dissolved in acetic anhydride (75 mL) and concentrated sulfuric acid is added in 500 uL portions five times over a four hour period. The reaction is monitored by HPLC. The reaction is then heated to 40° C. until the starting material is consumed. The reaction is then concentrated to dryness and purified by column chromatography. This procedure yielded (11.6 g, 37.4 mmol) 48.3% of the desired oxazole.

Step B

2-[2-(4-Bromo-Phenyl)-5-methyl-oxazol-4-yl]-propionic acid methyl ester

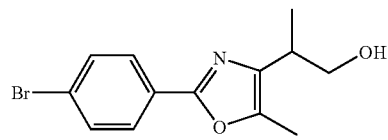

[2-(4-Bromo-phenyl)-5-methyl-oxazol-4-yl]-acetic acid methyl ester (11.6 g, 37.4 mmol) is dissolved in anhydrous tetrahydrofuran (150 mL) and allowed to stir under nitrogen. Lithium diisopropyl amide solution in tetrahydrofuran (28 mL of 2M soln., 56.1 mmol) is slowly added to the solution at room temperature. This is then heated to 50° C. for 6 hours. The solution is allowed to cool to room temperature and methyl iodide (7.0 mL, 112 mmol) is added in one portion. The mixture is allowed to stir under nitrogen at room temperature overnight. The solution is quenched with a saturated solution of ammonium chloride, diluted with ethyl acetate, and then enough water added to dissolve the solids. The two phases are separated and the organic layer is washed with water and brine, dried over anhydrous sodium sulfate, filtered, and concentrated. The pure 2-[2-(4-Bromo-phenyl)-5-methyl-oxazol-4-yl]-propionic acid methyl ester (5.57 g, 17.19 mmol) is isolated in 46% yield after column chromatography. The racemic 2-[2-(4-Bromo-phenyl)-5-methyl-oxazol-4-yl)-propionic acid methyl ester is resolved on a Chiralcel OJ column (4.6×250 mm). Eluted with 40% isopropanol in heptane with 0.2% dimethy-ethylamine at 1 mL per minute with detection at 260 nM and concentrated the fractions to provide the pure enantiomer esters (isomer 1, 99.8% ee; isomer 2, 99.4% ee).

Step C

2-[2-(4-Bromo-phenyl)-5-methyl-oxazol-4-yl]-propan-1-ol

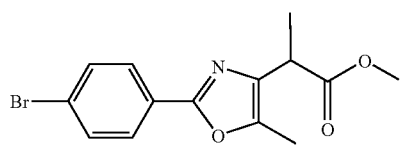

2-[2-(4-Bromo-phenyl)-5-methyl-oxazol-4-yl]-propionic acid methyl ester (1.59 g, 5.13 mmol) is dissolved in anhydrous tetrahydrofuran at room temperature. The atmosphere is replaced with nitrogen and the solution is cooled to 0° C. in an ice water bath. Lithium aluminum hydride solution (5.2 mL of 1M solution in THF, 5.2 mmol) is slowly added to the solution, and the reaction is monitored by HPLC. Upon complete conversion, the reaction is quenched with a saturated solution of Rochelle's salt. The ice bath is removed and the mixture is warmed to room temperature. The reaction is diluted with diethyl ether and water to dissolve any solids. The two phases are separated and the organic phase is washed with water and brine, dried over anhydrous sodium sulfate, filtered, and concentrated. The 2-[2-(4-Bromo-phenyl)-5-methyl-oxazol-4-yl]-propan-1-ol (1.25 g, 4.22 mmol) is used without further purification. 82% yield.

Step D 3-(4-{2-[2-(4-Bromo-phenyl)-S-methyl-oxazol-4-yl]-propoxy}-2-methylphenyl)propionic acid methyl ester

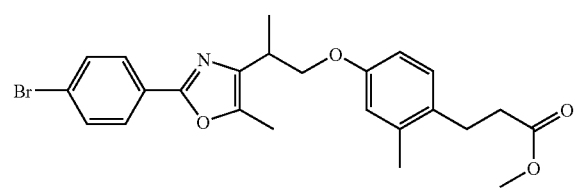

A solution of 2-[2-(4-Bromo-phenyl)-5-methyl-oxazol-4-yl]-propan-1-ol (1.25 g, 4.22 mmol) in anhydrous toluene (20 mL) is degassed and filled with nitrogen for three times, and cooled to 0° C. in an ice water bath. Tri-n-butylphosphine (1.50 mL, 6.0 mmol) is added to the reaction mixture under nitrogen at 0° C., followed by addition of of 1,1'-(azodicarbonyl)-dipiperidine (1.5 g, 6.0 mmol), and 3-(4-Hydroxy-2-methyl-phenyl)-propionic acid methyl ester (989 mg, 5.07 mmol). The reaction mixture is allowed to warm to room temperature and stirred overnight, the mixture is loaded on silica gel column. Chromatography gave the title compound (592 mg, 1.25 mmol) in 31% yield.

Preparation 85

[2-(6-Chloro-pyridin-3-yl)-5-methyl-oxazol-4-yl]-acetic acid methyl ester

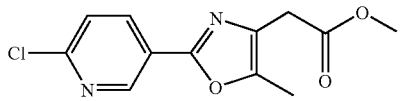

Step A

Aspartic acid methyl ester hydrochloride salt (57 g, 310 mmol) is dissolved in dichloromethane (500 mL) and cooled to 0° C. in an ice water bath. Triethylamine (75 mL, 444 mmol) is slowly added in several portions and the mixture is allowed to stir at 0° C. Meanwhile, 6-chloronicotinic acid (35 g, 222 mmol) is dissolved into dichloromethane (500 mL) with a drop of dimethylformamide and cooled to 0° C. in an ice water bath. After one hour at 0° C. the ice bath is removed and the solution allowed to warm to room temperature. The solvent is evaporated, the solution concentrated to about 100 mL, and then transferred to an addition funnel. This solution is then slowly added to the amino acid solution over two hours at 0° C. After two hours, the ice bath is removed. Upon reaching room temperature, the reaction is complete. The reaction is acidified with concentrated hydrochloric acid. The two phases are separated and the organic layer is washed with water and brine. The organic layer is then dried over anhydrous sodium sulfate, filtered, and concentrated. The white solid is used without further purification.

Step B

2-[(6-Chloro-pyridine-3-carbonyl)-amino]-succinic acid 4-methyl ester (222 mmol) is dissolved in ethyl acetate (300 mL) at room temperature and pyridine (90 mL, 1.11 mol), acetic anhydride (94 mL, 1.0 mol), and dimethyl amino pyridine (3.5 g, 22.2 mmol) are added. The reaction is heated to 90° C. under nitrogen. The reaction is monitored by HPLC and upon complete consumption of the starting material, is allowed to cool to room temperature. The reaction is diluted with additional ethyl acetate and the two phases are separated. The organic layer is washed a few times with 1N HCl, then saturated sodium bicarbonate solution, and finally brine. The organic layer is then dried over anhydrous sodium sulfate, filtered, and concentrated. The 3-[(6-Chloro-pyridine-3-carbonyl)-amino]-4-oxo-pentanoic acid methyl ester is used in the next step without further purification.

Step C

3-[(6-Chloro-pyridine-3-carbonyl)-amino]-4-oxo-pentanoic acid methyl ester is dissolved in acetic anhydride (75 mL) and concentrated sulfuric acid is added in 500 uL portions five times over a four hour period. The reaction is monitored by HPLC. The reaction is then heated to 40° C. until the starting material is consumed. The reaction is allowed to proceed at room temperature overnight. The reaction is then concentrated to dryness and purified by column chromatography. This procedure yielded (12.8 g, 48 mmol) 22% of the desired oxazole over four steps.

Preparation 86

[5-Methyl-2-(6-phenylsulfanyl-pyridin-3-yl)-oxazol-4-yl]-acetic acid methyl ester

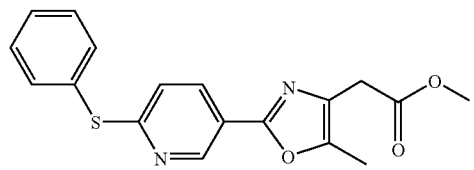

[2-(6-Chloro-pyridin-3-yl)-5-methyl-oxazol-4-yl]-acetic acid methyl ester (4.8 g, 17.98 mmol) is dissolved in anhydrous dimethylformamide (100 mL) and allowed to stir under nitrogen. Benzenethiol (2.78 mL, 27 mmol) is added by syringe, followed by anhydrous cesium carbonate (12.6 g, 36 mmol). The mixture is allowed to stir under nitrogen 50° C. and monitored by HPLC. After complete consumption of strating material, the solution is quenched with 1N sodium hydroxide solution, diluted with ethyl acetate, and then enough water added to dissolve the solids. The two phases are separated and the organic layer is washed with water and brine, dried over anhydrous sodium sulfate, filtered, and concentrated. The pure (5-Methyl-2-(6-phenylsulfanyl-pyridin-3-yl)-oxazol-4-yl]-acetic acid methyl ester (4.51 g, 13.2 mmol) is isolated in 74% yield after column chromatography.

The following compound is made in a similar manner:

Preparation 87

[5-Methyl-2-(6-phenylsulfanyl-pyridin-3-yl)-oxazol-4-yl]-acetic acid methyl ester

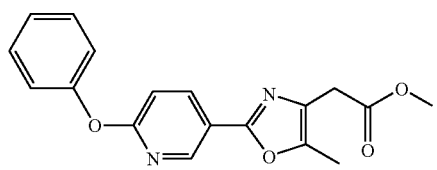

Preparation 88

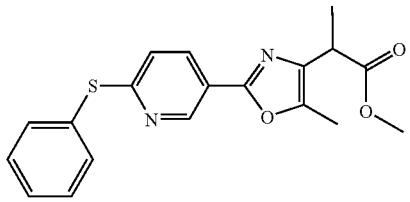

2-[5-Methyl-2-(6-phenylsulfanyl-pyridin-3-yl)-oxazol-4-yl]-propionic acid methyl ester

[5-Methyl-2-(6-phenylsulfanyl-pyridin-3-yl)-oxazol-4-yl]-acetic acid methyl ester (4.51 g, 13.25 mmol) is dissolved in anhydrous tetrahydrofuran (200 mL) and allowed to stir under nitrogen. Lithium diisopropyl amide solution in tetrahydrofuran (6.63 mL of 2M soln., 13.25 mmol) is slowly added to the solution at room temperature. This is allowed to stir under nitrogen for 6 hours at room temperature. Hexamethylphosphor-amide (9.2 mL, 53 mmol) is added to the reaction followed by methyl iodide (1.74 mL, 26.5 mmol), added in one portion. The mixture is allowed to stir under nitrogen at room temperature overnight. The solution is quenched with a saturated solution of ammonium chloride, diluted with ethyl acetate, and then enough water added to dissolve the solids. The two phases are separated and the organic layer is washed with water and brine, dried over anhydrous sodium sulfate, filtered, and concentrated. The pure 2-[5-Methyl-2-(6-phenylsulfanyl-pyridin-3-yl)-oxazol-4-yl]-propionic acid methyl ester (1.6 g, 4.51 mmol) is isolated in 34% yield after column chromatography. The racemic 2-[5-Methyl-2-(6-phenylsulfanyl-pyridin-3-yl)-oxazol-4-yl]-propionic acid methyl ester is resolved on a Chiralpak AD column (4.6×150 mm). Eluted with 15% 3A alcohol in heptane with 0.2% dimethy-ethylamine at 0.6 mL per minute with detection at 260 nm and concentrated the fractions to provide the pure enantiomer esters (isomer 1, 98.9% ee; isomer 2, 96.4% ee).

Preparation 89

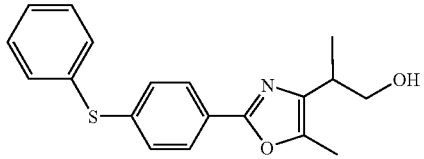

2-[5-Methyl-2-(4-phenylsulfanyl-phenyl)-oxazol-4-yl]-propan-1-ol

2-[5-Methyl-2-(6-phenylsulfanyl-pyridin-3-yl)-oxazol-4-yl]-propionic acid methyl ester (507 mg, 1.43 mmol) is dissolved in anhydrous tetrahydrofuran (5 mL) at room temperature. The atmosphere is replaced with nitrogen and the solution is cooled to 0° C. in an ice water bath. Lithium aluminum hydride solution (1.43 mL of 1M soln., 1.43 mmol) is slowly added to the solution, and the reaction is monitored by HPLC. Upon complete conversion, the reaction is quenched with a saturated solution of Rochelle's salt. The ice bath is removed and the mixture is warmed to room temperature. The reaction is diluted with ethyl acetate and water to dissolve any solids. The two phases are separated and the organic phase is washed with water and brine, dried over anhydrous sodium sulfate, filtered, and concentrated. The 2-[5-Methyl-2-(4-phenylsulfanyl-phenyl)-oxazol-4-yl]-propan-1-ol (457 mg, 1.40 mmol) is used without further purification (98% yield).

The following compound is made in a similar manner:

Preparation 90

[5-Methyl-2-(6-phenylsulfanyl-pyridin-3-yl)-oxazol-4-yl]-acetic acid methyl ester

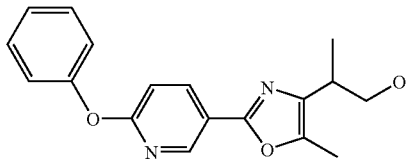

Example 1

(4-{1-[4-[2-(2-Chloro-6-fluoro-phenyl)-ethyl]-2-(4-trifluoromethyl-phenyl)-thiazol-5-yl]-ethylsulfanyl}-2-methyl-phenoxy)-acetic acid

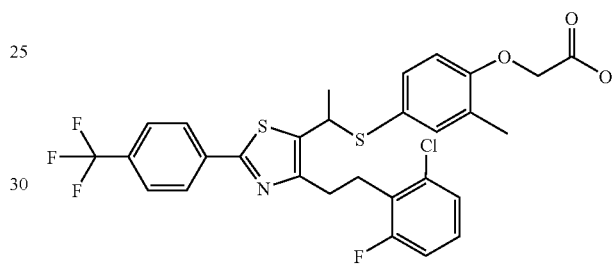

Step A (4-{1-[4-[2-(2-Chloro-6-fluoro-phenyl)-ethyl]-2-(4-trifluoromethyl-phenyl)-thiazol-5-yl]-ethylsulfan yl}-2-methyl-phenoxy)-acetic acid ethyl ester A solution of (4-Mercapto-2-methyl-phenoxy)-acetic acid (158 mg, 0.7 mmol) and 1-[4-[2-(2-Chloro-6-fluoro-phenyl)-ethyl]-2-(4-trifluoromethyl-phenyl)-thiazol-5-yl]-ethanol (200 mg, 0.465 mmol) in toluene (3.0 mL) is degassed and filled with nitrogen for 3 times. Tributylphosphine (0.174 mL, 0.7 mmol) is added to the reaction mixture under nitrogen at 0° C., followed by addition of of 1,1'-(azodicarbonyl)-dipiperidine (177 mg, 0.7 mmol). The reaction mixture is allowed to warm to room temperature and stirred overnight, the mixture is loaded on silica gel column. Chromatography gave the title compound (160 mg).

Step B (4-{1-[4-[2-(2-Chloro-6-fluoro-phenyl)-ethyl]-2-(4-trifluoromethyl-phenyl)-thiazol-5-yl]-ethylsulfan yl}-2-methyl-phenoxy)-acetic acid (4-{1-[4-[2-(2-Chloro-6-fluoro-phenyl)-ethyl]-2-(4-trifluoromethyl-phenyl)-thiazol-5-yl]-ethylsulfan yl}-2-methyl-phenoxy)-acetic acid ethyl ester (30 mg) is taken into THF (0.5 mL and treated with LiOH (1.0 N, 0.5 mL for 2 hrs. The reaction mixture is acidified with 5 N HCl, extracted with ethyl ether, dried over sodium sulfate. Concentration gave the title compound. MS (ES): 610.1 ($M^{+}+1$, $^{35}Cl$), 612.1 ($M^{+}+1$, $^{37}Cl$), the structure is also confirmed by proton NMR.

The following compounds are made in a similar manner:

Example 2

(2-Methyl-4-{1-[4-methyl-2-(4-trifluoromethyl-phenyl)-thiazol-5-yl]-2-phenyl-ethylsulfanyl}-phenoxy)-acetic acid

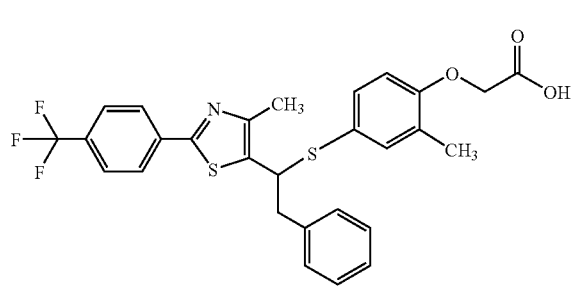

MS (ES): 544.2 (M⁺+1, the structure is also confirmed by proton NMR.

Example 3

3-(2-Methyl-4-{1-[4-methyl-2-(4-trifluoromethyl-phenyl)-thiazol-5-yl]-2-phenyl-ethoxy}-phenyl)-propionic acid

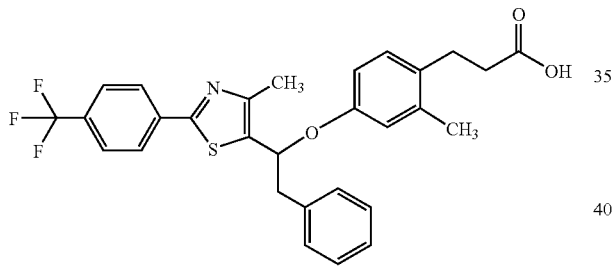

MS (ES): 526.2 (M⁺+1), the structure is also confirmed by proton NMR.

Example 4

(4-{1-[4-[2-(2-Chloro-6-fluoro-phenyl)-ethyl]-2-(4-trifluoromethyl-phenyl)-thiazol-5-yl]-ethoxy}-2-methyl-phenoxy)-acetic acid

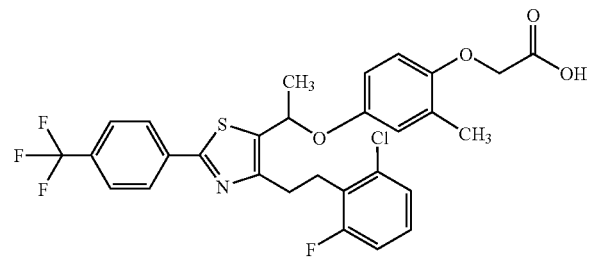

MS (ES): 594.2 (M⁺+1, ³⁵Cl), 596.2 (M⁺+1, ³⁷Cl), the structure is also confirmed by proton NMR.

Example 5

3-(4-{1-[4-[2-(2-Chloro-6-fluoro-phenyl)-ethyl]-2-(4-trifluoromethyl-phenyl)-thiazol-5-yl]-ethoxy}-2-methyl-phenyl)-propionic acid

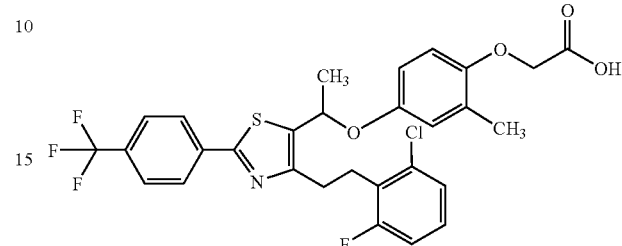

MS (ES): 592.2 (M⁺+1, ³⁵Cl), 594.2 (M⁺+1, ³⁷ Cl) the structure is also confirmed by proton NMR.

Example 6

(2-Methyl-4-{1-[4-phenethyl-2-(4-trifluoromethyl-phenyl)-thiazol-5-yl]-ethylsulfanyl}-phenoxy)-acetic acid

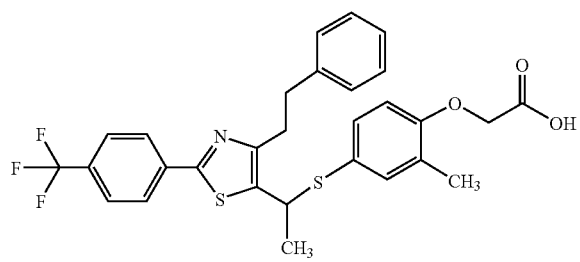

MS (ES): 558.2 (M⁺+1), the structure is also confirmed by proton NMR.

Example 7

(2-Methyl-4-{1-[4-phenethyl-2-(4-trifluoromethyl-phenyl)-thiazol-5-yl]-ethoxy}-phenoxy)-acetic acid

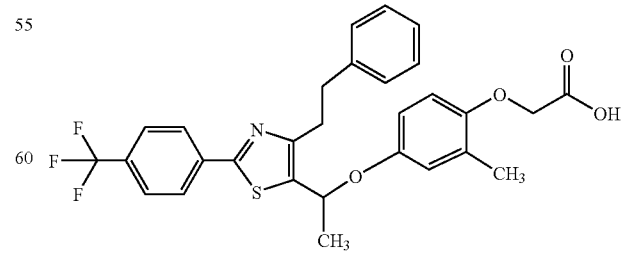

MS (ES): 542.2 (M⁺+1), the structure is also confirmed by proton NMR.

Example 8

3-(2-Methyl-4-{1-[4-phenethyl-2-(4-trifluoromethyl-phenyl)-thiazol-5-yl]-ethoxy}-phenyl)-propionic acid

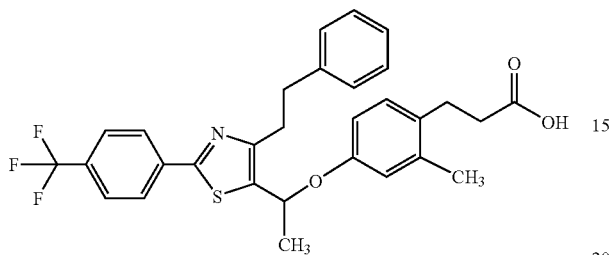

MS (ES): 540.2 (M$^+$+1), the structure is also confirmed by proton NMR.

Example 9

(2-Methyl-4-{1-[4-phenyl-2-(4-trifluoromethyl-phenyl)-thiazol-5-yl]-ethylsulfanyl}-phenoxy)-acetic acid

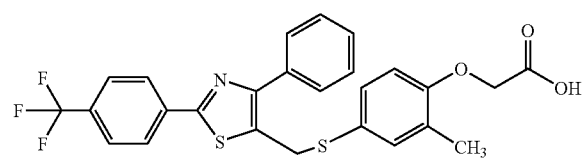

MS (ES): 530.2 (M$^+$+1), the structure is also confirmed by proton NMR.

Example 10

3-(2-Methyl-4-{1-[4-phenyl-2-(4-trifluoromethyl-phenyl)-thiazol-5-yl]-ethoxy}-phenyl)-propionic acid

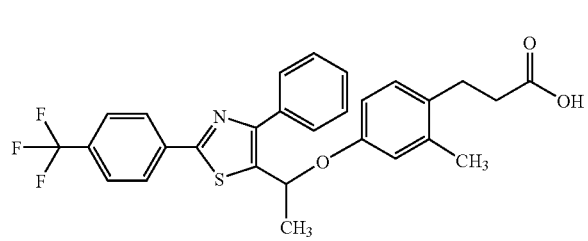

MS (ES): 512.2 (M$^+$+1), the structure is also confirmed by proton NMR.

Example 11

(4-{1-[4-Isopropyl-2-(4-trifluoromethyl-phenyl)-thiazol-5-yl]-ethylsulfanyl}-2-methyl-phenoxy)-acetic acid

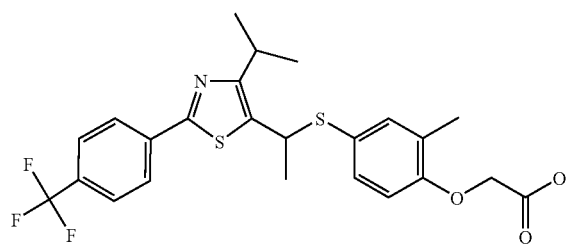

MS (ES): 496.7 (M$^+$+1), the structure is also confirmed by proton NMR.

Example 12

(4-{1-[4-Isopropyl-2-(4-trifluoromethyl-phenyl)-thiazol-5-yl]-ethoxy}-2-methyl-phenoxy)-acetic acid

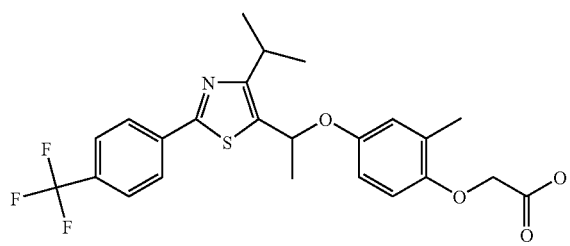

MS (ES): 480.6 (M$^+$+1), the structure is also confirmed by proton NMR.

Example 13

3-(4-{1-[4-Isopropyl-2-(4-trifluoromethyl-phenyl)-thiazol-5-yl]-ethoxy}-2-methyl-phenyl)-propionic acid

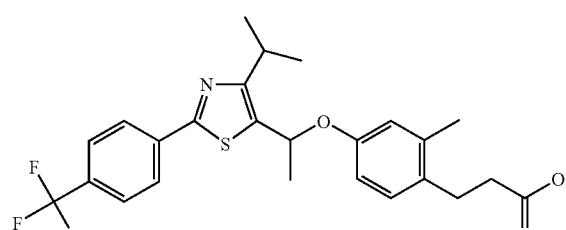

MS (ES): 478.6 (M$^+$+1), the structure is also confirmed by proton NMR.

Example 14

3-(4-{1-[4-Isopropyl-2-(4-trifluoromethyl-phenyl)-thiazol-5-yl]-ethylsulfanyl}-2-methyl-phenyl)-propionic acid

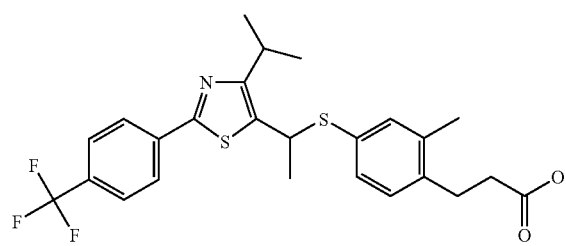

MS (ES) 494.7 (M$^+$+1), the structure is also confirmed by proton NMR.

Example 15

(2-Methyl-4-{1-[4-phenylsulfanylmethyl-2-(4-trifluoromethyl-phenyl)-thiazol-5-yl]-ethylsulfanyl}-phenoxy)-acetic acid

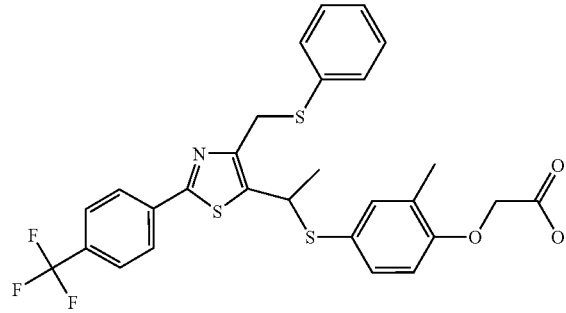

MS (ES): 576.8 (M$^+$+1), the structure is also confirmed by proton NMR.

Example 16

(4-{1-[4-(3,5-Bis-trifluoromethyl-phenoxymethyl)-2-(4-trifluoromethyl-phenyl)-thiazol-5-yl]-ethylsulfanyl}-2-methyl-phenoxy)-acetic acid

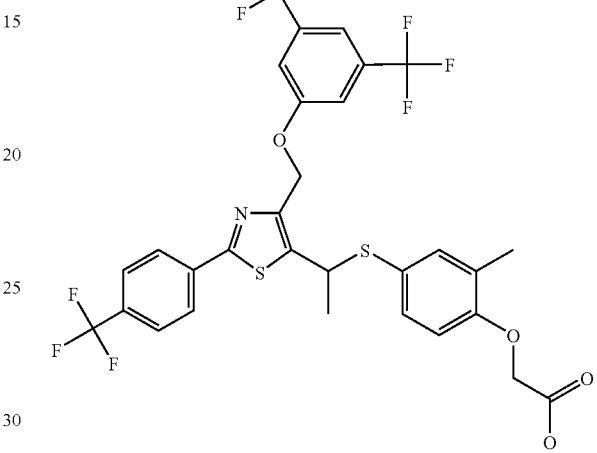

MS (ES) 696.7 (M$^+$+1), the structure is also confirmed by proton NMR.

Example 17

(4-{1-[4-(2-Chloro-6-fluoro-phenoxymethyl)-2-(4-trifluoromethyl-phenyl)-thiazol-5-yl]-ethylsulfanyl}-2-methyl-phenoxy)-acetic acid

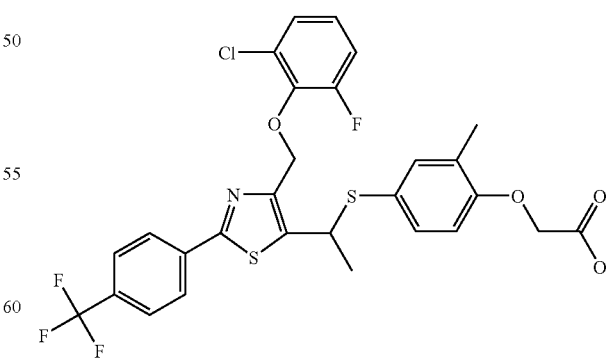

MS (ES): 613.2 (M$^+$+1), the structure is also confirmed by proton NMR.

Example 18

3-(4-{1-[4-(3,5-Bis-trifluoromethyl-phenoxymethyl)-2-(4-trifluoromethyl-phenyl)-thiazol-5-yl]-ethoxy}-2-methyl-phenyl)-propionic acid

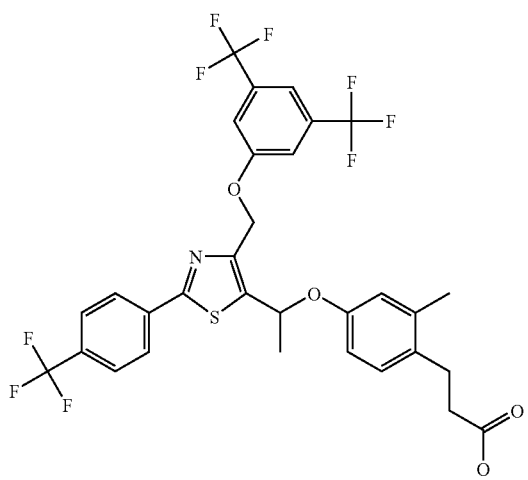

MS (ES): 678.7 (M⁺+1), the structure is also confirmed by proton NMR.

Example 19

3-(4-{1-[4-(2-Chloro-6-fluoro-phenoxymethyl)-2-(4-trifluoromethyl-phenyl)-thiazol-5-yl]-ethoxy}-2-methyl-phenyl)-propionic acid

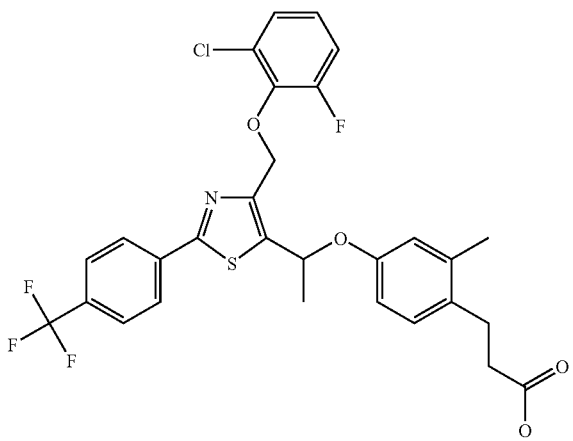

MS (ES): 595.1 (M⁺+1), the structure is also confirmed by proton NMR.

Example 20

3-(2-Methyl-4-{1-[4-methyl-2-(4-trifluoromethyl-phenyl)-thiazol-5-yl]-ethoxy}-phenyl)-propionic acid

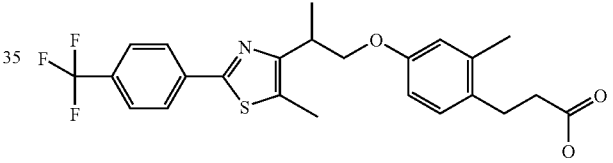

MS (ES): 450.6 (M⁺+1), the structure is also confirmed by proton NMR.

Example 21

3-(2-Methyl-4-{2-[5-methyl-2-(4-trifluoromethyl-phenyl)-thiazol-4-yl]-propoxy}-phenyl)-propionic acid MS (ES): 464.6 (M⁺+1), the structure is also confirmed by proton NMR.

Example 22

3-(2-Methyl-4-{2-methyl-2-[5-methyl-2-(4-trifluoromethyl-phenyl)-thiazol-4-yl]-propoxy}-phenyl)-propionic acid

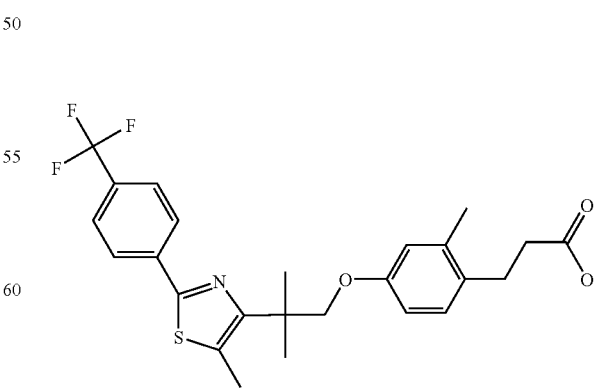

MS (ES): 478.6 (M⁺+1), the structure is also confirmed by proton NMR.

Example 23

3-(2-Methyl-4-{2-[5-methyl-2-(4-trifluoromethyl-phenyl)-oxazol-4-yl]-propoxy}-phenyl)-propionic acid

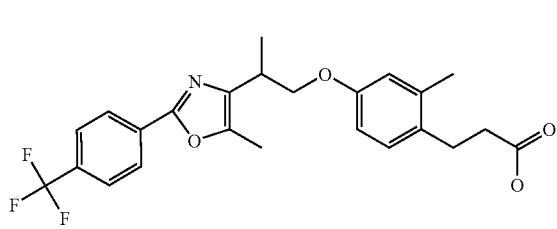

MS (ES): 448.5 (M$^+$+1), the structure is also confirmed by proton NMR.

Example 24

(S)-3-(2-Methyl-4-{2-[5-methyl-2-(4-trifluoromethyl-phenyl)-thiazol-4-yl]-propoxy}-phenyl)-propionic acid

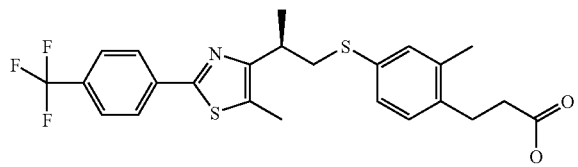

This compound is made in a similar manner using the chiral alcohol as starting material. MS (ES): 480.7 (M$^+$+1), the structure is also confirmed by proton NMR.

Example 25

(R)-3-(2-Methyl-4-{2-[5-methyl-2-(4-trifluoromethyl-phenyl)-thiazol-4-yl]-propylsulfanyl}-phenyl)-propionic acid

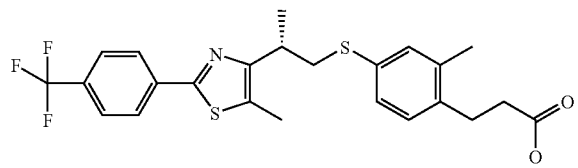

This compound is made in a similar manner using the chiral alcohol as starting material. MS (ES): 480.7 (M$^+$+1), the structure is also confirmed by proton NMR.

Example 26

(4-{1R-[4-[2-(2-Chloro-6-fluoro-phenyl)-ethyl]-2-(4-trifluoromethyl-phenyl)-thiazol-5-yl]-ethylsulfanyl}-2-methyl-phenoxy)-acetic acid

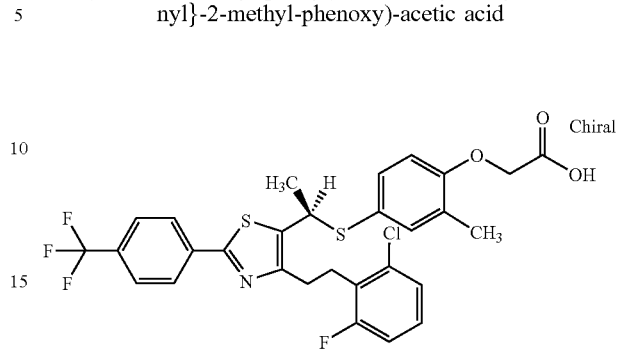

The racemic ethyl ester of 4-{1R-[4-[2-(2-Chloro-6-fluoro-phenyl)-ethyl]-2-(4-trifluoromethyl-phenyl)-thiazol-5-yl]-ethylsulfanyl}-2-methyl-phenoxy)-acetic acid is resolved on a Chiralcel OD column (2.1×25 cm). Eluted with ethanol in heptane and concentrated the fractions to provide a pure enantiomer ester (isomer 1, 100% ee). Hydrolysis of the pure enantiomer of the ester provided the title compound as a white solid.

The following enantiomeric pure compounds are obtained by similar chiral separation using Chiralcel OD column (2.1×25 cm) or using Chiralcel OJ column (2.1×25 cm):

Example 27

(4-{1S-[4-[2-(2-Chloro-6-fluoro-phenyl)-ethyl]-2-(4-trifluoromethyl-phenyl)-thiazol-5-yl]-ethylsulfanyl}-2-methyl-phenoxy)-acetic acid

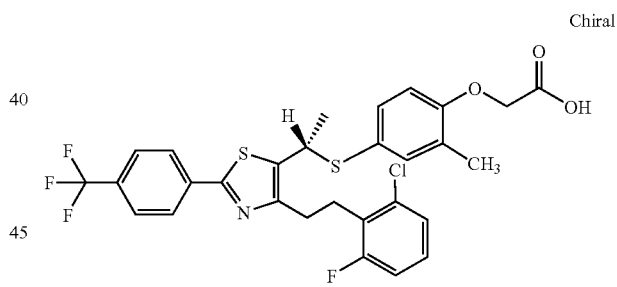

Example 28

(2-Methyl-4-{1S-[4-phenethyl-2-(4-trifluoromethyl-phenyl)-thiazol-5-yl]-ethoxy}-phenoxy)-acetic acid

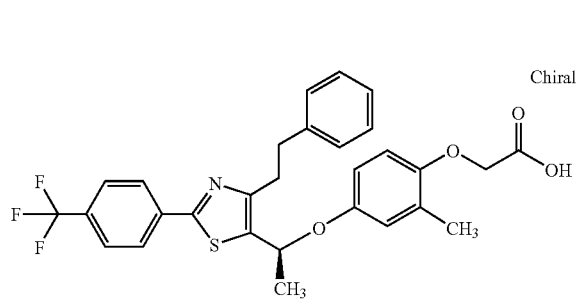

Example 29

(2-Methyl-4-{1R-[4-phenethyl-2-(4-trifluoromethyl-phenyl)-thiazol-5-yl]-ethoxy}-phenoxy)-acetic acid

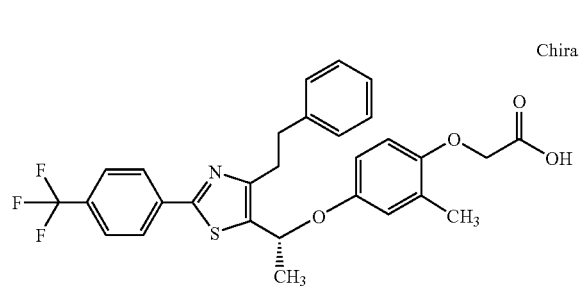

Example 30

(2-Methyl-4-{1S-[4-phenethyl-2-(4-trifluoromethyl-phenyl)-thiazol-5-yl]-ethylsulfanyl}-phenoxy)-acetic acid

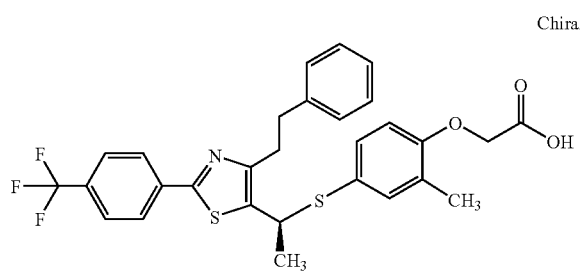

Example 31

(2-Methyl-4-{1R-[4-phenethyl-2-(4-trifluoromethyl-phenyl)-thiazol-5-yl]-ethylsulfanyl}-phenoxy)-acetic acid

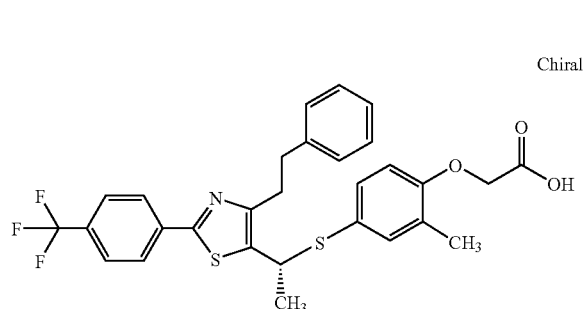

Example 32

(R)-(4-{1-[4-Isopropyl-2-(4-trifluoromethyl-phenyl)-thiazol-5-yl]-ethylsulfanyl}-2-methyl-phenoxy)-acetic acid

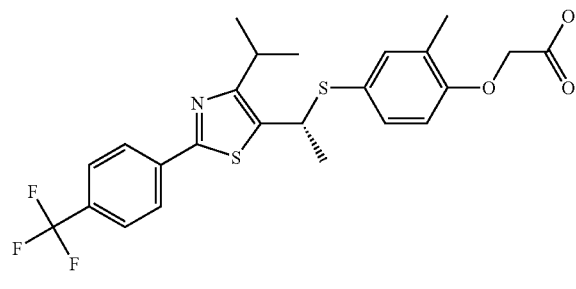

MS (ES): 496.7 (M$^+$+1), the structure is also confirmed by proton NMR.

Example 33

(S)-(4-{1-[4-Isopropyl-2-(4-trifluoromethyl-phenyl)-thiazol-5-yl]-ethylsulfanyl}-2-methyl-phenoxy)-acetic acid

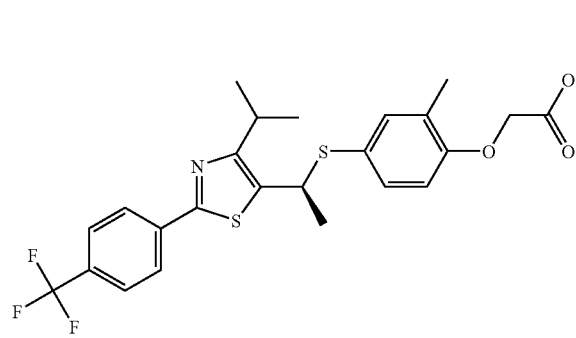

MS (ES): 496.7 (M$^+$+1), the structure is also confirmed by proton NMR.

Example 34

(S)-(4-{1-[4-Isopropyl-2-(4-trifluoromethyl-phenyl)-thiazol-5-yl]-ethoxy}-2-methyl-phenoxy)-acetic acid

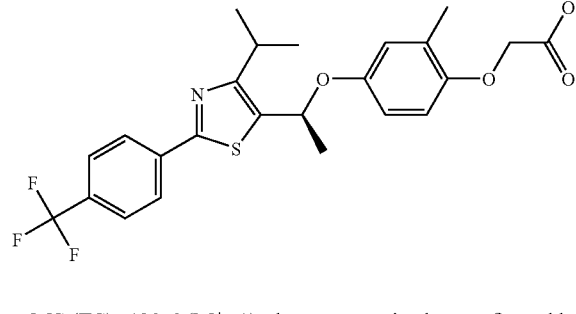

MS (ES): 480.6 (M$^+$+1), the structure is also confirmed by proton NMR.

Example 35

(R)-(4-{1-[4-Isopropyl-2-(4-trifluoromethyl-phenyl)-thiazol-5-yl]-ethoxy}-2-methyl-phenoxy)-acetic acid

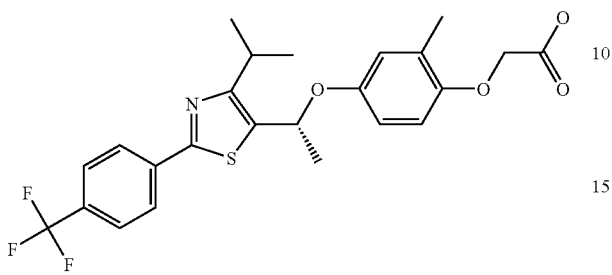

MS (ES): 480.6 (M⁺+1), the structure is also confirmed by proton NMR.

Example 36

(S)-3-(4-{1-[4-Isopropyl-2-(4-trifluoromethyl-phenyl)-thiazol-5-yl]-ethoxy}-2-methyl-phenyl)-propionic acid

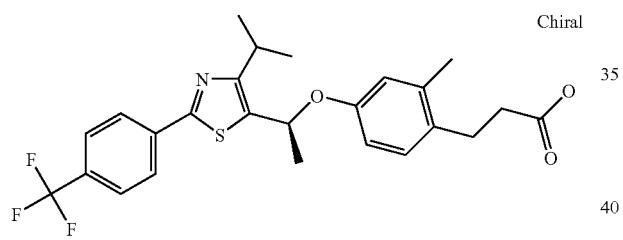

MS (ES): 478.6 (M⁺+1), the structure is also confirmed by proton NMR.

Example 37

(R)-3-(4-{1-[4-Isopropyl-2-(4-trifluoromethyl-phenyl)-thiazol-5-yl]-ethoxy}-2-methyl-phenyl)-propionic acid

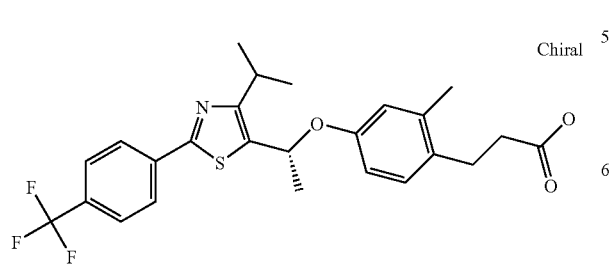

MS (ES): 478.6 (M⁺+1), the structure is also confirmed by proton NMR.

Example 38

(R)-3-(4-{1-[4-(2-Chloro-6-fluoro-phenoxymethyl)-2-(4-trifluoromethyl-phenyl)-thiazol-5-yl]-ethoxy}-2-methyl-phenyl)-propionic acid

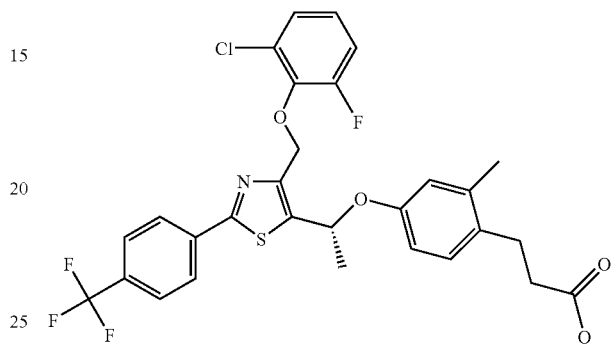

MS (ES): 595.1 (M⁺+1), the structure is also confirmed by proton NMR.

Example 39

(S)-3-(4-{1-[4-(2-Chloro-6-fluoro-phenoxymethyl)-2-(4-trifluoromethyl-phenyl)-thiazol-5-yl]-ethoxy}-2-methyl-phenyl)-propionic acid

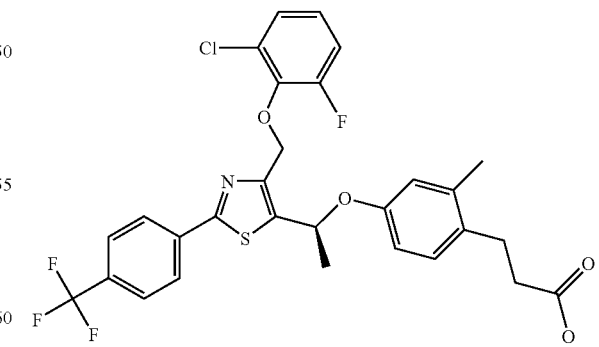

MS (ES): 595.1 (M⁺+1), the structure is also confirmed by proton NMR.

Example 40

(R)-(4-{1-[4-(2-chloro-6-fluoro-phenoxymethyl)-2-(4-trifluoromethyl-phenyl)-thiazol-5-yl]-ethylsulfanyl}-2-methyl-phenoxy)-acetic acid

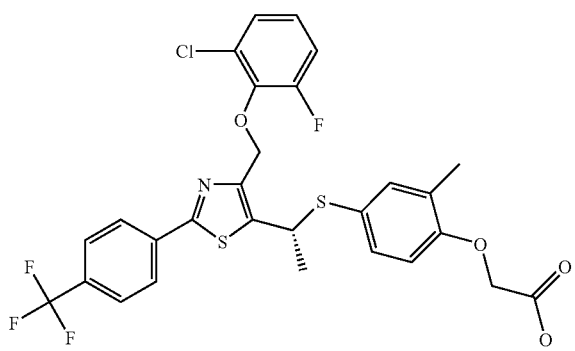

MS (ES): 612.1 (M$^+$+1), the structure is also confirmed by proton NMR.

Example 41

(S)-(4-{1-[4-(2-Chloro-6-fluoro-phenoxymethyl)-2-(4-trifluoromethyl-phenyl)-thiazol-5-yl]-ethylsulfanyl}-2-methyl-phenoxy)-acetic acid

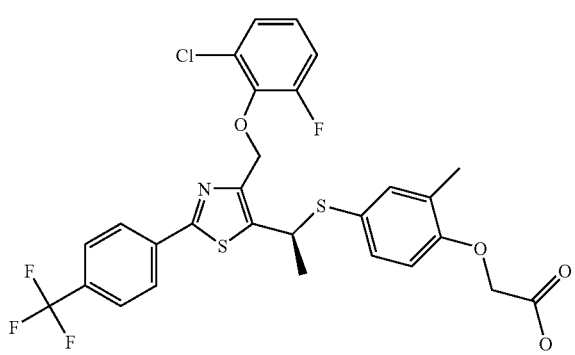

MS (ES): 612.1 (M$^+$+1), the structure is also confirmed by proton NMR.

Example 42

(S)-(2-Methyl-4-{1-[4-phenylsulfanylmethyl-2-(4-trifluoromethyl-phenyl)-thiazol-5-yl]-ethylsulfanyl}-phenoxy)-acetic acid MS (ES): 576.07 (M$^+$+1), the structure is also confirmed by proton NMR.

Example 43

(R)-(2-Methyl-4-{1-[4-phenylsulfanylmethyl-2-(4-trifluoromethyl-phenyl)-thiazol-5-yl]-ethylsulfanyl}-phenoxy)-acetic acid MS (ES): 576.07 (M$^+$+1), the structure is also confirmed by proton NMR.

Example 44

(R)-3-(2-Methyl-4-{1-[4-methyl-2-(4-trifluoromethyl-phenyl)-thiazol-5-yl]-ethoxy}-phenyl)-propionic acid MS (ES): 450.6 (M$^+$+1), the structure is also confirmed by proton NMR.

Example 45

(S)-3-(2-Methyl-4-{1-[4-methyl-2-(4-trifluoromethyl-phenyl)-thiazol-5-yl]-ethoxy}-phenyl)-propionic acid

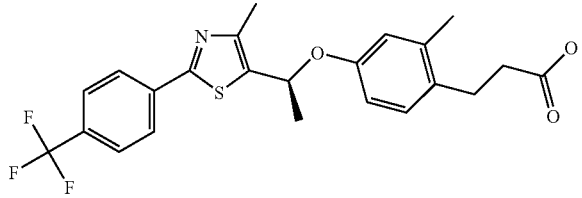

MS (ES): 450.6 (M⁺+1), the structure is also confirmed by proton NMR.

Example 46

(S)-3-(2-Methyl-4-{2-[5-methyl-2-(4-trifluoromethyl-phenyl)-thiazol-4-yl]-propoxy}-phenyl)-propionic acid

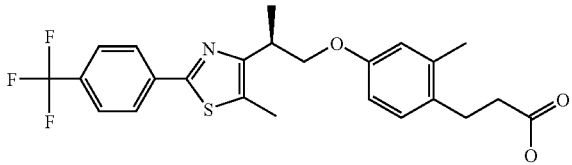

MS (ES): 464.2 (M⁺+1), the structure is also confirmed by proton NMR.

Example 47

(R)-3-(2-Methyl-4-{2-[5-methyl-2-(4-trifluoromethyl-phenyl)-thiazol-4-yl]-propoxy}-phenyl)-propionic acid

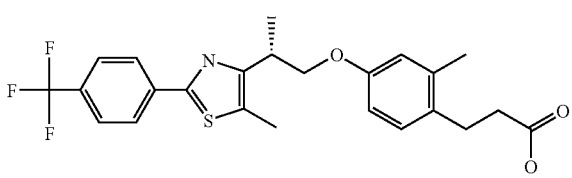

MS (ES) 464.2 (M⁺+1) the structure is also confirmed by proton NMR.

Example 48

3-(4-{1-[4-Ethyl-2-(4-trifluoromethyl-phenyl)-oxazol-5-yl]-ethoxy}-2-methyl-phenyl)-propionic acid

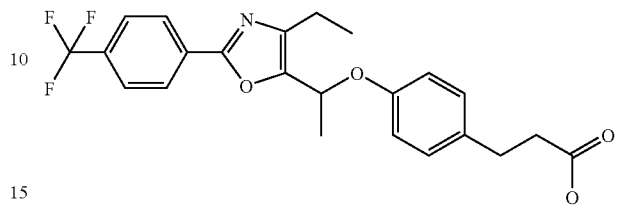

Step A 3-(4-{1-[4-Ethyl-2-(4-trifluoromethyl-phenyl)-oxazol-5-yl]-ethoxy}-2-methyl-phenyl)-propionic acid methyl ester

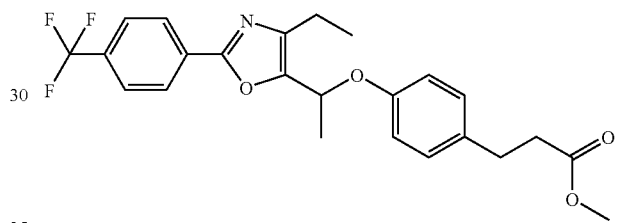

To a solution of 1-[4-ethyl-2-(4-trifluoromethyl-phenyl)-oxazol-5-yl]-ethanol (0.114 g, 0.400 mmole) and 3-(4-Hydroxy-2-methyl-phenyl)-propionic acid methyl ester (0.0789, 0.400 mmole) in toluene (2 mL) at room temperature, is added tributylphosphine (0.200 mL, 0.800 mmole) followed by a solution of 1,1'-(azodicarbonyl)-dipiperidine (0.201 g, 0.800 mmole) in toluene (2 mL). The reaction is stirred overnight, then diluted with hexane (10 mL). The precipitate is removed through filtration and the filtrate is concentrated, loaded to a silica gel column, eluted with ethyl acetate in hexane (0–15%) and concentrated to provide the titled compound as a white solid. Mass [EI+] 462 (M+H)⁺.

Step B 3-(4-{1-[4-Ethyl-2-(4-trifluoromethyl-phenyl)-oxazol-5-yl]-ethoxy}-2-methyl-phenyl)-propionic acid 3-(4-{1-[4-Ethyl-2-(4-trifluoromethyl-phenyl)-oxazol-5-yl]-ethoxy}-2-methyl-phenyl)-propionic acid methyl ester (0.095 g, 0.206 mmole) is treated with a mixture of NaOH$_{(aq)}$ (1 mL)/THF (3 mL)/MeOH (3 mL) at room temperature overnight. The organic solvents are removed on rota-vapor. The residue is diluted with water (10 mL), acidified to pH=2 with 6N HCl$_{(aq)}$. The precipitate is collected through filtration, washed with cold water (30 mL) and dried to provide the titled compound as a white solid. Mass [EI+] 448 (M⁺+H), 446 (M⁺−H).

Example 49

(4-{1-[4-Ethyl-2-(4-trifluoromethyl-phenyl)-oxazol-5-yl]-ethoxy}-2-methyl-phenoxy)-acetic acid

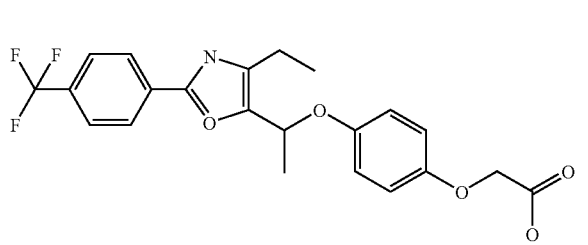

White solid. Mass [EI+] 450 (M$^+$+H), 448 (M$^+$–H).

Example 50

(4-{1-[4-Ethyl-2-(4-trifluoromethyl-phenyl)-oxazol-5-yl]-ethylsulfanyl}-2-methyl-phenoxy)-acetic acid

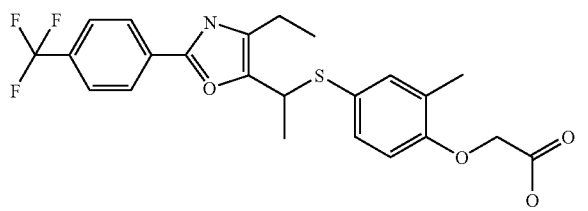

White solid. Mass [EI+] 466 (M$^+$+H), 464 (M$^+$–H).

Example 51

(4-{1R-[4-Ethyl-2-(4-trifluoromethyl-phenyl)-oxazol-5-yl]-ethylsulfanyl}-2-methyl-phenoxy)-acetic acid

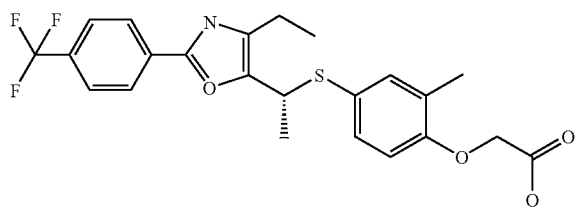

The racemic methyl ester of (4-{1-[4-ethyl-2-(4-trifluoromethyl-phenyl)-oxazol-5-yl]-ethylsulfanyl}-2-methyl-phenoxy)-acetic acid is resolved on a Chiralcel OJ column (2.1×25 cm). Eluted with 40% ethanol in heptane and concentrated the fractions to provide a pure enantiomer ester (isomer 1, 100% ee). Hydrolysis of the pure enantiomer of the ester provides the titled compound as a white solid. Mass [EI+] 466 (M$^+$+H), 464 (M$^+$–H).

Example 52

(4-{1S-[4-Ethyl-2-(4-trifluoromethyl-phenyl)-oxazol-5-yl]-ethylsulfanyl}-2-methyl-phenoxy)-acetic acid

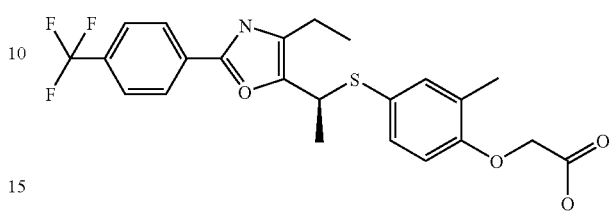

From the chiral separation in previous example also gave the ester of this enantiomer. Hydrolysis of the pure enantiomer of the ester provides the titled compound as a white solid. Mass [EI+] 466 (M+H)$^+$, 464 (M+H)$^-$.

Example 53

3-(2-Methyl-4-{1S-[4-methyl-2-(4-trifluoromethyl-phenyl)-oxazol-5-yl]-2-phenyl-ethoxy}-phenyl)-propionic acid

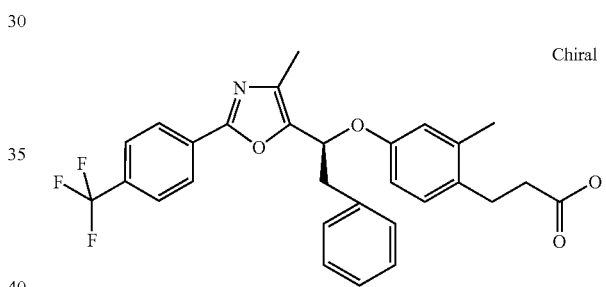

To a solution of 1-[4-Methyl-2-(4-trifluoromethyl-phenyl)-oxazol-5-yl]-2-phenyl-ethanone (1.2 g, 3.5 mmol) in 50 mL MeOH at 0° C. is added LiBH$_4$ (0.086 g, 3.50 mmol) portionwise. After gas evolution had ceased a tic indicated that the reaction is complete and 50 mL of NH$_4$Cl (aq.) is added and the resultant solution extraxted with ethyl acetate (3×50 mL). The combined organics are dried (Na$_2$SO$_4$), filtered and concentrated under vacuo. The resultant crude oil is purified by flash column chromatography (10%–20%) ethyl acetate/hexane to provide 1.1 g 1-[4-Methyl-2-(4-trifluoromethyl-phenyl)-oxazol-5-yl]-2-phenyl-ethanol. To a solution of 1-[4-Methyl-2-(4-trifluoromethyl-phenyl)-oxazol-5-yl]-2-phenyl-ethanol (0.50 g, 1.44 mmol), 3-(4-Hydroxy-2-methyl-phenyl)-propionic acid methyl ester (0.28 g, 1.44 mmol) and 1,1'-(azodicarbonyl)-dipiperidine (0.54 g, 2.16 mmol) in 15 mL toluene is added tributylphosphine (0.5 mL, 2.16 mmol). After 1 hr the volatiles are removed and the crude ester purified by flash column chromatography (10%–25%) ethyl acetate/hexane to provide 0.34 g (45%) of 3-(2-Methyl-4-{1-[4-methyl-2-(4-trifluoromethyl-phenyl)-oxazol-5-yl]-2-phenyl-ethoxy}-phenyl)-propionic acid methyl ester as the racemate. The ester is separated by HPLC utilizing a chiral column with ethanol as the eluent. This enatiomerically pure ester (0.097 g, 0.18 mmol) is hydrolyzed in the usual manner 3 eq. 1N LiOH in 0.5 mL 3:2:1 solution of THF:MeOH:H$_2$O to provide 0.09 g (93%) of the title compound. MS (M$^+$+1) 510.

Example 54

3-(2-Methyl-4-{1R-[4-methyl-2-(4-trifluoromethyl-phenyl)-oxazol-5-yl]-2-phenyl-ethoxy}-phenyl)-propionic acid

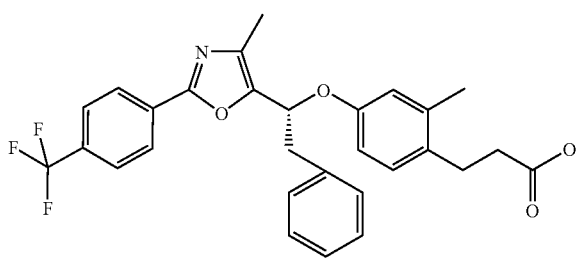

3-(2-Methyl-4-{1R-[4-methyl-2-(4-trifluoromethyl-phenyl)-oxazol-5-yl]-2-phenyl-ethoxy}-phenyl)-propionic acid ethyl ester (0.09 g, 0.17 mmol) obtained as described above is hydrolyzed in the usual manner 3 eq. 1N LiOH in 0.5 mL 3:2:1 solution of THF:MeOH:H$_2$O to provide 0.08 g (89%) of the title compound. MS (M$^+$+1) 510.

Example 55

3-(2-Methyl-4-{1-[4-methyl-2-(4-trifluoromethyl-phenyl)-oxazol-5-yl]-ethoxy}-phenyl)-propionic acid

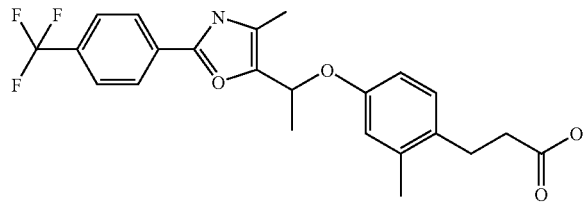

Step 1

3-(2-Methyl-4-{1-[4-methyl-2-(4-trifluoromethyl-phenyl)-oxazol-5-yl]-ethoxy}-phenyl)-propionic acid methyl ester 1-[4-Methyl-2-(4-trifluoromethyl-phenyl)-oxazol-5-yl]-ethanol (0.15 g, 0.553 mmol) and 3-(4-Hydroxy-2-methyl-phenyl)-propionic acid methyl ester (0.12 g, 0.610 mmol) are stirred in 10 mL toluene at 0° C. under a nitrogen atmosphere. Tri-n-butylphosphine (0.21 mL, 0.83 mmol) is added followed by 1,1'-(Azodicarbonyl)dipiperidine (0.21 g, 0.83 mmol). The mixture is allowed to stir at room temperature for 20 hr. The resulting slurry is concentrated under reduced pressure. 50 mL of a 1:1 solution of ethyl acetate: hexanes is added, and the slurry is filtered. The resulting solution is concentrated and purified by silica gel chromatography eluting with a mixture of 8:2 hexanes:ethyl acetate yielding 3-(2-Methyl-4-{1-[4-methyl-2-(4-trifluoromethyl-phenyl)-oxazol-5-yl]-ethoxy}-phenyl)-propionic acid methyl ester as a white solid, 0.176 g (71%) MS (M$^+$+1) 446.

Step 2

3-(2-Methyl-4-{1-[4-methyl-2-(4-trifluoromethyl-phenyl)-oxazol-5-yl]-ethoxy}-phenyl)-propionic acid 3-(2-Methyl-4-{1-[4-methyl-2-(4-trifluoromethyl-phenyl)-oxazol-5-yl]-ethoxy}-phenyl)-propionic acid methyl ester (0.176 g, 0.393 mmol) is dissolved in 20 mL of a 3:2:1 mixture of THF:MeOH:H$_2$O. Lithium hydroxide (0.050 g, 2.08 mmol) is added and the resulting mixture is heated to 60° C. for 1 hr. The mixture is cooled to room temperature, diluted with 50 mL water and the pH is adjusted to 2–3 with 1M HCl. The product is extracted with two 50 mL portions of ethyl acetate. The combined organic extracts are washed with 50 mL water, dried over anhydrous magnesium sulfate, filtered, and concentrated to yield the title compound, 3-(2-Methyl-4-{1-[4-methyl-2-(4-trifluoromethyl-phenyl)-oxazol-5-yl]-ethoxy}-phenyl)-propionic acid as a white solid, 0.12 g (71%). MS (M$^+$+1) 434.

The following compounds are made in a similar manner as Example 55:

Example 56

3-(2-Methyl-4-{1-[4-methyl-2-(4-trifluoromethyl-phenyl)-oxazol-5-yl]-propoxy}-phenyl)-propionic acid

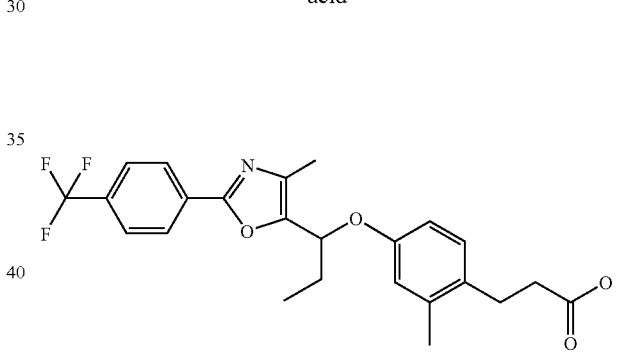

The structure is confirmed by MS. MS (M$^+$–1) 448.

Example 57

3-(2-Methyl-4-{1-[4-methyl-2-(4-trifluoromethyl-phenyl)-oxazol-5-yl]-but-3-enyloxy}-phenyl)-propionic acid

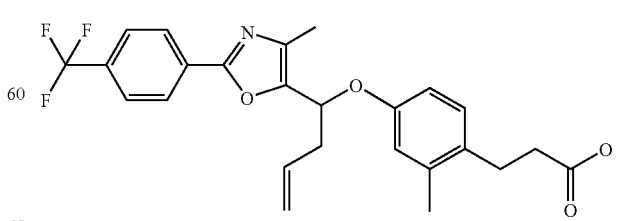

The structure is confirmed by MS. MS (M$^+$+1) 460.

Example 58

3-(2-Methyl-4-{1-[4-methyl-2-(4-trifluoromethyl-phenyl)-oxazol-5-yl]-pentyloxy}-phenyl)-propionic acid

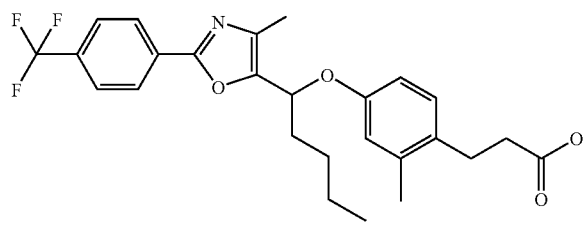

The structure is confirmed by MS. MS (M⁺+1) 476.

Example 59

3-(4-{1-[4-tert-Butyl-2-(4-trifluoromethyl-phenyl)-oxazol-5-yl]-ethoxy}-2-methyl-phenyl)-propionic acid

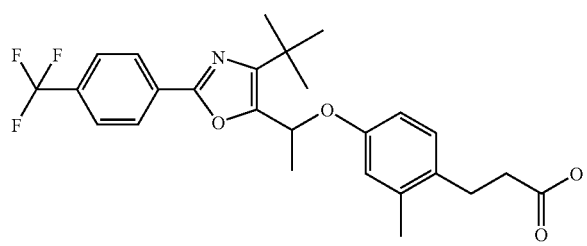

The structure is confirmed by MS. MS (M⁺+1) 476.

Example 60

3-(4-{1-[4-Isopropyl-2-(4-trifluoromethyl-phenyl)-oxazol-5-yl]-ethoxy}-2-methyl-Phenyl)-propionic acid

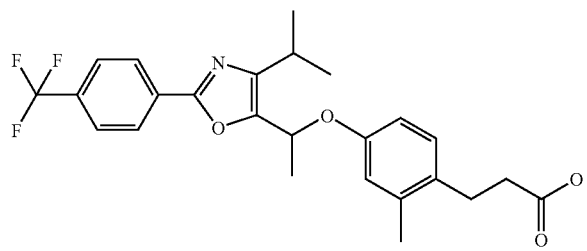

The structure is confirmed by MS. MS (M⁺+1) 462.

Example 61

3-(4-{2-[4-Isopropyl-2-(4-trifluoromethyl-phenyl)-oxazol-5-yl]-propoxy}-2-methyl-phenyl)-propionic acid

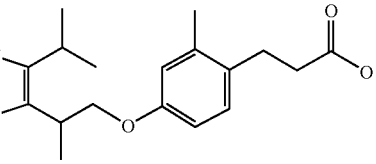

The structure is confirmed by MS. MS (M⁺+1) 476.

Example 62

3-(2-Methyl-4-{2-methyl-2-[5-methyl-2-(4-trifluoromethyl-phenyl)-thiazol-4-yl]-propylsulfanyl}-phenyl)-propionic acid

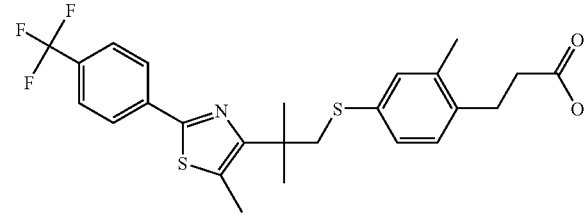

MS (ES): 494.07 (M⁺+1).

Example 63

(R)-(3-{2-[5-Methyl-2-(4-trifluoromethyl-phenyl)-thiazol-4-yl]-propoxy}-phenyl)-acetic acid

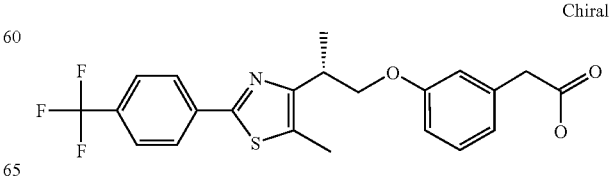

MS (ES): 436.1 (M⁺+1).

Example 64

3-(2-Methyl-4-{2-methyl-2-[5-methyl-2-(4-trifluoromethyl-phenyl)-oxazol-4-yl]-propylsulfanyl}-phenyl)-propionic acid

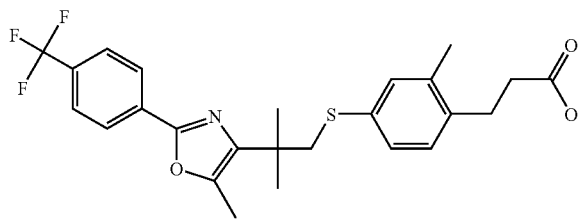

MS (ES) 478.11 (M⁺+1).

Example 65

3-(4-{2-[4-Isopropyl-2-(4-trifluoromethyl-phenyl)-thiazol-5-yl]-propoxy}-2-methyl-phenyl)-propionic acid

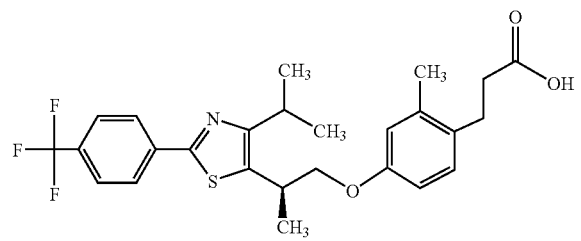

Step 1

2-[4-Isopropyl-2-(4-trifluoromethyl-phenyl)-thiazol-5-yl]-propan-1-ol (329 mg, 1.0 mmol) is dissolved into anhydrous toluene (5 mL) and cooled in an ice bath to 0° C. with stirring under nitrogen. Tributyl phosphine (400 uL, 1.50 mmol) is added by syringe followed by 1-1'-azodicarbonyl-dipiperidine (405 mg, 1.50 mmol). Finally, 3-(4-Hydroxy-2-methyl-phenyl)-propionic acid methyl ester (200 mg, 1.20 mmol) is then added. The reaction is allowed to stir under nitrogen at 0° C. for 1 hour, then room temperature and monitored by TLC and HPLC. Upon completion, the reaction is diluted with hexanes and allowed to stir vigorously for 10 min. The resulting white precipitate is then filtered away and the solution is concentrated under vacuum. The residue is further purified using either EtOAc/Hexanes (1:9) or Acetone/Hexanes (1:9) gradients on silica gel chromatography to yield 3-(4-{2-[4-Isopropyl-2-(4-trifluoromethyl-phenyl)-thiazol-5-yl]-propoxy}-2-methyl-phenyl)-propionic acid methyl ester (239 mg, 0.4725 mmol) or 45%.

Step 2

3-(4-{2-[4-Isopropyl-2-(4-trifluoromethyl-phenyl)-thiazol-5-yl]-propoxy}-2-methyl-phenyl)-propionic acid methyl ester (239 mg, 0.4725 mmol) is dissolved in tetrahydrofuran (1 mL) and 5N NaOH (1 mL) is added. The mixture is heated to reflux until the conversion is complete. Upon complete conversion, the reaction is cooled to room temperature and 5N HCl (1 mL) is added. The mixture is diluted with diethyl ether and extracted with 1N HCl. The organic layer is washed with water and brine, then dried over anhydrous sodium sulfate. Concentration of the solvent reveals the pure 3-(4-{2-[4-Isopropyl-2-(4-trifluoromethyl-phenyl)-thiazol-5-yl]-propoxy}-2-methyl-phenyl)-propionic acid in near quantitative yield (221 mg, 0.4489 mmol).

The following compounds are made in a substantially similar manner:

Example 66

Racemic-3-(2-Methyl-4-{2-[5-methyl-2-(4-trifluoromethyl-phenyl)-oxazol-4-yl]-propoxy}-phenyl)-propionic acid

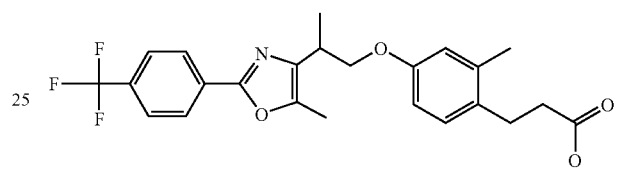

MS (ES): 448.24 (M⁺+1).

Example 67

(S)-3-(2-Methyl-4-{2-[5-methyl-2-(4-trifluoromethyl-phenyl)-oxazol-4-yl]-propoxy}-phenyl)-propionic acid

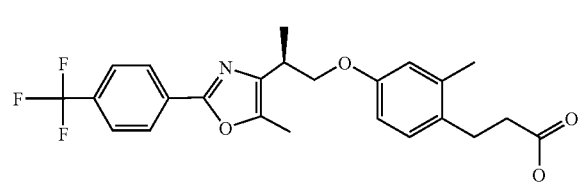

MS (ES): 448.15 (M⁺+1).

Example 68

(R)-3-(2-Methyl-4-{2-[5-methyl-2-(4-trifluoromethyl-phenyl)-oxazol-4-yl]-propoxy}-phenyl)-propionic acid

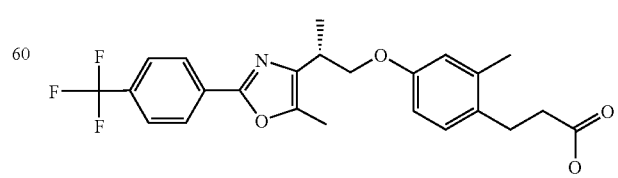

MS (ES): 448.15 (M⁺+1).

Example 69

2-Methoxy-3-(4-{2-[5-methyl-2-(4-trifluoromethyl-phenyl)-oxazol-4-yl]-propoxy}-phenyl)-propionic acid

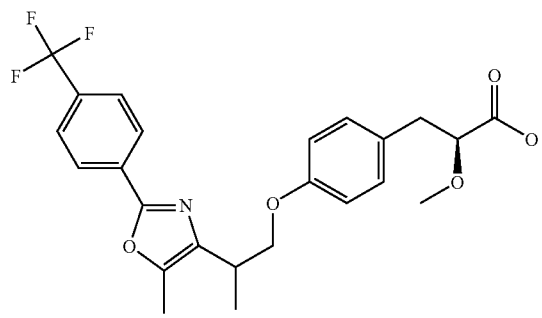

MS (ES): 464.1 (M⁺+1).

Example 70

Racemic-(3-{2-[5-Methyl-2-(4-trifluoromethyl-phenyl)-oxazol-4-yl]-propylsulfanyl}-phenyl)-acetic acid

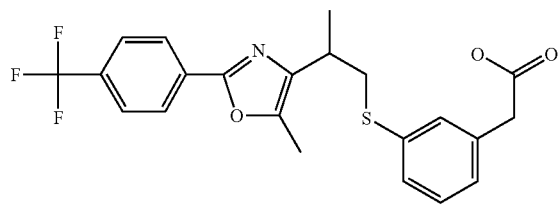

MS (ES): 436.11 (M⁺+1).

Example 71

2-Methoxy-3-(4-{2-[5-methyl-2-(4-trifluoromethyl-phenyl)-oxazol-4-yl]-propoxy}-phenyl)-propionic acid

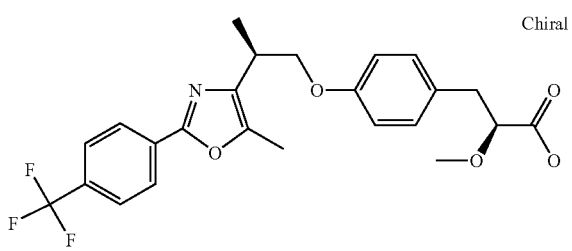

MS (ES): 464.13 (M⁺+1).

Example 72

2-Methoxy-3-(4-{2-[5-methyl-2-(4-trifluoromethyl-phenyl)-oxazol-4-yl]-propoxy}-phenyl)-propionic acid

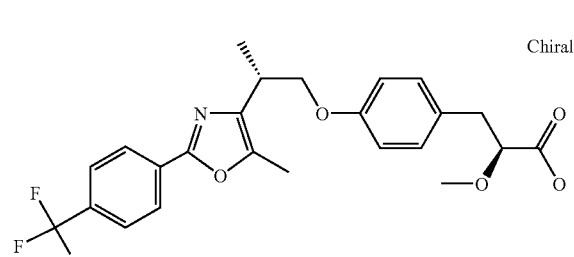

MS (ES): 464.13 (M⁺+1).

Example 73

3-(4-{2-[4-Isopropyl-2-(4-trifluoromethyl-phenyl)-thiazol-5-yl]-propoxy}-2-methyl-phenyl)-propionic acid

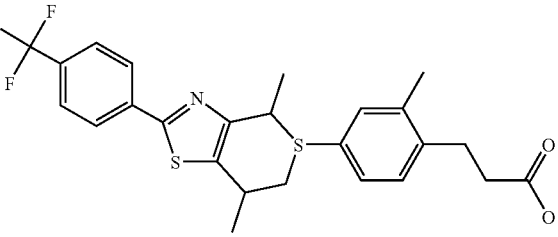

MS (ES): 492.13 (M⁺+1).

Example 74

3-(4-{2-[4-Isopropyl-2-(4-trifluoromethyl-phenyl)-thiazol-5-yl]-propylsulfanyl}-2-methyl-phenyl)-propionic acid

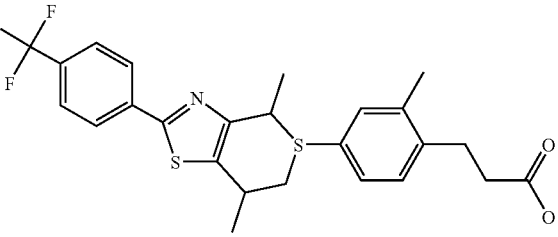

MS (ES): 508.12 (M⁺+1).

Example 75

(4-{2-[4-Isopropyl-2-(4-trifluoromethyl-phenyl)-thiazol-5-yl]-propylsulfanyl}-2-methyl-phenoxy)-acetic acid

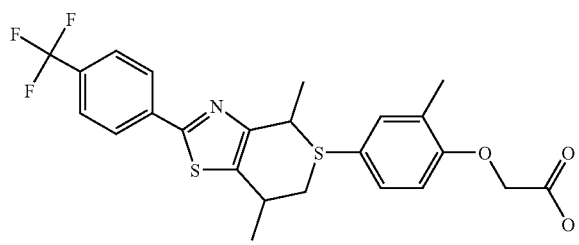

MS (ES): 510.09 (M$^+$+1).

Example 76

(3-{2-[4-Isopropyl-2-(4-trifluoromethyl-phenyl)-thiazol-5-yl]-propoxy}-phenyl)-acetic acid

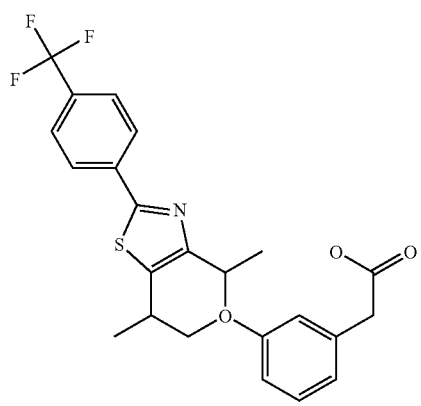

MS (ES): 464.13 (M$^+$+1).

Example 77

(R)-3-(4-{2-[4-Isopropyl-2-(4-trifluoromethyl-phenyl)-thiazol-5-yl]-propoxy}-2-methyl-phenyl)-propionic acid

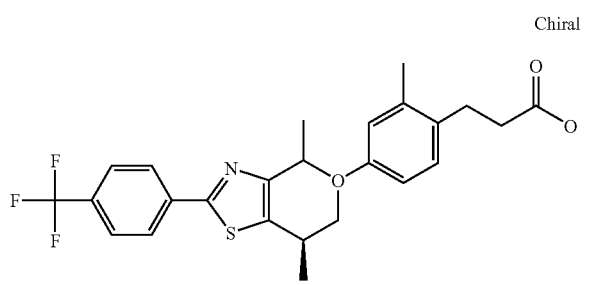

MS (ES): 492.16 (M$^+$+1).

Example 78

(S)-3-(4-{2-[4-Isopropyl-2-(4-trifluoromethyl-phenyl)-thiazol-5-yl]-propoxy}-2-methyl-phenyl)-propionic acid

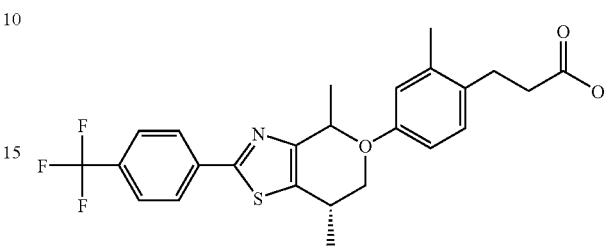

MS (ES): 492.13 (M$^+$+1).

Example 78

3-(2-Methyl-4-{2-[4-methyl-2-(4-trifluoromethyl-phenyl)-thiazol-5-yl]-propoxy}-phenyl)-propionic acid

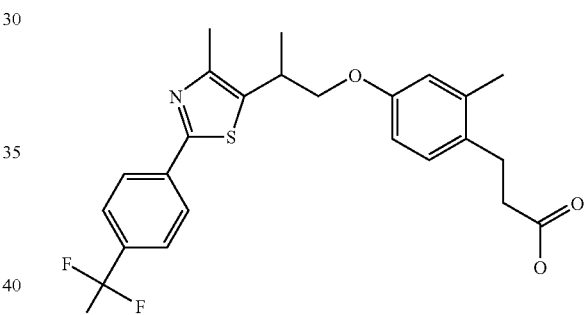

MS (ES): 464.11 (M$^+$+1).

Example 79

3-(2-Methyl-4-{2-[4-methyl-2-(4-trifluoromethyl-phenyl)-thiazol-5-yl]-propylsulfanyl}-phenyl)-propionic acid

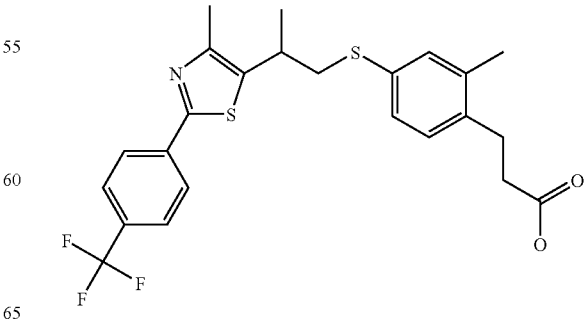

MS (ES): 480.1 (M$^+$+1).

Example 80

(3-{2-[4-Methyl-2-(4-trifluoromethyl-phenyl)-thiazol-5-yl]-propoxy}-phenyl)-acetic acid

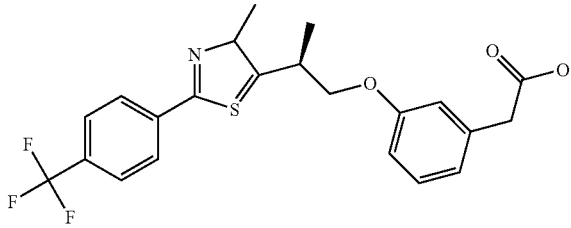

MS (ES): 436.09 (M$^+$+1).

Example 81

(R)-(3-{2-[4-Isopropyl-2-(4-trifluoromethyl-phenyl)-thiazol-5-yl]-propoxy}-phenyl)-acetic acid

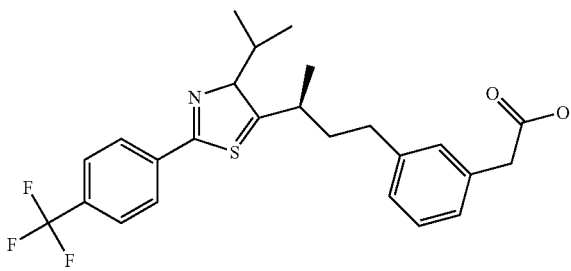

MS (ES): 464.08 (M$^+$+1).

Example 82

(R)-(3-{2-[4-Isopropyl-2-(4-trifluoromethyl-phenyl)-thiazol-5-yl]-propoxy}-phenyl)-acetic acid

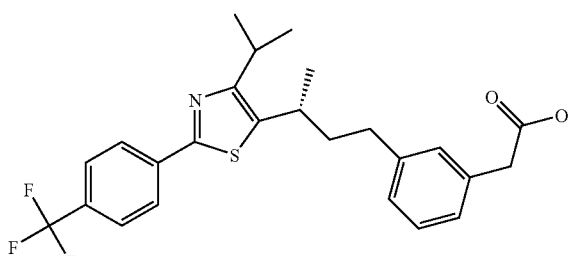

MS (ES): 464.09 (M$^+$+1).

Example 83

(S)-(3-{2-[5-Methyl-2-(4-trifluoromethyl-phenyl)-thiazol-4-yl]-propoxy}-phenyl)-acetic acid

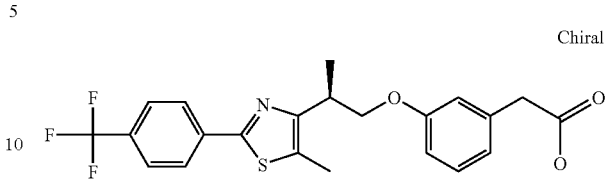

MS (ES): 434.07 (M$^+$−1).

Example 84

(R)-(3-{2-[5-Methyl-2-(4-trifluoromethyl-phenyl)-thiazol-4-yl]-propoxy}-phenyl)-acetic acid

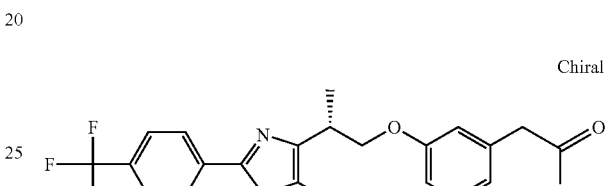

MS (ES): 436.1 (M$^+$+1).

Example 85

3-(4-{2-[5-Ethyl-2-(4-trifluoromethyl-phenyl)-thiazol-4-yl]-propoxy}-2-methyl-phenyl)-propionic acid

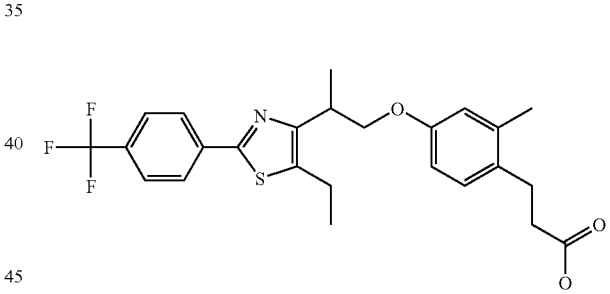

MS (ES): 478.1 (M$^+$+1).

Example 86

3-(4-{2-[5-Ethyl-2-(4-trifluoromethyl-phenyl)-thiazol-4-yl]-propylsulfanyl}-2-methyl-phenyl)-propionic acid

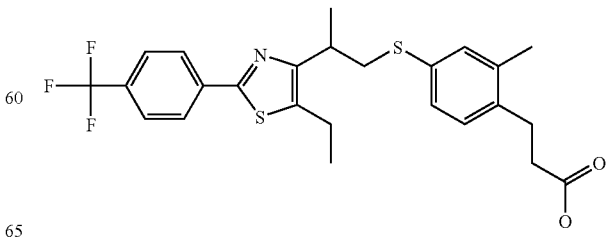

MS (ES): 494.1 (M$^+$+1).

Example 87

(4-{2-[5-Ethyl-2-(4-trifluoromethyl-phenyl)-thiazol-4-yl]-propylsulfanyl}-2-methyl-phenoxy)-acetic acid

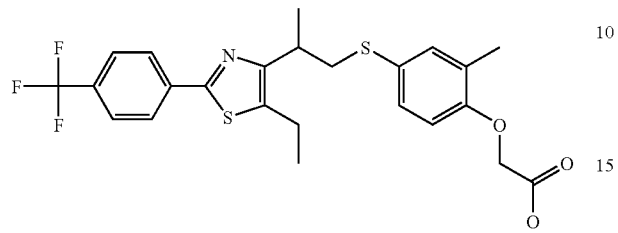

MS (ES): 496.0 (M$^+$+1).

Example 88

(3-{2-[5-Ethyl-2-(4-trifluoromethyl-phenyl)-thiazol-4-yl]-propoxy}-phenyl)-acetic acid

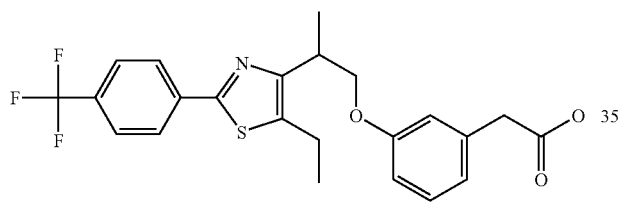

MS (ES): 450.11 (M$^+$+1).

Example 89

(S)-3-(4-{2-[4-Isopropyl-2-(4-trifluoromethyl-phenyl)-thiazol-5-yl]-propylsulfanyl}-2-methyl-phenyl)-propionic acid

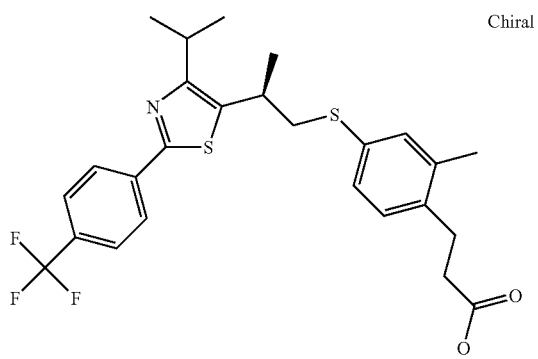

MS (ES): 508.07 (M$^+$+1).

Example 90

(R)-3-(4-{2-[4-Isopropyl-2-(4-trifluoromethyl-phenyl)-thiazol-5-yl]-propylsulfanyl}-2-methyl-phenyl)-propionic acid

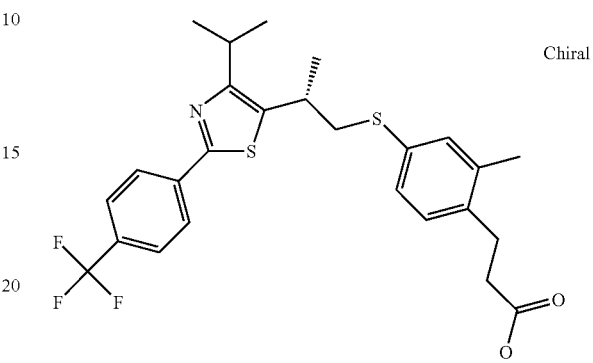

MS (ES): 508.07 (M$^+$+1).

Example 91

(R)-(4-{2-[4-Isopropyl-2-(4-trifluoromethyl-phenyl)-thiazol-5-yl]-propylsulfanyl}-2-methyl-phenoxy)-acetic acid

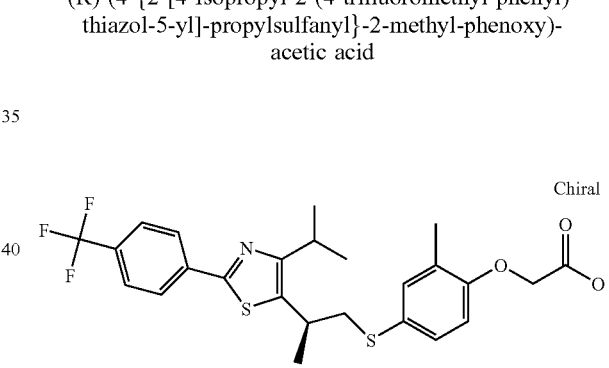

MS (ES): 510.08 (M$^+$+1).

Example 92

(R)-(4-{2-[4-Isopropyl-2-(4-trifluoromethyl-phenyl)-thiazol-5-yl]-propylsulfanyl}-2-methyl-phenoxy)-acetic acid

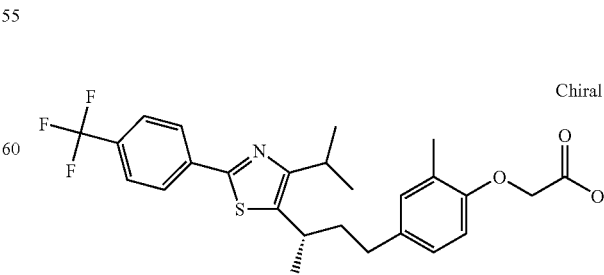

MS (ES): 510.09 (M$^+$+1).

Example 93

(3-{2-[4-Isopropyl-2-(4-trifluoromethyl-phenyl)-thiazol-5-yl]-propylsulfanyl}-phenyl)-acetic acid

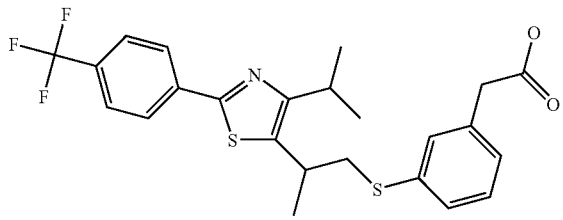

MS (ES): 480.12 (M⁺+1).

Example 94

3-(4-{2-[4-Isopropyl-2-(4-trifluoromethyl-phenyl)-thiazol-5-yl]-propoxy}-phenyl)-2-methoxy-propionic acid

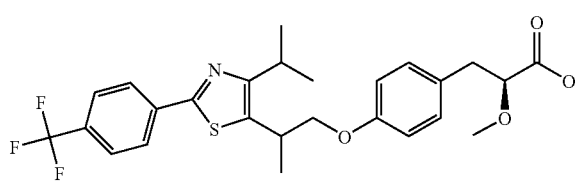

MS (ES): 506.15 (M⁺+1).

Example 95

2-(4-{2-[4-Isopropyl-2-(4-trifluoromethyl-phenyl)-thiazol-5-yl]-propoxy}-2-methyl-phenoxy)-2-methyl-propionic acid

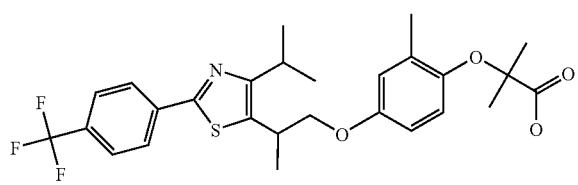

MS (ES): 522.1 (M⁺+1).

Example 96

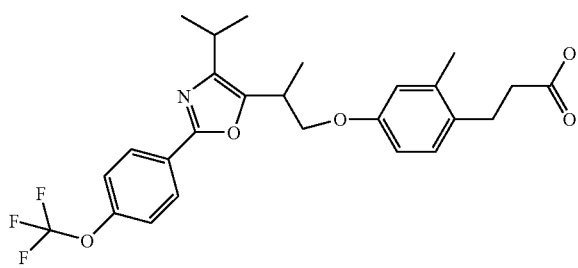

3-(4-{2-[4-Isopropyl-2-(4-trifluoromethoxy-phenyl)-oxazol-5-yl]-propoxy}-2-methyl-phenyl)-propionic acid

Step A

A solution of 2-[4-isopropyl-2-(4-trifluoromethoxy-phenyl)-oxazol-5-yl]-propan-1-ol (230 mg, 0.699 mmol) and 2,6-di-t-butyl-4-methylpyridine (229 mg, 1.12 mmol) in $CH_2Cl_2$ (20 mL) at −40° C. is treated with triflic anhydride (0.165 mL, 0.979 mmol). The reaction mixture is stirred at −40° C. for 20 minutes and then quenched with MeOH (0.2 mL). The mixture is immediately concentrated to crude triflate and it is dissolved in THF (5 mL) and cooled to 0° C. In the meantime, a solution of 3-(4-hydroxy-2-methyl-phenyl)-propionic acid methyl ester (165 mg, 0.839 mmol) in THF (5 mL) is treated with LiHMDS (0.84 mL, 1.0 M in THF) and stirred for 5 minutes. Cannula this phenoxide solution to the crude triflate solution and the resulting mixture is stirred for 12 hours while warmed up to room temperature. The mixture is concentrated and purified on silica gel chromatography with 10–15% EtOAc/Hexanes to afford the intermediate compound (239 mg, 68%).

Step B

A solution of 3-(4-{2-[4-isopropyl-2-(4-trifluoromethoxy-phenyl)-oxazol-5-yl]-propoxy}-2-methyl-phenyl)-propionic acid methyl ester (239 mg, 0.473) in MeOH (1.0 mL) and THF (0.5 mL) is treated with NaOH (1.5 mL, 2.0 M) and stirred at room temperature for 12 hours. The mixture is neutralized to pH=4 with HCl (5 N) and extracted with EtOAc (20 mL×2), and the combined organics are dried ($Na_2SO_4$), concentrated and purified on silica gel chromatography column with EtOAc/Hexanes (50/50) to yield the acid as white solid (202 mg, 87%). MS (ES): 492.2; the structure is also confirmed by proton NMR.

Example 97

3-(4-{1-[4-Isopropyl-2-(4-trifluoromethoxy-phenyl)-oxazol-5-yl]-ethoxy}-2-methyl-phenyl)-propionic acid

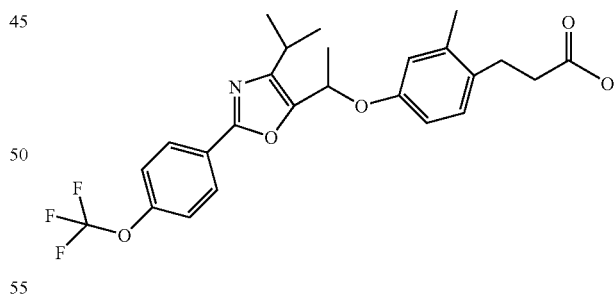

Step A 3-(4-{1-[4-Isopropyl-2-(4-trifluoromethoxy-phenyl)-oxazol-5-yl]-ethoxy}-2-methyl-phenyl)-propionic acid methyl ester A solution of 1-[4-isopropyl-2-(4-trifluoromethoxy-phenyl)-oxazol-5-yl]-ethanol (140 mg, 0.446 mmol) and 3-(4-hydroxy-2-methyl-phenyl)-propionic acid methyl ester (122 mg, 0.624 mmol) in toluene (15 mL) is degassed and filled with nitrogen for 3 times. Tributylphosphine (144 mg, 0.713 mmol) is added to the reaction mixture under nitrogen at 0° C., followed by addition of of 1,1'-(azodicarbonyl)-dipiperidine (169 mg, 0.669 mmol). The reaction mixture is allowed to warm to room temperature and stirred for 4 hours. The mixture is loaded directly on silica gel column chromatography with 10–25% EtOAc/Hexanes to afford the title compound (25 mg, 11%).

Step B 3-(4-{1-[4-Isopropyl-2-(4-trifluoromethoxy-phenyl)-oxazol-5-yl]-ethoxy}-2-methyl-phenyl)-propionic acid A solution of 3-(4-{1-[4-Isopropyl-2-(4-trifluoromethoxy-phenyl)-oxazol-5-yl]-ethoxy}-2-methyl-phenyl)-propionic acid methyl ester in MeOH (1.0 mL) and THF (0.5 mL) is treated with NaOH (1.5 mL, 2.0 M) and stirred at room temperature for 2 hours. The mixture is neutralized to pH=6 with HCl (5 N) and extracted with EtOAc (20 mL×2), and the combined organics are dried ($Na_2SO_4$), concentrated and purified on silica gel chromatography column with EtOAc/Hexanes (50/50) to yield the acid as white solid (14 mg). MS (ES): 478.2; the structure is also confirmed by proton NMR.

The following compounds are made in a similar manner:

Example 98

(4-{1-[4-Isopropyl-2-(4-trifluoromethoxy-phenyl)-oxazol-5-yl]-ethylsulfanyl}-2-methyl-phenoxy)-acetic acid

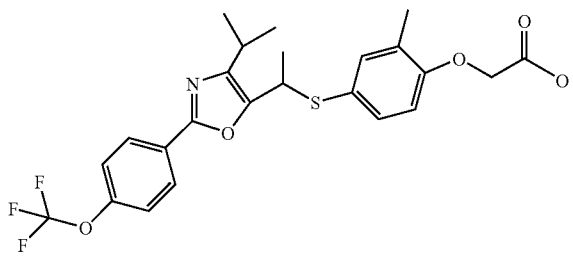

MS (ES): 496.1; the structure is also confirmed by proton NMR.

Example 99

(4-{1-[4-Isopropyl-2-(4-trifluoromethoxy-phenyl)-oxazol-5-yl]-ethoxy}-2-methyl-phenoxy)-acetic acid

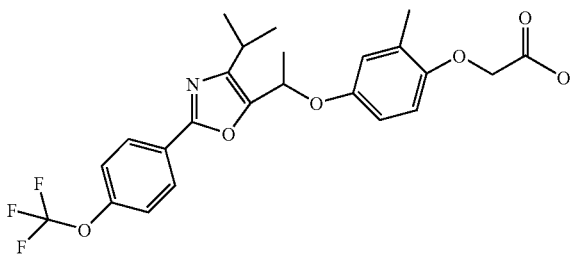

MS (ES): 480.2; the structure is also confirmed by proton NMR.

Example 100

3-(4-{2-[4-Isopropyl-2-(4-phenoxy-phenyl)-oxazol-5-yl]-propoxy}-2-methyl-phenyl)-propionic acid

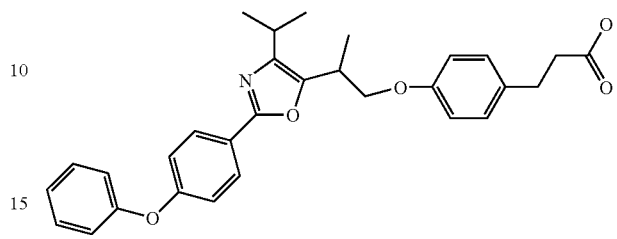

A solution of 1-[4-isopropyl-2-(4-phenoxyphenyl)-oxazol-5-yl]-ethanol (160 mg, 0.474 mmol) and 3-(4-hydroxy-2-methyl-phenyl)-propionic acid methyl ester (120 mg, 0.614 mmol) in toluene (10 mL) is degassed and filled with nitrogen for 3 times. Tributylphosphine (153 mg, 0.759 mmol) is added to the reaction mixture under nitrogen at 0° C., followed by addition of of 1,1'-(azodicarbonyl)-dipiperidine (167 mg, 0.614 mmol). The reaction mixture is allowed to warm to room temperature and stirred for 2 hours. The mixture is loaded directly on silica gel column chromatography with 10–25% EtOAc/Hexanes to afford the intermediate compound.

The intermediate is then dissolved in MeOH (1.0 mL) and THF (0.5 mL) and is treated with NaOH (1.5 mL, 2.0 M) and stirred at room temperature for 2 hours. The mixture is neutralized to pH=6 with HCl (5 N) and extracted with EtOAc (20 mL×2), and the combined organics are dried ($Na_2SO_4$), concentrated to yield the acid as white solid (55 mg, 23%). MS (ES): 500.2; the structure is also confirmed by proton NMR.

Example 101

3-(4-{2-[2-(4-Bromo-phenyl)-4-isopropyl-oxazol-5-yl]-propoxy}-2-methyl-phenyl)-propionic acid methyl ester

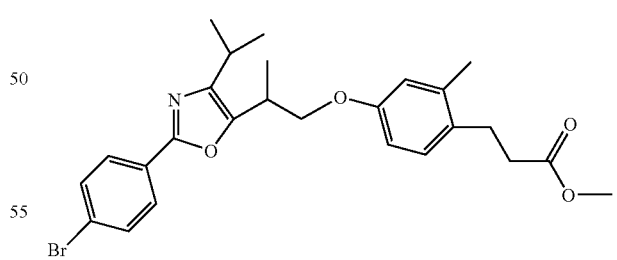

A solution of 2-[2-(4-bromo-phenyl)-4-isopropyl-oxazol-5-yl]-propan-1-ol (225 mg, 0.694 mmol) and 3-(4-hydroxy-2-methyl-phenyl)-propionic acid methyl ester (190 mg, 0.972 mmol) in toluene (15 mL) is degassed and filled with nitrogen for 3 times. Tributylphosphine (224 mg, 1.11 mmol) is added to the reaction mixture under nitrogen at 0° C., followed by addition of of 1,1'-(azodicarbonyl)-dipiperidine (280 mg, 1.11 mmol). The reaction mixture is allowed to warm to room temperature and stirred overnight, the mixture is loaded directly on silica gel column chromatography with 10–15% EtOAc/Hexanes to afford the title compound (320 mg, 92%).

Example 102

3-[4-(2-{4-Isopropyl-2-[4-(4,4,5,5-tetramethyl-[1,3,2]dioxaborolan-2-yl)-phenyl]-oxazol-5-yl}-propoxy)-2-methyl-phenyl]-propionic acid methyl ester

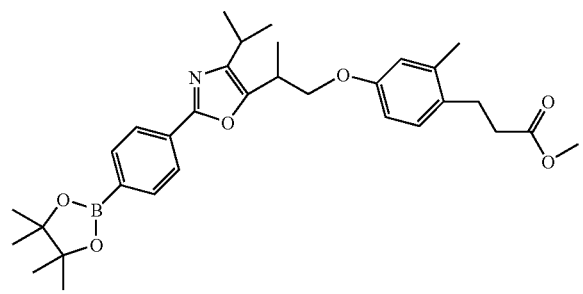

To a solution of 3-(4-{2-[2-(4-Bromo-phenyl)-4-isopropyl-oxazol-5-yl]-propoxy}-2-methyl-phenyl)-propionic acid methyl ester (0.871 g, 1.74 mmol) in DMSO (10 mL) is added bis(pinacolato)diboron (0.663 g, 2.61 mmol) and KOAc (0.682 g, 6.96 mmol). The suspension is bubbled with nitrogen gas for 10 minutes and then is treated with Pd(dppf)Cl$_2$ (20 mg) The mixture is then stirred and heated at 85° C. for 6 hours. The reaction is quenched water (50 mL) and extracted with EtOAc (50 mL×2) and the combined organics are dried (Na$_2$SO$_4$), concentrated and purified on silica gel chromatography column with 20% EtOAc/Hexanes to yield the title compound as yellowish oil (0.825 g, 87%). MS (ES): 548.3.

Example 103

3-(4-{2-[4-Isopropyl-2-(4-pyrimidin-2-yl-phenyl)-oxazol-5-yl]-propoxy}-2-methyl-phenyl)-propionic acid

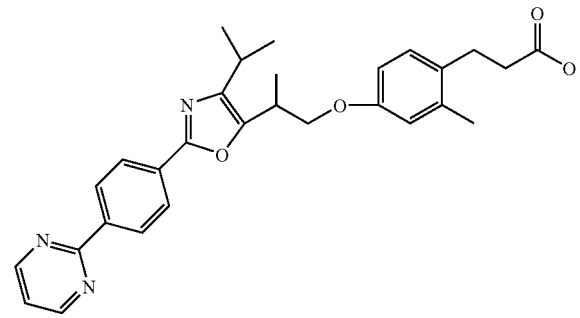

A solution of 3-[4-(2-{4-isopropyl-2-[4-(4,4,5,5-tetramethyl-[1,3,2]dioxaborolan-2-yl)-phenyl]-oxazol-5-yl}-propoxy)-2-methyl-phenyl]-propionic acid methyl ester (91 mg, 0.166 mmol) in toluene (4.0 mL) is bubbled with nitrogen gas for 10 minutes. To this, Pd(dppf)Cl$_2$ (10 mg), Na$_2$CO$_3$ (1.0 mL, 2.0 M), 2-bromopyrimidine (53 mg, 0.333 mmol) are added. The resulting suspension is stirred and heated at 90° C. for 48 hours. It is then concentrated, purified on silica gel chromatography column with 20–40% EtOAc/Hexanes to yield the pyrimidine intermediate.

The pyrimidine intermediate is dissolved in MeOH (1.0 mL) and THF (0.5 mL) and treated with NaOH (1.5 mL, 2.0 M) and stirred at room temperature for 2 hours. The mixture is neutralized to pH=6 with HCl (5 N) and extracted with EtOAc (20 mL×2), and the combined organics are dried (Na$_2$SO$_4$), concentrated and purified on silica gel chromatography column with EtOAc/Hexanes/HOAc (50/50/2) to yield the acid as white solid (14 mg, 18%). MS (ES): 486.2; the structure is also confirmed by proton NMR.

The following compounds are made in a similar manner:

Example 104

3-(4-{1-[4-Isopropyl-2-(4-pyridin-2-yl-phenyl)-oxazol-5-yl]-ethoxy}-2-methyl-phenyl)-propionic acid

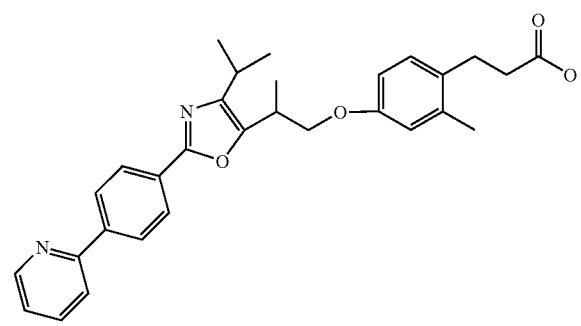

MS (ES): 485.2; the structure is also confirmed by proton NMR.

Example 105

3-(4-{2-[4-Isopropyl-2-(4-pyrazin-2-yl-phenyl)-oxazol-5-yl]-propoxy}-2-methyl-phenyl)-propionic acid

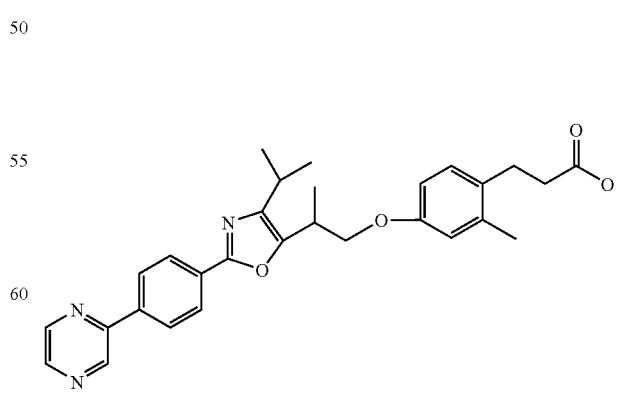

MS (ES): 486.2; the structure is also confirmed by proton NMR.

Example 106

(R)-3-(2-Methyl-4-{1-r[4-methyl-2-(4-trifluorom-ethyl-phenyl)-oxazol-5-yl]-ethoxy}-phenyl)-propionic acid

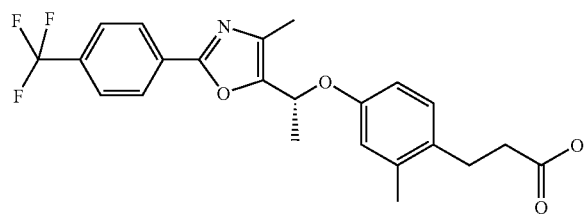

Racemic 3-(2-Methyl-4-{1-[4-methyl-2-(4-trifluoromethyl-phenyl)-oxazol-5-yl]-ethoxy}-phenyl)-propionic acid methyl ester is separated into its enantiomers using Ethanol as eluent on a Chiralpak AD at 1.0 mL/min to afford (R)-3-(2-Methyl-4-{1-[4-methyl-2-(4-trifluoromethyl-phenyl)-oxazol-5-yl]-ethoxy}-phenyl)-propionic acid methyl ester. Hydrolysis of the ester gave the title compound, (R)-3-(2-Methyl-4-{1-[4-methyl-2-(4-trifluoromethyl-phenyl)-oxazol-5-yl]-ethoxy}-phenyl)-propionic acid as a white solid MS (M$^+$+1) 434.

Example 107

(S)-3-(2-Methyl-4-{1-[4-methyl-2-(4-trifluorom-ethyl-phenyl)-oxazol-5-yl]-ethoxy}-phenyl)-propionic acid

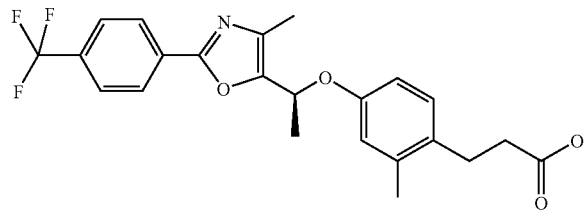

Racemic 3-(2-Methyl-4-{1-[4-methyl-2-(4-trifluoromethyl-phenyl)-oxazol-5-yl]-ethoxy}-phenyl)-propionic acid methyl ester is separated into its enantiomers using Ethanol as eluent on a Chiralpak AD at 1.0 mL/min to afford (S)-3-(2-Methyl-4-{1-[4-methyl-2-(4-trifluoromethyl-phenyl)-oxazol-5-yl]-ethoxy}-phenyl)-propionic acid methyl ester. Hydrolysis of the ester gave the title compound, (S11)-3-(2-Methyl-4-{1-[4-methyl-2-(4-trifluoromethyl-phenyl)-oxazol-5-yl]-ethoxy}-phenyl)-propionic acid as a white solid MS (M$^+$+1) 434.

The following compounds are made in a similar manner via chiral separation:

Example 108

(S)-3-(4-{2-[4-Isopropyl-2-(4-trifluoromethyl-phe-nyl)-oxazol-5-yl]-propoxy}-2-methyl-phenyl)-propionic acid

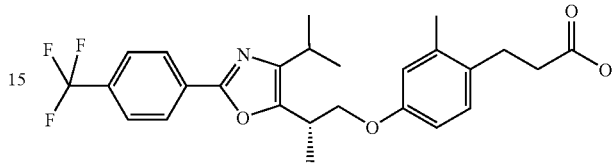

The structure is confirmed by MS. MS (M$^+$+1) 476.

Example 109

(R)-3-(4-{2-[4-Isopropyl-2-(4-trifluoromethyl-phe-nyl)-oxazol-5-yl]-propoxy}-2-methyl-phenyl)-propionic acid

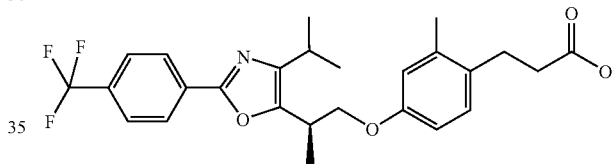

The structure is confirmed by MS. MS (M$^+$+1) 476.

Example 110

3-(2-Methyl-4-{1-[4-methyl-2-(4-trifluoromethyl-phenyl)-oxazol-5-yl]-butoxy}-phenyl)-propionic acid

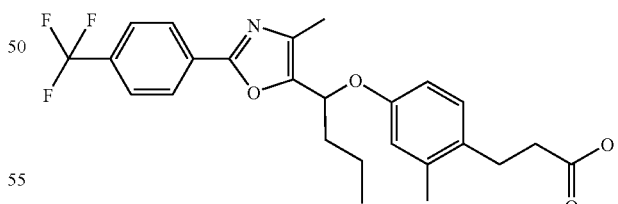

3-(2-Methyl-4-{1-[4-methyl-2-(4-trifluoromethyl-phenyl)-oxazol-5-yl]-but-3-enyloxy}-phenyl)-propionic acid (30 mg, 0.065 mmol), 10% Palladium on charcoal (30 mg) and tetrahydrofuran (30 mL) is stirred under a hydrogen balloon 30 min. The solution is filtered over celite and concentrated in vacuo to afford the title compound, 3-(2-Methyl-4-{1-[4-methyl-2-(4-trifluoromethyl-phenyl)-oxazol-5-yl]-butoxy}-phenyl)-propionic acid as a white solid, 30 mg 100%. MS (M$^+$+1) 462.

Example 111

3-(4-{1-[2-(4-bromo-phenyl)-4-isopropyl-oxazol-5-yl]-ethoxy}-2-methyl-phenyl)-propionic acid methyl ester

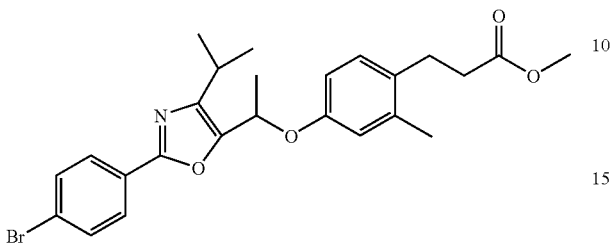

To a solution of 1-[2-(4-bromo-phenyl)-4-isopropyl-oxazol-5-yl]-ethanol (9.05 g, 29.2 mmol) in toluene (300 ml) at 0° C. is added tri-n-butylphosphine (7.70 g, 38.1 mmol) and 1,1'-(azodicarbonyl)-dipiperidine (8.84 g, 35.0 mmol), followed by addition of 3-(4-hydroxy-2-methyl-phenyl)-propionic acid methyl ester (6.30 g, 32.1 mmol). The resulting mixture is stirred for 18 hours while warmed up to room temperature. The reaction is quenched with water (100 ml) and the aqueous layer is extracted with EtOAc (2×100 ml). The combined organics are dried over $Na_2SO_4$ and concentrated, purified by silica gel chromatography (Hexanes/EtOAc, 9/1 to 8.5/1.5) to afford the 3-(4-{1-[2-(4-bromo-phenyl)-4-isopropyl-oxazol-5-yl]-ethoxy}-2-methyl-phenyl)-propionic acid methyl ester as a colorless oil (11.4 g, 80%). MS (MH+): 488.1.

Example 112

3-[4-(1-{4-Isopropyl-2-[4-(4,4,5,5-tetramethyl-[1,3,2]dioxaborolan-2-yl)-phenyl]-oxazol-5-yl}-ethoxy)-2-methyl-phenyl]-propionic acid methyl ester

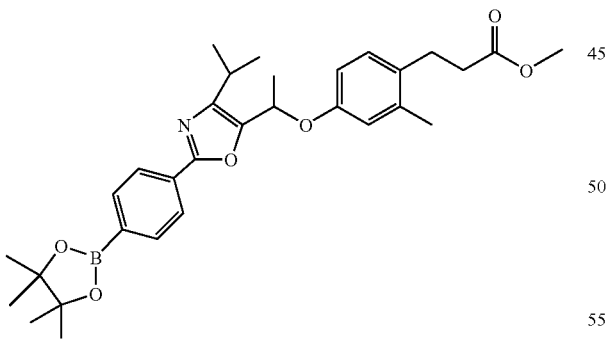

To a solution of 3-(4-{1-[2-(4-bromo-phenyl)-4-isopropyl-oxazol-5-yl]-ethoxy}-2-methyl-phenyl)-propionic acid methyl ester (2.50 g, 5.14 mmol) in DMSO (50 ml) is added the bis(pinacolato)diboron (1.88 g, 7.40 mmol) and potassium acetate (1.94 g, 19.8 mmol). The suspension is bubbled with $N_2$ for 10 minutes, and then $Pd_2Cl_2$ (dppf) is added. The mixture is stirred and heated to 85° C. for 4 hours. The reaction mixture is quenched with $H_2O$ (100 mL) and extracted with EtOAc (3×100 mL). The combined organics are dried over $Na_2SO_4$ and concentrated, purified by silica gel chromatography (Hexanes/EtOAc, 8/2) to afford the borane intermediate as a colorless oil (1.68 g, 61%). MS (MH+): 534.3.

Example 113

3-(4-{1-[2-(4-Hydroxy-phenyl)-4-isopropyl-oxazol-5-yl]-ethoxy}-2-methyl-phenyl)-propionic acid methyl ester

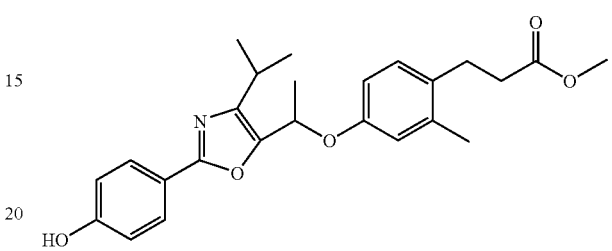

A solution of 3-[4-(1-{4-Isopropyl-2-[4-(4,4,5,5-tetramethyl-[1,3,2]dioxaborolan-2-yl)-phenyl]-oxazol-5-yl}-ethoxy)-2-methyl-phenyl]-propionic acid methyl ester (0.88 g, 1.69 mmol) in THF (5 ml) at 0° C. is treated with HOAc (150 mg, 2.54 mmol), followed by addition of mixture of $H_2O_2$ (4.0 ml, 30%) in $H_2O$ (0.8 ml). The reaction mixture is stirred for 2 hours while warmed to room temperature. The mixture is then cooled back to 0° C. and treated with saturated aqueous $Na_2S_2O_3$ (30 ml) carefully. The mixture is then extracted with EtOAc (3×100 mL) and the combined organics are dried over $Na_2SO_4$ and concentrated, purified by silica gel chromatography (Hexanes/EtOAc, 7/3 to 5/5) to afford the phenol as a colorless oil (0.62 g, 87%). MS (MH+): 424.4.

Example 114

3-(4-{1-[4-Isopropyl-2-(4-methoxy-phenyl)-oxazol-5-yl]-ethoxy}-2-methyl-phenyl)-propionic acid

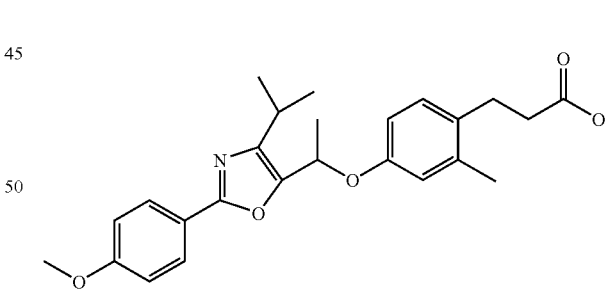

A solution of 3-(4-{1-[2-(4-Hydroxy-phenyl)-4-isopropyl-oxazol-5-yl]-ethoxy}-2-methyl-phenyl)-propionic acid methyl ester (42 mg, 0.10 mmol) in DMF (1.0 ml) is treated with iodomethane (0.20 ml) and $K_2CO_3$ (100 mg). The suspension is stirred at room temperature for 24 hours and then quenched with water (5 ml). The mixture is then extracted with EtOAc (3×10 mL) and the combined organics are dried over $Na_2SO_4$ and concentrated, purified by silica gel chromatography (Hexanes/EtOAc, 7/3) to afford the phenol ether as a colorless oil. The ester is then dissolved in MeOH (1.0 ml) and THF (0.5 ml) and treated with NaOH (2.0 N, 1.5 ml). The mixture is stirred at room temperature for 2 hours and concentrated to an aqueous residue. It is then neutralized with 5 N HCl to pH-4 and extracted with EtOAc (3×5 ml). The combined organics are dried over Na₂SO₄ and concentrated, purified by silica gel chromatography (Hexanes/EtOAc, 5/5, then Hexanes/EtOAc/HOAc 5/5/0.02) to afford the acid as a colorless oil (10 mg, 25%). MS (MH+): 424.2.

The following compounds are made in a similar manner:

Example 115

3-(4-{1-[4-Isopropyl-2-(3-methoxy-phenyl)-oxazol-5-yl]-ethoxy}-2-methyl-phenyl)-propionic acid

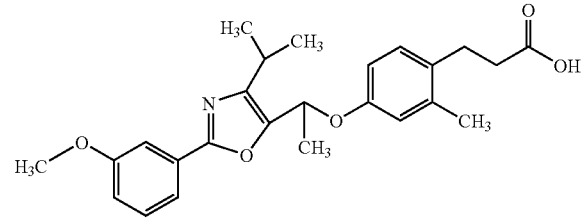

MS (ES): 424.2 (M⁺+H).

Example 116

3-(4-{1-[2-(3-Isopropoxy-phenyl)-4-isopropyl-oxazol-5-yl]-ethoxy}-2-methyl-phenyl)-propionic acid

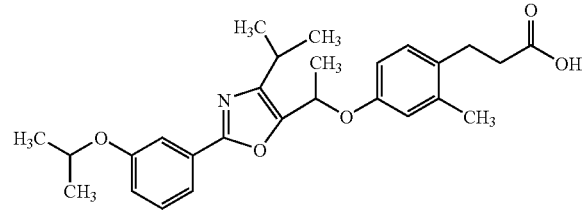

MS (ES): 452.3 (M⁺+H).

Example 117

3-(4-{1-[2-(3-Cyclopentyloxy-phenyl)-4-isopropyl-oxazol-5-yl]-ethoxy}-2-methyl-phenyl)-propionic acid

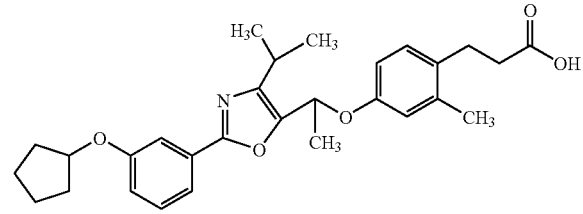

MS (ES): 478.3 (M⁺+H).

Example 118

3-(4-{1-[2-(4-Isopropoxy-phenyl)-4-isopropyl-oxazol-5-yl]-ethoxy}-2-methyl-phenyl)-propionic acid

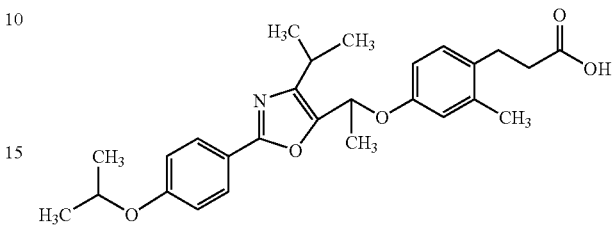

MS (ES): 452.3 (M⁺+H).

Example 119

3-[4-(1-{4-Isopropyl-2-[3-(tetrahydro-pyran-4-yloxy)-phenyl]-oxazol-5-yl}-ethoxy)-2-methyl-phenyl]-propionic acid

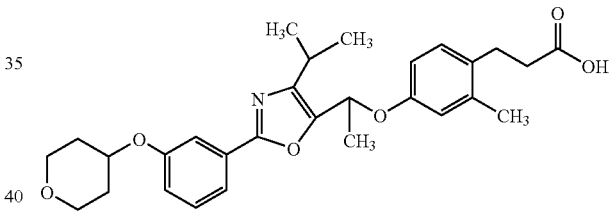

MS (ES): 494.2 (M⁺+H).

Example 120

3-(4-{1-[2-(4-Cyclopentyloxy-phenyl)-4-isopropyl-oxazol-5-yl]-ethoxy}-2-methyl-phenyl)-propionic acid

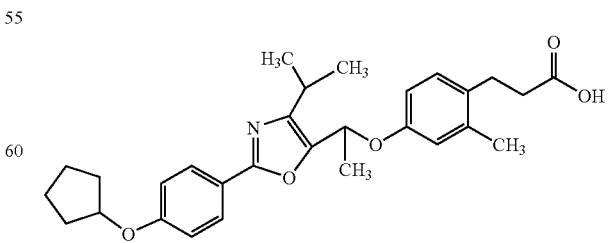

MS (ES): 478.3 (M⁺+H).

Example 121

3-(4-{1-[4-Isopropyl-2-(3-methoxy-phenyl)-oxazol-5-yl]-ethoxy}-2-methyl-phenyl)-propionic acid

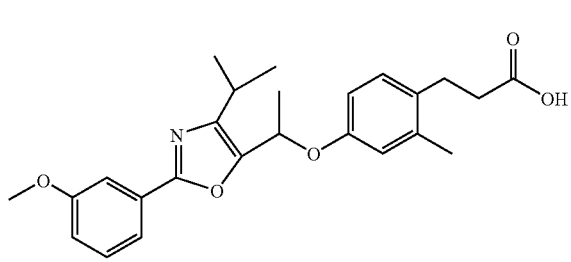

MS (ES): 424.2; the structure is also confirmed by proton NMR.

Example 122

3-(4-{1-[2-(3-Isopropoxy-phenyl)-4-isopropyl-oxazol-5-yl]-ethoxy}-2-methyl-phenyl)-propionic acid

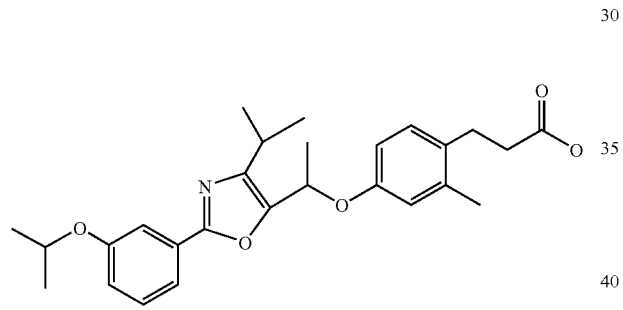

MS (ES): 452.3; the structure is also confirmed by proton NMR.

Example 123

3-(4-{1-[2-(3-Cyclopentyloxy-phenyl)-4-isopropyl-oxazol-5-yl]-ethoxy}-2-methyl-phenyl)-propionic acid

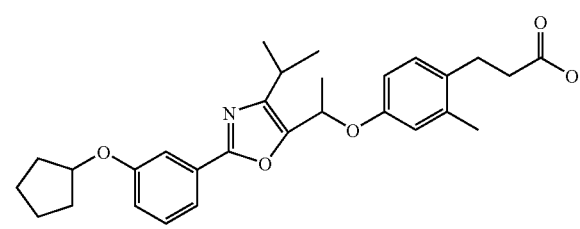

MS (ES): 478.3; the structure is also confirmed by proton NMR.

Example 124

3-[4-(1-{4-Isopropyl-2-[4-(tetrahydro-pyran-4-yloxy)-phenyl]-oxazol-5-yl}-ethoxy)-2-methyl-phenyl]-propionic acid

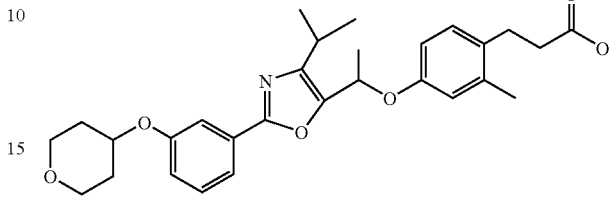

MS (ES): 494.2; the structure is also confirmed by proton NMR.

Example 125

3-(4-{1-[4-Isopropyl-2-(4-piperidin-1-yl-phenyl)-oxazol-5-yl]-ethoxy}-2-methyl-phenyl)-propionic acid

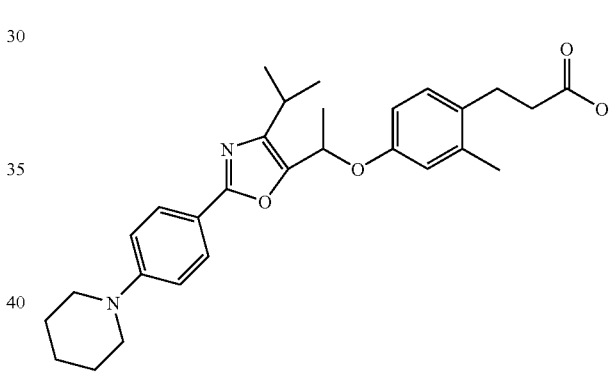

A solution of 3-(4-{1-[2-(4-bromo-phenyl)-4-isopropyl-oxazol-5-yl]-ethoxy}-2-methyl-phenyl)-propionic acid methyl ester (97 mg, 0.200 mmol) in toluene (5 ml) is bubbled with nitrogen for 10 minutes. To this solution is added piperidine (34 mg, 0.40 mmol), Pd(OAc)$_2$ (10 mg), 2-(di-t-butylphosphino)-biphenyl (10 mg) and sodium tert-butoxide (38 mg, 0.40 mmol). The suspension is heated to 100° C. for 8 hours and quenched with water (5 ml). The mixture is then extracted with EtOAc (3×10 mL) and the combined organics are dried over Na$_2$SO$_4$ and concentrated, purified by silica gel chromatography (Hexanes/EtOAc, 7.5/2.5) to afford the piperidine aniline intermediate as a colorless oil. The ester is then dissolved in MeOH (1.0 ml) and THF (0.5 ml) and treated with NaOH (2.0 N, 1.5 ml). The mixture is stirred at room temperature for 2 hours and concentrated to an aqueous residue. It is then neutralized with 5 N HCl to pH-4 and extracted with EtOAc (3×5 ml). The combined organics are dried over Na$_2$SO$_4$ and concentrated, purified by silica gel chromatography (Hexanes/EtOAc, 5/5, then Hexanes/EtOAc/HOAc 5/5/0.02) to afford the acid as a colorless oil (25 mg, 26%). MS (ES): 477.3 (M$^+$+1).

The following compounds are made in a similar manner:

Example 126

3-(4-{1-[4-Isopropyl-2-(3-morpholin-4-yl-phenyl)-oxazol-5-yl]-ethoxy}-2-methyl-phenyl)-propionic acid

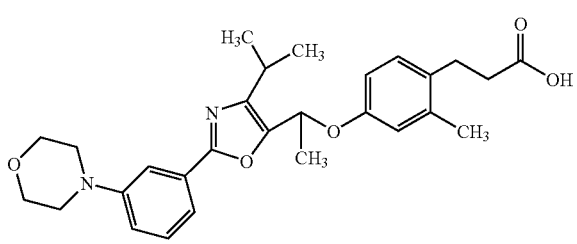

MS (ES): 479.3 (M⁺+1).

Example 127

3-(4-{1-[4-Isopropyl-2-(4-morpholin-4-yl-phenyl)-oxazol-5-yl]-ethoxy}-2-methyl-phenyl)-propionic acid

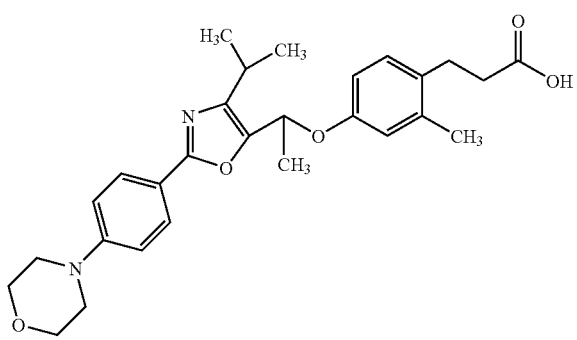

MS (ES): 479.3 (M⁺+1).

Example 128

3-(4-{1-[4-Isopropyl-2-(3-piperidin-1-yl-phenyl)-oxazol-5-yl]-ethoxy}-2-methyl-phenyl)-propionic acid

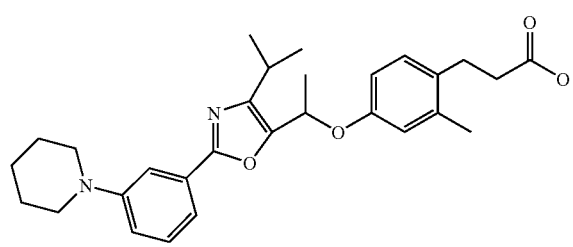

MS (ES): 477.4; the structure is also confirmed by proton NMR.

Example 129

3-{4-[1-(2-Biphenyl-4-yl-4-isopropyl-oxazol-5-yl)-ethoxy]-2-methyl-phenyl}-propionic acid

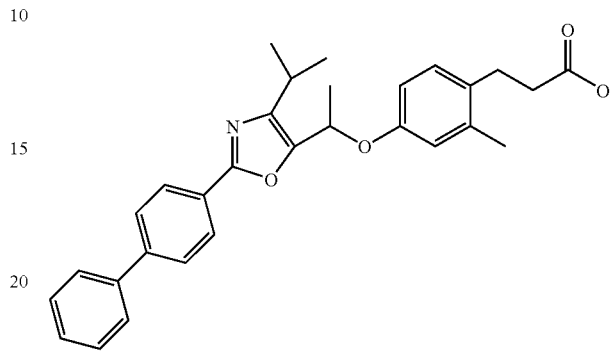

A solution of 3-(4-{1-[2-(4-bromo-phenyl)-4-isopropyl-oxazol-5-yl]-ethoxy}-2-methyl-phenyl)-propionic acid methyl ester (150 mg, 0.308 mmol) in toluene (4 ml) and THF (0.5 ml) is bubbled with nitrogen for 10 minutes. To this solution is added phenyl boronic acid (56 mg, 0.46 mmol), Pd(OAc)$_2$ (10 mg), and sodium carbonate (1.0 ml, 2.0 N). The suspension is heated to 85° C. for 8 hours and the mixture is then extracted with EtOAc (3×10 mL). The combined organics are dried over Na$_2$SO$_4$ and concentrated, purified by silica gel chromatography (Hexanes/EtOAc, 7.5/2.5) to afford the biphenyl intermediate as a colorless oil. The ester is then dissolved in MeOH (1.0 ml) and THF (0.5 ml) and treated with NaOH (2.0 N, 1.5 ml). The mixture is stirred at room temperature for 2 hours and concentrated to an aqueous residue. It is then neutralized with 5 N HCl to pH~4 and extracted with EtOAc (3×5 ml). The combined organics are dried over Na$_2$SO$_4$ and concentrated, purified by silica gel chromatography (Hexanes/EtOAc, 5/5, then Hexanes/EtOAc/HOAc 5/5/0.02) to afford the acid as a colorless oil (35 mg, 24%). MS (ES): 470.1 (M⁺+1).

Example 130

3-{4-[1-(2-Biphenyl-3-yl-4-isopropyl-oxazol-5-yl)-ethoxy]-2-methyl-phenyl}-propionic acid

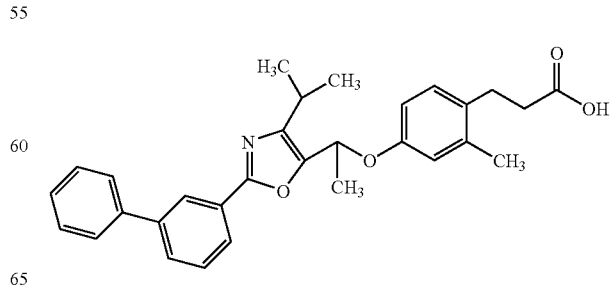

MS (ES): 470.2 (M⁺+1).

Example 131

3-(4-{1-[2-(3'-Fluoro-biphenyl-4-yl)-4-isopropyl-oxazol-5-yl]-ethoxy}-2-methyl-phenyl)-propionic acid

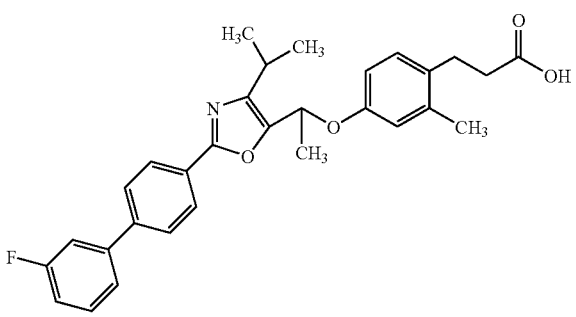

MS (ES): 488.2 (M⁺+1).

Example 132

3-(4-{1-[4-Isopropyl-2-(4'-methoxy-biphenyl-4-yl)-oxazol-5-yl]-ethoxy}-2-methyl-phenyl)-propionic acid

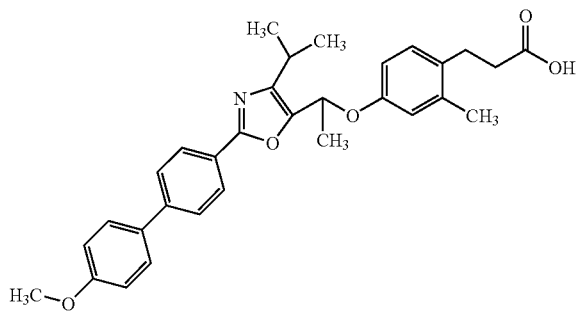

MS (ES) 500.2 (M⁺+1).

Example 133

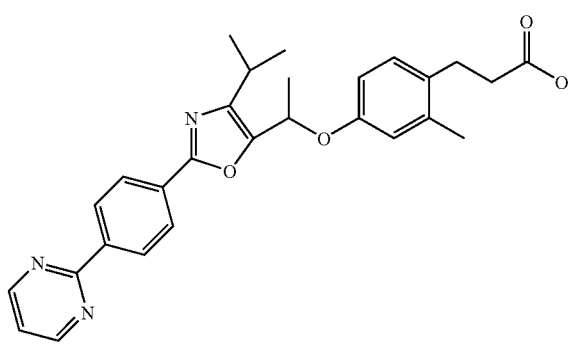

Example 134

3-(4-{1-[4-Isopropyl-2-(4-pyrimidin-2-yl-phenyl)-oxazol-5-yl]-ethoxy}-2-methyl-phenyl)-propionic acid A solution of 3-[4-(1-{4-isopropyl-2-[4-(4,4,5,5-tetramethyl-[1,3,2]dioxaborolan-2-yl)-phenyl]-oxazol-5-yl}-ethoxy)-2-methyl-phenyl]-propionic acid methyl ester (130 mg, 0.250 mmol) in toluene (3 mL) is bubbled with nitrogen gas for 10 minutes. To this, Pd(dppf)Cl₂ (10 mg), Na₂CO₃ (1.0 mL, 2.0 M), 2-chloropyrimidine (43 mg, 0.375 mmol) are added. The resulting suspension is stirred and heated at 100° C. for 8 hours and quenched with water (1.0 mL). The mixture is extracted with EtOAc (20 mL×2) and the combined organics are dried (Na₂SO₄), concentrated, and purified on silica gel chromatography column with 20–50% EtOAc/Hexanes to yield the pyrimidine intermediate.

The pyrimidine intermediate is dissolved in MeOH (1.0 mL) and THF (0.5 mL) and treated with NaOH (1.5 mL, 2.0 M) and stirred at room temperature for 12 hours. The mixture is neutralized to pH=6 with HCl (5 N) and extracted with EtOAc (20 mL×2), and the combined organics are dried (Na₂SO₄), concentrated to yield the acid as white solid (3.0 mg, 2.5%).

MS (ES): 472.3; the structure is also confirmed by proton NMR.

Example 134

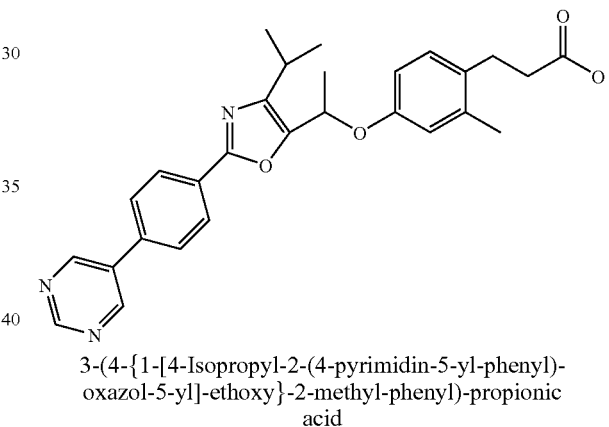

3-(4-{1-[4-Isopropyl-2-(4-pyrimidin-5-yl-phenyl)-oxazol-5-yl]-ethoxy}-2-methyl-phenyl)-propionic acid MS (ES): 472.3; the structure is also confirmed by proton NMR.

Example 135

3-(4-{1-[4-Isopropyl-2-(4-pyrazin-2-yl-phenyl)-oxazol-5-yl]-ethoxy}-2-methyl-phenyl)-propionic acid

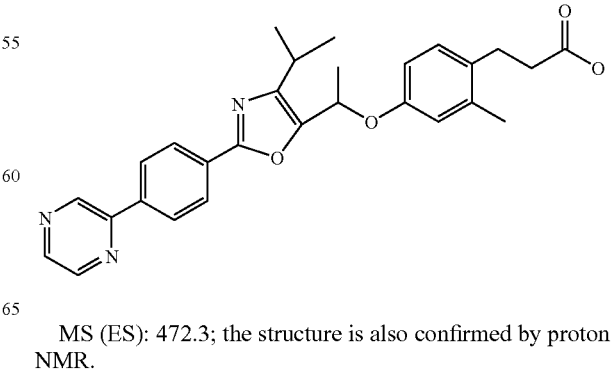

MS (ES): 472.3; the structure is also confirmed by proton NMR.

Example 136

3-(4-{1-[2-(4-Hexylcarbamoyl-phenyl)-4-isopropyl-oxazol-5-yl]-ethoxy}-2-methyl-phenyl)-propionic acid

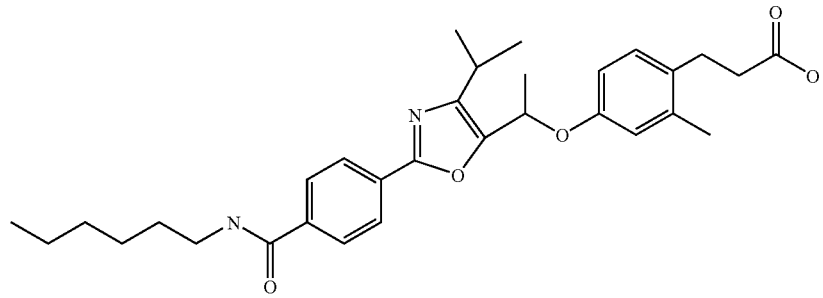

To a solution of of 3-(4-{1-[2-(4-bromo-phenyl)-4-isopropyl-oxazol-5-yl]-ethoxy}-2-methyl-phenyl)-propionic acid methyl ester (280 mg, 0.576 mmol) in acetonitrile (30 ml) is added the Pd$_2$Cl$_2$ (dppf) (15 mg) and hexyl amine (117 mg, 1.15 mmol). Triethyl amine (0.50 ml) is added and the mixture is stirred and heated to 75° C. under the balloon pressure of CO for 16 hours. The reaction mixture is filtered through a pad of celite and purified by silica gel chromatography (Hexanes/EtOAc, 6/4) to afford the amide ester intermediate as a colorless oil. The ester is then dissolved in MeOH (1.0 ml) and THF (0.5 ml) and treated with NaOH (2.0 N, 1.5 ml). The mixture is stirred at room temperature for 2 hours and concentrated to an aqueous residue. It is then neutralized with 5 N HCl to pH-4 and extracted with EtOAc (3×5 ml). The combined organics are dried over Na$_2$SO$_4$ and concentrated, purified by chromato lab with HPLC to afford the final product (3.9 mg, 1.3%).

Example 137

(4-{2-[4-Isopropyl-2-(4-trifluoromethyl-phenyl)-oxazol-5-yl]-propoxy}-2-methyl-phenyl)-acetic acid

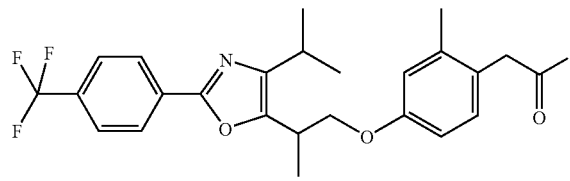

Step A (4-{2-[4-Isopropyl-2-(4-trifluoromethyl-phenyl)-oxazol-5-yl]-propoxy}-2-methyl-phenyl)-acetic acid methyl ester A mixture of 2-[4-Isopropyl-2-(4-trifluoromethyl-phenyl)-oxazol-5-yl]-propan-1-ol, (0.18 g, 0.5745 mmol), (4-Hydroxy-2-methyl-phenyl)-acetic acid methyl ester (0.114 g) and toluene (10 mL) and azodicarboxylic dipiperidide (0.19 g, 0.747 mmol) is stirred at −20 deg C. Neat tri-n-butyl phosphine (0.19 mL, 0.747 mmol) is added dropwise and the resulting mixture is allowed to reach room temperature with stirring 18 hr. The mixture is diluted with ether (25 mL) and cooled in ice/water for 30 min. The mixture is filtered, concentrated, and purified via silica gel chromatography eluting with 95:5 hexanes:ethyl acetate to afford the title compound as a thick oil, 0.065 g, 24%. MS M$^+$+1 476. The structure is confirmed by $^1$H NMR spectroscopy.

Step B (4-{2-[4-Isopropyl-2-(4-trifluoromethyl-phenyl)-oxazol-5-yl]-propoxy}-2-methyl-phenyl)-acetic acid (4-{2-[4-Isopropyl-2-(4-trifluoromethyl-phenyl)-oxazol-5-yl]-propoxy}-2-methyl-phenyl)-acetic acid methyl ester (0.065 g, 0.1367 mmol), lithium hydroxide (0.020 g, 0.8333 mmol) and 3:2:1 tetrahydrofuran:methanol:water (15 mL) is stirred at 60 deg C. 1 hr. The mixture is cooled on ice/water and diluted with 0.2 N aqueous hydrochloric acid. The product is extracted to ethyl acetate (2×50 mL), the extracts combined, dried over anhydrous magnesium sulfate, filtered and concentrated to afford the title compound as a white solid, 55 mg, 87%. MS M$^+$+1 462. The structure is confirmed by $^1$H NMR spectroscopy.

The following compounds are prepared in a similar manner.

Example 138

(2-Methyl-4-{1-[4-methyl-2-(4-trifluoromethyl-phenyl)-oxazol-5-yl]-ethoxy}-phenyl)-acetic acid

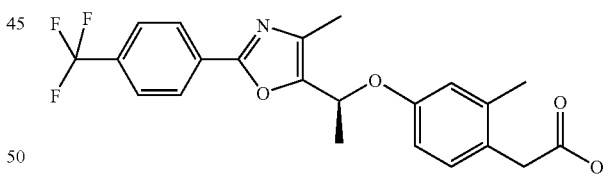

MS M$^+$+1 420. The structure is confirmed by $^1$H NMR spectroscopy.

Example 139

(3-{2-[4-Isopropyl-2-(4-trifluoromethyl-phenyl)-oxazol-5-yl]-propoxy}-phenyl)-acetic acid

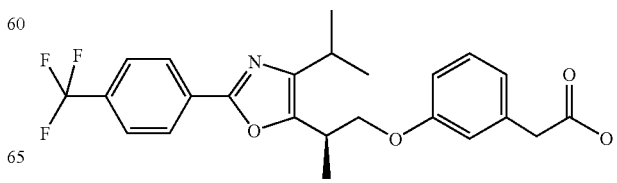

Step A (3-{2-[4-Isopropyl-2-(4-trifluoromethyl-phenyl)-oxazol-5-yl]-propoxy}-phenyl)-acetic acid methyl ester Azodicarboxylic dipiperidide (0.31 g, 1.23 mmol) is stirred in 5 mL toluene at −30 to −20 deg C. Tri-n-butyl phosphine (0.31 mL, 1.23 mmol) is added dropwise and the mixture is stirred at −30 to −20 deg C. 10–15 min. An intimate mixture of (3-hydroxy-phenyl)-acetic acid methyl ester (0.13 g, 0.77 mmol) and 2-[4-isopropyl-2-(4-trifluoromethyl-phenyl)-oxazol-5-yl]-propan-1-ol (0.20 g, 0.701 mmol) in toluene (5 mL) is added dropwise and the resulting mixture is stirred 18 hr at room temperature. The thick suspension is diluted with 25 mL ether and cooled on ice/water for 30 min. The mixture is filtered, concentrated, and purified via silica gel chromatography eluting with 98:2 hexanes:acetone to afford the title compound as a colorless thick oil, 0.10 g, 31%. MS M$^+$+1 462. The structure is confirmed by $^1$H NMR spectroscopy.

Step B (3-{2-[4-Isopropyl-2-(4-trifluoromethyl-phenyl)-oxazol-5-yl]-propoxy}-phenyl)-acetic acid Hydrolysis of the ester from step A gave the title compound. MS M$^+$+1 448. The structure is confirmed by $^1$H NMR spectroscopy.

The following examples are prepared in a similar manner:

Example 140

(3-{1-[4-Methyl-2-(4-trifluoromethyl-phenyl)-oxazol-5-yl]-ethoxy}-phenyl)-acetic acid

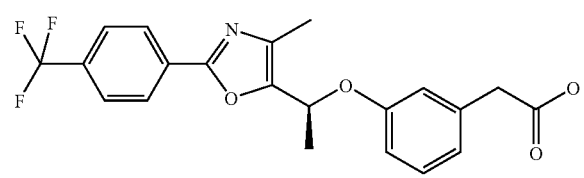

MS M$^+$+1 406. The structure is confirmed by $^1$H NMR spectroscopy.

Example 141

(3-{2-[5-Methyl-2-(4-trifluoromethyl-phenyl)-oxazol-4-yl]-propoxy}-phenyl)-acetic acid, enantiomer 1

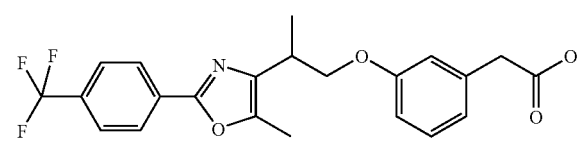

MS M$^+$+1 419. The structure is confirmed by $^1$H NMR spectroscopy.

Example 142

(3-{2-[5-Methyl-2-(4-trifluoromethyl-phenyl)-oxazol-4-yl]-propoxy}-phenyl)-acetic acid, enantiomer 2

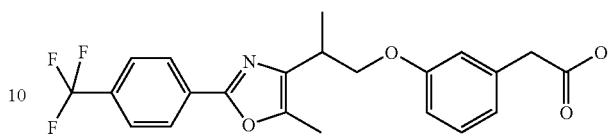

MS M$^+$+1 419. The structure is confirmed by $^1$H NMR spectroscopy.

Example 143

(3-{2-[4-Isopropyl-2-(4-trifluoromethyl-phenyl)-oxazol-5-yl]-propoxy}-4-methoxy-phenyl)-acetic acid

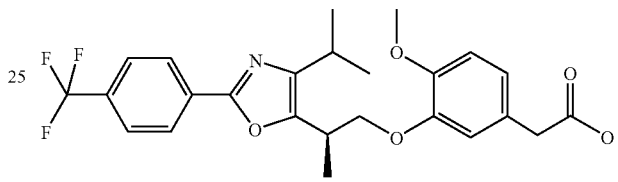

MS M$^+$+1 478. The structure is confirmed by $^1$H NMR spectroscopy.

Example 144

3-(3-{2-[4-Isopropyl-2-(4-trifluoromethyl-phenyl)-oxazol-5-yl]-propoxy}-phenyl)-propionic acid

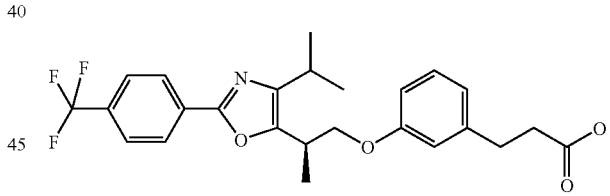

MS M$^+$+1 462. The structure is confirmed by $^1$H NMR spectroscopy.

The following example is prepared in a similar manner:

Example 145

3-(3-{1-[4-Methyl-2-(4-trifluoromethyl-phenyl)-oxazol-5-yl]-ethoxy}-phenyl)-propionic acid

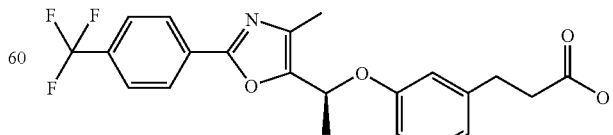

MS M$^+$+1 420. The structure is confirmed by $^1$H NMR spectroscopy.

Example 146

(3-{2-[4-Isopropyl-2-(4-trifluoromethyl-phenyl)-oxazol-5-yl]-propylsulfanyl}-phenyl)-acetic acid

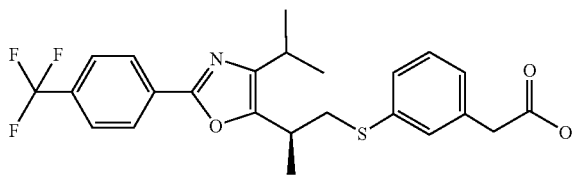

MS M⁺+1 464. The structure is confirmed by ¹H NMR spectroscopy.

Example 147

(3-{1-[4-Methyl-2-(4-trifluoromethyl-phenyl)-oxazol-5-yl]-ethylsulfanyl}-phenyl)-acetic acid

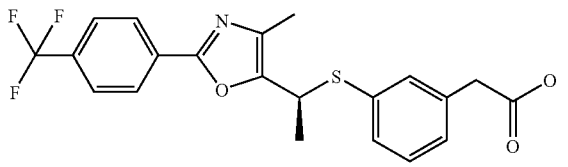

MS M⁺+1 422. The structure is confirmed by ¹H NMR spectroscopy.

Example 148

(3-{1-Methyl-1-[4-methyl-2-(4-trifluoromethyl-phenyl)-oxazol-5-yl]-ethylsulfanyl}-phenyl)-acetic acid

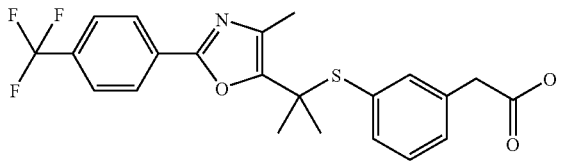

Step A

2-[4-Methyl-2-(4-trifluoromethyl-phenyl)-oxazol-5-yl]-propan-2-ol

1-[4-Methyl-2-(4-trifluoromethyl-phenyl)-oxazol-5-yl]-ethanone (0.58 g, 2.15 mmol) is stirred in tetrahydrofuran (25 mL) at zero deg. C. Methyl magnesium bromide (1.1 mL, 3.23 mmol, 3 M in ether) is added and the reaction stirred at room temperature 2 hr. The mixture is cooled on ice/water and quenched with saturated ammonium chloride (5 mL). The product is extracted with ethyl acetate (3×50 mL), dried over anhydrous magnesium sulfate, filtered and concentrated to afford the product as a tan solid, 0.40 g, 65%). MS M⁺+1 286. The structure is confirmed by ¹H NMR spectroscopy.

Step B (3-{1-Methyl-1-[4-methyl-2-(4-trifluoromethyl-phenyl)-oxazol-5-yl]-ethylsulfanyl}-phenyl)-acetic acid methyl ester A mixture of 2-[4-methyl-2-(4-trifluoromethyl-phenyl)-oxazol-5-yl]-propan-2-ol (0.1 g, 0.351 mmol), (3-Mercapto-phenyl)-acetic acid methyl ester (0.070 g, 0.386 mmol), zinc (I) iodide (0.056 g, 0.176 mmol), and 1,2-dichloroethane (2 mL) is stirred at room temperature 24 hr. The reaction mixture is diluted with ethyl acetate (25 mL), and washed with aqueous saturated sodium hydrogen carbonate, water, brine (25 mL each), dried over anhydrous magnesium sulfate, filtered, concentrated, and purified via silica chromatography eluting with 8:2 hexanes:ethyl acetate to afford the product as a colorless film, 0.105 g, 66%. MS M⁺+1 286. The structure is confirmed by ¹H NMR spectroscopy.

Step C (3-{1-Methyl-1-[4-methyl-2-(4-trifluoromethyl-phenyl)-oxazol-5-yl]-ethylsulfanyl}-phenyl)-acetic acid MS M⁺+1 436. The structure is confirmed by ¹H NMR spectroscopy.

Example 149

3-(2-Methyl-4-{1-[4-methyl-2-(4-trifluoromethyl-phenyl)-oxazol-5-yl]-ethoxymethyl}-phenyl)-propionic acid A mixture of 1-[4-Methyl-2-(4-trifluoromethyl-phenyl)-oxazol-5-yl]-ethanol (0.132 g, 0.487 mmol), sodium hydride (0.05 g, 1.25 mmol) and N,N-dimethyl formamide (5 mL) is stirred at room temperature. 3-(4-Iodomethyl-2-methyl-phenyl)-propionic acid methyl ester (0.17 g, 0.535 mmol) is added and the mixture is heated to 65 deg C., 2 hr. The reaction is cooled to room temperature and diluted with aqueous sodium hydroxide (10 mL, 5M) and stirred 1 hr. The pH is adjusted with aqueous hydrochloric acid until pH is 2–3. The product is extracted into ethyl acetate (3×25 mL). The combined extracts are dried over anhydrous magnesium sulfate, filtered and concentrated. The residue is purified via silica chromatography eluting with 7:3 hexanes: ethyl acetate to 1:1 hexanes:ethyl acetate to afford the title compound as a white solid, 0.027 g, 12%. MS M⁺+1 448. The structure is confirmed by ¹H NMR spectroscopy.

The following examples are prepared in a similar manner:

Example 150

3-(4-{1-[4-Isopropyl-2-(4-trifluoromethyl-phenyl)-oxazol-5-yl]-ethoxymethyl}-2-methyl-phenyl)-propionic acid

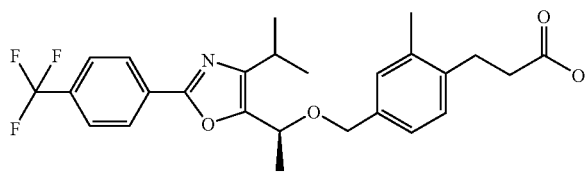

MS M$^+$+1 476. The structure is confirmed by $^1$H NMR spectroscopy.

Example 151

3-(4-{2-[2-(4-Difluoromethyl-phenyl)-4-isopropyl-oxazol-5-yl]-propoxymethyl}-2-methyl-phenyl)-propionic acid

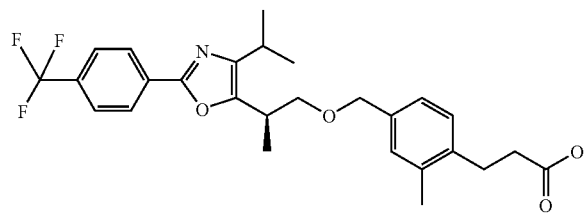

MS M$^+$+1 472. The structure is confirmed by $^1$H NMR spectroscopy.

Example 152

(4-{2-[4-Isopropyl-2-(4-trifluoromethyl-phenyl)-oxazol-5-yl]-propyl}-2-methyl-phenoxy)-acetic acid

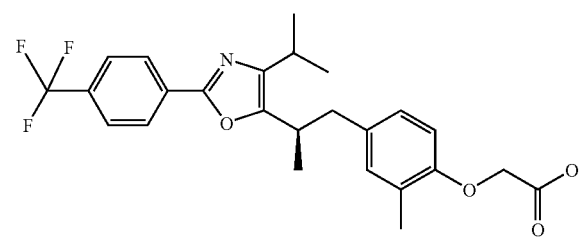

Step A

5-Isopropenyl-4-isopropyl-2-(4-trifluoromethyl-phenyl)-oxazole

4-Isopropyl-2-(4-trifluoromethyl-phenyl)-oxazole-5-carboxylic acid methyl ester (5.0 g, 15.3 mmol) and tetrahydrofuran (100 mL) are stirred in ice/water. Methyl magnesium bromide (12.7 mL, 38.2 mmol, 3M in ether) is added and the mixture is stirred at room temperature 3 hr. The reaction is cooled on ice/water and quenched with aqueous saturated ammonium chloride (15 mL). The product is extracted into ethyl acetate (3×50 mL). The combined extracts are dried over anhydrous magnesium sulfate, filtered, and concentrated. The residue is taken up in toluene (50 mL) and p-toluenesulfonic acid monohydrate (0.2 g, 1.05 mmol) is added and the mixture is heated to reflux for 1 hr. The mixture is concentrated and the residue is purified via silica chromatography eluting the product with hexanes to afford the product as a yellow solid, 4.17 g, 92%. MS M$^+$+1 296. The structure is confirmed by $^1$H NMR spectroscopy.

Step B (4-{2-[4-Isopropyl-2-(4-trifluoromethyl-phenyl)-oxazol-5-yl]-propyl}-2-methyl-phenoxy)-acetic acid methyl ester A mixture of 5-Isopropenyl-4-isopropyl-2-(4-trifluoromethyl-phenyl)-oxazole (0.5 g, 1.695 mmol), 9-BBN dimer (0.46 g, 1.865 mmol), and tetrahydrofuran (5 mL) is stirred at room temperature 6 hr. The mixture is diluted with water (1 mL). In another flask, a mixture of (4-bromo-2-methyl-phenoxy)-acetic acid methyl ester (0.53 g, 2.03 mmol), [1,1'-bis(diphenylphosphino)-ferrocene]dichloropalladium (II) complex with dichloromethane (1:1) (0.14 g, 0.17 mmol), triphenylarsine (0.1 g, 0.339 mmol), and N,N-dimethylformamide (5 mL) is stirred in ice/water. The previously described 9-BBN solution is added via cannula and the resulting mixture is stirred at room temperature 18 hr. The black reaction mixture is diluted with water (50 mL) and brine (50 mL), and the product is extracted to ethyl acetate (3×75 mL). The combined extracts are dried over anhydrous magnesium sulfate, filtered, and concentrated. The black residue is purified via silica chromatography eluting with 1:1 hexanes:dichloromethane to 1:1:0.5 hexanes:dichloromethane:ethyl acetate to afford the product as a colorless oil, 0.136 g, 17%. MS M$^+$+1 476. The structure is confirmed by $^1$H NMR spectroscopy.

Step C (4-{2-[4-Isopropyl-2-(4-trifluoromethyl-phenyl)-oxazol-5-yl]-propyl}-2-methyl-phenoxy)-acetic acid Hydrolysis of the ester from step B gave the title compound (0.015 g, 75%). MS M$^+$+1 462. The structure is confirmed by $^1$H NMR spectroscopy.

Example 153

3-(4-{2-[5-Ethyl-2-(4-trifluoromethyl-phenyl)-thiazol-4-yl]-propionylamino}-2-methyl-phenyl)-propionic acid

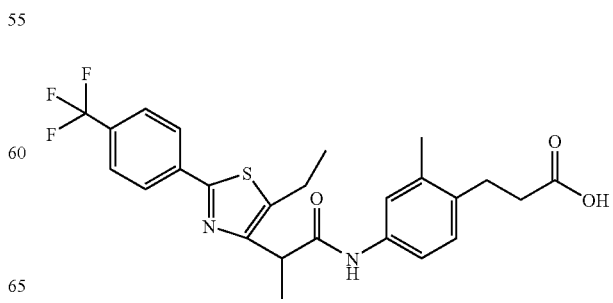

Step A

3-(4-{2-[5-Ethyl-2-(4-trifluoromethyl-phenyl)-thiazol-4-yl]-propionylamino}-2-methyl-phenyl)-propionic-acid methyl ester To a mixture of 2-[5-Ethyl-2-(4-trifluoromethyl-phenyl)-thiazol-4-yl]-propionic acid (0.35 mmol), 3-(4-Amino-2-methyl-phenyl)-propionic acid methyl ester (0.35 mmol), and DMAP (0.01 g, 0.082 mmol) in CH$_2$Cl$_2$ (5 mL) is added EDCI (0.08 g, 0.42 mmol). After stirring for 2 h at RT, the mixture is concentrated. The residue is redissolved in EtOAc, and the organics are washed with 1N HCl (1×), 2N NaOH (2×), water, and brine, and dried with MgSO$_4$. The crude material is purified by flash chromatography to yield the title compound.

Step B

3-(4-{2-[5-Ethyl-2-(4-trifluoromethyl-phenyl)-thiazol-4-yl]-propionylamino}-2-methyl-phenyl)-propionic acid Hydrolysis of the product from step one in the presence of sodium hydroxide gave the title compound. MS (ES): 491 (M$^+$+1); the structure is also confirmed by $^1$H NMR.

Example 154

3-[4-({2-[5-Ethyl-2-(4-trifluoromethyl-phenyl)-thiazol-4-yl]-propionyl}-methyl-amino)-2-methyl-phenyl]-propionic acid

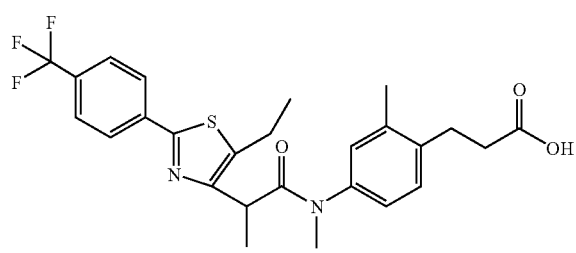

Step A

3-[4-({2-[5-Ethyl-2-(4-trifluoromethyl-phenyl)-thiazol-4-yl]-propionyl}-methyl-amino)-2-methyl-phenyl]-propionic acid methyl ester To a solution of 3-(4-{2-[5-Ethyl-2-(4-trifluoromethyl-phenyl)-thiazol-4-yl]-propionylamino}-2-methyl-phenyl)-propionoc acid methyl ester (0.09 g, 0.17 mmol) and methyl iodide (11 μL, 0.17 mmol) in DMF is added NaH (12 mg, 0.29 mmol). The mixture is stirred at RT for 12 h. Water is added, and the mixture is extracted with EtOAc. The organics are washed with brine and dried with MgSO$_4$. The crude material is purified by flash chromatography to yield the title compound (65 mg, 75%).

Step B

3-[4-({2-[5-Ethyl-2-(4-trifluoromethyl-phenyl)-thiazol-4-yl]-propionyl}-methyl-amino)-2-methyl-phenyl]-propionic acid A similar hydrolysis procedure is followed to yield the title compound (51 mg, 81%). MS (ES): 505 (M$^+$+1); the structure is also confirmed by $^1$H NMR.

Example 155

3-(4-{2-[4-Isopropyl-2-(4-trifluoromethyl-phenyl)-thiazol-5-yl]-propylamino}-2-methyl-phenyl)-propionic acid TFA salt

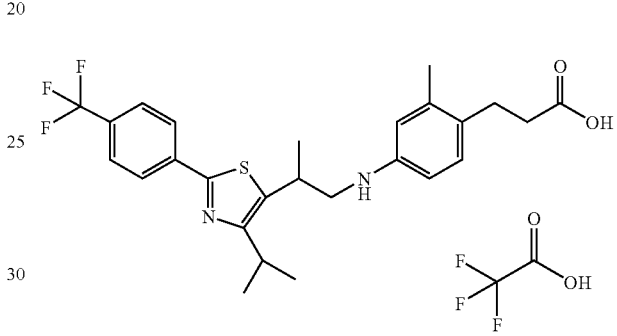

Step A

3-(4-{2-[4-Isopropyl-2-(4-trifluoromethyl-phenyl)-thiazol-5-yl]-propylamino}-2-methyl-phenyl)-propionic acid methyl ester To a solution of 3-(4-Amino-2-methyl-phenyl)-propionic acid methyl ester (0.7.0 mmol) and 2-[4-Isopropyl-2-(4-trifluoromethyl-phenyl)-thiazol-5-yl]-propionaldehyde (0.71 mmol) in anhydrous CH$_2$Cl$_2$ (5 mL) is added 4 Å molecular sieves followed by acetic acid (50 μL, 0.87 mmol). The mixture is stirred at RT for 2 h. Sodium triacetoxyborohydride (0.22 g, 1.04 mmol) is added, and the mixture is stirred at RT for 12 h. The reaction is quenched with saturated NaHCO$_3$. The organics are separated and washed with saturated NaHCO$_3$ and brine, and dried with MgSO$_4$. The crude material is purified by flash chromatography to yield the title compound (0.21 g, 68%).

Step B

3-(4-{2-[4-Isopropyl-2-(4-trifluoromethyl-phenyl)-thiazol-5-yl]-propylamino}-2-methyl-phenyl)-propionic acid TFA salt Hydrolysis of the ester product form step A foloowed by reversed phse HPLC purification gave the title compound. MS (ES): 491 (M$^+$); the structure is also confirmed by $^1$H NMR.

Example 156

3-{4-[({2-[4-Isopropyl-2-(4-trifluoromethyl-phenyl)-thiazol-5-yl]-propyl}-methyl-amino)-methyl]-2-methyl-phenyl}-propionic acid TFA salt

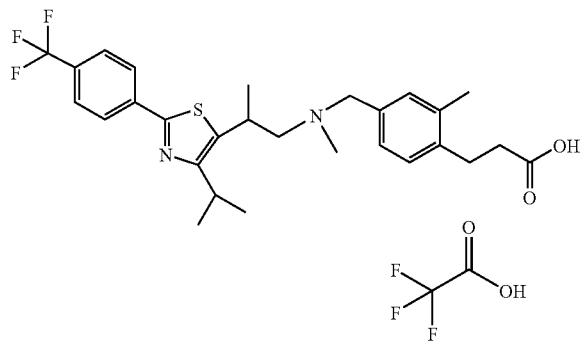

MS (ES): 519 (M$^+$); the structure is also confirmed by $^1$H NMR.

Example 157

3-[4-(2-{2-[6-(2-Fluoro-phenyl)-pyridin-3-yl]-5-methyl-thiazol-4-yl}-propoxy)-2-methyl-phenyl]-propionic acid

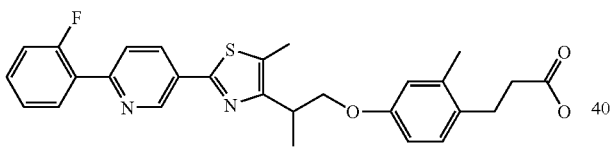

Step A 6-(2-Fluoro-phenyl)-nicotinonitrile

A mixture of 6-Chloro-nicotinonitrile (7.26 g, 52.4 mmol) and 2-fluorophenyl boronic acid (11 g, 78.6 mmol) and Na2CO3 (11 g, 103 mmol) in toluene (200 mL) and water (10 mL) is degassed and filled with nitrogen for three times, then Pd(PPh3)4 (0.73 g) is added under nitrogen. The reaction mixture is heated at 90° C. After 12 hrs, the reaction mixture is cooled to room temperature, diluted with ethyl acetate, washed with water, dried, concentrated. Column chromatography on silica gel (Hexane/ethyl acetate as eluent) gave 9.8 g of 6-(2-Fluoro-phenyl)-nicotinonitrile.

Step B 6-(2-Fluoro-phenyl)-thionicotinamide

A mixture of 6-(2-Fluoro-phenyl)-nicotinonitrile (9.8 g, 49.4 mmol) and thioacetamide (5.94 g, 79.1 mmol) in 4.0 M HCl in dioxane (200 mL) is heated at 100° C. for 3 days, cooled to room temperature. The raction mixture is poured into old saturated sodium bicarbonate and stirred for 30 min. Solid product is collected by filtration and dried under vacuum giving the title compound (11.4 g).

Step C

2-{2-[6-(2-Fluoro-phenyl)-pyridin-3-yl]-5-methyl-thiazol-4-yl}-propionic acid ethyl ester A mixture of 6-(2-Fluoro-phenyl)-thionicotinamide (3.0 g, 12 mmol) and 4-bromo-3-oxo-2-methyl-pentanoic acid methyl ester (3.2 g, 14.4 mmol) in ethanol (100 mL) is heated to reflux for 24 h, and concentrated. The residue is purified by column chromatography on silica gel yielding 2.6 g of the product.

Step D

2-{2-[6-(2-Fluoro-phenyl)-pyridin-3-yl]-5-methyl-thiazol-4-yl}-propan-1-ol

To a solution of 2-{2-[6-(2-Fluoro-phenyl)-pyridin-3-yl]-5-methyl-thiazol-4-yl}-propionic acid ethyl ester (2.6 g, 7.03 mmol) in THF (15 mL) is added LiAlH4 (1.0 M in THF, 7.1 mL, 7.1 mmol) at 0–5° C., and then stirred for 2 h. The reaction is then quenched by water and 5 N NaOH, diluted with THF and filtered through a pad of celite. The filtrate is concentrated and purified by column yielding 1.8 g of the product.

Step E

3-[4-(2-{2-[6-(2-Fluoro-phenyl)-pyridin-3-yl]-5-methyl-thiazol-4-yl}-ethoxy)-2-methyl-phenyl]-propionic acid tert-butyl ester A solution of 3-(4-hydroxy-2-methyl-phenyl)-propionic acid tert-butyl ester (120 mg, 0.5 mmol) and 2-{2-[6-(2-fluoro-phenyl)-pyridin-3-yl]-5-methyl-thiazol-4-yl}-ethanol (106 mg, 0.323 mmol) in toluene (3.0 mL) is degassed and filled with nitrogen for 3 times. Tributylphosphine (0.124 mL, 0.5 mmol) is added to the reaction mixture under nitrogen at 0° C., followed by addition of of 1,1'-(azodicarbonyl)-dipiperidine (120 mg, 0.5 mmol). The reaction mixture is allowed to warm to room temperature and stirred overnight, the mixture is loaded on silica gel column. Chromatography gave the title compound (150 mg).

Step F

3-[4-(2-{2-[6-(2-Fluoro-phenyl)-pyridin-3-yl]-5-methyl-thiazol-4-yl}-propoxy)-2-methyl-phenyl]-propionic acid To a solution of 3-[4-(2-{2-[6-(2-Fluoro-phenyl)-pyridin-3-yl]-5-methyl-thiazol-4-yl}-ethoxy)-2-methyl-phenyl]-propionic acid tert-butyl ester (120 mg) in methylene chloride (1 mL) is added TFA (0.8 mL) and two drops of water. The mixture is stirred for 2 h, and concentrated and purified by reversed phase HPLC (water-acetonitrile with 0.1% TFA). MS (ES): 491.4 (M$^+$+1).

The following compounds are made in substantially similar method:

Example 158

3-[4-(2-{2-[6-(3-Fluoro-phenyl)-pyridin-3-yl]-5-methyl-thiazol-4-yl}-propoxy)-2-methyl-phenyl]-propionic acid

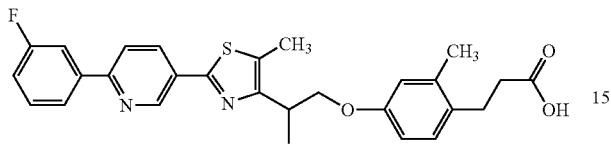

MS (ES): 491.3 (M$^+$+1).

Example 159

3-[4-(2-{2-[6-(4-Fluoro-phenyl)-pyridin-3-yl]-5-methyl-thiazol-4-yl}-propoxy)-2-methyl-phenyl]-propionic acid

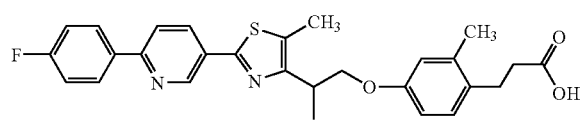

MS (ES): 491.3 (M$^+$+1).

Example 160

3-[4-(2-{2-[6-phenyl-pyridin-3-yl]-5-methyl-thiazol-4-yl}-propoxy)-2-methyl-phenyl]-propionic acid

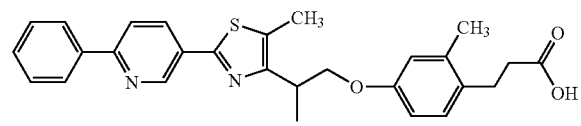

MS (ES): 473.5 (M$^+$+1).

Example 161

3-[4-(2-{2-[6-(2-Methyl-phenyl)-pyridin-3-yl]-5-methyl-thiazol-4-yl}-propoxy)-2-methyl-phenyl]-propionic acid

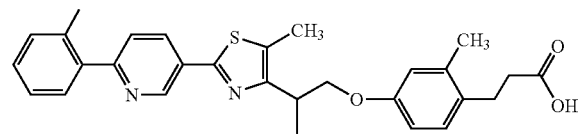

MS (ES): 487.4 (M$^+$+1).

Example 162

3-[4-(2-{2-[6-(3-Methyl-phenyl)-pyridin-3-yl]-5-methyl-thiazol-4-yl}-propoxy)-2-methyl-phenyl]-propionic acid

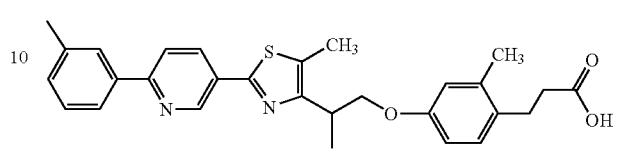

MS (ES): 487.5 (M$^+$+1).

Example 163

3-[4-(2-{2-[6-(4-Methyl-phenyl)-pyridin-3-yl]-5-methyl-thiazol-4-yl}-propoxy)-2-methyl-phenyl]-propionic acid

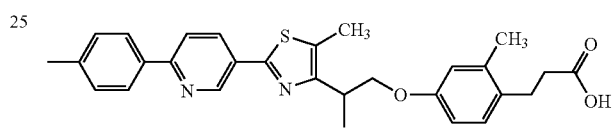

MS (ES): 487.5 (M$^+$+1).

Example 164

3-{4-[2-(2-[2,2']Bipyridinyl-5-yl-5-methyl-thiazol-4-yl)-propoxy]-2-methyl-phenyl}-propionic acid

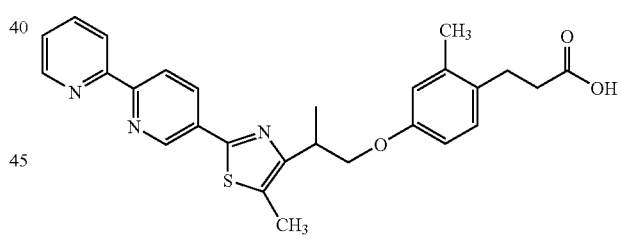

MS (ES): 474.4 (M$^+$+1).

Example 165

3-(2-Methyl-4-{2-[5-methyl-2-(6-phenoxy-pyridin-3-yl)-thiazol-4-yl]-propoxy}-phenyl)-propionic acid

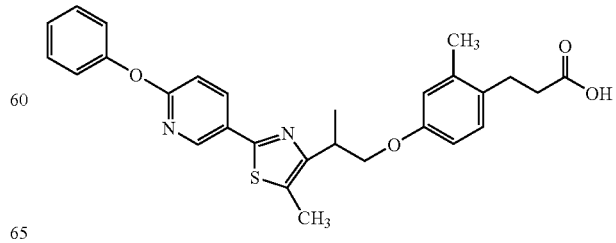

MS (ES): 489.5 (M$^+$+1).

Example 166

3-(2-Methyl-4-{2-[5-methyl-2-(4-pyridin-2-yl-phenyl)-oxazol-4-yl]-propoxy}phenyl)propionic acid

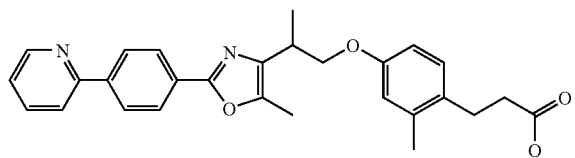

Step A 3-(2-Methyl-4-{2-[5-methyl-2-(4-pyridin-2-yl-phenyl)-oxazol-4-yl]-propoxy}phenyl)propionic acid methyl ester

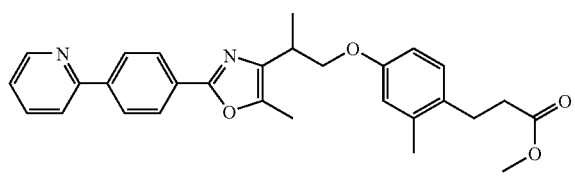

3-(4-{2-[2-(4-Bromo-phenyl)-5-methyl-oxazol-4-yl]-propoxy}-2-methylphenyl)-propionic acid methyl ester (592 mg, 1.25 mmol) is dissolved in anhydrous toluene (5 mL), degassed, and filled with nitrogen three times. Palladium tetrakis triphenyl phosphine [Pd(PPh$_3$)$_4$, 25 mg, 0.025 mmol] is added, and the degassing procedure is repeated. 2-tributylstannylpyridine (635 uL, 2.5 mmol) is then added via syringe and the reaction is heated to reflux. The reaction is monitored by HPLC. Upon complete consumption of starting material, the reaction is allowed to cool to room temperature and diluted with ethyl acetate. Celite is added and the mixture is filtered and rinsed with more ethyl acetate and water. The solution is further diluted with water and the two phases are separated. The organic layer is washed with water and brine, dried over anhydrous sodium sulfate, filtered, and concentrated. The pure 3-(2-Methyl-4-{2-[5-methyl-2-(4-pyridin-2-yl-phenyl)-oxazol-4-yl]-propoxy}-phenyl)-propionic acid methyl ester is obtained after column chromatography.

Step B 3-(2-Methyl-4-{2-[5-methyl-2-(4-pyridin-2-yl-phenyl)-oxazol-4-yl]-propoxy}-phenyl)-propionic acid methyl ester from step A is dissolved in tetrahydrofuran (1 mL) and 5N sodium hydroxide (1 mL) solution is added with stirring at room temperature. The reaction is heated to reflux and monitored by HPLC. Upon complete conversion, the reaction is allowed to cool to room temperature and neutralized with 5N hydrochloric acid (1 mL), diluted with ethyl acetate, and extracted. The organic layer is washed with water and brine, dried over anhydrous sodium sulfate, filtered, and concentrated. The pure 3-(2-Methyl-4-{2-[5-methyl-2-(4-pyridin-2-ylphenyl)oxazol-4yl]propoxy}phenyl)propionic acid (400 mg, 0.875 mmol) may also be obtained by recrystalization from ethyl acetate. 70% yield 2 steps, MS (ES): 457.2 (M$^+$+1).

The following compounds are made in a similar manner:

Example 167

3-(2-Methyl-4-{2-[5-methyl-2-(4-pyridin-2-yl-phenyl)-oxazol-4-yl]-butoxy}-phenyl)-propionic acid

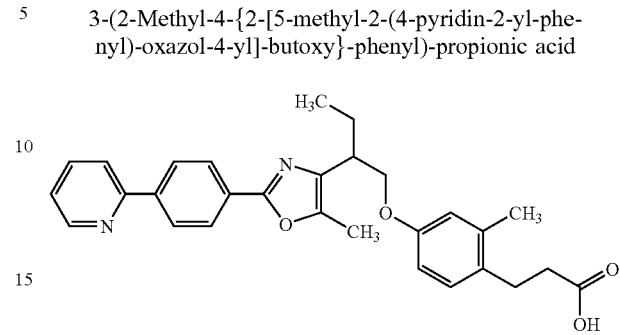

MS (ES): 471.3 (M$^+$+1).

Example 168

3-(2-Methyl-4-{1-methyl-2-[5-methyl-2-(4-pyridin-2-yl-phenyl)-oxazol-4-yl]-ethoxy}-phenyl)-propionic acid

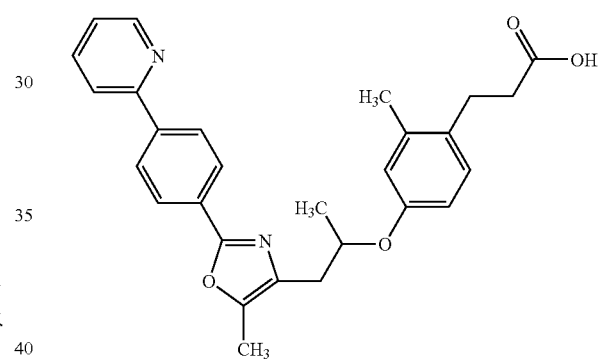

MS (ES): 457.3 (M$^+$+1).

Example 169

3-(2-Methyl-4-{2-[5-methyl-2-(4-pyridin-2-yl-phenyl)-thiazol-4-yl]-propoxy}-phenyl)-propionic acid, HCl salt

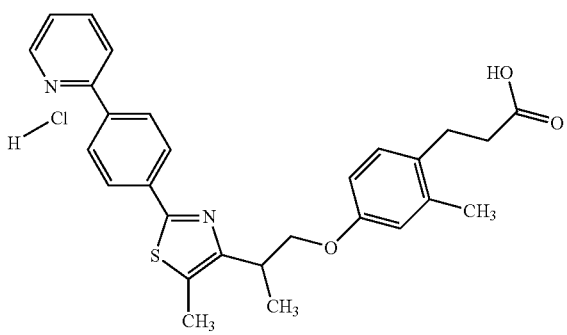

MS (ES): 457.3 (M$^+$+1-HCl).

Example 170

3-(2-Methyl-4-{2-[5-methyl-2-(4-pyridin-2-yl-phenyl)-thiazol-4-yl]-butoxy}-phenyl)-propionic acid, HCl salt

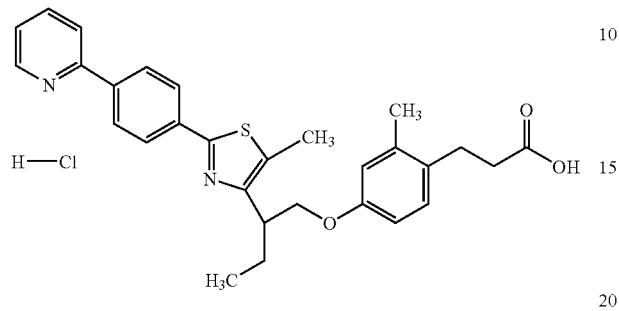

MS (ES): 487.5 (M+1-HCl).

Example 171

3-(2-Methyl-4-{2-[5-methyl-2-(4-pyrimidin-2-yl-phenyl)-thiazol-4-yl]-propoxy}-phenyl)-propionic acid

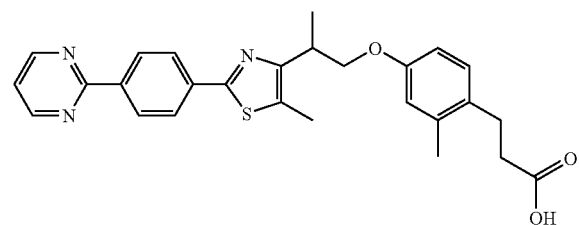

Step A

3-[2-Methyl-4-(2-{5-methyl-2-[4-(4,4,5,5-tetramethyl-[1,3,2]dioxaborolan-2-yl)-phenyl]-thiazol-4-yl}-propoxy)-phenyl]-propionic acid methyl ester

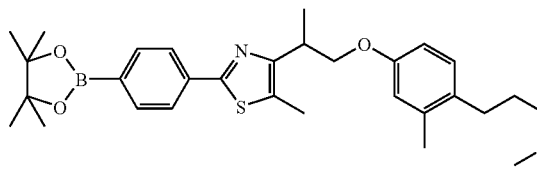

3-(4-{2-[2-(4-Bromo-phenyl)-5-methyl-thiazol-4-yl]-propoxy}-2-methyl-phenyl)-propionic acid methyl ester (3.38 g, 6.92 mmol) is dissolved in anhydrous methyl sulfoxide (25 mL), degassed, and filled with nitrogen three times. [1,1'-Bis-(diphenylphosphino)ferrocene]dichloropalladium(II) (330 mg, 0.346 mmol) bis(pinacolato)diboron (3.5 g, 13.84 mmol), and potassium acetate (2.0 g, 20.7 mmol) are added, and the degassing procedure is repeated. The reaction is heated to 90° C. and monitored by HPLC. Upon complete consumption of starting material, the reaction is allowed to cool to room temperature and diluted with ethyl acetate. Celite is added and the mixture is filtered and rinsed with more ethyl acetate and water. The solution is further diluted with water and the two phases are separated. The organic layer is washed with water and brine, dried over anhydrous sodium sulfate, filtered, and concentrated. The pure 3-[2-Methyl-4-(2-{5-methyl-2-[4-(4,4,5,5-tetramethyl-[1,3,2]dioxaborolan-2-yl)-phenyl]-thiazol-4-yl}-propoxy)-phenyl]-propionic acid methyl ester (5.2 g, 6.92 mmol) is obtained after column chromatography. 200% yield.

Step B 3-(2-Methyl-4-{2-[5-methyl-2-(4-pyrimidin-2-yl-phenyl)-thiazol-4-yl]-propoxy}-phenyl)-propionic acid methyl ester

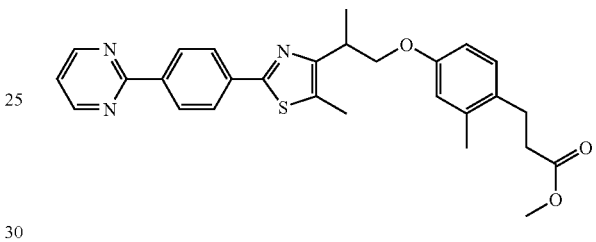

3-[2-Methyl-4-(2-{5-methyl-2-[4-(4,4,5,5-tetramethyl-[1,3,2]dioxaborolan-2-yl)-phenyl]-thiazol-4-yl)-propoxy)-phenyl]-propionic acid methyl ester (5.2 g, 6.92 mmol) is dissolved in anhydrous toluene (30 mL), degassed, and filled with nitrogen three times. [1,1'-Bis-(diphenylphosphino)ferrocene]dichloropalladium(II) (330 mg, 0.346 mmol), 2-bromopyrimidine (2.24 g, 14 mmol), and sodium carbonate (3.71 g in 5 mL water, 35 mmol) are added, and the degassing procedure is repeated. The reaction is heated to 100° C. and monitored by HPLC. Upon complete consumption of starting material, the reaction is allowed to cool to room temperature and diluted with ethyl acetate. Celite is added and the mixture is filtered and rinsed with more ethyl acetate and water. The solution is further diluted with water and the two phases are separated. The organic layer is washed with water and brine, dried over anhydrous sodium sulfate, filtered, and concentrated. The pure 3-(2-Methyl-4-{2-[5-methyl-2-(4-pyrimidin-2-yl-phenyl)-thiazol-4-yl]-propoxy}-phenyl)-propionic acid methyl ester (1.3 g, 2.87 mmol) is obtained after column chromatography (65% yield).

Step C 3-(2-Methyl-4-{2-[5-methyl-2-(4-pyrimidin-2-yl-phenyl)-thiazol-4-yl]-propoxy}-phenyl)-propionic acid methyl ester (698 mg, 1.43 mmol) is dissolved in tetrahydrofuran (2 mL) and 5N sodium hydroxide (2 mL) solution is added with stirring at room temperature. The reaction is heated to reflux and monitored by HPLC. Upon complete conversion, the reaction is allowed to cool to room temperature and neutralized with 5N hydrochloric acid (2 mL), diluted with ethyl acetate, and extracted. The organic layer is washed with water and brine, dried over anhydrous sodium sulfate, filtered, and concentrated. The pure 3-(2-Methyl-4-{2-[5-methyl-2-(4-pyrimidin-2-yl-phenyl)-thiazol-4-yl]-propoxy}-phenyl)-propionic acid (462 mg, 0.9755 mmol) may also be obtained by recrystalization from ethyl acetate (68% yield), MS (ES): ?? (M$^+$+1).

The following compounds are made in a similar manner:

Example 172

3-[2-Methyl-4-(2-{4-methyl-2-[4-(3-methyl-pyridin-2-yl)-phenyl]-thiazol-5-yl}-propoxy)-phenyl]-propionic acid

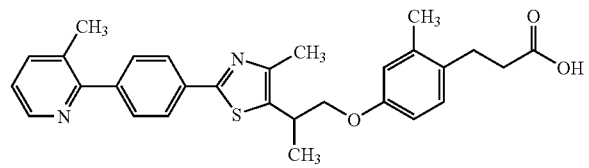

MS (ES) 487.2 (M$^+$+1).

Example 173

3-[2-Methyl-4-(2-{4-methyl-2-[4-(5-methyl-pyridin-2-yl)-phenyl]-thiazol-5-yl}-propoxy)-phenyl]-propionic acid

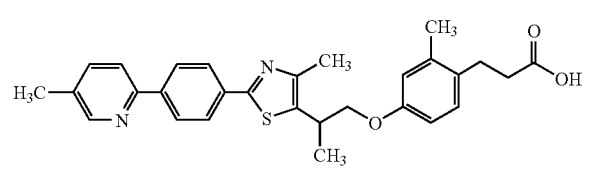

MS (ES): 487.3 (M$^+$+1).

Example 174

3-(2-Methyl-4-{2-[4-methyl-2-(4-pyridin-2-yl-phenyl)-thiazol-5-yl]-propoxy}-phenyl)-propionic acid

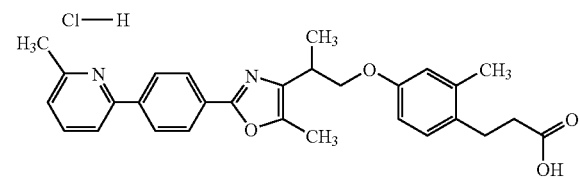

MS (ES): 473.2 (M$^+$+1).

Example 175

3-[2-Methyl-4-(2-{5-methyl-2-[4-(6-methyl-pyridin-2-yl)-phenyl]-oxazol-4-yl}-propoxy)-phenyl]-propionic acid, HCl salt

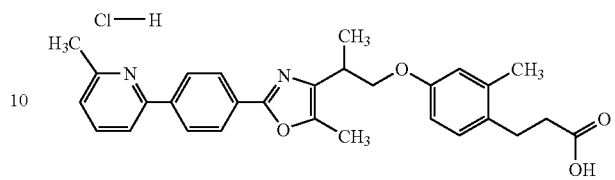

MS (ES): 471.2 (M$^+$+1-HCl).

Example 176

3-[2-Methyl-4-(2-{5-methyl-2-[4-(5-methyl-pyridin-2-yl)-phenyl]-oxazol-4-yl}-propoxy)-phenyl]-propionic acid, HCl salt

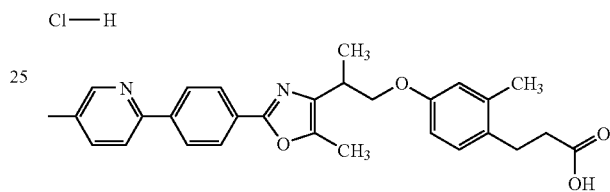

MS (ES): 471.2 (M$^+$+1-HCl).

Example 177

3-[2-Methyl-4-(2-{5-methyl-2-[4-(3-methyl-pyridin-2-yl)-phenyl]-oxazol-4-yl}-propoxy)-phenyl]-propionic acid, HCl salt

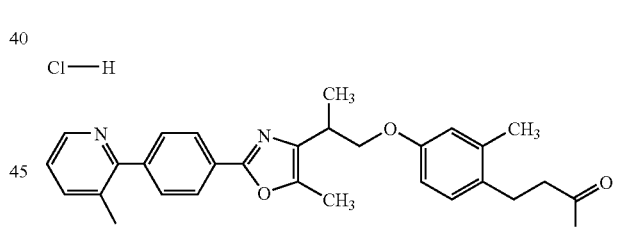

MS (ES): 471.2 (M$^+$+1-HCl).

Example 178

3-[2-Methyl-4-(2-{5-methyl-2-[4-(5-trifluoromethyl-pyridin-2-yl)-phenyl]-oxazol-4-yl}-propoxy)-phenyl]-propionic acid, HCl salt

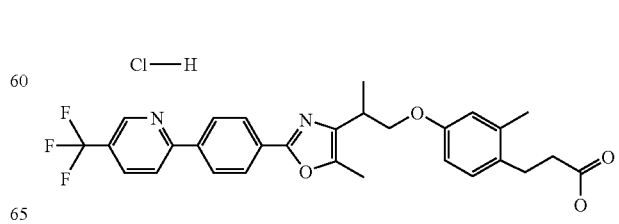

MS (ES) 525.6 (M$^+$+1-HCl).

Example 179

3-(4-{2-[4-Isopropyl-2-(4-pyridin-3-yl-phenyl)-thiazol-5-yl]-propoxy}-2-methyl-phenyl)-propionic acid, HCl salt

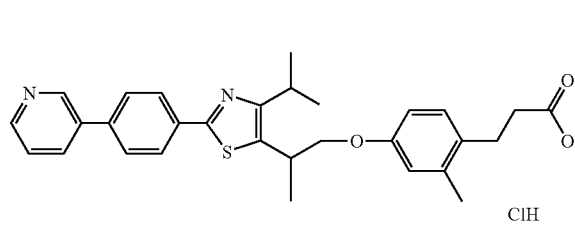

Step A 3-(4-{2-[2-(4-Bromo-phenyl)-4-isopropyl-thiazol-5-yl]-propoxy}-2-methyl-phenyl)-propionic acid methyl ester (333 mg, 0.645 mmol) is dissolved in toluene (3 mL), degassed, and filled with nitrogen three times. Palladium tetrakistriphenyl phosphine (10 mg, 0.010 mmol), 3-pyridylboronic acid (159 mg, 1.29 mmol), and sodium carbonate (320 uL of a 10M solution, 3.22 mmol) are added, and the degassing procedure is repeated. Ethanol (1 mL) is added to dissolve the boronic acid. The reaction is heated to 100° C. and monitored by HPLC. Upon complete consumption of starting material, the reaction is allowed to cool to room temperature and diluted with ethyl acetate. Celite is added and the mixture is filtered and rinsed with more ethyl acetate and water. The solution is further diluted with water and the two phases are separated. The organic layer is washed with water and brine, dried over anhydrous sodium sulfate, filtered, and concentrated. The pure 3-(4-{2-[4-Isopropyl-2-(4-pyridin-3-yl-phenyl)-thiazol-5-yl]-propoxy)-}-2-methyl-phenyl)-propionic acid methyl ester is obtained after column chromatography.

Step B 3-(4-{2-[4-Isopropyl-2-(4-pyridin-3-yl-phenyl)-thiazol-5-yl]-propoxy}-2-methyl-phenyl)-propionic acid methyl ester from step A is dissolved in tetrahydrofuran (1 mL) and 5N sodium hydroxide (1 mL) solution is added at room temperature. The reaction is heated to reflux and monitored by HPLC. Upon complete conversion, the reaction is allowed to cool to room temperature and neutralized with 5N hydrochloric acid (1 mL), diluted with ethyl acetate, and extracted. The organic layer is washed with water and brine, dried over anhydrous sodium sulfate, filtered, and concentrated. The pure 3-(4-{2-[4-Isopropyl-2-(4-pyridin-3-yl-phenyl)-thiazol-5-yl]-propoxy}-2-methyl-phenyl)-propionic acid (86 mg, 0.172 mmol, 27% yield) may also be obtained by recrystalization from ethyl acetate. MS (ES): 501.1 (M$^+$+1-HCl).

The following compound is made in a similar manner:

Example 180

3-(4-{2-[4-Isopropyl-2-(4-pyridin-4-yl-phenyl)-thiazol-5-yl]-propoxy}-2-methyl-phenyl)-propionic acid, HCl salt

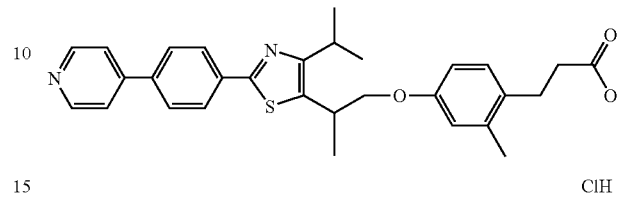

MS (ES): 501.1 (M$^+$+1-HCl).

Example 181

3-(2-Methyl-4-{2-[5-methyl-2-(4-phenylsulfanyl-phenyl)-oxazol-4-yl]-propoxy}-phenyl)-propionic acid

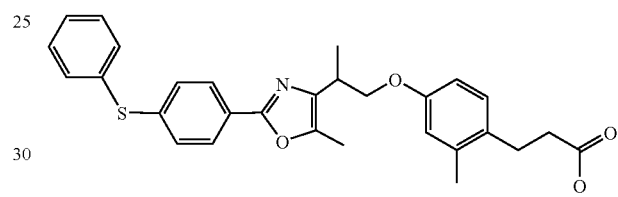

Step A

A solution of 2-[5-Methyl-2-(4-phenylsulfanyl-phenyl)-oxazol-4-yl]-propan-1-ol (457 mg, 1.40 mmol) in anhydrous toluene (20 mL) is degassed and filled with nitrogen for three times, and cooled to 0° C. in an ice water bath. Tri-n-butylphosphine (530 uL, 2.1 mmol) is added to the reaction mixture under nitrogen at 0° C., followed by addition of of 1,1'-(azodicarbonyl)-dipiperidine (530 mg, 2.1 mmol), and 3-(4-Hydroxy-2-methyl-phenyl)-propionic acid methyl ester (339 mg, 1.75 mmol). The reaction mixture is allowed to warm to room temperature and stirred overnight, the mixture is loaded on silica gel column. Chromatography gave 3-(2-Methyl-4-{2-[5-methyl-2-(4-phenyl-sulfanyl-phenyl)-oxazol-4-yl]-propoxy)-phenyl)-propionic acid methyl ester.

Step B 3-(2-Methyl-4-{2-[5-methyl-2-(4-phenyl-sulfanyl-phenyl)-oxazol-4-yl]-propoxy}-phenyl)-propionic acid methyl ester from step A is dissolved in tetrahydrofuran (1 mL) and 5N sodium hydroxide (1 mL) solution is added with stirring at room temperature. The reaction is heated to reflux and monitored by HPLC. Upon complete conversion, the reaction is allowed to cool to room temperature and neutralized with 5N hydrochloric acid (1 mL), diluted with ethyl acetate, and extracted. The organic layer is washed with water and brine, dried over anhydrous sodium sulfate, filtered, and concentrated. The pure 3-(2-Methyl-4-(2-[5-methyl-2-(4-phenylsulfanyl-phenyl)-oxazol-4-yl]-propoxy}-phenyl)-propionic acid (150 mg, 0.308 mmol) may also be obtained by recrystalization from ethyl acetate (22% yield 2 steps), MS (ES): 489.2 (M$^+$+1).

The following compounds are made in a similar manner:

Example 182

(S)-3-(2-Methyl-4-{2-[5-methyl-2-(4-phenylsulfanyl-phenyl)-oxazol-4-yl]-propoxy}-phenyl)-propionic acid

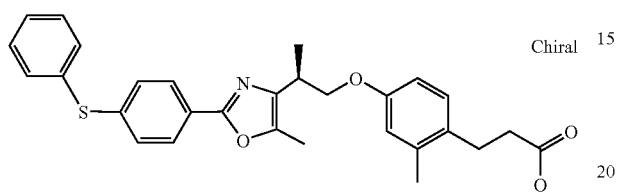

Chiral

MS (ES) 489.1 (M$^+$+1).

Example 183

(R)-3-(2-Methyl-4-{2-[5-methyl-2-(4-phenylsulfanyl-phenyl)-oxazol-4-yl]-propoxy}-phenyl)-propionic acid

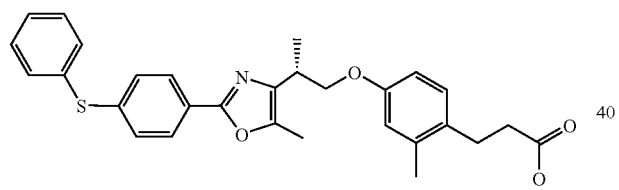

MS (ES): 489.1 (M$^+$+1).

Example 184

3-(2-Methyl-4-{2-[5-methyl-2-(4-phenylsulfanyl-phenyl)-oxazol-4-yl]-propoxy}-phenyl)-propionic acid

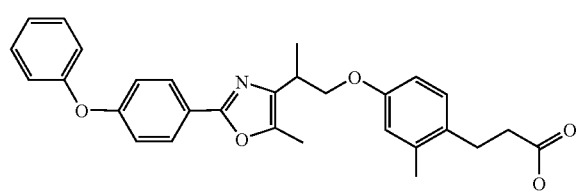

MS (ES): 473.6 (M$^+$+1).

Example 185

3-(2-Methyl-4-{2-[5-methyl-2-(6-phenyl-pyridin-3-yl)-oxazol-4-yl]-propoxy}-phenyl)-propionic acid

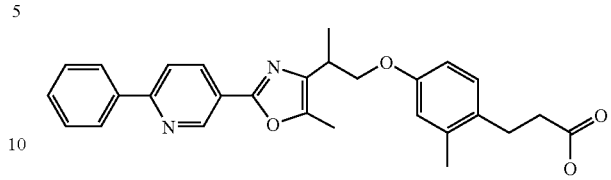

MS (ES): 457.2 (M$^+$+1).

Example 186

3-(4-{2-[4-Isopropyl-2-(4-pyrimidin-2-yl-phenyl)-oxazol-5-yl]-propoxy}-2-methyl-phenyl)-propionic acid

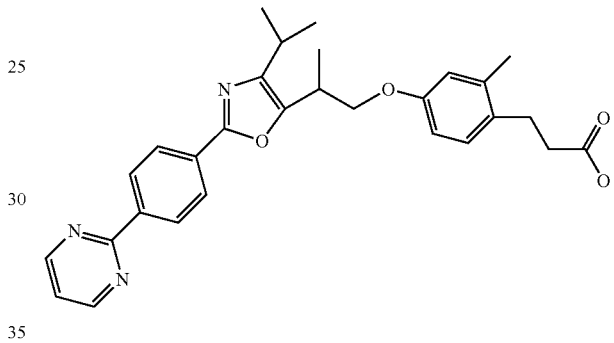

Step A 3-(4-{2-[2-(4-Bromo-phenyl)-4-isopropyl-oxazol-5-yl]-propoxy}-2-methyl-phenyl)-propionic acid methyl ester

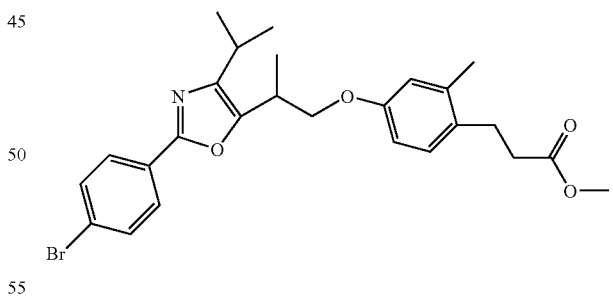

A solution of 2-[2-(4-bromo-phenyl)-4-isopropyl-oxazol-5-yl]-propan-1-ol (225 mg, 0.694 mmol) and 3-(4-hydroxy-2-methyl-phenyl)-propionic acid methyl ester (190 mg, 0.972 mmol) in toluene (15 mL) is degassed and filled with nitrogen for 3 times. Tributylphosphine (224 mg, 1.11 mmol) is added to the reaction mixture under nitrogen at 0° C., followed by addition of of 1,1'-(azodicarbonyl)-dipiperidine (280 mg, 1.11 mmol). The reaction mixture is allowed to warm to room temperature and stirred overnight, the mixture is loaded directly on silica gel column chromatography with 10–15% EtOAc/Hexanes to afford the title compound (320 mg, 92%).

Step B

3-[4-(2-{4-Isopropyl-2-[4-(4,4,5,5-tetramethyl-[1,3,2]dioxaborolan-2-yl)-phenyl]-oxazol-5-yl}-propoxy)-2-methyl-phenyl]-propionic acid methyl ester

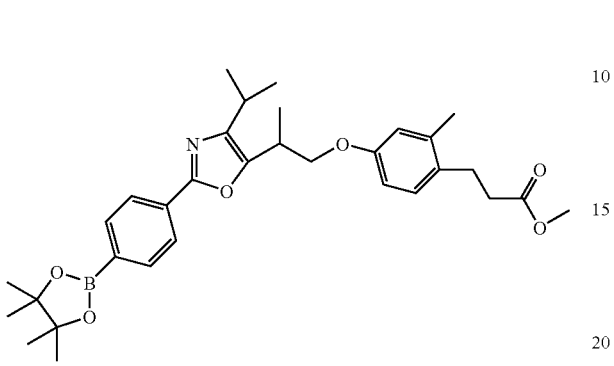

To a solution of 3-(4-{2-[2-(4-Bromo-phenyl)-4-isopropyl-oxazol-5-yl]-propoxy}-2-methyl-phenyl)-propionic acid methyl ester (0.871 g, 1.74 mmol) in DMSO (10 mL) is added bis(pinacolato)diboron (0.663 g, 2.61 mmol) and KOAc (0.682 g, 6.96 mmol). The suspension is bubbled with nitrogen gas for 10 minutes and then is treated with Pd(dppf)Cl$_2$ (20 mg) The mixture is then stirred and heated at 85° C. for 6 hours. The reaction is quenched water (50 mL) and extracted with EtOAc (50 mL×2) and the combined organics are dried (Na$_2$SO$_4$), concentrated and purified on silica gel chromatography column with 20% EtOAc/Hexanes to yield the title compound as yellowish oil (0.825 g, 87%). MS (ES): 548.3.

Step C 3-(4-{2-[4-Isopropyl-2-(4-pyrimidin-2-yl-phenyl)-oxazol-5-yl]-propoxy}-2-methyl-phenyl)-propionic acid A solution of 3-[4-(2-{4-isopropyl-2-[4-(4,4,5,5-tetramethyl-[1,3,2]dioxaborolan-2-yl)-phenyl]-oxazol-5-yl}-propoxy)-2-methyl-phenyl]-propionic acid methyl ester (91 mg, 0.166 mmol) in toluene (4.0 mL) is bubbled with nitrogen gas for 10 minutes. To this, Pd(dppf)Cl$_2$ (10 mg), Na$_2$CO$_3$ (1.0 mL, 2.0 M), 2-bromopyrimidine (53 mg, 0.333 mmol) are added. The resulting suspension is stirred and heated at 90° C. for 48 hours. It is then concentrated, purified on silica gel chromatography column with 20–40% EtOAc/Hexanes to yield the pyrimidine intermediate.

The pyrimidine intermediate is dissolved in MeOH (1.0 mL) and THF (0.5 mL) and treated with NaOH (1.5 mL, 2.0 M) and stirred at room temperature for 2 hours. The mixture is neutralized to pH=6 with HCl (5 N) and extracted with EtOAc (20 mL×2), and the combined organics are dried (Na$_2$SO$_4$), concentrated and purified on silica gel chromatography column with EtOAc/Hexanes/HOAc (50/50/2) to yield the acid as white solid (14 mg, 18%). MS (ES): 486.2; the structure is also confirmed by proton NMR.

The following compounds are made in a similar manner:

Example 187

3-(4-{1-[4-Isopropyl-2-(4-pyridin-2-yl-phenyl)-oxazol-5-yl]-ethoxy}-2-methyl-phenyl)-propionic acid

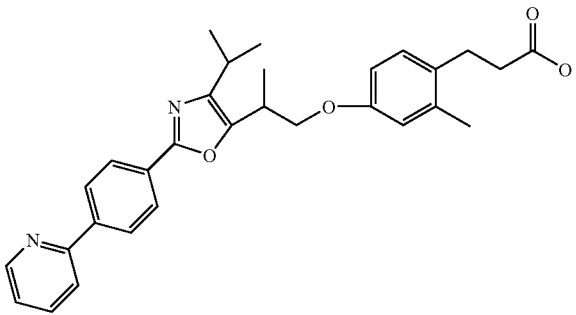

MS (ES): 485.2; the structure is also confirmed by proton NMR.

Example 188

3-(4-{2-[4-Isopropyl-2-(4-pyrazin-2-yl-phenyl)-oxazol-5-yl]-propoxy}-2-methyl-phenyl)-propionic acid

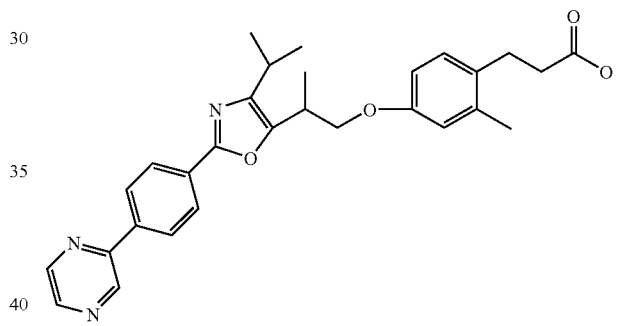

MS (ES): 486.2; the structure is also confirmed by proton NMR.

Example 189

3-(4-{1-[4-Isopropyl-2-(4-pyrimidin-2-yl-phenyl)-oxazol-5-yl]-ethoxy}-2-methyl-phenyl)-propionic acid

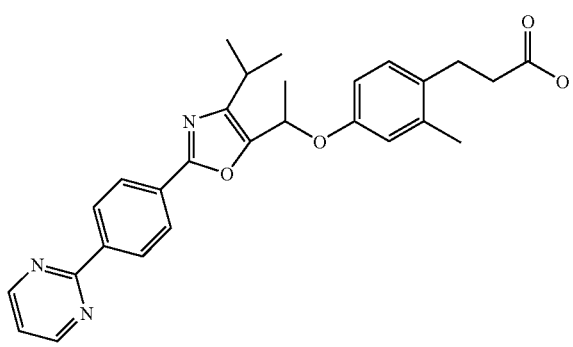

Step A 3-(4-{1-[2-(4-Bromo-phenyl)-4-isopropyl-oxazol-5-yl]-ethoxy}-2-methyl-phenyl)-propionic acid methyl ester

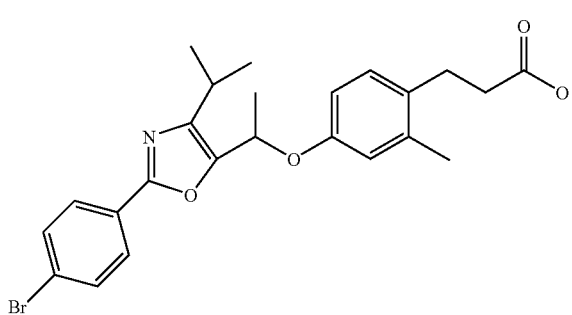

A solution of 3-(4-hydroxy-2-methyl-phenyl)-propionic acid methyl ester (6.30 g, 32.1 mmol) and 1-[2-(4-bromo-phenyl)-4-isopropyl-oxazol-5-yl]-ethanol (9.05 g, 29.2 mmol) in toluene (300 mL) is degassed and filled with nitrogen for 3 times. Tributylphosphine (7.70 g, 38.1 mmol) is added to the reaction mixture under nitrogen at 0° C., followed by addition of of 1,1'-(azodicarbonyl)-dipiperidine (8.84 g, 35.0 mmol). The reaction mixture is allowed to warm to room temperature and stirred overnight, the mixture is loaded directly on silica gel column chromatography with 10–15% EtOAc/Hexanes to afford the title compound (11.8 g, 79%).

Step B

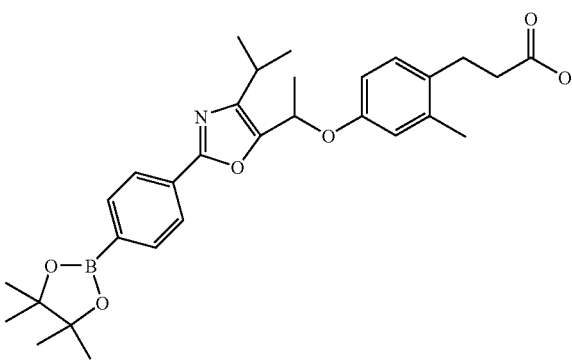

3-[4-(1-{4-Isopropyl-2-[4-(4,4,5,5-tetramethyl-[1,3,2]dioxaborolan-2-yl)-phenyl]-oxazol-5-yl}-ethoxy)-2-methyl-phenyl]-propionic acid methyl ester To a solution of 3-(4-{1-[2-(4-bromo-phenyl)-4-isopropyl-oxazol-5-yl]-ethoxy}-2-methyl-phenyl)-propionic acid methyl ester (2.50 g, 5.14 mmol) in DMSO (50 mL) is added bis(pinacolato)diboron (1.88 g, 7.40 mmol) and KOAc (1.94 g, 19.8 mmol). The suspension is bubbled with nitrogen gas for 10 minutes and then is treated with Pd(dppf)Cl₂ (100 mg) The mixture is then stirred and heated at 85° C. for 4 hours. The reaction is quenched water and extracted with EtOAc (50 mL×3) and the combined organics are dried (Na₂SO₄), concentrated and purified on silica gel chromatography column with 10–20% EtOAc/Hexanes to yield the title compound as yellow oil (1.68 g, 61%).

Step C 3-(4-{1-[4-Isopropyl-2-(4-pyrimidin-2-yl-phenyl)-oxazol-5-yl]-ethoxy}-2-methyl-phenyl)-propionic acid A solution of 3-[4-(1-{4-isopropyl-2-[4-(4,4,5,5-tetramethyl-[1,3,2]dioxaborolan-2-yl)-phenyl]-oxazol-5-yl}-ethoxy)-2-methyl-phenyl]-propionic acid methyl ester (130 mg, 0.250 mmol) in toluene (3 mL) is bubbled with nitrogen gas for 10 minutes. To this, Pd(dppf)Cl₂ (10 mg), Na₂CO₃ (1.0 mL, 2.0 M), 2-chloropyrimidine (43 mg, 0.375 mmol) are added. The resulting suspension is stirred and heated at 100° C. for 8 hours and quenched with water (1.0 mL). The mixture is extracted with EtOAc (20 mL×2) and the combined organics are dried (Na₂SO₄), concentrated, and purified on silica gel chromatography column with 20–50% EtOAc/Hexanes to yield the pyrimidine intermediate.

The pyrimidine intermediate is dissolved in MeOH (1.0 mL) and THF (0.5 mL) and treated with NaOH (1.5 mL, 2.0 M) and stirred at room temperature for 12 hours. The mixture is neutralized to pH=6 with HCl (5 N) and extracted with EtOAc (20 mL×2), and the combined organics are dried (Na₂SO₄), concentrated to yield the acid as white solid (3.0 mg, 2.5%). MS (ES): 472.3; the structure is also confirmed by proton NMR.

The following compounds are made in a similar manner:

Example 190

3-(4-{1-[4-Isopropyl-2-(4-pyrimidin-5-yl-phenyl)-oxazol-5-yl]-ethoxy}-2-methyl-phenyl)-propionic acid

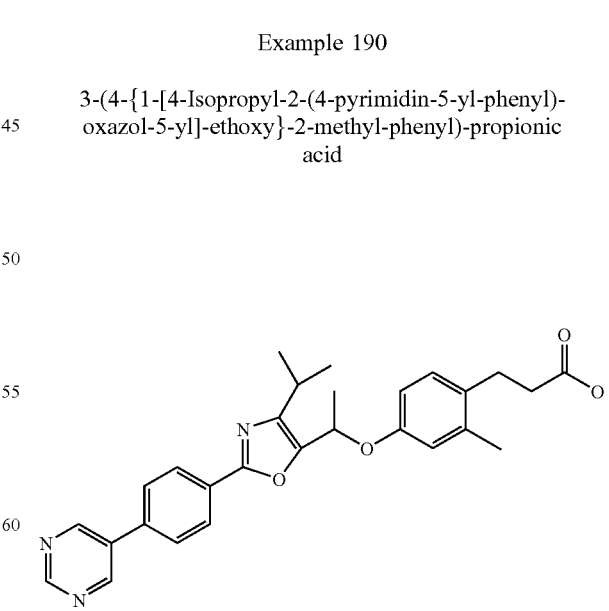

MS (ES): 472.3; the structure is also confirmed by proton NMR.

Example 191

3-(4-{1-[4-Isopropyl-2-(4-pyrazin-2-yl-phenyl)-oxazol-5-yl]-ethoxy}-2-methyl-phenyl)-propionic acid

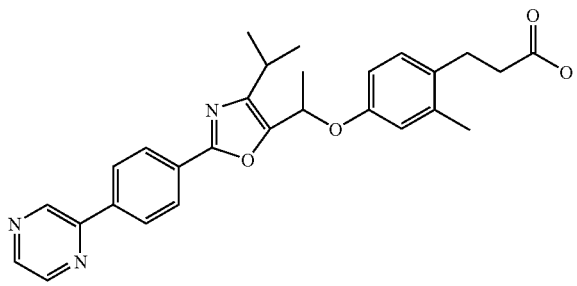

MS (ES): 472.3; the structure is also confirmed by proton NMR.

Example 192

3-(4-{2-[4-Isopropyl-2-(4-pyrimidin-5-yl-phenyl)-thiazol-5-yl]-propoxy}-2-methyl-phenyl)-propionic acid

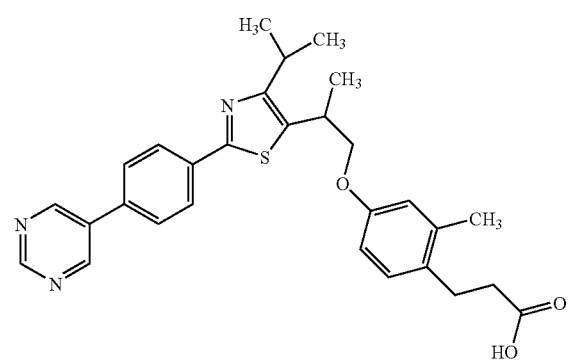

MS (ES): 502.1 (M$^+$+1).

Example 193

3-(2-Methyl-4-{2-[5-methyl-2-(4-pyrimidin-2-yl-phenyl)-oxazol-4-yl]-propoxy}-phenyl)-propionic acid

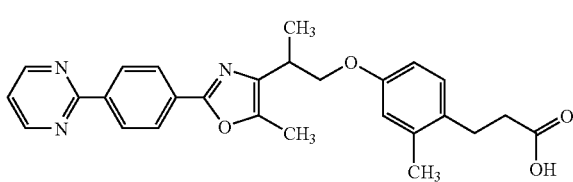

MS (ES): 458.2 (M$^+$+1).

Example 194

3-(2-Methyl-4-{2-[5-methyl-2-(4-pyrimidin-2-yl-phenyl)-thiazol-4-yl]-propoxy}-phenyl)-propionic acid

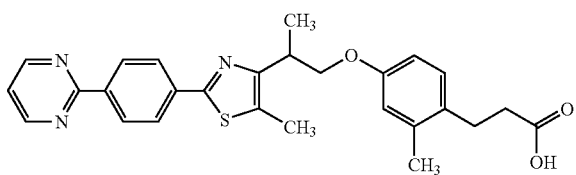

MS (ES): 447.0 (M$^+$+1).

Example 195

3-(2-Methyl-4-{2-[4-methyl-2-(4-pyrimidin-2-yl-phenyl)-oxazol-5-yl]-propoxy}-phenyl)-propionic acid

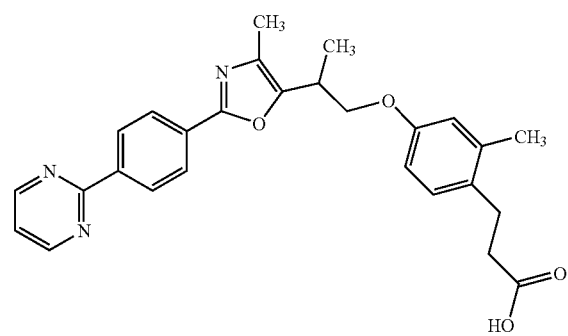

MS (ES): 458.3 (M$^+$+1).

Example 196

3-(2-Methyl-4-{2-[4-methyl-2-(4-pyrimidin-2-yl-phenyl)-thiazol-5-yl]-propoxy}-phenyl)-propionic acid

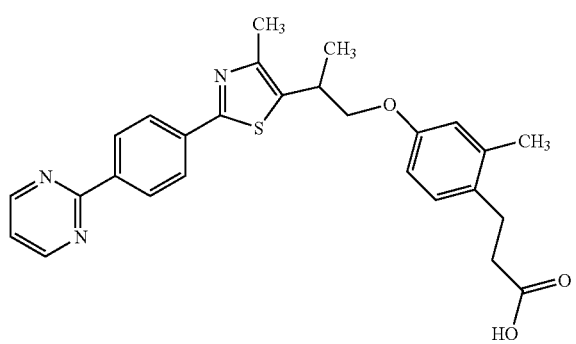

MS (ES): 474.2 (M$^+$+1).

Example 197

3-(2-Methyl-4-{2-[5-methyl-2-(4-pyrimidin-2-yl-phenyl)-oxazol-4-yl]-butoxy}-phenyl)-propionic acid

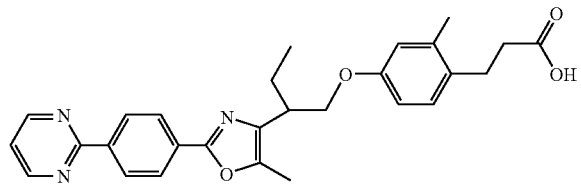

MS (ES): 472.3 (M$^+$++1).

Example 198

3-(2-Methyl-4-{2-[5-methyl-2-(4-pyrimidin-2-yl-phenyl)-thiazol-4-yl]-propoxy}-phenyl)-propionic acid

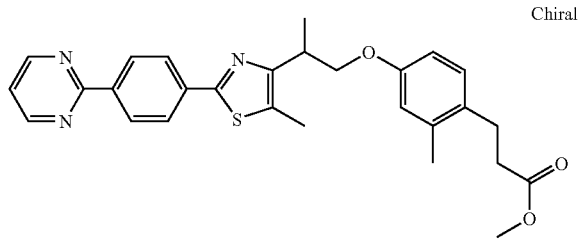

The racemic 3-(2-methyl-4-{2-[5-methyl-2-(4-pyrimidin-2-yl-phenyl)-thiazol-4-yl]-propoxy}-phenyl)-propionic acid methyl ester is resolved on a Chiralpak AD column (4.6×250 mm). Eluted with 15% 3A in heptane with 0.2% dimethy-ethylamine at 1 mL per minute with detection at 300 nM and concentrated the fractions to provide the pure enantiomer esters (isomer 1, 99.8% ee; isomer 2, 97.8% ee).

The following compounds are made in a similar manner:

Example 199

(R)-3-(2-Methyl-4-{2-[5-methyl-2-(4-pyridin-2-yl-phenyl)-thiazol-4-yl]-propoxy}-phenyl)-propionic acid

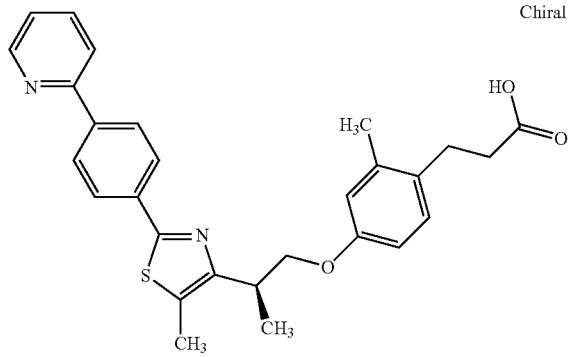

MS (ES): 473.2 (M$^+$+1).

Example 200

(S)-3-(2-Methyl-4-{2-[5-methyl-2-(4-pyridin-2-yl-phenyl)-thiazol-4-yl]-propoxy}-phenyl)-propionic acid

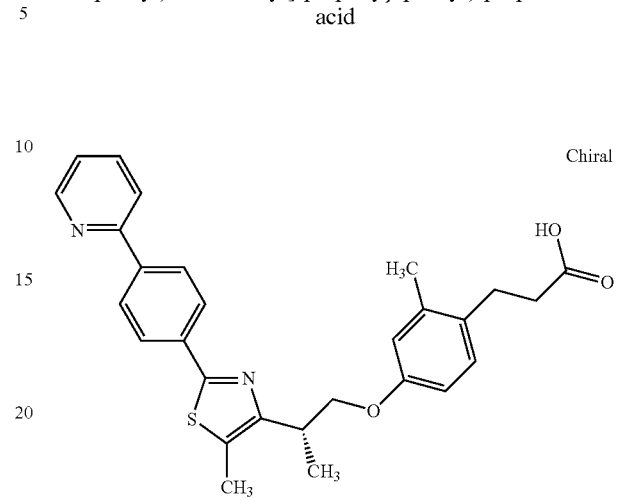

MS (ES): 473.2 (M$^+$+1).

Example 201

(R)-3-(2-Methyl-4-{2-[5-methyl-2-(4-pyridin-2-yl-phenyl)-oxazol-4-yl]-propoxy}-phenyl)-propionic acid

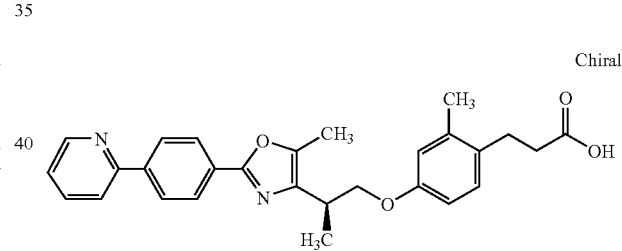

MS (ES): 457.3 (M$^+$+1).

Example 202

(S)-3-(2-Methyl-4-{2-[5-methyl-2-(4-pyridin-2-yl-phenyl)-oxazol-4-yl]-propoxy}-phenyl)-propionic acid

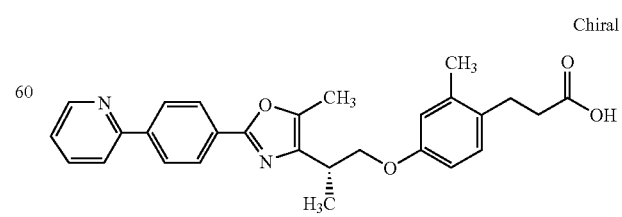

MS (ES): 457.3 (M$^+$+1).

Example 203

(R)-3-(2-Methyl-4-{2-[5-methyl-2-(4-pyrimidin-2-yl-phenyl)-oxazol-4-yl]-propoxy}-phenyl)-propionic acid

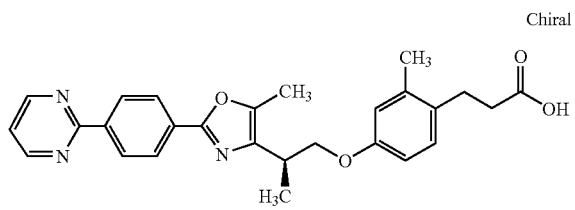

MS (ES): 458.3 (M$^+$+1).

Example 204

(S)-3-(2-Methyl-4-{2-[5-methyl-2-(4-pyrimidin-2-yl-phenyl)-oxazol-4-yl]-propoxy}-phenyl)-propionic acid

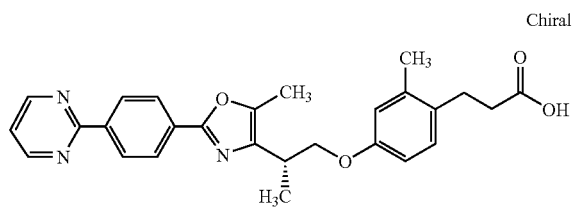

MS (ES): 458.3 (M$^+$+1).

Example 205

(R)-3-(2-Methyl-4-{2-[5-methyl-2-(4-pyrimidin-2-yl-phenyl)-oxazol-4-yl]-propoxy}-phenyl)-propionic acid

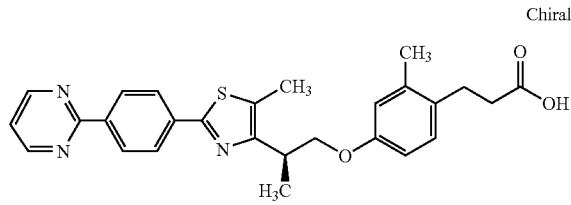

MS (ES): 474.3 (M$^+$+1).

Example 206

(S)-3-(2-Methyl-4-{2-[5-methyl-2-(4-pyrimidin-2-yl-phenyl)-thiazol-4-yl]-propoxy}-phenyl)-propionic acid

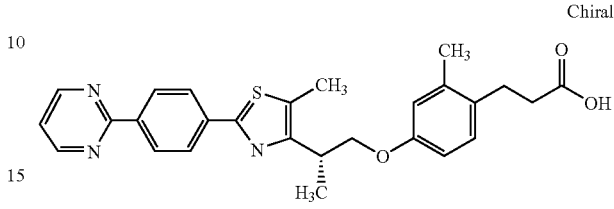

MS (ES): 474.3 (M$^+$+1).

Biological Assays

Binding and Cotransfection Studies

The in vitro potency of compounds in modulating PPAR receptors are determined by the procedures detailed below. DNA-dependent binding (ABCD binding) is carried out using SPA technology with PPAR receptors. Tritium-labeled PPAR selective agonists are used as radioligands for generating displacement curves and IC$_{50}$ values with compounds of the invention. Cotransfection assays are carried out in CV-1 cells. The reporter plasmid contained an acyl-CoA oxidase (AOX) PPRE and TK promoter upstream of the luciferase reporter cDNA. Appropriate PPARs are constitutively expressed using plasmids containing the CMV promoter. For PPARα, interference by endogenous PPARγ in CV-1 cells is an issue. In order to eliminate such interference, a GAL4 chimeric system is used in which the DNA binding domain of the transfected PPAR is replaced by that of GAL4, and the GAL4 response element is utilized in place of the AOX PPRE. Cotransfection efficacy is determined relative to PPARα agonist reference molecules. Efficacies are determined by computer fit to a concentration-response curve, or in some cases at a single high concentration of agonist (10 μM). These studies are carried out to evaluate the ability of compounds of the invention to bind to and/or activate various nuclear transcription factors, particularly huPPARα ("hu" indicates "human"). These studies provide in vitro data concerning efficacy and selectivity of compounds of the invention. Furthermore, binding and cotransfection data for compounds of the invention are compared with corresponding data for marketed compounds that act on huPPARα.

The binding and cotransfection efficacy values found, for compounds of the invention and compounds of this invention which are useful for modulating a PPAR alpha receptor, are ≦100 nM and ≧50%, respectively.

Binding Assay:

DNA-dependent binding is carried out using Scintillation Proximity Assay (SPA) technology (Amersham Pharmacia Biotech). PPAR•, PPAR• and PPAR• receptors as well as their heterodimer partner RXR••receptor are prepared using a baculovirus expression system. Biotinylated oligonucleotide 5'TAATGTAGGTAATAGTTCAATAGGT-CAAAGGG3' is used for binding of receptor dimers to Yttrium silicate streptavidin-coated SPA beads. PPAR• labeled ligand is $^3$H-reference, and PPAR• and PPAR•• labeled ligands is ³H-reference with specific activity of 52 Ci/mmol and 90 Ci/mmol, respectively. Competition binding reactions are carried out in 10 mM HEPES pH 7.8, 80 mM KCl, 0.5 mM MgCl$_2$, 1 mM DTT, 0.5% CHAPS, 14% glycerol, using 2.5 •g of each of PPAR•, • or • and RXR• receptors, 5 nM to 10 •M of competing compounds and 30,000 cpm of corresponding labeled ligand.

Co-Transfection Assay:

Co-transfection assays are performed in CV-1 cells using calcium phosphate coprecipitation as previously described (Berger et al. Steroid Biochem. Mol. Biol. 41:733, 1992; Mukherjee et al. Nature 386:407–410, 1997). The reporter plasmid contained an acylCoA oxidase (AOX) PPRE and TK promoter upstream of the luciferase reporter cDNA. PPARs and RXR• are constitutively expressed using plasmids containing the CMV promoter. For PPAR••or••, interference by endogenous PPARs in CV-1 cells is eliminated by using a GAL4 chimeric system in which the DNA binding domain of the transfected PPAR••or•••is replaced by that of GAL4, and the GAL4 response element is utilized in place of the AOX PPRE. CV-1 cells are transfected in T225 cm$^2$ flasks in DMEM with 10% Fetal Bovine Serum (FBS). After an overnight incubation, transfected cells are trypsinized and plated in 96 well dishes in DMEM media containing 10% charcoal-stripped FBS. After a 6 h incubation, cells are exposed to 0.1 nM to 10•M of test compounds. Co-transfection efficacy is determined using reference compounds. Compounds of this invention that are selective for the PPAR• are at least 10-fold selective for PPAR•• over PPARα and PPARγ.

Evaluation of Triglyceride Reduction and HDL Cholesterol Elevation in HuapoAI Transgenic Mice Seventeen different series of studies are performed to evaluate the effect of compounds of the present invention upon HDL and triglyceride levels in human apoAI mice. For each compound tested, seven to eight week old male mice, transgenic for human apoAI (C57BL/6-tgn(apoa1)1rub, Jackson Laboratory, Bar Harbor, Me.) are acclimated in individual cages for two weeks with standard chow diet (Purina 5001) and water provided ad libitum. After the acclimation, mice and chow are weighed and assigned to test groups (n=5) with randomization by body weight. Mice are dosed daily by oral gavage for 8 days using a 29 gauge, 1½ inch curved feeding needle (P*opper* & S*ons*). T*he* vehicle for the *controls*, test compounds and the positive control (*fenofibrate* 100 mg/kg) is 1% carboxymethylcellulose (w/v) with 0.25% tween 80 (w/v). All mice are dosed daily between 6 and 8 a.m. with a dosing volume of 0.2 ml. Prior to termination, animals and diets are weighed and body weight change and food consumption are calculated. Three hours after last dose, mice are euthanized with CO$_2$ and blood is removed (0.5–1.0 ml) by cardiac puncture. After sacrifice, the liver, heart, and epididymal fat pad are excised and weighed. Blood is permitted to clot and serum is separated from the blood by centrifugation.

Cholesterol and triglycerides are measured colorimetrically using commercially prepared reagents (for example, as available from Sigma #339–1000 and Roche-#450061 for triglycerides and cholesterol, respectively). The procedures are modified from published work (McGowan M. W. et al., Clin Chem 29:538–542,1983; Allain C. C. et al., Clin Chem 20:470–475,1974. Commercially available standards for triglycerides and total cholesterol, respectively, commercial quality control plasma, and samples are measured in duplicate using 200 μl of reagent. An additional aliquot of sample, added to a well containing 200 μl water, provided a blank for each specimen. Plates are incubated at room temperature on a plate shaker and absorbance is read at 500 nm and 540 nm for total cholesterol and triglycerides, respectively. Values for the positive control are always within the expected range and the coefficient of variation for samples is below 10%. All samples from an experiment are assayed at the same time to minimize inter-assay variability.

Serum lipoproteins are separated and cholesterol quantitated by fast protein liquid chromatography (PPLC) coupled to an in line detection system. Samples are applied to a Superose 6 HR size exclusion column (Amersham Pharmacia Biotech) and eluted with phosphate buffered saline-EDTA at 0.5 ml/min. Cholesterol reagent (for example, Roche Diagnostics Chol/HP 704036) at 0.16 ml/min mixed with the column effluent through a T-connection and the mixture passed through a 15 m×0.5 mm id knitted tubing reactor immersed in a 37 C water bath. The colored product produced in the presence of cholesterol is monitored in the flow strem at 505 nm and the analog voltage from the monitor is converted to a digital signal for collection and analysis. The change in voltage corresponding to change in cholesterol concentration is plotted vs time and the area under the curve corresponding to the elution of very low density lipoprotein (VLDL), low density lipoprotein (LDL) and high density lipoprotein (HDL) is calculated using Perkin Elmer Turbochrome software.

Triglyceride Serum Levels in Mice Dosed with a Compound of the Invention is compared to Mice Receiving the Vehicle to identify compounds that could be particularly useful for lowering triglycerides. Generally, triglyceride decreases of greater than or equal to 30% (thirty percent) compared to control following a 30 mg/kg dose suggests a compound that can be especially useful for lowering triglyceride levels.

The percent increase of HDLc serum levels in mice receiving a compound of the invention is compared to mice receiving vehicle to identify compounds of the invention that could be particularly useful for elevating HDL levels. Generally, and increase of greater than or equal to 25% (twenty five percent) increase in HDLc level following a 30 mg/kg dose suggests a compound that can be especially useful for elevating HDLc levels.

It may be particularly desirable to select compounds of this invention that both lower triglyceride levels and increase HDLc levels. However, compounds that either lower triglyceride levels or increase HDLc levels may be desirable as well.

Evaluation of Glucose Levels in db/db Mice

The effects, upon plasma glucose of administering various dose levels of five different compounds of the present invention and the PPAR gamma agonist rosiglitazone or the PPAR alpha agonist fenofibrate, and the control, to male db/db mice, are studied.

Five week old male diabetic (db/db) mice [for example, C57BlKs/j-m+/+Lepr(db), Jackson Laboratory, Bar Harbor, Me.] or lean littermates are housed 6 per cage with food and water available at all times. After an acclimation period of 2 weeks, animals are individually identified by ear notches, weighed, and bled via the tail vein for determination of initial glucose levels. Blood is collected (100 μl) from unfasted animals by wrapping each mouse in a towel, cutting the tip of the tail with a scalpel, and milking blood from the tail into a heparinized capillary tube. Sample is discharged into a heparinized microtainer with gel separator and retained on ice. Plasma is obtained after centrifugation at 4° C. and glucose measured immediately. Remaining plasma is frozen until the completion of the experiment, when glucose and triglycerides are assayed in all samples. Animals are grouped based on initial glucose levels and body weights. Beginning the following morning, mice are dosed daily by oral gavage for 7 days. Treatments are test compounds (30 mg/kg), a positive control agent (30 mg/kg) or vehicle [1% carboxymethylcellulose (w/v)/0.25% Tween80 (w/v); 0.3 ml/mouse]. On day 0.7, mice are weighed and bled (tail vein) 3 hours after dosing. Twenty-four hours after the $7^{th}$ dose (i.e., day 8), animals are bled again (tail vein). Samples obtained from conscious animals on days 0, 7 and 8 are assayed for glucose. After the 24 hour bleed, animals are weighed and dosed for the final time. Three hours after dosing on day 8, animals are anesthetized by inhalation of isoflurane and blood obtained via cardiac puncture (0.5–0.7 ml). Whole blood is transferred to serum separator tubes, chilled on ice and permitted to clot. Serum is obtained after centrifugation at 4° C. and frozen until analysis for compound levels. After sacrifice by cervical dislocation, the liver, heart and epididymal fat pads are excised and weighed.

Glucose is measured colorimetrically using commercially purchased reagents. According to the manufacturers, the procedures are modified from published work (McGowan, M. W., Artiss, J. D., Strandbergh, D. R. & Zak, B. Clin Chem, 20:470-5 (1974) and Keston, A. Specific colorimetric enzymatic analytical reagents for glucose. Abstract of papers 129th Meeting ACS, 31C (1956).); and depend on the release of a mole of hydrogen peroxide for each mole of analyte, coupled with a color reaction first described by Trinder (Trinder, P. Determination of glucose in blood using glucose oxidase with an alternative oxygen acceptor. Ann Clin Biochem, 6:24 (1969)). The absorbance of the dye produced is linearly related to the analyte in the sample. The assays are further modified in our laboratory for use in a 96 well format. The commercially available standard for glucose, commercially available quality control plasma, and samples (2 or 5 µl/well) are measured in duplicate using 200 µl of reagent. An additional aliquot of sample, pipetted to a third well and diluted in 200 µl water, provided a blank for each specimen. Plates are incubated at room temperature for 18 minutes for glucose on a plate shaker (DPC Micormix 5) and absorbance read at 500 nm on a plate reader. Sample absorbances are compared to a standard curve (100–800 for glucose). Values for the quality control sample are always within the expected range and the coefficient of variation for samples is below 10%. All samples from an experiment are assayed at the same time to minimize inter-assay variability.

The results of the study, suggest compounds of the present invention that significantly reduced db/db mouse plasma glucose levels while resulting in body weight gains that are generally less than those observed for rosiglitazone.

Evaluation of the Effects of Compounds of the Present Invention Upon $A^y$ Mice Body Weight, Fat Mass, Glucose and Insulin Levels Female $A^y$ Mice Female $A^y$ mice are singly housed, maintained under standardized conditions (22° C., 12 h light:dark cycle), and provided free access to food and water throughout the duration of the study. At twenty weeks of age the mice are randomly assigned to vehicle control and treated groups based on body weight and body fat content as assessed by DEXA scanning (N=6). Mice are then dosed via oral gavage with either vehicle or a Compound of this invention (50 mg/kg) one hour after the initiation of the light cycle (for example, about 7 A.M.) for 18 days. Body weights are measured daily throughout the study. On day 14 mice are maintained in individual metabolic chambers for indirect calorimetry assessment of energy expenditure and fuel utilization. On day 18 mice are again subjected to DEXA scanning for post treatment measurement of body composition.

The results of p.o. dosing of compound for 18 days on body weight, fat mass, and lean mass are evaluated and suggest which compounds of this invention can be especially useful for maintaining desirable weight and/or promoting desired lean to fat mass.

Indirect calorimetry measurements revealed a significant reduction in respiratory quotient (RQ) in treated animals during the dark cycle [0.864±0.013 (Control) vs. 0.803±0.007 (Treated); p<0.001]. This reduction in RQ is indicative of an increased utilization of fat during the animals' active (dark) cycle. Additionally, treated animals displayed significantly higher rates of energy expenditure than control animals (17.40±0.49 vs. 13.62±0.26 kcal/kg/hr, respectively).

Male KK/$A^y$ Mice

Male KK/$A^y$ mice are singly housed, maintained under standardized conditions (22° C., 12 h light:dark cycle), and provided free access to food and water throughout the duration of the study. At twenty-two weeks of age the mice are randomly assigned to vehicle control and treated groups based on plasma glucose levels. Mice are then dosed via oral gavage with either vehicle or a Compound of this invention (30 mg/kg) one hour after the initiation of the light cycle (7 A.M.) for 14 days. Plasma glucose, triglyceride, and insulin levels are assessed on day 14.

The results of p.o. dosing of compound for 14 days on plasma glucose, triglycerides, and insulin are evaluated to identify compounds of this invention that may be especially desired.

Method to Elucidate the LDL-cholesterol Total-cholesterol and Triglyceride Lowering Effect Male Syrian hamsters (Harlan Sprague Dawley) weighing 80–120 g are placed on a high-fat cholesterol-rich diet for two to three weeks prior to use. Feed and water are provided ad libitum throughout the course of the experiment. Under these conditions, hamsters become hypercholesterolemic showing plasma cholesterol levels between 180–280 mg/dl. (Hamsters fed with normal chow had a total plasma cholesterol level between 100–150 mg/dl.) Hamsters with high plasma cholesterol (180 mg/dl and above) are randomized into treatment groups based on their total cholesterol level using the GroupOptimizeV211.xls program.

A Compound of this invention is dissolved in an aqueous vehicle (containing CMC with Tween 80) such that each hamster receives once a day approx. 1 ml of the solution by garvage at doses 3 and 30 mg/kg body weight. Fenofibrate (Sigma Chemical, prepared as a suspension in the same vehicle) is given as a known alpha-agonist control at a dose of 200 mg/kg, and the blank control is vehicle alone. Dosing is performed daily in the early morning for 14 days.

Quantification of Plasma Lipids:

On the last day of the test, hamsters are bled (400 ul) from the suborbital-sinus while under isoflurane anesthesia 2 h after dosing. Blood samples are collected into heparinized microfuge tubes chilled in ice bath. Plasma samples are separated from the blood cells by brief centrifugation. Total cholesterol and triglycerides are determined by means of enzymatic assays carried out automatically in the Monarch equipment (Instrumentation Laboratory) following the manufacturer's precedure. Plasma lipoproteins (VLDL, LDL and HDL) are resolved by injecting 25 ul of the pooled plasma samples into an FPLC system eluted with phosphate buffered saline at 0.5 ml/min through a Superose 6 HR 10/30 column (Pharmacia) maintained room temp. Detection and characterization of the isolated plasma lipids are accomplished by postcolumn incubation of the effluent with a Cholesterol/HP reagent (for example, Roche Lab System; infused at 0.12 ml/min) in a knitted reaction coil maintained at 37° C. The intensity of the color formed is proportional to the cholesterol concentration and is measured photometrically at 505 nm.

The effect of administration of a Compound of this invention for 14 days is studied for the percent reduction in LDL level with reference to the vehicle group. The LDL-lowering efficacy for certain compounds of this invention is markedly more potent than that of fenofibrate. Compounds of this invention that decrease LDL greater than or equal to 30% (thirty percent) compared to vehicle can be especially desired.

The total-cholesterol and triglyceride lowering effects of a Compound of this invention is also studied. The data for reduction in total cholesterol and triglyceride levels after treatment with a compound of this invention for 14 days is compared to the vehicle to suggest compounds that can be particularly desired.

Method to Elucidate the Fibrinogen-lowering Effect of PPAR•Modulators

Zucker Fatty Rat Model:

The life phase of the study on fibrinogen-lowering effect of compounds of this invention is part of the life phase procedures for the antidiabetic studies of the same compounds. On the last (14th) day of the treatment period, with the animals placed under surgical anesthesia, ~3 ml of blood is collected, by cardiac puncture, into a syringe containing citrate buffer. The blood sample is chilled and centrifuged at 4° C. to isolate the plasma that is stored at −70° C. prior to fibrinogen assay.

Quantification of Rat Plasma Fibrinogen:

Rat plasma fibrinogen levels are quantified by using a commercial assay system consists of a coagulation instrument following the manufacturer's protocol. In essence, 100 ul of plasma is sampled from each specimen and a 1/20 dilution is prepared with buffer. The diluted plasma is incubated at 37° C. for 240 seconds. Fifty microliters of clotting reagent thrombin solution (provided by the instrument's manufacturer in a standard concentration) is then added. The instrument monitores the clotting time, a function of fibrinogen concentration quantified with reference to standard samples.

RESULTS

Compounds of this invention are capable of lowering fibrinogen level in vivo. Compounds that lower fibrinogen level greater than vehicle can be especially desired.

Cholesterol and triglyceride lowering effects of compounds of this invention are also produced in Zucker rats.

Method to Elucidate the Anti-body Weight Gain and Anti-appetite Effects of Compounds of this Invention Fourteen-Day Study in Zucker Fatty Rat[1] or ZDF Rat[2] Models:

Male Zucker Fatty rats, non-diabetic (Charles River Laboratories, Wilmington, Mass.) or male ZDF rats (Genetic Models, Inc, Indianapolis, Ind.) of comparable age and weight are acclimated for 1 week prior to treatment. Rats are on normal chow and water is provided ad libitum throughout the course of the experiment.

Test compounds are dissolved in an aqueous vehicle such that each rat receives once a day approximately 1 ml of the solution by garvage at doses 0.1, 0.3, 1 and 3 mg/kg body weight. Fenofibrate (Sigma Chemical, prepared as a suspension in the same vehicle) a known alpha-agonist given at doses of 300 mg/kg, as well as the vehicle are controls. Dosing is performed daily in the early morning for 14 days. Over the course of the experiment, body weight and food consumption are monitored.

Using this assay, compounds of this invention can result in significant weight reduction.

EQUIVALENTS

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound of the formula Formula I:

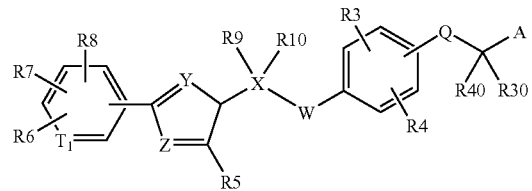

and pharmaceutically acceptable salts thereof, wherein;
(a) R3 is selected from the group consisting of hydrogen, ($C_1$–$C_4$)alkyl, halo, and ($C_1$–$C_6$)alkoxy;
(b) R4 is methyl;
(c) R30 and R40 are each hydrogen;
(d) R5 is selected from the group consisting of ($C_2$–$C_4$) alkyl, ($C_1$–$C_6$)alkenyl, aryl($C_0$–$C_4$)alkyl, aryloxy ($C_0$–$C_4$)alkyl, arylthio($C_0$–$C_4$)alkyl, wherein said aryl ($C_0$–$C_4$)alkyl, aryloxy($C_0$–$C_4$)alkyl, and arylthio ($C_0$–$C_4$)alkyl are each independently optionally substituted with from one to three substituents each independently selected from R5', and further wherein when R5 is alkyl, R5 can optionally combine with W to form a 6 membered cycloheteroalkyl ring that is fused with the oxazole or thiazole ring to which the R5 group is attached;
(e) R5' are each independently selected from the group consisting of halo, —(O)—($C_1$–$C_5$)alkylCOOH, $C_1$–$C_5$alkyl, $C_1$–$C_5$alkylCOOH, and $CF_3$;
(f) R6 is selected from the group consisting of trihalomethyl, trihalomethoxy, hydroxyl($C_0$–$C_3$)alkyl, ($C_1$–$C_4$) alkyl, ($C_1$–$C_6$)alkyINC(O)—, tetramethyldioxaborolanyl, halo, —C(O)($C_1$–$C_4$)alkyl, —O—($C_1$–$C_2$)alkyl-$CO_2$H, aryloxy, arylthio, —C(O)N($C_1$–$C_6$)alkyl, ($C_1$–$C_4$)alkoxy, tetrahydropyranyloxy, morpholinyl, ($C_5$–$C_6$)cycloalkyloxy, ($C_5$–$C_6$)heterocyclo-oxy, pyridinyl, pyrimidinyl, pyrazinyl and aryl($C_0$–$C_4$)alkyl, wherein said pyridinyl, pyrimidinyl, pyrazinyl, aryl ($C_0$–$C_4$)alkyl, aryloxy, ($C_5$–$C_6$)heterocyclo-oxy, and arylthio are each optionally substituted with from one to three substituents independently selected from R6';

(g) R6' and R9' are each independently selected from the group consisting of $CF_3$, $C_1$–$C_4$alkyl, halo, hydroxy ($C_1$–$C_3$)alkyl, $C_1$–$C_3$alkoxy, and —C(O)$CH_3$;

(h) R7 and R8 are each independently selected from the group consisting of hydrogen, $CF_3$, and ($C_1$–$C_3$)alkyl;

(i) R9 is selected from the group consisting of $C_1$–$C_5$alkyl, $C_1$–$C_5$alkenyl, and aryl$C_0$–$C_3$alkyl, wherein said arylalkyl is optionally substituted with from one to three substituents each independently selected from R9';

(j) R10 is selected from the group consisting of hydrogen, and $C_1$–$C_5$alkyl;

(k) Q is selected from the group consisting of O, a single bond, and $CH_2$;

(l) $T_1$ is C;

(m) W is selected from the group consisting of $CH_2$, C(O)N(R21), N(R21), N(R21)$CH_2$, O, $OCH_2$, S, and $SO_2$;

(n) R21 is selected from the group consisting of hydrogen and $C_1$–$C_2$alkyl;

(o) X is selected from the group consisting of C, $CH_2$C, and $CCH_2$;

(p) Y and Z are each independently selected from the group consisting of O, N and S, wherein at least one of Y and Z is selected from the group consisting of O and S;

(q) A is an functional group selected from the group consisting of carboxyl, $C_1$–$C_3$alkylnitrile, carboxamide, and $(CH_2)_n$ COOR19;

(r) n is 0, 1, 2 or 3;

(s) R19 is selected from the group consisting of hydrogen, and $C_1$–$C_3$alkyl; and (t) Further provided that when O is O and R5 is methyl, then R9 is benzyl.

2. A compound as claimed by claim 1 wherein W is O.

3. A compound as claimed by claim 1 wherein W is S.

4. A compound as claimed by claim 3 wherein Q is O.

5. A compound as claimed by claim 3 wherein Q is C.

6. A compound as claimed by claim 4 or 5 wherein Q bonded to the phenyl ring in a meta orientation with respect to W.

7. A compound as claimed by claim 4 or 5 wherein R3 is methyl.

8. A compound as claimed by claim 4 or 5 wherein X is C.

9. A compound as claimed by claim 2 wherein X is $CH_2$C.

10. A compound as claimed by claim 4 or 5 wherein R9 is $C_1$–$C_3$alkyl.

11. A compound as claimed by claim 2 wherein R9 is benzyl.

12. A compound as claimed by claim 8 or 9 wherein Y is N.

13. A compound as claimed by claim 8 or 9 wherein Z is O.

14. A compound as claimed by claim 8 or 9 wherein Z is S.

15. A compound as claimed by claim 12 wherein R5 is $C_2$–$C_4$alkyl.

16. A compound as claimed by claims 8 or 9 wherein R6 is selected from the group consisting of trihalomethoxy, ($C_1$–$C_6$)alkylNC(O)—, tetramethyldioxaborolanyl, —C(O)($C_1$–$C_4$)alkyl, —O—($C_1$–$C_2$)alkyl-$CO_2$H, aryloxy, arylthio, —C(O)N($C_1$–$C_6$)alkyl, morpholinyl, and ($C_5$–$C_6$)cycloalkyloxy.

17. A compound as claimed by claim 12 wherein R6 is $CF_3$.

18. A compound as claimed by claim 12 wherein A is COOH.

19. A compound as claimed by claim 1 wherein the compound is selected from the group consisting of (4-{1-[4-[2-(2-Chloro-6-fluoro-phenyl)-ethyl]-2-(4-trifluoromethyl-phenyl)-thiazol-5-yl]-ethylsulfanyl}-2-methyl-phenoxy)-acetic acid, (4-{1-[4-[2-(2-Chloro-6-fluoro-phenyl)-ethyl]-2-(4-trifluoromethyl-phenyl)-thiazol-5-yl]-ethoxy}-2-methyl-phenoxy)-acetic, 3-(4-{1-[4-[2-(2-Chloro-6-fluoro-phenyl)-ethyl]-2-(4-trifluoromethyl-phenyl)-thiazol-5-yl]-ethoxy}-2-methyl-phenyl)-propionic acid, (2-Methyl-4-{1-[4-phenethyl-2-(4-trifluoromethyl-phenyl)-thiazol-5-yl]-ethylsulfanyl}-phenoxy)-acetic acid, (2-Methyl-4-{1-[4-phenethyl-2-(4-trifluoromethyl-phenyl)-thiazol-5-yl]-ethoxy}-phenoxy)-acetic acid, 3-(2-Methyl-4-{1-[4-phenethyl-2-(4-trifluoromethyl-phenyl)-thiazol-5-yl]-ethoxy}-phenyl)-propionic acid, (2-Methyl-4-{1-[4-phenyl-2-(4-trifluoromethyl-phenyl)-thiazol-5-yl]-ethylsulfanyl}-phenoxy)-acetic acid, 3-(2-Methyl-4-{1-[4-phenyl-2-(4-trifluoromethyl-phenyl)-thiazol-5-yl]-ethoxy}-phenyl)-propionic acid, (4-{1-[4-Isopropyl-2-(4-trifluoromethyl-phenyl)-thiazol-5-yl]-ethylsulfanyl}-2-methyl-phenoxy)-acetic acid, (4-{1-[4-Isopropyl-2-(4-trifluoromethyl-phenyl)-thiazol-5-yl]-ethoxy}-2-methyl-phenoxy)-acetic acid, 3-(4-{1-[4-Isopropyl-2-(4-trifluoromethyl-phenyl)-thiazol-5-yl]-ethoxy}-2-methyl-phenyl)-propionic acid, 3-(4-{1-[4-Isopropyl-2-(4-trifluoromethyl-phenyl)-thiazol-5-yl]-ethylsulfanyl}-2-methyl-phenyl)-propionic acid, (2-Methyl-4-{1-[4-phenylsulfanylmethyl-2-(4-trifluoromethyl-phenyl)-thiazol-5-yl]-ethylsulfanyl}-phenoxy)-acetic acid, (4-{1-[4-(3,5-Bis-trifluoromethyl-phenoxymethyl)-2-(4-trifluoromethyl-phenyl)-thiazol-5-yl]-ethylsulfanyl}-2-methyl-phenoxy)-acetic acid, (4-{1-[4-(2-Chloro-6-fluoro-phenoxymethyl)-2-(4-trifluoromethyl-phenyl)-thiazol-5-yl]-ethylsulfanyl}-2-methyl-phenoxy)-acetic acid, 3-(4-{1-[4-(3,5-Bis-trifluoromethyl-phenoxymethyl)-2-(4-trifluoromethyl-phenyl)-thiazol-5-yl]-ethoxy}-2-methyl-phenyl)-propionic acid, 3-(4-{1-[4-(2-Chloro-6-fluoro-phenoxymethyl)-2-(4-trifluoromethyl-phenyl)-thiazol-5-yl]-ethoxy}-2-methyl-phenyl)-propionic acid, (4-{1R-[4-[2-(2-Chloro-6-fluoro-phenyl)-ethyl]-2-(4-trifluoromethyl-phenyl)-thiazol-5-yl]-ethylsulfanyl}-2-methyl-phenoxy)-acetic acid, (4-{1S-[4-[2-(2-Chloro-6-fluoro-phenyl)-ethyl]-2-(4-trifluoromethyl-phenyl)-thiazol-5-yl]-ethylsulfanyl}-2-methyl-phenoxy)-acetic acid, (2-Methyl-4-{1S-[4-phenethyl-2-(4-trifluoromethyl-phenyl)-thiazol-5-yl]-ethoxy}-phenoxy)-acetic acid, (2-Methyl-4-{1 R-[4-phenethyl-2-(4-trifluoromethyl-phenyl)-thiazol-5-yl]-ethoxy}-phenoxy)-acetic acid, (2-Methyl-4-{1R-[4-phenethyl-2-(4-trifluoromethyl-phenyl)-thiazol-5-yl]-ethylsulfanyl}-phenoxy)-acetic acid, (R)-(4-{1-[4-Isopropyl-2-(4-trifluoromethyl-phenyl)-thiazol-5-yl]-ethylsulfanyl}-2-methyl-phenoxy)-acetic acid, (S)-4-{1-[4-Isopropyl-2-(4-trifluoromethyl-phenyl)-thiazol-5-yl]-ethylsulfanyl}-2-methyl-phenoxy)-acetic acid, (S)-(4-{1-[4-Isopropyl-2-(4-trifluoromethyl-phenyl)-thiazol-5-yl]-ethoxy}-2-methyl-phenoxy)-acetic acid, (R)-4-{1-[4-Isopropyl-2-(4-trifluoromethyl-phenyl)-thiazol-5-yl]-ethoxy}-2-methyl-phenoxy)-acetic acid, (S)-3-(4-{1-[4-Isopropyl-2-(4-trifluoromethyl-phenyl)-thiazol-5-yl]-ethoxy}-2-methyl-phenyl)-propionic acid, (R)-3-(4-{1-[4-Isopropyl-2-(4-trifluoromethyl-phenyl)-thiazol-5-yl]-ethoxy}-2-methyl-phenyl)-propionic acid, (R)-3-(4-{1-[4-(2-Chloro-6-fluoro-phenoxymethyl)-2-(4-trifluoromethyl-phenyl)-thiazol-5-yl]-ethoxy}-2-methyl-phenyl)-propionic acid, (S)-3-(4-{1 -[4-(2-Chloro-6-fluoro-phenoxymethyl)-2-(4-trifluoromethyl-phenyl)-thiazol-5-yl]-ethoxy}-2-methyl-phenyl-propionic acid, (R)-4-{1-[4-(2-Chloro-6-fluoro-phenoxymethyl)-2-(4-trifluoromethyl-phenyl)-thiazol-5-yl]-ethylsulfanyl}-2-methyl-phenoxy)-acetic acid, (S)-(4-{1-[4-(2-Chloro-6-fluoro-phenoxymethyl)-2-(4-trifluoromethyl-phenyl)-thiazol-5-yl]-ethylsulfanyl}-2-methyl-phenoxy)-acetic acid, (S)-(2-Methyl-4-{1-[4-phenylsulfanylmethyl-2-(4-trifluoromethyl-phenyl)-thiazol-5-yl]-ethylsulfanyl}-phenoxy)-acetic acid, (R)-2-Methyl-4-{1-[4-phenylsulfanylmethyl-2-(4-trifluoromethyl-phenyl)-thiazol-5-yl]-4ethylsulfanyl}-phenoxy)-acetic acid, (S)-3-(2-Methyl-4-{1-[4-methyl-2-(4-trifluoromethyl-phenyl)-thiazol-5-yl]-ethoxy}-phenyl)-propionic acid, 3-(4-{1-[4-Ethyl-2-(4-trifluoromethyl-phenyl)-oxazol-5-yl]-ethoxy}-2-methyl-phenyl)-propionic acid, (4-{1-[4-Ethyl-2-(4-trifluoromethyl-phenyl)-oxazol-5-yl]-ethoxy}-2-methyl-phenoxy)-acetic acid, (4-{1-[4-Ethyl-2-(4-trifluoromethyl-phenyl)-oxazol-5-yl]-ethylsulfanyl}-2-methyl-phenoxy)-acetic acid, (4-{1R-[4-Ethyl-2-(4-trifluoromethyl-phenyl)-oxazol-5-yl]-ethylsulfanyl}-2-methyl-phenoxy)-acetic acid, (4-{1S-[4-Ethyl-2-(4-trifluoromethyl-phenyl)-oxazol-5-yl]-ethylsulfanyl}-2-methyl-phenoxy)-acetic acid, 3-(4-{1-[4-tert-Butyl-2-(4-trifluoromethyl-phenyl)-oxazol-5-yl]-ethoxy}-2-methyl-phenyl)-propionic acid, 3-(4-{1-[4-Isopropyl-2-(4-trifluoromethyl-phenyl)-oxazol-5-yl]-ethoxy}-2-methyl-phenyl)-propionic acid, 3-(4-{2-[4-Isopropyl-2-(4-trifluoromethyl-phenyl)-oxazol-5-yl]-propoxy}-2-methyl-phenyl)-propionic acid, 3-[4-( 1-{4-Isopropyl-2-[4-(4,4,5,-tetramethyl-[1,3,2] dioxaborolan-2-yl)-phenyl]-oxazol-5-yl}-ethoxy)-2-methyl-phenyl]-propionic acid methyl ester, 3-(4-{1-[2-(4-Hydroxy-phenyl)-4-isopropyl-oxazol-5-yl]-ethoxy}-2-methyl-phenyl)-propionic acid methyl ester, 3-(4-{1-[4-Isopropyl-2-(4-methoxy-phenyl)-oxazol-5-yl]-ethoxy}-2-methyl-phenyl)-propionic acid, 3-(4-{1-[2-(3-Cyclopentyloxy-phenyl)-4-isopropyl-oxazol-5-yl]-ethoxy}-2-methyl-phenyl)-propionic acid, 3-[4-(1-{4-Isopropyl-2-[3-(tetrahydro-pyran-4-yloxy)-phenyl]-oxazol-5-yl}-ethoxy)-2-methyl-phenyl]-propionic acid, 3-(4-{1-[2-(4-Cyclopentyloxy-phenyl)-4-isopropyl-oxazol-5-yl]-ethoxy}-2-methyl-phenyl)-propionic acid, 3-(4-{1-[4-Isopropyl-2-(4-piperidin-1-yl-phenyl)-oxazol-5-yl]-ethoxy}-2-methyl-phenyl)-propionic acid, 3-(4-{1-[4-Isopropyl-2-(3-piperidin-1-yl-phenyl)-oxazol-5-yl]-ethoxy}-2-methyl-phenyl)-propionic acid, 3-(4-{1-[4-Isopropyl-2-(3-morpholin-4-yl-phenyl)-oxazol-5-yl]-ethoxy}-2-methyl-phenyl)-propionic acid, 3-(4-{1-[4-Isopropyl-2-(4-morpholin-4-yl-phenyl)-oxazol-5-yl]-ethoxy}-2-methyl-phenyl)-propionic acid, and 3-(4-{1-[2-(4-Hexylcarbamoyl-phenyl)-4-isopropyl-oxazol-5-yl]-ethoxy}-2-methyl-phenyl)-propionic acid.

20. A compound as claimed by claim 1 wherein the compound is the S conformation.

21. A compound as claimed by claim 1 wherein the compound is the R conformation.

22. A pharmaceutical composition, comprising a pharmaceutically acceptable carrier and at least one compound as claimed by claim 1.

23. A method of treating diabetes mellitus in a mammal, comprising the step of administering to the mammal in need thereof, a therapeutically effective amount of at least one compound of claim 1.

24. A method of creating Syndrome X in a mammal, comprising the step of administering to the mammal in need thereof, a therapeutically effective amount of at least one compound of claim 1.

25. A method of treating atherosclerosis in a mammal, comprising the step of administering to the mammal in need thereof, a therapeutically effective amount of at least one compound of claim 1.

* * * * *